United States Patent
Van Berkel et al.

(10) Patent No.: US 9,988,661 B2
(45) Date of Patent: Jun. 5, 2018

(54) PROCESS FOR THE MODIFICATION OF A GLYCOPROTEIN USING A GLYCOSYLTRANSFERASE THAT IS OR IS DERIVED FROM A β(1,4)-N-ACETYLGALACTOSAMINYL-TRANSFERASE

(71) Applicant: SynAffix B.V., Oss (NL)

(72) Inventors: Sander Sebastiaan Van Berkel, Lent (NL); Remon Van Geel, Lithoijen (NL); Maria Antonia Wijdeven, Lent (NL); Floris Louis Van Delft, Nijmegen (NL)

(73) Assignee: SynAffix B.V., Oss (NL)

( * ) Notice: Subject to any disclaimer, the term of this patent is extended or adjusted under 35 U.S.C. 154(b) by 0 days. days.

(21) Appl. No.: 15/318,248

(22) PCT Filed: Apr. 25, 2016

(86) PCT No.: PCT/EP2016/059194
§ 371 (c)(1),
(2) Date: Dec. 12, 2016

(87) PCT Pub. No.: WO2016/170186
PCT Pub. Date: Oct. 27, 2016

(65) Prior Publication Data
US 2017/0130256 A1    May 11, 2017

(30) Foreign Application Priority Data
Apr. 23, 2015 (EP) .................... 15164864

(51) Int. Cl.
*C12P 21/00* (2006.01)
*C07K 16/32* (2006.01)
(Continued)

(52) U.S. Cl.
CPC ...... *C12P 21/005* (2013.01); *A61K 47/48384* (2013.01); *A61K 47/48561* (2013.01);
(Continued)

(58) Field of Classification Search
CPC ............. C12P 21/005; C12N 9/1051; C12Y 204/01092; C07K 16/32; C07K 16/2878;
(Continued)

(56) References Cited

U.S. PATENT DOCUMENTS 8,697,061 B2   4/2014   Natunen et al.
2008/0108557 A1   5/2008   Behrens et al.

FOREIGN PATENT DOCUMENTS

WO   WO-2004/024938 A2   3/2004
WO   WO-2007/095506 A1   8/2007
(Continued)

OTHER PUBLICATIONS

Rendic et al. The Glycosylation Capacity of Insect Cells. Croatica Chemica Acta 81(1):7-21 (2008) (Year: 2008).*
Bosco et al., "6-Azido D-galactose transfer to N-acetyl-D-glucosamine derivative using commercially available beta-1,4-galactosyltransferase", Tetrahedron Letters, 2008, vol. 49, pp. 2294-2297.
Bulter et al., "Chemoenzymatic synthesis of biotinylated nucleotide sugars as substrates for glycosyltransferases", ChemBioChem, 2001, vol. 2, pp. 884-894.
Burnham-Marusich et al., "Metabolic labeling of Caenorhabditis elegans primary embryonic cells with azid-sugars as a tool for glycoprotein discovery", Plos One, Nov. 2012, vol. 7, No. 11, p. e49020 (10 pages).
Clark et al., "Direct in-gel fluorescence detection and cellular imaging of O-GlcNAc-Modified proteins", J. Am. Chem. Soc., 2008, vol. 130, pp. 11576-11577.
Hoskins et al., "Sequence finishing and mapping of *Drosophila melanogaster* Heterochromatin", Science, Jun. 2007, vol. 316, No. 5831, pp. 1625-1628.
(Continued)

*Primary Examiner* — Yih-Horng Shiao
(74) *Attorney, Agent, or Firm* — Gilberto M. Villacorta; Sunit Talapatra; Foley & Lardner LLP

(57) ABSTRACT

The present invention relates to a process for the enzymatic modification of a glycoprotein. The process comprises the step of contacting a glycoprotein comprising a glycan comprising a terminal GlcNAc-moiety, in the presence of glycosyltransferase that is, or is derived from, a β-(1,4)-N-acetylgalactosaminyltransferase, with a non-natural sugar-derivative nucleotide. The non-natural sugar-derivative nucleotide is according to formula (3): wherein A is selected from the group consisting of $-N_3$, $-C(O)R^3$, $-(CH_2)_i$ $C\equiv C-R^4$, $-SH$, $-SC(O)R^8$, $-SC(O)OR8$, $-SC(S)OR8$, $-F$, $-Cl$, $-Br$, $-I$, $-OS(O)_2R^5$, terminal $C_2$-$C_{24}$ alkenyl groups, $C_3$-$C_5$ cycloalkenyl groups, $C_4$-$C_8$ alkadienyl groups, terminal $C_3$-$C_{24}$ allenyl groups and amino groups. The invention further relates to a glycoprotein obtainable by the process according to the invention, to a bioconjugate that can be obtained by conjugating the glycoprotein with a linker-conjugate, and to β-(1,4)-N-acetylgalactosaminyltransferases that can be used in preparing the the glycoprotein according to the invention.

11 Claims, 4 Drawing Sheets

(51) Int. Cl.
*C07K 16/28* (2006.01)
*C12N 9/10* (2006.01)
*A61K 47/48* (2006.01)

(52) U.S. Cl.
CPC .......... *C07K 16/2878* (2013.01); *C07K 16/32* (2013.01); *C12N 9/1051* (2013.01); *C12Y 204/01092* (2013.01); *C07K 2317/14* (2013.01); *C07K 2317/41* (2013.01)

(58) Field of Classification Search
CPC ............ C07K 2317/14; C07K 2317/41; A61K 47/48561; A61K 47/48384
USPC ................................. 514/20.9; 435/68.1, 69.1
See application file for complete search history.

(56) References Cited

FOREIGN PATENT DOCUMENTS

| WO | WO-2008/029281 A2 | 3/2008 |
|----|-------------------|--------|
| WO | WO-2010/130683 A1 | 11/2010 |
| WO | WO-2014/065661 A1 | 5/2014 |

OTHER PUBLICATIONS

Kawar et al., "Molecular cloning and enzymatic characterization of a UDP-GalNAc: GlGNAcbeta-R beta1,4-N-Acetylgalactosaminyltransferase from Caenorhabditis elegans", The Journal of Biological Chemistry, Sep. 2002, vol. 277, No. 38, pp. 34924-34932.
Khidekel et al., "A chemoenzymatic approach toward the rapid and sensitive detection of O-GlcNAc posttranslational modifications" J. Am. Chem. Soc., 2003, vol. 125, pp. 16162-16163.
Laughlin et al., "In Vivo imaging of Caenorhabditis elegans Glycans", ACS Chemical Biology, 2009, vol. 4, No. 12, pp. 1068-1072.
Mercer et al. "Use of novel mutant galactosyltransferase for the bioconjugation of terminal N-acetylglucosamine (GlcNAc) residues on live cell surface", Bioconjugate Chemistry, 2013, vol. 24, pp. 144-152.
Miller et al., "A necessary and sufficient determinant for protein-selective glycosylation in Vivo", The Journal of Biological Chemistry, 2008, vol. 283, No. 4, pp. 1985-1991.
Ramakrishnan et al., "Effect of the Met344His mutation on the conformational dynamics of bovine beta-1,4-galactosyltransferase: Crystal structure of the Met344His mutant in complex with chitobiose", Biochemistry, 2004, vol. 43, pp. 12513-12522.
Ramakrishnan et al., "Role of a single amino acid in the evolution of glycans of invertebrates and vertebrates", J. Mol. Biol., 2007, vol. 365, pp. 570-576.
Ramakrishnan et al., "Structure-based design of beta-1,4-Galactosyltransferase I (Beta4Gal-T1) with equally efficient N-Acetylgalactosaminylstransferase activity", The Journal of Biological Chemistry, 2002, vol. 277, No. 23, pp. 20833-20839.
Vadaie et al., "Molecular cloning and functional characterization of a lepidopteran insect beta4-N-Acetylgalactosaminyltransferase with broad substrate specificity, a functional role in glycoprotein biosynthesis, and a potential functional role in glycolipid biosynthesis", The Journal of Biological Chemistry, 2004, vol. 279, No. 32, pp. 33501-33518.
Vainauskas et al., "In vivo incorporation of an azide-labeled sugar analog to detect mammalian glycosylphosphatidylinositol molecules isolated from the cell surface", Carbohydrate Research, 2012, vol. 362, pp. 62-69.
Zeglis et al., "Enzyme-mediated methodology for the site-specific radiolabeling of antibodies based on catalyst-free click chemistry", Bioconjugate Chemistry, 2013, vol. 24, pp. 1057-1067.
International Search Report issued in International Patent Application No. PCT/EP2016/059194, dated Jun. 28, 2016.

\* cited by examiner

PROCESS FOR THE MODIFICATION OF A GLYCOPROTEIN USING A GLYCOSYLTRANSFERASE THAT IS OR IS DERIVED FROM A β(1,4)-N-ACETYLGALACTOSAMINYL- TRANSFERASE

CROSS-REFERENCE TO RELATED APPLICATIONS

This application is the National Phase of International Patent Application No. PCT/EP2016/059194, filed Apr. 25, 2016, published on Oct. 27, 2016 as WO 2016/170186 A1, which claims priority to European Patent Application No. 15164864.9, filed Apr. 23, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Dec. 12, 2016, is named 069818-2220Sequence_Listing.txt and is 260 KB.

TECHNICAL FIELD OF THE INVENTION

The present invention relates to a process for the enzymatic modification of a glycoprotein. More in particular, the invention relates to a process for the modification of a glycoprotein with a sugar-derivative nucleotide, using a glycosyltransferase enzyme that is or is derived from a β-(1,4)-N-acetylgalactosaminyltransferase. The invention also relates to a glycoprotein obtainable by the process, to a bioconjugate that can be obtained by conjugating the glycoprotein with a linker-conjugate, and to β-(1,4)-N-acetylgalactosaminyltransferases that can be used in preparing the the glycoprotein according to the invention.

BACKGROUND OF THE INVENTION

Glycosyltransferases constitute a superfamily of enzymes that are involved in the synthesis of complex carbohydrates present on glycoproteins and glycolipids. The fundamental role of a glycosyltransferase is to transfer the glycosyl moiety of a nucleotide derivative to a specific sugar acceptor. β-1,4-Galactosyltransferases (β4GalTs) (EC 2.4.1.38) constitute one of the subfamilies of glycosyltransferase superfamily—comprising at least seven members Gal-T1 to Gal-T7—which catalyze the transfer of galactose (Gal) from UDP-Gal to different sugar acceptors. A common motif resulting from a galactose transferase onto a terminal GlcNAc residue is the lactosamine sequence Galβ4GlcNAc-R (LacNAc or LN), which is subsequently modified in a variety of ways by the additions of other sugars and sulfate groups. The most common and important sugar structure of membrane glycoconjugates is poly-N-acetyllactosamine (poly-LN), which linked to proteins (or lipids), plays an important role in cellular communication, adhesion, and signalling and are key molecules in regulation of immune responses.

Another common terminal motif found in vertebrate and invertebrate glycoconjugates is the GalNAcβ4GlcNAc-R (LacdiNAc or LDN) sequence. The LDN motif occurs in mammalian pituitary glycoprotein hormones, where the terminal GalNAc residues are 4-O-sulfated and function as recognition markers for clearance by the endothelial cell Man/S4GGnM receptor. However, non-pituitary mammalian glycoproteins also contain LDN determinants. In addition, LDN and modifications of LDN sequences are common antigenic determinants in many parasitic nematodes and trematodes. The biosynthesis of LDN involves the transfer of GalNAc to a terminal GlcNAc, a process executed by highly specific GalNAc-transferases. For example it was reported by Miller et al. in *J. Biol. Chem.* 2008, 283, p. 1985, incorporated by reference, that two closely related β1,4-N-acetylgalactosaminyltransferases, β4GalNAc-T3 and β4GalNAc-T4, are thought to account for the protein-specific addition of β1,4-linked GalNAc to Asn-linked oligosaccharides on a number of glycoproteins including the glycoprotein luteinizing hormone (LH) and carbonic anhydrase-6 (CA6).

β-(1,4)-Acetylgalactosaminyltransferases (β-(1,4)-Gal-NAcTs) have been identified in a range of organisms, including humans, *Caenorhabditis elegans* (Kawar et al., *J. Biol. Chem.* 2002, 277, 34924, incorporated by reference), *Drosophila melanogaster* (Hoskins et al. *Science* 2007, 316, 1625, incorporated by reference) and *Trichoplusia ni* (Vadaie et al., *J. Biol. Chem.* 2004, 279, 33501, incorporated by reference).

Finally, besides GalTs and GalNAcTs involved in N-glycoprotein modification, a non-related class of enzymes called UDP-N-acetylgalactosamine:polypeptide N-acetylgalactosaminyltransferases (also referred to as ppGalNAcTs) is responsible for the biosynthesis of mucin-type linkages (GalNAc-α-1-O-Ser/Thr). These enzymes transfer GalNAc from the sugar donor UDP-GalNAc to serine and threonine residues, forming an alpha anomeric linkage typical in O-glycoproteins. Despite the seeming simplicity of ppGalNAcTs catalytic function, it is estimated on the basis of in silico analysis that there are 24 unique ppGalNAcTs human genes alone. Because O-linked glycosylation proceeds stepwise, addition of GalNAc to serine or threonine represents the first committed step in mucin biosynthesis. Despite this seeming simplicity, multiple ppGalNAcTs family members appear to be necessary to fully glycosylate their protein substrates.

It has been shown that galactosyltransferases are able to transfer, besides the natural substrate UDP-Gal, a range of unnatural galactose derivatives to an acceptor GlcNAc substrate. For example, Elling et al. in *ChemBioChem* 2001, 2, 884, incorporated by reference, showed that terminal GlcNAc-containing proteins can be biotinylated by transfer of a 6-modified galactose from an UDP-sugar under the action of a range of galactosyltransferases. Similarly, it was demonstrated by Pannecoucke et al. in *Tetrahedron Lett.* 2008, 49, 2294, incorporated by reference, that 6-azido-6-deoxygalactose can be transferred (to some extent) from the corresponding UDP-sugar to a small molecule GlcNAc substrate upon subjection to bovine β1,4-galactosyltransferase. The use of glycosyltransferases for modified galactose derivatives was also reported earlier in US 2008/0108557 (WO 2006/035057, Novo Nordisk A/S), where it is claimed that a wide range of galactose derivatives modified at C-6 (e.g. thiol, azide, O-propargyl, aldehyde) can be transferred to a GlcNAc substrate under the action of (bovine or human) β1,4-galactosyltransferase, using 2-10 equivalents of UDP-sugars. However, the data provided to support such claims concern only the 6-O-propargyl and 6-aldehydo variant of galactose. A range of GalNAc derivatives with a chemical handle at C2 is also claimed as substrates for glycosyltransferases but no examples were provided.

In particular the mutation of the Tyr-289 residue to Leu-289 in bovine β4Gal-T1, as reported by Ramakrishnan et al. *J. Biol. Chem.* 2002, 23, 20833, incorporated by reference, creates a catalytic pocket of the enzyme that can facilitate a UDP-Gal molecule carrying a chemical handle at C2, such as 2-keto-Gal. By a two-step procedure involving first transfer of the unnatural galactose moiety followed by oxime ligation onto the C-2 handle, this mutant enzyme, β4GalT(Y289L), has been used for in vitro detection of O-GlcNAc residues on proteins or the presence of a terminal GlcNAc moiety on the cell surface glycans of normal and malignant tumor tissues.

For example Khidekel et al., *J. Am. Chem. Soc.* 2003, 125, 16162, incorporated by reference, discloses chemoselective installation of an unnatural ketone functionality to O-GlcNAc modified proteins with β4GalT(Y289L). The ketone moiety serves as a unique marker to "tag" O-GlcNAc glycosylated proteins with biotin using oxime ligation. Once biotinylated, the glycoconjugates can be readily detected by chemiluminescence using streptavidin conjugated to horseradish peroxidase (HRP).

For example WO 2007/095506, WO 2008/029281 (both Invitrogen Corporation), WO 2014/065661 (SynAffix B.V.) and Clark et al. *J. Am. Chem. Soc.* 2008, 130, 11576, all incorporated by reference, report a similar approach, using β4GalT(Y289L) and azidoacetyl variants of galactosamine, with similar success.

For example U.S. Pat. No. 8,697,061 (Glykos), incorporated by reference, reports a similar approach, using β4GalT (Y289L) and 2-modified sugars, with similar success.

Mutant β4GalT(Y289L) has also been applied most recently in a preparative fashion for the site-selective radiolabeling of antibodies on the heavy chain glycans, as reported by Zeglis et al. in *Bioconj. Chem.* 2013, 24, 1057, incorporated by reference. In particular, the incorporation of azide-modified N-acetylgalactosamine monosaccharides (GalNAz) into the glycans of the antibody allowed the controlled labeling with $^{89}$Zr upon after click chemistry introduction of the appropriate chelator.

Ramakrishnan et al. in *Biochemistry* 2004, 43, 12513, incorporated by reference, describe that the double mutant β4GalT(Y289L,M344H) loses 98% of its $Mn^{2+}$-dependent activity, but nevertheless shows 25-30% activity in the presence of $Mg^{2+}$, including a capability to transfer C-2 modified galactose substrates. The double mutant β4GalT (Y289L,M344H) was found useful for in vitro galactosylation assays, because the typical requirement of 5-10 mM $Mn^{2+}$ is known to have potential cytotoxic effects for the cells.

Mercer et al., *Bioconjugate Chem.* 2013, 24, 144, incorporated by reference, describe that a double mutant Y289L-M344H-β4Gal-T1 enzyme transfers GalNAc and analogue sugars to the acceptor GlcNAc in the presence of $Mg^{2+}$.

Attempts to employ a wild-type β-(1,4)-N-acetylgalactosaminyltransferase, herein also referred to as β-(1,4)-GalNAcT, for the transfer of C-2 modified GalNAc have met little success to date.

Bertozzi et al. in *ACS Chem. Biol.* 2009, 4, 1068, incorporated by reference herein, applied the bioorthogonal chemical reporter technique for the molecular imaging of mucin-type O-glycans in live *C. elegans*. Worms were treated with the azido-sugar variant of N-acetylgalactosamine (GalNAz) allowing the in vivo incorporation of this unnatural sugar. Although metabolic incorporation of GalNAz into glycoproteins was observed, both chondroitinase ABC and peptide N-glycosidase F (PNGase F) digestion of *C. elegans* lysate, followed by the Staudinger ligation using a phosphine-Flag tag and subsequent probing of the glycoproteins by Western blotting utilizing an α-Flag antibody, indicated that the majority of GalNAz residues on glycoproteins were situated in other types of glycans than N-glycans. In addition, no detectable binding of azide-labeled glycoproteins to the N-glycan specific lectin concanavalin A (ConA) was observed, consistent with the hypothesis that the vast majority of labelled glycans are O-linked and not N-linked. Based on these observations, one may conclude that GalNAz does not metabolically incorporate onto N-GlcNAcylated proteins in this organism.

A similar conclusion was drawn most recently by Burnham-Marusich et al. in *Plos One* 2012, 7, e49020, incorporated by reference herein, where lack of signal reduction upon PNGase treatment—indicating no apparent incorporation of GalNAz in N-glycoproteins—was also observed. Burnham-Marusich et al. describe a study using the Cu(I)-catalyzed azide-alkyne cycloaddition reaction of a terminal alkyne-probe with an azido-labeled glycoprotein to detect metabolically labelled glycoproteins. Results indicated that the majority of the GalNAz label is incorporated into glycan classes that are insensitive to PNGase F, hence are not N-glycoproteins.

High substrate specificity of a β-(1,4)-GalNAcT for UDP-GalNAc becomes apparent from the poor recognition of UDP-GlcNAc, UDP-Glc and UDP-Gal, for which only 0.7%, 0.2% and 1% transferase activity remains, respectively, as was reported by Kawar et al., *J. Biol. Chem.* 2002, 277, 34924, incorporated by reference.

Based on the above, it is not surprising that no in vitro method for modification of glycoproteins has been reported by means of GalNAc-transferase of an unnatural GalNAc derivative such as a 2-keto or 2-azidoacetyl derivative.

At the same time, it has been reported by Qasba et al., *J. Mol. Biol.* 2007, 365, 570, incorporated by reference, that substitution of the Ile or Leu active site residue in invertebrate GalNAcTs—corresponding to the Tyr-289 residue in human β4Gal-T1 ortholog enzymes—for a Tyr residue, converts the enzyme to a β(1,4)galactosyltransferase by reducing its N-Acetylgalactosaminyltransferase activity by nearly 1000-fold, while enhancing its galactosyltransferase activity by 80-fold.

Taron et al., *Carbohydr. Res.* 2012, 362, 62, incorporated by reference, describe the in vivo metabolic incorporation of GalNAz in GPI-anchors.

SUMMARY OF THE INVENTION

The present invention relates to a process for the modification of a glycoprotein, the process comprising contacting a glycoprotein comprising a glycan comprising a terminal GlcNAc moiety, with a sugar-derivative nucleotide Su(A)-Nuc in the presence of a glycosyltransferase, wherein:
(i) the glycosyltransferase is, or is derived from, a β-(1, 4)-N-acetylgalactosaminyltransferase;
(ii) the glycan comprising a terminal GlcNAc-moiety is according to formula (1) or (2):

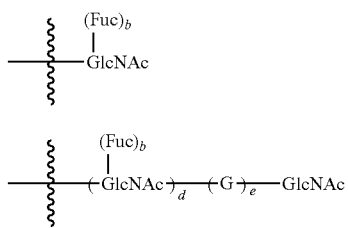

wherein:
b is 0 or 1;
d is 0 or 1;
e is 0 or 1; and
G is a monosaccharide, or a linear or branched oligosaccharide comprising 2 to 20 sugar moieties; and
(iii) the sugar-derivative nucleotide Su(A)-Nuc is according to formula (3):

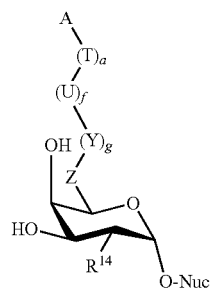

3 wherein:
a is 0 or 1;
f is 0 or 1;
g is 0 or 1;
Nuc is a nucleotide;
U is $[C(R^1)_2]_n$ or $[C(R^1)_2]_p$—O—$[C(R^1)_2C(R^1)_2O]_o$—$[C(R^1)_2]_q$, wherein n is an integer in the range of 1 to 24; o is an integer in the range of 0 to 12; p and q are independently 0, 1 or 2; and $R^1$ is independently selected from the group consisting of H, F, Cl, Br, I, OH and an optionally substituted $C_1$-$C_{24}$ alkyl group;
T is a $C_3$-$C_{12}$ (hetero)arylene group, wherein the (hetero)arylene group is optionally substituted;
A is selected from the group consisting of:
(a) —$N_3$
(b) —C(O)$R^3$
  wherein $R^3$ is an optionally substituted $C_1$-$C_{24}$ alkyl group;
(c) (hetero)cycloalkynyl group or a —$(CH_2)_iC\equiv C$—$R^4$ moiety
  wherein i is 0-10 and $R^4$ is hydrogen or an optionally substituted $C_1$-$C_{24}$ alkyl group;
(d) —SH
(e) —SC(O)$R^8$
  wherein $R^8$ is an, optionally substituted, $C_1$-$C_{24}$ alkyl group or phenyl group;
(f) —SC(V)O$R^8$
  wherein V is O or S, and $R^8$ is an, optionally substituted, $C_1$-$C_{24}$ alkyl group or phenyl group;
(g) —X
  wherein X is selected from the group consisting of F, Cl, Br and I;
(h) —OS(O)$_2R^5$
  wherein $R^5$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups, the alkyl groups, aryl groups, alkylaryl groups and arylalkyl groups being optionally substituted;
(i) $R^{12}$
  wherein $R^{12}$ is selected from the group consisting of, optionally substituted, terminal $C_2$-$C_{24}$ alkenyl groups, $C_3$-$C_5$ cycloalkenyl groups and $C_4$-$C_8$ alkadienyl groups; and
(j) $R^{13}$
  wherein $R^{13}$ is an optionally substituted terminal $C_3$-$C_{24}$ allenyl group; and
(k) $N(R^{17})_2$
  wherein $R^{17}$ is independently selected from the group consisting of H and $C_1$-$C_{12}$ alkyl groups;
Z is $CH_2$, $CF_2$ or C(O); or Z is CHOH with the proviso that when Z is CHOH, g is 0, f is 1 and a is 0 or 1;
Y is selected from the group consisting of O, S, $N(R^{15})$, $N(R^{15})C(O)$, $N(R^{15})C(O)N(R^{15})$, $N(R^{15})C(O)O$, $OC(O)N(R^{15})S(O)_2N(R^{15})$ and $N(R^{15})C(O)N(R^{15})S(O)_2O$, wherein $R^{15}$ is independently selected from the group consisting of H, $C_1$-$C_{12}$ alkyl groups and $(U)_f$-$(T)_a$-A wherein f, a, U, T and A are as defined above; and
$R^{14}$ is selected from the group consisting of:

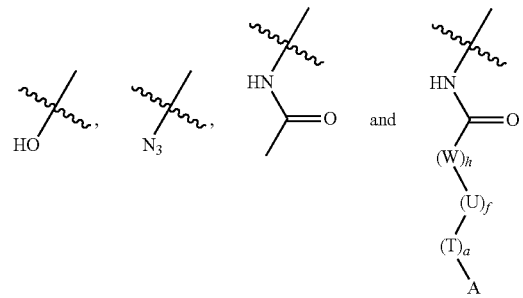

wherein:
a, f, T, A and U are as defined above;
h is 0 or 1; and
W is selected from the group consisting of O, S, $NR^{15}$, $NHS(O)_2O$ and $NHS(O)_2NR^5$, wherein $R^{15}$ is as defined above.

The invention further relates to a glycoprotein obtainable by the process according to the invention.

or (1) with an azido-modified UDP-GalNAc derivative, e.g. 6-azidoGalNAc, leads to an azido-modified glycoprotein (33) or (32), respectively.

Figure 5:
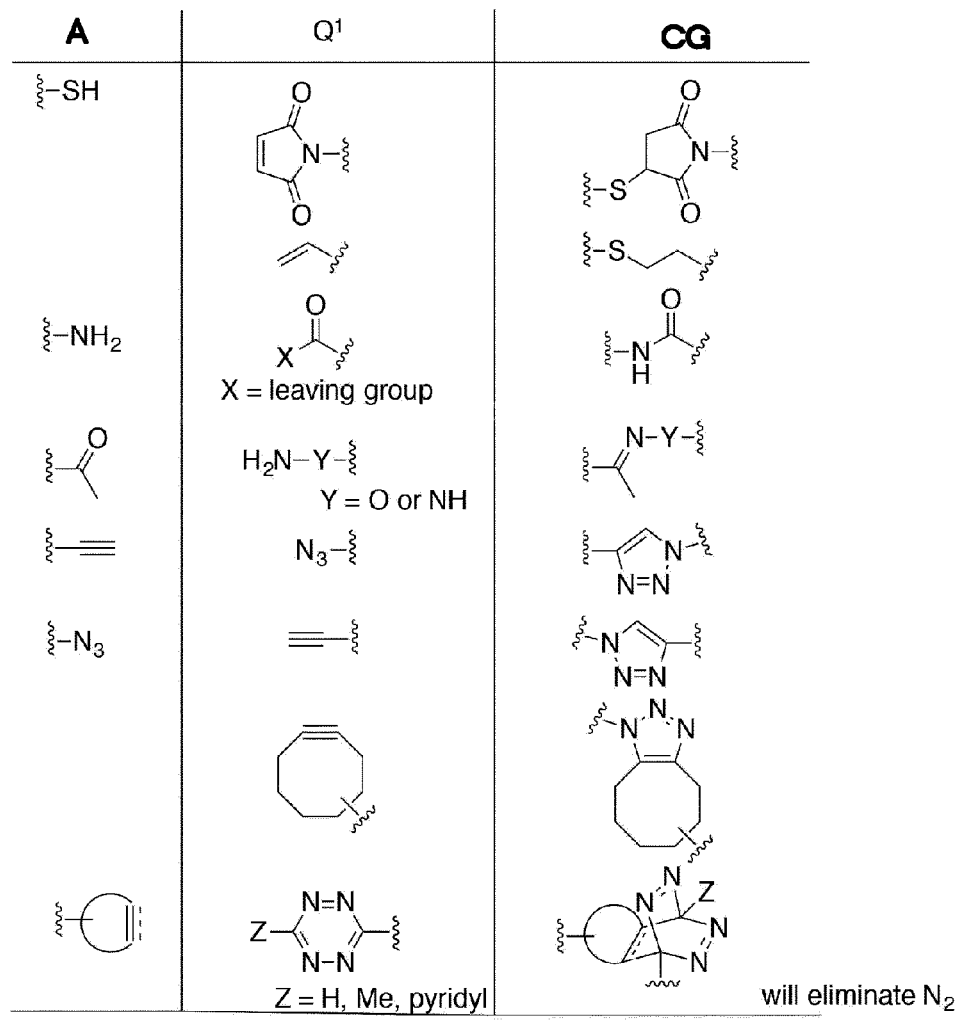

FIG. 5 shows a representative set of functional groups (A) in the modified glycoprotein according to the invention, which upon reaction with a reactive group $Q^1$ lead to connecting group CG and a functionalized glycoprotein.

DETAILED DESCRIPTION OF THE INVENTION

Definitions

The verb "to comprise" as is used in this description and in the claims, and its conjugations, is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

Unsubstituted alkyl groups have the general formula $C_nH_{2n+1}$ and may be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

Unless stated otherwise, alkyl groups, alkenyl groups, alkenes, alkynes, (hetero)aryl groups, (hetero)arylalkyl groups, alkyl(hetero)aryl groups, alkylene groups, alkenylene groups, cycloalkylene groups, (hetero)arylene groups, alkyl(hetero)arylene groups, (hetero)arylalkylene groups, alkenyl groups, alkynyl groups, cycloalkyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^2)_3Si$—, wherein $R^2$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

An alkynyl group comprises a carbon-carbon triple bond. An unsubstituted alkynyl group comprising one triple bond has the general formula $C_nH_{2n-3}$. A terminal alkynyl is an alkynyl group wherein the triple bond is located at a terminal position of a carbon chain. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero) cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to a nitrogen function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (*candida antartica* lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan.

A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein.

A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar.

A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The end of an oligosaccharide that is directly attached to the protein is called the reducing end of a glycan. The other end of the oligosaccharide is called the non-reducing end of a glycan.

For O-linked glycans, a wide diversity of chains exist. Naturally occurring O-linked glycans typically feature a serine or threonine-linked α-O-GalNAc moiety, further substituted with another GalNAc, galactose, GlcNAc, sialic acid and/or fucose. The hydroxylated amino acid that carries the glycan substitution may be part of any amino acid sequence in the protein.

For N-linked glycans, a wide diversity of chains exist. Naturally occurring N-linked glycans typically feature an asparagine-linked β-N-GlcNAc moiety, in turn further substituted at its 4-OH with β-GlcNAc, in turn further substituted at its 4-OH with β-Man, in turn further substituted at its 3-OH and 6-OH with α-Man, leading to the glycan pentasaccharide $Man_3GlcNAc_2$. The core GlcNAc moiety may be further substituted at its 6-OH by α-Fuc. The pentasaccharide $Man_3GlcNAc_2$ is the common oligosaccharide scaffold of nearly all N-linked glycoproteins and may carry a wide variety of other substituents, including but not limited to Man, GlcNAc, Gal and sialic acid. The asparagine that is substituted with the glycan on its side-chain is typically part of the sequence Asn-X-Ser/Thr, with X being any amino acid except proline and Ser/Thr being either serine or threonine.

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, $F(ab')_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Suitable marketed antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

Identity/Similarity

In the context of the invention, a protein or a protein fragment is represented by an amino acid sequence.

It is to be understood that each protein or protein fragment or peptide or derived peptide or polypeptide as identified herein by a given Sequence Identity Number (SEQ ID NO) is not limited to this specific sequence as disclosed. "Sequence identity" is herein defined as a relationship between two or more amino acid (polypeptide or protein) sequences, as determined by comparing the sequences. In the art, "identity" also means the degree of sequence similarity between amino acid sequences, as the case may be, as determined by the match between strings of such sequences. Unless otherwise indicated herein, identity or similarity with a given SEQ ID NO means identity or similarity based on the full length of said sequence (i.e. over its whole length or as a whole).

Any enzyme encompassed by the invention that has less than 100% sequence identity to the specifically indicated sequence defined by its SEQ ID NO, preferably has enzyme activity that is at least 10%, 20%, 30%, 40%, 50%, 60%, 70% or preferably at least 80% or 90% or at least 100% of the enzyme activity of the enzyme having 100% identity to said sequence defined by the SEQ ID NO.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between two or more sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr or His; Tyr to Trp or Phe; and, Val to Ile or Leu.

Process for the Modification of a Glycoprotein

The present invention relates to a process for the modification of a glycoprotein, under the action of a glycosyltransferase, wherein the glycosyltransferase is or is derived from a β-(1,4)-N-acetylgalactosaminyltransferase, in order to obtain a modified glycoprotein. Preferably the process is an in vitro process.

In particular, the invention relates to a process for the modification of a glycoprotein, the process comprising contacting a glycoprotein comprising a glycan comprising a terminal GlcNAc moiety, with a sugar-derivative nucleotide Su(A)-Nuc in the presence of a glycosyltransferase, wherein:

(i) the glycosyltransferase is or is derived from a β-(1,4)-N-acetylgalactosaminyltransferase;
  (ii) the glycan comprising a terminal GlcNAc-moiety is according to formula (1) or (2):

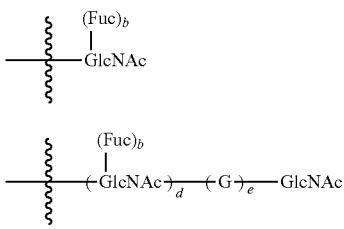

wherein:
b is 0 or 1;
d is 0 or 1;
e is 0 or 1; and
G is a monosaccharide, or a linear or branched oligosaccharide comprising 2 to 20 sugar moieties; and
(iii) the sugar-derivative nucleotide Su(A)-Nuc is according to formula (3):

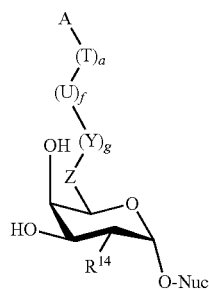

wherein:
a is 0 or 1;
f is 0 or 1;
g is 0 or 1;
Nuc is a nucleotide;
U is $[C(R^1)_2]_n$ or $[C(R^1)_2]_p$—O—$[C(R^1)_2C(R^1)_2O]_o$—$[C(R^1)_2]_q$, wherein n is an integer in the range of 1 to 24; o is an integer in the range of 0 to 12; p and q are independently 0, 1 or 2; and $R^1$ is independently selected from the group consisting of H, F, Cl, Br, I, OH and an optionally substituted $C_1$-$C_{24}$ alkyl group;
T is a $C_3$-$C_{12}$ (hetero)arylene group, wherein the (hetero)arylene group is optionally substituted;
A is selected from the group consisting of:
  (a) —$N_3$
  (b) —C(O)$R^3$
    wherein $R^3$ is an optionally substituted $C_1$-$C_{24}$ alkyl group;
  (c) (hetero)cycloalkynyl group or a —$(CH_2)_i$C≡C—$R^4$ moiety
    wherein i is 0-10 and $R^4$ is hydrogen or an optionally substituted $C_1$-$C_{24}$ alkyl group;
  (d) —SH
  (e) —SC(O)$R^8$
    wherein $R^8$ is an, optionally substituted, $C_1$-$C_{24}$ alkyl group or phenyl group;
  (f) —SC(V)O$R^8$
    wherein V is O or S, and $R^8$ is an, optionally substituted, $C_1$-$C_{24}$ alkyl group or phenyl group;
  (g) —X
    wherein X is selected from the group consisting of F, Cl, Br and I;
  (h) —OS(O)$_2R^5$
    wherein $R^5$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups, the alkyl groups, aryl groups, alkylaryl groups and arylalkyl groups being optionally substituted;
  (i) $R^{12}$
    wherein $R^{12}$ is selected from the group consisting of, optionally substituted, terminal $C_2$-$C_{24}$ alkenyl groups, $C_3$-$C_5$ cycloalkenyl groups and $C_4$-$C_8$ alkadienyl groups; and
  (j) $R^{13}$
    wherein $R^{13}$ is an optionally substituted terminal $C_3$-$C_{24}$ allenyl group; and
  (k) $N(R^{17})_2$
    wherein $R^{17}$ is independently selected from the group consisting of H and $C_1$-$C_{12}$ alkyl groups;
Z is $CH_2$, $CF_2$ or C(O); or Z is CHOH with the proviso that when Z is CHOH, g is 0, f is 1 and a is 0 or 1;
Y is selected from the group consisting of O, S, $N(R^{15})$, $N(R^{15})C(O)$, $N(R^{15})C(O)N(R^5)$, $N(R^{15})C(O)O$, $OC(O)N(R^{15})S(O)_2N(R^{15})$ and $N(R^{15})C(O)N(R^{15})S(O)_2O$, wherein $R^{15}$ is independently selected from the group consisting of H, $C_1$-$C_{12}$ alkyl groups and $(U)_f$-$(T)_a$-A wherein f, a, U, T and A are as defined above; and
$R^{14}$ is selected from the group consisting of:

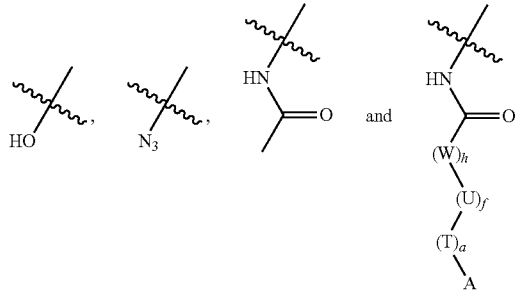

wherein:
a, f, T, A and U are as defined above;
h is 0 or 1; and
W is selected from the group consisting of O, S, $NR^{15}$, $NHS(O)_2O$ and $NHS(O)_2NR^{15}$, wherein $R^{15}$ is as defined above.

In one embodiment, A in Su(A)-Nuc is according to formula (3) is selected from the group consisting of options (a) to (j) as defined above. In another embodiment, A in Su(A)-Nuc is according to formula (3) is selected from the group consisting of options (a) to (d) and (g) to (k) as defined above, more preferably from the group consisting of options (a) to (d) and (g) to (j).

As described above, the process according to the invention for the modification of a glycoprotein provides a modified glycoprotein. A modified glycoprotein is herein defined as a glycoprotein comprising a glycan according to formula (4) or (5):

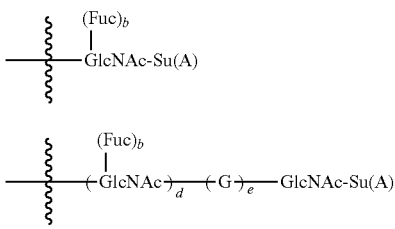

(4)

(5)

wherein:
b, d, e and G are as defined above; and
Su(A) is a sugar-derivative according to formula (6):

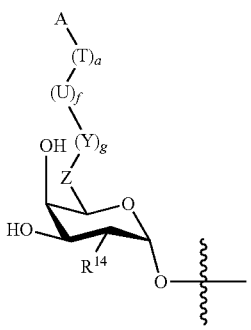

(6)

wherein:
$R^{14}$, Z, Y, U, T, A, g, f and a are as defined above.

In the modified glycoprotein glycan according to formula (4) and (5), C1 of sugar-derivative Su(A) is connected to C4 of the GlcNAc moiety via a β-1,4-O-glycosidic bond.

The process for the modification of a glycoprotein may further comprise the step of providing a glycoprotein comprising a glycan comprising a terminal GlcNAc-moiety. The invention therefore also relates to a process for the modification of a glycoprotein comprising the steps of:

(1) providing a glycoprotein comprising a glycan comprising a terminal GlcNAc moiety, wherein the glycan comprising a terminal GlcNAc-moiety is according to formula (1) or (2) as defined above; and (2) contacting said glycoprotein with a sugar-derivative nucleotide Su(A)-Nuc, in the presence of, more particular under the action of, a glycosyltransferase, wherein the glycosyltransferase is or is derived from a β-(1,4)-N-acetylgalactosaminyltransferase, and wherein Su(A)-Nuc is according to formula (3) as defined above.

The glycoprotein comprising a glycan comprising a terminal GlcNAc moiety, the sugar-derivative nucleotide Su(A)-Nuc and the modified glycoprotein, and preferred embodiments thereof, are described in more detail below.

The glycosyltransferase that is or is derived from a β-(1,4)-N-acetylgalactosaminyltransferase is described in more detail below.

In a preferred embodiment of the process according to the invention, the β-(1,4)-N-acetylgalactosaminyltransferase is or is derived from a sequence selected from the group consisting of SEQ ID NO: 2, 3, 4, 5, 6, 7, 8, 9, 10, 11, 12, 13, 14, 15, 16, 17, 18, 19, 20, 21, 22, 23, 25, 26, 27, 28, 29, 30, 31, 32, 33, 34, 46, 47, 49, 50, 51, 52, 53, 54, 55, 56, 57, 58, 59, 71, 72 and 73. This embodiment is particularly preferred when $R^{14}$ is —NHC(O)CH$_3$, —NHC(O)—(W)$_h$—(U)$_f$-(T)$_a$-A or —N$_3$.

In another preferred embodiment of the process according to the invention, the β-(1,4)-N-acetylgalactosaminyltransferase is or is derived from the group consisting of SEQ ID NO: 35, 36, 37, 38, 39, 40, 41, 42, 43, 44, 45, 48, 60, 61, 62, 63, 64, 65, 66, 67, 68, 69, 70 and 74. This embodiment is particularly preferred when $R^{14}$ is —OH.

In another preferred embodiment of the process according to the invention, the β-(1,4)-N-acetylgalactosaminyltransferase has at least 50% identity to a sequence selected from the group consisting of SEQ ID NO: 2, 3, 4, 5, 6, 7, 8, 9, 10, 11, 12, 13, 14, 15, 16, 17, 18, 19, 20, 21, 22, 23, 25, 26, 27, 28, 29, 30, 31, 32, 33, 34, 46, 47, 49, 50, 51, 52, 53, 54, 55, 56, 57, 58, 59, 71, 72 and 73. In this embodiment it is further preferred that the β-(1,4)-N-acetylgalactosaminyltransferase has at least 55% sequence identity, preferably at least 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2, 3, 4, 5, 6, 7, 8, 9, 10, 11, 12, 13, 14, 15, 16, 17, 18, 19, 20, 21, 22, 23, 25, 26, 27, 28, 29, 30, 31, 32, 33, 34, 46, 47, 49, 50, 51, 52, 53, 54, 55, 56, 57, 58, 59, 71, 72 and 73. These embodiments are particularly preferred when $R^{14}$ is —NHC(O)CH$_3$, —NHC(O)—(W)$_h$—(U)$_f$-(T)$_a$-A or —N$_3$.

In another preferred embodiment of the process according to the invention, the β-(1,4)-N-acetylgalactosaminyltransferase has at least 50% identity to a sequence selected from the group consisting of SEQ ID NO: 35, 36, 37, 38, 39, 40, 41, 42, 43, 44, 45, 48, 60, 61, 62, 63, 64, 65, 66, 67, 68, 69, 70 and 74. In this embodiment it is further preferred that the β-(1,4)-N-acetylgalactosaminyltransferase has at least 55% sequence identity, preferably at least 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 35, 36, 37, 38, 39, 40, 41, 42, 43, 44, 45, 48, 60, 61, 62, 63, 64, 65, 66, 67, 68, 69, 70 and 74. These embodiments are particularly preferred when $R^{14}$ is —OH.

Glycoprotein

The glycoprotein to be modified in the process according to the invention comprises a glycan, said glycan comprising a terminal GlcNAc moiety, i.e. a GlcNAc moiety that is present at the non-reducing end of the glycan. Said glycan comprises one or more saccharide moieties, and may be linear or branched. The glycan comprising a terminal GlcNAc-moiety is according to formula (1) or (2):

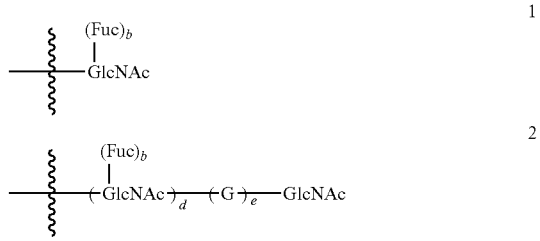

(1)

(2)

wherein:
b is 0 or 1;
d is 0 or 1;
e is 0 or 1; and
G is a monosaccharide, or a linear or branched oligosaccharide comprising 2 to 20 sugar moieties.

The glycoprotein to be modified may comprise more than one glycan comprising a terminal GlcNAc moiety. When this is the case, the two or more glycans may differ from each other. The glycoprotein may also comprise one or more additional glycans that do not comprise a terminal GlcNAc moiety.

The core-GlcNAc moiety, i.e. the GlcNAc moiety that is attached to the protein, is optionally fucosylated (b is 0 or 1). When a core-GlcNAc moiety is fucosylated, fucose is most commonly linked α-1,6 to C6 of said GlcNAc-moiety.

It should be noted that the GlcNAc moiety of a glycan according to formula (1) wherein b is 1, i.e. the GlcNAc moiety in a glycan consisting of a fucosylated GlcNAc, is herein also considered a terminal GlcNAc moiety.

In one embodiment, the glycan comprising a terminal GlcNAc moiety consists of one GlcNAc moiety, and the glycan is a glycan according to formula (1) wherein b is 0. In another embodiment, said glycan consists of a fucosylated GlcNAc moiety, and the glycan is a glycan according to formula (1) wherein b is 1.

In another embodiment, said glycan is a glycan according to formula (2), wherein the core-GlcNAc, if present, is optionally fucosylated (b is 0 or 1). In a glycan according to formula (2), G represents a monosaccharide, or a linear or branched oligosaccharide comprising 1 to 20, preferably 1 to 12, more preferably 1 to 10, even more preferably 1, 2, 3, 4, 5, 6, 7 or 8, and most preferably 1, 2, 3, 4, 5 or 6 sugar moieties. When G is a branched oligosaccharide, G may comprise one or more terminal GlcNAc-moieties. A glycan according to formula (2) may thus comprise more than one terminal GlcNAc moieties. In glycan (2) it is preferred that when d is 0 then e is 1, and when e is 0 then d is 1. More preferably, in glycan (2) d is 1, and even more preferably d is 1 and e is 1.

Sugar moieties that may be present in a glycan are known to a person skilled in the art, and include e.g. glucose (Glc), galactose (Gal), mannose (Man), fucose (Fuc), N-acetylglucosamine (GlcNAc), N-acetylgalactosamine (GalNAc), N-acetylneuraminic acid (NeuNAc) or sialic acid and xylose (Xyl).

In a preferred embodiment of the process according to the invention, the glycan comprising a terminal GlcNAc moiety is according to formula (1), as defined above. In another preferred embodiment, the glycan comprising a terminal GlcNAc moiety is according to formula (2). It is further preferred that the glycan is an N-linked glycan. When the glycan is an N-linked glycan according to formula (2), it is preferred that d is 1.

When the glycan comprising a terminal GlcNAc moiety is according to formula (2), it is further preferred that the glycan according to formula (2) is a glycan according to formula (9), (10), (11), (12), (13) or (14):

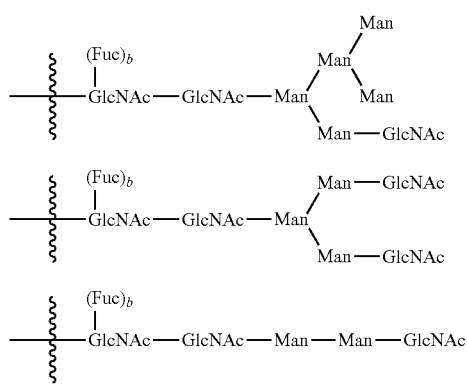
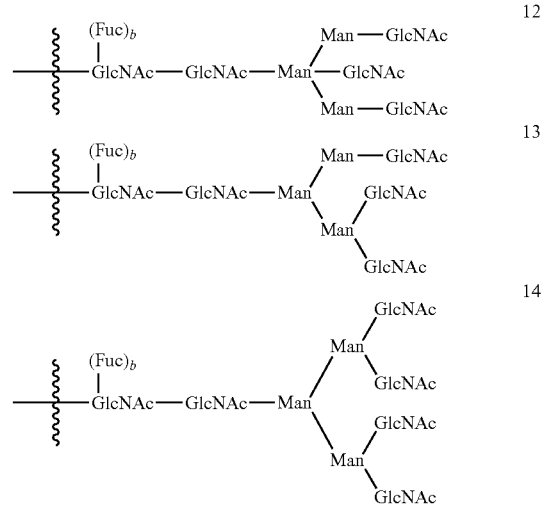

wherein b is 0 or 1.

In a preferred embodiment of the process according to the invention, the glycan comprising a terminal GlcNAc moiety is a glycan according to formula (1), (9), (10), (11), (12), (13) or (14), more preferably an N-linked glycan according to formula (1), (9), (10), (11), (12), (13) or (14). In a further preferred embodiment, the glycan comprising a terminal GlcNAc moiety is a glycan according to formula (1), (9), (10) or (11), more preferably an N-linked glycan according to formula (1), (9), (10) or (11). Most preferably the glycan comprising a terminal GlcNAc-moiety is a glycan according to formula (1) or (10), more preferably an N-linked glycan according to formula (1).

The glycoprotein comprising a glycan comprising a terminal GlcNAc moiety is preferably according to formula (7), (8) or (8b):

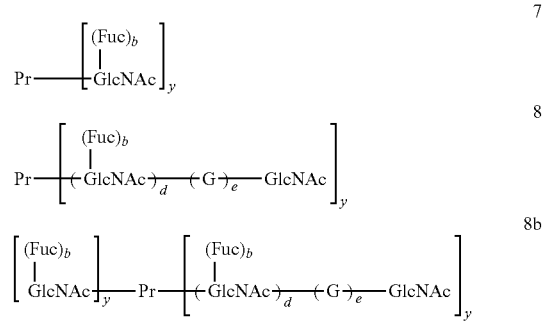

wherein:
b, d, e and G, and preferred embodiments thereof, are as defined above;
y is independently an integer in the range of 1 to 24; and
Pr is a protein.

The glycoprotein to be modified in the process according to the invention comprises one or more glycans comprising a terminal GlcNAc moiety (y is 1 to 24). Preferably y is an integer in the range of 1 to 12, more preferably an integer in the range of 1 to 10. More preferably, y is 1, 2, 3, 4, 5, 6, 7 or 8, and yet more preferably y is 1, 2, 3, 4, 5 or 6. Even more preferably, y is 1, 2, 3 or 4. When the glycoprotein to be modified comprises more than one glycan (y is 2 or more), the glycans may differ from each other. As was described above, the glycoprotein may further comprise one or more glycans not having a terminal GlcNAc moiety.

When the glycoprotein to be modified in the process according to the invention is according to formula (7), (8) or (8b), it is also preferred that the glycan comprising a terminal GlcNAc moiety is a glycan, preferably an N-linked glycan, according to formula (1), (9), (10), (11), (12), (13) or (14) as described above, more preferably a glycan, preferably an N-linked glycan according to formula (1), (9), (10) or (11) and even more preferably according to formula (1) or (10). Most preferably the glycan comprising a terminal GlcNAc moiety is an N-linked glycan according to formula (1).

In a preferred embodiment of the process according to the invention, the glycoprotein comprising a glycan comprising a terminal GlcNAc moiety is an antibody, more preferably an antibody according to formula (7), (8) or (8b), wherein the protein (Pr) is an antibody (Ab). Also when the glycoprotein to be modified is an antibody and the antibody comprises more than one glycan (y is 2 or more), the glycans may differ from each other. The antibody may further comprise one or more glycans not having a terminal GlcNAc-moiety. Also when the glycoprotein to be modified is an antibody, it is preferred that the glycan comprising a terminal GlcNAc moiety is a glycan according to formula (1), (9), (10), (11), (12), (13) or (14) as defined above, more preferably according to formula (1), (9), (10) or (11), even more preferably according to formula (1) or (10). In this embodiment it is further preferred that the glycan comprising a terminal GlcNAc moiety is an N-linked glycan according to formula (1), (9), (10), (11), (12), (13) or (14), more preferably an N-linked glycan according to formula (1), (9), (10) or (11), and most preferably an N-linked glycan according to formula (1) or (10).

When the glycoprotein to be modified is an antibody, it is preferred that y is 1, 2, 3, 4, 5, 6, 7 or 8, more preferably y is 1, 2, 4, 6 or 8, even more preferably y is 1, 2 or 4, and most preferably y is 1 or 2.

As was defined above, said antibody may be a whole antibody, but also an antibody fragment. When the antibody is a whole antibody, said antibody preferably comprises one or more, more preferably one, terminal non-reducing GlcNAc glycan on each heavy chain. Said whole antibody thus preferably comprises 2 or more, preferably 2, 4, 6 or 8 of said glycans, more preferably 2 or 4, and most preferably 2 glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a preferred embodiment, said antibody is a monoclonal antibody (mAb). Preferably, said antibody is selected from the group consisting of IgA, IgD, IgE, IgG and IgM antibodies. More preferably, said antibody is an IgG1, IgG2, IgG3 or IgG4 antibody, and most preferably said antibody is an IgG1 antibody.

In the process according to the invention, a glycoprotein mixture comprising fucosylated as well as non-fucosylated glycans may be used as the starting glycoprotein. Said mixture may e.g. comprise glycoproteins comprising one or more fucosylated (b is 1) glycans (1) and/or (2) and/or one or more non-fucosylated (b is 0) glycans (1) and/or (2). Removal of fucose from a fucosylated glycan prior to the process according to the invention is therefore not necessary, but optional.

A glycoprotein comprising a glycan comprising a terminal GlcNAc moiety is herein also referred to as a "terminal non-reducing GlcNAc protein", and a glycan comprising a terminal GlcNAc moiety is herein also referred to as a "terminal non-reducing GlcNAc glycan". It should be noted that the term "terminal non-reducing GlcNAc protein" includes a protein of formula (7) wherein b is 1, and that the term "terminal non-reducing GlcNAc glycan" includes a glycan of formula (1) wherein b is 1.

The terminal non-reducing GlcNAc protein may comprise one or more linear and/or one or more branched terminal non-reducing GlcNAc glycans. A glycan is bonded to the protein via C1 of the glycan core-sugar moiety, and said core-sugar moiety preferably is a core-GlcNAc moiety. Consequently, when the terminal non-reducing GlcNAc-glycan bonded to the protein is a glycan according to formula (2), it is preferred that d is 1. More preferably, when the glycan is according to formula (2), d is 1 and e is 1.

In a preferred embodiment, C1 of the core-sugar moiety of the terminal non-reducing GlcNAc glycan is bonded to the protein via an N-glycosidic bond to a nitrogen atom in an amino acid residue in said protein, more preferably to the nitrogen atom in the side chain of an asparagine (Asn) or an arginine (Arg) amino acid. However, C1 of the core-sugar moiety of the non-reducing GlcNAc glycan may also be bonded to the protein via an O-glycosidic bond to an oxygen atom in an amino acid residue in said protein, more preferably to an oxygen atom in the side chain of a serine (Ser) or threonine (Thr) amino acid. In this embodiment, it is preferred that the core-sugar moiety of said glycan is a GlcNAc moiety or a GalNAc moiety, preferably a GlcNAc moiety. C1 of the core-sugar moiety of the non-reducing GlcNAc glycan may also be bonded to the protein via a C-glycosidic bond to a carbon atom on the protein, e.g. to tryptophan (Trp). As described above, a glycoprotein may comprise more than one glycan, and may comprise a combination of N-linked, O-linked and/or C-linked glycans.

The terminal non-reducing GlcNAc glycan may be present at a native glycosylation site of a protein, but may also be introduced on a different site of a protein.

When the glycoprotein is an antibody, it is preferred that the glycan comprising a terminal GlcNAc moiety is attached to the conserved N-glycosylation site in the Fc-fragment at asparagine in the region 290-305, typically at N297.

Figure 1:
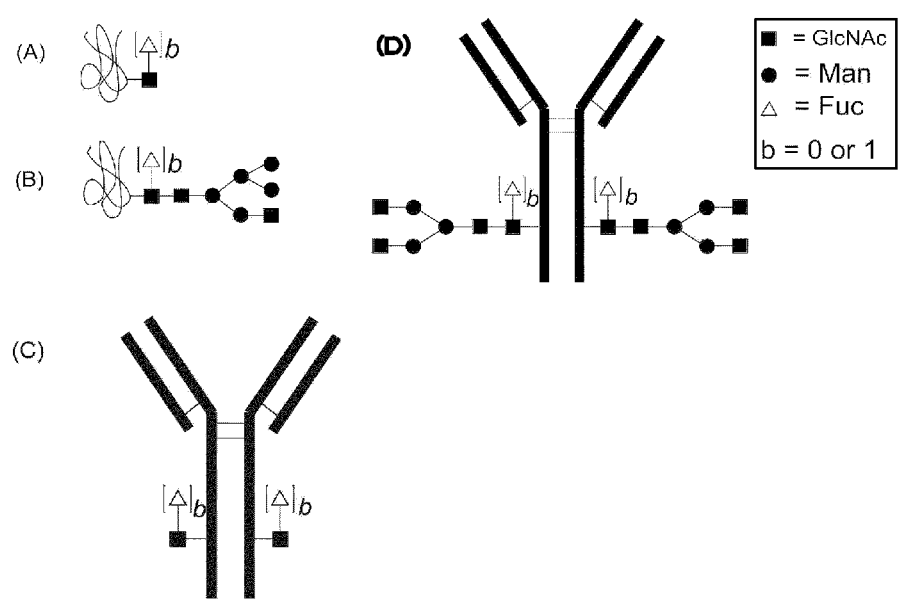
In FIG. 1 several examples of a glycoprotein comprising a glycan comprising a terminal GlcNAc moiety, that may be modified by the process according to the invention, are shown.

Several examples of a terminal non-reducing GlcNAc protein that may be modified in the process according to the invention are shown in FIG. 1. FIG. 1 (A) shows a glycoprotein comprising a single, optionally fucosylated, GlcNAc moiety. This GlcNAc glycan may for example be linked to the protein via an N-glycosidic or an O-glycosidic bond. The glycoprotein in FIG. 1(A) may for example be obtained by regular expression followed by trimming with an endoglycosidase or a combination of endoglycosidases. FIG. 1(B) shows a glycoprotein comprising a branched oligosaccharide glycan wherein one of the branches comprises a terminal GlcNAc moiety (this glycan is also referred to as $GnM_s$). The core-GlcNAc moiety may optionally be fucosylated. The glycoprotein in FIG. 1(B) may for example be obtained by expression of a glycoprotein in a mammalian system in the presence of swainsonine or by expression in an engineered host organism, e.g. Lec1 CHO or *Pichia*. FIG. 1 (C) shows an antibody comprising a single, optionally fucosylated, GlcNAc moiety. This GlcNAc glycan is preferably linked to the antibody via an N-glycosidic bond. The glycoprotein in FIG. 1(C) may for example be obtained by regular expression followed by trimming with an endoglycosidase or a combination of endoglycosidases. FIG. 1(D)

shows an antibody comprising a branched oligosaccharide glycan, wherein the core-GlcNAc moiety is optionally fucosylated and wherein all branches comprise a terminal GlcNAc moiety. The glycoprotein in FIG. 1(D) may for example be obtained by trimming of the regular mixture of antibody glycoforms (G0, G1, G2, G0F, G1F and G2F) upon combined action of sialidase and galactosidase.

Figure 2:
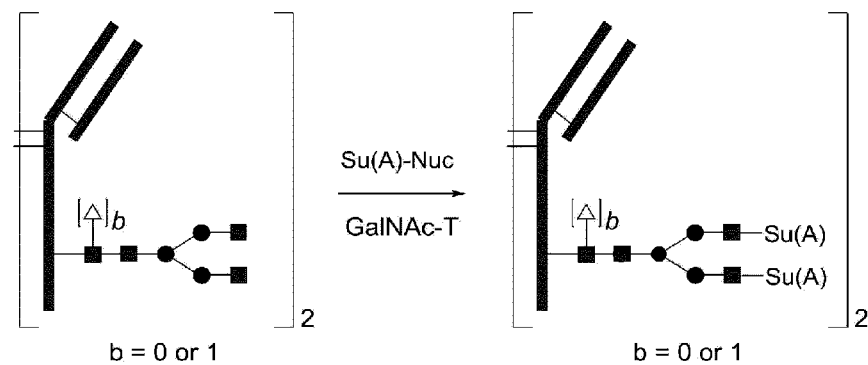
In FIG. 2, an embodiment of the process for the modification of a glycoprotein, wherein the glycoprotein is an antibody is shown. In this embodiment a sugar-derivative Su(A)-Nuc is attached to the terminal GlcNAc-moiety of an antibody glycan under the action a glycosyltransferase, wherein the glycosyltransferase is, or is derived from, a β-(1,4)-N-acetylgalactosaminyltransferase, to form a modified antibody.

In FIG. 2 an embodiment of the process for the modification of a glycoprotein, wherein the glycoprotein is an antibody, is shown. In this embodiment a sugar-derivative Su(A) is transferred from Su(A)-Nuc to a terminal GlcNAc moiety of an antibody glycan, under the action of a glycosyltransferase that is or is derived from a β-(1,4)-N-acetylgalactosaminyltransferase, to form a modified antibody.

As was described above, the process according to the invention for the modification of a glycoprotein may further comprise the step of providing a glycoprotein comprising a glycan comprising a terminal GlcNAc moiety, and the invention therefore also relates to a process for the modification of a glycoprotein comprising the steps of:
  (1) providing a glycoprotein comprising a glycan comprising a terminal GlcNAc moiety, wherein the glycan comprising a terminal GlcNAc moiety is according to formula (1) or (2) as defined above; and
  (2) contacting said glycoprotein with a sugar-derivative nucleotide Su(A)-Nuc, in the presence of, more in particular under the action of, a glycosyltransferase, wherein the glycosyltransferase is or is derived from a β-(1,4)-N-acetylgalactosaminyltransferase, and wherein Su(A)-Nuc is according to formula (3) as defined above.

When for example the glycoprotein to be modified in the process according to the invention comprises a glycan according to formula (1), in step (1) of the process the glycoprotein to be modified may be provided by a process comprising the step of trimming a glycoprotein comprising an oligosaccharide glycan by the action of a suitable enzyme, preferably an endoglycosidase.

In a large number of glycans, a second GlcNAc-residue is bonded to the GlcNAc-residue that is directly bonded to the glycoprotein, as is also seen in FIGS. 1(B) and (C). A glycan wherein a second GlcNAc-residue is bonded to the GlcNAc-residue that is directly bonded to the glycoprotein can be trimmed in order to obtain a glycoprotein comprising a glycan according to formula (1). Trimming occurs in between said two GlcNAc-residues.

A "suitable enzyme" is defined as an enzyme for which the glycan that is to be trimmed is a substrate. The preferred type of enzyme that is to be used in step (1) of this particular embodiment of the process according to the invention depends on the specific glycan or glycans that is or are trimmed. In a preferred embodiment of this particular embodiment of the process according to the invention, the enzyme in step (1) of this particular embodiment of the process is selected from the group of endoglycosidases.

Endoglycosidases are capable of cleaving internal glycosidic linkages in glycan structures, which provides a benefit to remodeling and synthetic endeavors. For example, endoglycosidases can be employed for facile homogenization of heterogeneous glycan populations, when they cleave at predictable sites within conserved glycan regions. One of the most significant classes of endoglycosidases in this respect comprises the endo-β-N-acetylglucosaminidases (EC 3.2.1.96, commonly known as Endos and ENGases), a class of hydrolytic enzymes that remove N-glycans from glycoproteins by hydrolyzing the β-1,4-glycosidic bond in the N,N'-diacetylchitobiose core (reviewed by Wong et al. *Chem. Rev.* 2011, 111, 4259, incorporated by reference herein), leaving a single core N-linked GlcNAc residue. Endo-β-N-acetylglucosaminidases are found widely distributed through Nature with common chemoenzymatic variants including Endo D, which is specific for pauci mannose; Endo A and Endo H, which are specific for high mannose; Endo F subtypes, which range from high mannose to biantennary complex; and Endo M, which can cleave most N-glycan structures (high mannose/complex-type/hybrid-type), except fucosylated glycans, and the hydrolytic activity for the high-mannose type oligosaccharides is significantly higher than that for the complex- and hybrid-type oligosaccharides. These ENGases show specificity toward the distal N-glycan structure and not the protein displaying it, making them useful for cleaving most N-linked glycans from glycoproteins under native conditions.

Endoglycosidases F1, F2, and F3 are most suitable for deglycosylation of native proteins. The linkage specificities of endo F1, F2, and F3 suggest a general strategy for deglycosylation of proteins that may remove all classes of N-linked oligosaccharides without denaturing the protein. Biantennary and triantennary structures can be immediately removed by endoglycosidases F2 and F3, respectively. Oligo-mannose and hybrid structures can be removed by Endo F1.

Endo F3 is unique in that its cleavage is sensitive to the state of peptide linkage of the oligosaccharide, as well as the state of core fucosylation. Endoglycosidase F3 cleaves asparagine-linked biantennary and triantennary complex oligosaccharides. It will cleave non-fucosylated biantennary and triantennary structures at a slow rate, but only if peptide-linked. Core fucosylated biantennary structures are efficient substrates for Endo F3, with an activity up to 400-fold higher. There is no activity on oligomannose and hybrid molecules. See for example Tarentino et al. *Glycobiology* 1995, 5, 599, incorporated by reference herein.

Endo S is a secreted endoglycosidase from *Streptococcus pyogenes*, and also belongs to the glycoside hydrolase family 18, as disclosed by Collin et al. (*EMBO J.* 2001, 20, 3046, incorporated by reference herein). In contrast to the ENGases mentioned above, Endo S has a more defined specificity and is specific for cleaving only the conserved N-glycan in the Fc domain of human IgGs (no other substrate has been identified to date), suggesting that a protein-protein interaction between the enzyme and IgG provides this specificity.

Endo S49, also known as Endo S2, is described in WO 2013/037824 (Genovis AB), incorporated by reference herein. Endo S49 is isolated from *Streptococcus* poyogenes NZ131 and is a homologue of Endo S. Endo S49 has a specific endoglycosidase activity on native IgG and cleaves a larger variety of Fc glycans than Endo S.

In a preferred embodiment, the enzyme in step (1) of this embodiment is an endo-β-N-acetylglucosaminidase. In a further preferred embodiment, the endo-β-N-acetylglucosaminidase is selected from the group consisting of Endo S, Endo S49, Endo F1, Endo F2, Endo F3, Endo H, Endo M and Endo A, or a combination thereof.

When the glycan to be trimmed is a diantennary structure of the complex type, the endo-β-N-acetylglucosaminidase is preferably selected from the group consisting of Endo S, Endo S49, Endo F1, Endo F2 and Endo F3, or a combination thereof.

When the glycoprotein is an antibody and the oligosaccharide to be trimmed is a diantennary structure of the complex type (i.e. according to FIG. 1(C)), and it is present at the IgG conserved N-glycosylation site at N297, the endo-β-N-acetylglucosaminidase is preferably selected from the group consisting of Endo S, Endo S49, Endo F1, Endo F2 and Endo F3, or a combination thereof, more preferably from the group consisting of Endo S and Endo S49, or a combination thereof.

When the glycoprotein is an antibody and the glycan to be trimmed is a diantennary structure of the complex type, and it is not present at the IgG conserved N-glycosylation site at N297, the endo-β-N-acetylglucosaminidase is preferably selected from the group consisting of Endo F1, Endo F2 and Endo F3, or a combination thereof.

When the glycan to be trimmed is a high mannose, the endo-β-N-acetylglucosaminidase is preferably selected from the group consisting of Endo H, Endo M, Endo A and Endo F1.

Therefore, when the glycoprotein to be modified in the process according to the invention comprises a glycan according to formula (1), in step (1) of the process the glycoprotein to be modified is preferably provided by a process comprising the step of trimming a glycan of a glycoprotein comprising an oligosaccharide glycan by the action of an endo-β-N-acetylglucosaminidase, in order to provide a glycoprotein comprising a glycan according to formula (1).

In a further preferred embodiment, the endo-β-N-acetylglucosaminidase is selected from the group consisting of Endo S, Endo S 49, Endo F1, Endo F2, Endo F3, Endo H, Endo M and Endo A, and any combination thereof. More preferably, the endo-3-N-acetylglucosaminidase is selected from the group consisting of Endo S, Endo S 49, Endo H, Endo F1, Endo F2 and Endo F3, and any combination thereof. Even more preferably, the endo-β-N-acetylglucosaminidase is Endo S or Endo S49. Most preferably, the endo-β-N-acetylglucosaminidase is a combination of Endo H and Endo S.

Figure 3:
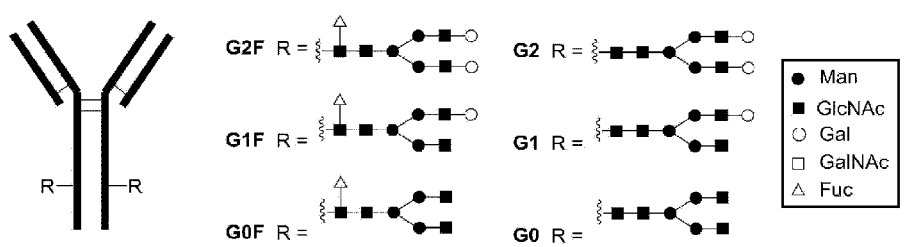
FIG. 3 shows different glycoforms of antibody glycans G0, G1, G2, G0F, G1F and G2F.
Figure 4:
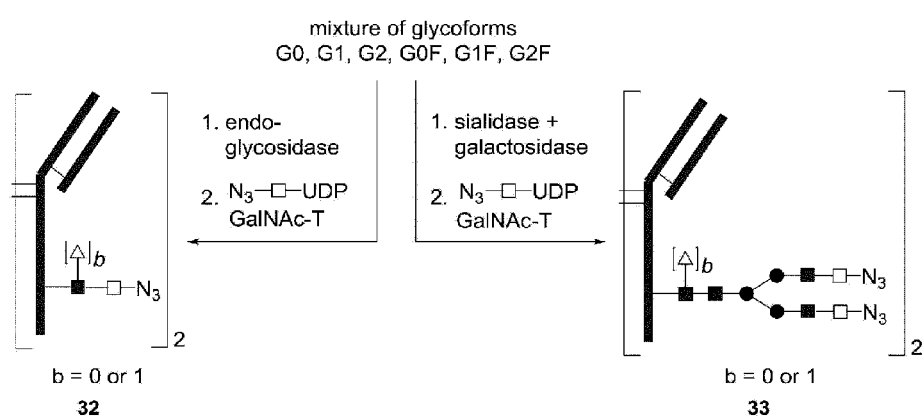
FIG. 4 shows a process for providing a glycoprotein comprising a glycan according to formula (10) by treatment of a mixture of glycoforms G0, G1, G2, G0F, G1F and G2F with sialidase and galactosidase, and a process for providing a glycoprotein comprising a glycan according to formula (1) by treatment of a mixture of glycoforms G0, G1, G2, G0F, G1F and G2F with an endoglycosidase. Incubation of the glycoproteins comprising a glycan according to formula (10)

The process for providing a glycoprotein comprising a glycan according to formula (1) by treatment of a mixture of glycoforms G0, G1, G2, G0F, G1F and G2F with an endoglycosidase is shown in FIG. 4. FIG. 4 shows that treatment of a glycoprotein, in this case an antibody, comprising a mixture of glycoforms G0, G1, G2, G0F, G1F and G2F (said glycoforms are shown in FIG. 3) with an endoglycosidase, followed by transfer of for example N-azido-acetylgalactosamine (GalNAz) from UDP-GalNAz using a β-(1,4)-GalNAcT enzyme, results in a modified antibody according to formula (32).

When for example the glycoprotein to be modified in the process according to the invention comprises a glycan according to formula (9), the glycoprotein comprising said glycan, also referred to as "GnM5", may be provided in various ways. In this embodiment, it is preferred that the glycoprotein is provided by an expression of hybrid N-glycoprotein in the presence of swainsonine, as for example described in Kanda et al., Glycobiology 2006, 17, 104, incorporated by reference, and if necessary followed by sialidase/galactosidase treatment. An alternative approach includes the genetic engineering of a host organism. For example, Lec1 CHO is a knock-out CHO cel-line lacking the gene for expression of Mns-II. As a consequence, biosynthesis of the N-glycan inevitable stops at the GnM$_5$-stage of the glycan, which can be isolated pure from the supernatant. A more extensive approach entails the engineering of host organisms not normally programmed to produce hybrid or complex N-glycans, such as yeast or insect cells. However, it has been amply demonstrated that these non-mammalian host cells (e.g. Glycoswitch™) can also be employed for the selective expression of a single glycoform of a particular N-glycoprotein, including glycans of the GnM$_5$-type and of the M$_5$-type.

Therefore, when the glycoprotein to be modified in the process according to the invention comprises a glycan according to formula (9), in step (1) of the process the glycoprotein comprising an optionally fucosylated glycan of formula (9) is preferably provided by a process comprising expression of the glycoprotein in a host organism, in the presence of swainsonine. Preferably, said host organism is a mammalian cell line, e.g. HEK293 or NS0 or a CHO-cell line. The resulting glycoproteins may be obtained as a mixture of proteins comprising a glycan of the formula (9) (also referred to as GnM$_5$), a glycan referred to as GalGnM$_5$, a sialylated glycan referred to as SiaGalGnM$_5$ and/or a mixture thereof. The non-reducing sialic acid and/or galactose moiety, if present, may be removed by processing of the glycoprotein with sialidase (removal of the sialic acid moiety) and/or β-galactosidase (removal of galactose moiety), whereby a glycoprotein comprising a glycan of formula (9) is obtained. Preferably, treatment with sialidase and β-galactosidase occurs in a single step in (1b). In this embodiment it is further preferred that in step (1) of the process the glycoprotein to be modified is provided by a process comprising the steps of:

(1a) expression of a glycoprotein in a host organism in the presence of swainsonine; and (1b) treatment of the obtained glycoprotein with sialidase and/or β-galactosidase in order to obtain a glycoprotein comprising a glycan of formula (9).

When the glycoprotein to be modified in the process according to the invention comprises a glycan according to formula (10), in step (1) of the process the glycoprotein to be modified may for example be provided by a process comprising a treatment of a mixture of glycoforms G0, G1, G2, G0F, G1F and G2F of the glycoprotein with sialidase and galactosidase. In FIG. 3 the glycoforms G0, G1, G2, G0F, G1F and G2F of an antibody comprising a biantennary glycan are shown.

FIG. 4 shows a process for providing a glycoprotein, in this case an antibody, comprising a glycan according to formula (10) by treatment of a mixture of glycoforms G0, G1, G2, G0F, G1F and G2F with sialidase and galactosidase, followed by transfer of the sugar moiety from a sugar-derivative nucleotide Su(A)-UDP wherein A is an azido group, e.g. 6-azido-GalNAc-UDP, under the action of a glycosyltransferase that is, or is derived from, a β-(1,4)-GalNAcT, providing a modified antibody according to formula (33).

Sugar Derivative Nucleotide Su(A)-Nuc

In the process for the modification of a glycoprotein according to the invention, a glycoprotein comprising a glycan according to formula (1) or (2) is contacted, under the action of a glycosyltransferase that is or is derived from a β-(1,4)-acetylgalactosaminyltransferase, with a sugar-derivative nucleotide Su(A)-Nuc. The sugar-derivative nucleotide Su(A)-Nuc is according to formula (3):

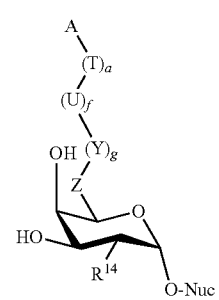

3 wherein Nuc, $R^{14}$, a, f, g, U, T, A, Z, Y and are as defined above.

Nuc is herein defined as a nucleotide. Nuc is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP) and cytidine diphosphate (CDP). Most preferably, Nuc is uridine diphosphate (UDP). Therefore, in a preferred embodiment of the process according to the invention, Su(A)-Nuc (3) is Su(A)-UDP (34):

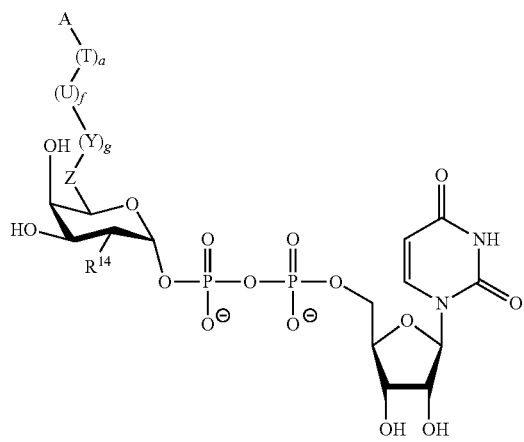

34 wherein $R^{14}$, a, f, g, U, T, A, Z, Y and are as defined above.

In one embodiment, A is an azido group —$N_3$.

In another embodiment, A is a keto group —C(O)$R^3$, wherein $R^3$ is an optionally substituted $C_1$-$C_{24}$ alkyl group, preferably an optionally substituted $C_1$-$C_{12}$ alkyl group, and more preferably an optionally substituted $C_1$-$C_6$ alkyl group. Even more preferably, $R^3$ is methyl, ethyl, n-propyl, i-propyl, n-butyl, s-butyl or t-butyl, and most preferably, $R^3$ is methyl.

In another embodiment, A is an alkynyl group. In other words, A is a functional moiety comprising a C≡C bond, preferably (hetero)cycloalkynyl group or a —(CH$_2$)$_i$C≡C—$R^4$ moiety. In one embodiment, the alkynyl group is a (hetero)cycloalkynyl group, preferably a (hetero)cyclooctynyl group. In a preferred embodiment, the alkynyl group is —(CH$_2$)$_i$C≡C—$R^4$, wherein i is 0-10 and $R^4$ is hydrogen or an optionally substituted $C_1$-$C_{24}$ alkyl group, preferably hydrogen or an optionally substituted $C_1$-$C_{12}$ alkyl group, and more preferably hydrogen or an optionally substituted $C_1$-$C_6$ alkyl group. Even more preferably, $R^4$ is hydrogen, methyl, ethyl, n-propyl, i-propyl, n-butyl, s-butyl or t-butyl and more preferably $R^4$ is hydrogen or methyl. Preferably, i is 0, 1, 2, 3, 4, 5 or 6, more preferably i is 0, 1, 2, 3 or 4, even more preferably i is 0, 1 or 2, yet even more preferably i is 0 or 1 and most preferably i is 1. More preferably, $R^4$ is hydrogen, methyl, ethyl, n-propyl, i-propyl, n-butyl, s-butyl or t-butyl and i is 0, 1 or 2. Even more preferably $R^4$ is hydrogen or methyl and i is 0, 1 or 2. In this embodiment, it is further preferred that the alkynyl group is a terminal alkynyl group, i.e. $R^4$ is most preferably hydrogen. In a particularly preferred embodiment the alkynyl group is —CH$_2$—C≡CH or —C≡CH, most preferably —CH$_2$—C≡CH.

In another embodiment, A is a thiol group —SH.

In another embodiment, A is a precursor of a thiol group —SC(O)$R^8$, wherein $R^8$ is an, optionally substituted, $C_1$-$C_{24}$ alkyl group or phenyl group. Preferably, $R^8$ is an, optionally substituted, $C_1$-$C_{12}$ alkyl group or phenyl group, more preferably $R^8$ is an, optionally substituted, $C_1$-$C_6$ alkyl group or phenyl group, and even more preferably $R^8$ is methyl, ethyl, n-propyl, i-propyl, n-butyl, s-butyl, t-butyl or phenyl. Even more preferably $R^8$ is methyl or phenyl, and most preferably, $R^8$ is methyl. In the process according to the invention for the modification of a glycoprotein, a sugar-derivative nucleotide wherein A is a precursor of a thiol group may be used. During the process, the thiol-precursor is converted to a thiol group.

In another embodiment, A is —SC(V)O$R^8$, wherein V is O or S, and $R^8$ is an, optionally substituted, $C_1$-$C_{24}$ alkyl group or phenyl group. In a preferred embodiment, A is —SC(O)O$R^8$. In another preferred embodiment, A is —SC(S)O$R^8$. Both when A is —SC(O)O$R^8$ and when A is —SC(S)O$R^8$, $R^8$ is preferably an, optionally substituted, $C_1$-$C_{12}$ alkyl group or phenyl group, more preferably $R^8$ is an, optionally substituted, $C_1$-$C_6$ alkyl group or phenyl group, and even more preferably $R^8$ is methyl, ethyl, n-propyl, i-propyl, n-butyl, s-butyl, t-butyl or phenyl. Even more preferably $R^8$ is methyl or phenyl and most preferably, $R^8$ is methyl.

In another embodiment, A is a halogen X. X is selected from the group consisting of F, Cl, Br and I, preferably from the group consisting of Cl, Br and I, more preferably from the group consisting of Cl and Br. Most preferably, X is Cl.

In another embodiment, A is a sulfonyloxy group —OS(O)$_2$$R^5$, wherein $R^5$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups, the alkyl groups, aryl groups, alkylaryl groups and arylalkyl groups being optionally substituted. Preferably, $R^5$ is a $C_1$-$C_{12}$ alkyl group, $C_6$-$C_{12}$ aryl group, $C_7$-$C_{12}$ alkylaryl group or a $C_7$-$C_{12}$ arylalkyl group. More preferably $R^5$ is selected from the group consisting of —CH$_3$, —C$_2$H$_5$, a $C_3$ linear or branched alkyl group, a $C_4$ linear or branched alkyl group, a $C_6$-$C_{10}$ aryl group and a $C_7$ alkylaryl group. Even more preferably, $R^5$ is a methyl group, an ethyl group, a phenyl group or a p-tolyl group. Most preferably the sulfonyloxy group is a mesylate group, —OS(O)$_2$CH$_3$, a benzenesulfonate group (—OS(O)$_2$(C$_6$H$_5$)) or a tosylate group (—OS(O)$_2$C$_6$H$_4$CH$_3$).

In another embodiment, A is $R^{12}$, wherein $R^{12}$ is selected from the group consisting of, optionally substituted, terminal $C_2$-$C_{24}$ alkenyl groups, $C_3$-$C_5$ cycloalkenyl groups and $C_4$-$C_8$ alkadienyl groups.

The term "terminal alkenyl group" herein refers to an alkenyl group wherein the carbon-carbon double bond is situated at a terminus of the alkenyl group. When $R^{12}$ is an, optionally substituted, terminal $C_2$-$C_{24}$ alkenyl group, the terminal $C_2$-$C_{24}$ alkenyl group preferably ends with a C=CH$_2$ moiety, more preferably a C(H)=CH$_2$ moiety. Preferably $R^{12}$ is an optionally substituted terminal $C_2$-$C_{12}$ alkenyl group, and more preferably an optionally substituted terminal $C_2$-$C_6$ alkenyl group. More preferably, the terminal alkenyl group is a linear alkenyl group, preferably an unsubstituted linear alkenyl group. Even more preferably $R^{12}$ is selected from the group consisting of —C(H)=CH$_2$, —CH$_2$—C(H)=CH$_2$, —CH$_2$—CH$_2$—C(H)=CH$_2$, —CH$_2$—CH$_2$—CH$_2$—C(H)=CH$_2$ and —CH$_2$—CH$_2$—

$CH_2$—$CH_2$—$C(H)$=$CH_2$. Yet even more preferably $R^{12}$ is selected from the group consisting of —$C(H)$=$CH_2$, —$CH_2$—$C(H)$=$CH_2$ and —$CH_2$—$CH_2$—$C(H)$=$CH_2$. Yet even more preferably $R^{12}$ is —$C(H)$=$CH_2$ or —$CH_2$—$C(H)$=$CH_2$, and most preferably, $R^{12}$ is —$C(H)$=$CH_2$.

When $R^{12}$ is an, optionally substituted, $C_3$-$C_5$ cycloalkenyl group, $R^{12}$ preferably comprises a cyclopropenyl group. More preferably the (optionally substituted) $C_3$-$C_5$ cycloalkenyl group is selected from the group consisting of:

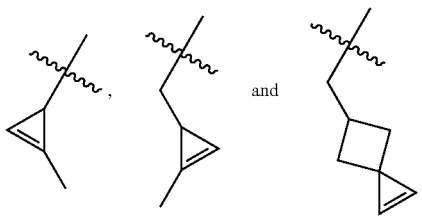

When $R^{12}$ is an, optionally substituted, $C_4$-$C_8$ alkadienyl group, it is preferred that the $C_4$-$C_8$ alkadienyl group ends with a C=$CH_2$ moiety, more preferably a C=$C(H)$—$C(H)$=$CH_2$ moiety. Preferably the $C_4$-$C_8$ alkadienyl group is selected from the group consisting of $C(H)$=$C(H)$—$C(H)$=$CH_2$, $CH_2$—C=$C(H)$—$C(H)$=$CH_2$ and $CH_2$—$CH_2$—C=$C(H)$—$C(H)$=$CH_2$, more preferably from $C(H)$=$C(H)$—$C(H)$=$CH_2$ and $CH_2$—C=$C(H)$—$C(H)$=$CH_2$. When $R^{12}$ is an optionally substituted $C_4$-$C_8$ alkadienyl group, most preferably $R^{12}$ is $C(H)$=$C(H)$—$C(H)$=$CH_2$.

In another embodiment, A is $R^{13}$, wherein $R^{13}$ is an optionally substituted terminal $C_3$-$C_{24}$ allenyl group. The term "terminal allenyl group" herein refers to an allenyl group wherein the C=C=C moiety is situated at a terminus of the allenyl group. The terminal $C_3$-$C_{24}$ alkenyl group preferably ends with a —$C(H)$=C=$CH_2$ moiety. Preferably $R^{13}$ is an optionally substituted terminal $C_3$-$C_{12}$ alkenyl group, and more preferably an optionally substituted terminal $C_3$-$C_6$ alkenyl group. More preferably, the terminal allenyl group is a linear allenyl group, preferably an unsubstituted linear allenyl group. Even more preferably $R^{13}$ is selected from the group consisting of —$C(H)$=C=$CH_2$, —$CH_2$—$C(H)$=C=$CH_2$, —$CH_2$—$CH_2$—$C(H)$=C=$CH_2$ and —$CH_2$—$CH_2$—$CH_2$—$C(H)$=C=$CH_2$. Yet even more preferably $R^{13}$ is selected from the group consisting of —$C(H)$=C=$CH_2$ and —$CH_2$—$C(H)$=C=$CH_2$. Most preferably, $R^{13}$ is —$C(H)$=C=$CH_2$. When A is $R^{13}$, it is particularly preferred that in Su(A)-Nuc (3), both U and T are absent, i.e. it is particularly preferred that a is 0 and f is 0.

In another embodiment, A is $N(R^{17})_2$, wherein $R^{17}$ is independently selected from the group consisting of H, $C_1$-$C_{12}$ alkyl groups. Preferred alkyl groups in the context of $R^{17}$ are $C_1$-$C_6$ alkyl groups, most preferably $C_1$-$C_4$ alkyl groups. Preferably, at least one of $R^{17}$ is H and A is $NHR^{17}$, most preferably both of $R^{17}$ are H and A is $NH_2$. When A is $N(R^{17})_2$, it is preferred that in Su(A)-Nuc (3), Y is absent, i.e. g is 0, more preferably both U and T are also absent, i.e. it is particularly preferred that g is 0, a is 0 and f is 0.

In a preferred embodiment of the process according to the invention, A in Su(A)-Nuc (3), and preferred embodiments of (3) as described in more detail below, is selected from the group consisting of —$N_3$, —$C(O)R^3$, —SH, —$(CH_2)_i$C=$CR^4$ and $R^{12}$, wherein i, $R^3$, $R^4$, $R^{12}$, and preferred embodiments thereof, are as defined above. More preferably, A is selected from the group consisting of —$N_3$, —$C(O)CH_3$, —SH, —CH=$CH_2$ and —$CH_2C$≡CH. Most preferably A is $N_3$.

In sugar derivative nucleotide Su(A)-Nuc (3) and preferred embodiments thereof such as e.g. (34), $R^{14}$ is selected from the group consisting of:

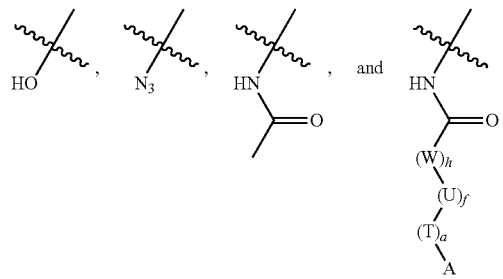

wherein W, h, a, f, T, A and U are as defined above.

In a preferred embodiment of sugar derivative nucleotide Su(A)-Nuc (3), $R^{14}$ is selected from the group consisting of:

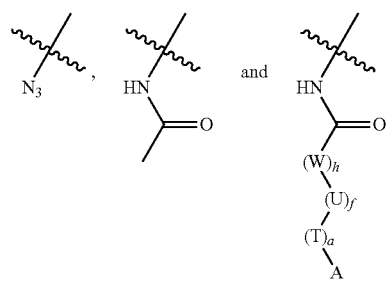

wherein W, h, a, f, T, A and U are as defined above.

Most preferably $R^{14}$ is —NHAc.

When $R^{14}$ is —NHC(O)—$(W)_h$—$(U)_f$-$(T)_a$-A, W, h, a, f, T, A and U are as defined above. Preferred embodiments of W, h, a, f, T and U are described in more detail below. Preferred embodiments of A are as described in more detail above.

In a preferred embodiment of the process according to the invention, $R^{14}$ in Su(A)-Nuc (3) is —NHC(O)$CH_3$. In this embodiment, sugar derivative nucleotide Su(A)-Nuc is according to formula (3a):

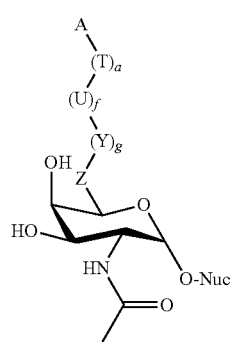

3a wherein Nuc, Z, Y, U, T, A, g, f and a are as defined above.

Also when sugar derivative nucleotide Su(A)-Nuc is according to formula (3a) or preferred embodiments thereof, it is preferred that Nuc is UDP.

Furthermore, also in Su(A)-Nuc (3a) A is preferably selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. More preferably, A is selected from the group consisting of —$N_3$, —$C(O)CH_3$, —SH, —CH=$CH_2$ and —$CH_2C\equiv CH$. Most preferably A is $N_3$.

In a particular preferred embodiment, in Su(A)-Nuc (3a) Nuc is UDP and A is selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. Even more preferably, Nuc is UDP and A is selected from the group consisting of —$N_3$, —$C(O)CH_3$, —SH, —CH=$CH_2$ and —$CH_2C\equiv CH$. Most preferably Nuc is UDP and A is $N_3$.

In another preferred embodiment of the process according to the invention, $R^{14}$ is —NHC(O)—(W)$_h$—(U)$_f$-(T)$_a$-A. In this embodiment, sugar derivative nucleotide Su(A)-Nuc is according to formula (3b):

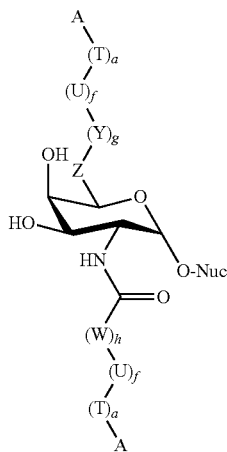

3b wherein Nuc, Z, Y, U, T, A, W, h, g, f and a are as defined above.

In sugar derivative nucleotide Su(A)-Nuc (3b), A, T, U, a and f are independently selected. In other words, A, T, U, a and f in the substituent on C2 of (3b) may differ from A, T, U, a and f in the substituent on C6 of (3b).

Also when Su(A)-Nuc is according to formula (3b), or preferred embodiments thereof, it is preferred that Nuc is UDP.

Furthermore, also in Su(A)-Nuc (3b) A is preferably selected from the group consisting of —$N_3$, —$C(O)R^3$, —SH, —$(CH_2)_iC\equiv CR^4$ and $R^{12}$, wherein i, R, $R^4$, $R^{12}$, and preferred embodiments thereof, are as defined above. More preferably, A is selected from the group consisting of —$N_3$, —$C(O)CH_3$, —SH, —CH=$CH_2$ and —$CH_2C\equiv CH$. Most preferably A is $N_3$.

In a particular preferred embodiment, in Su(A)-Nuc (3b) Nuc is UDP and A is selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. Even more preferably, Nuc is UDP and A is selected from the group consisting of —$N_3$, —$C(O)CH_3$, —SH, —CH=$CH_2$ and —$CH_2C\equiv CH$. Most preferably Nuc is UDP and A is $N_3$.

In another preferred embodiment of the process according to the invention, $R^{14}$ is —OH. In this embodiment, sugar derivative nucleotide Su(A)-Nuc is therefore according to formula (3c):

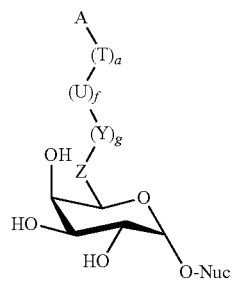

3c wherein Nuc, Z, Y, U, T, A, g, f and a are as defined above.

Also when sugar derivative nucleotide Su(A)-Nuc is according to formula (3c) or preferred embodiments thereof, it is preferred that Nuc is UDP.

Furthermore, also in Su(A)-Nuc (3c) A is preferably selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. More preferably, A is selected from the group consisting of —$N_3$, —$C(O)CH_3$, —SH, —CH=$CH_2$ and —$CH_2C\equiv CH$. Most preferably A is $N_3$.

In a particular preferred embodiment, in Su(A)-Nuc (3c) Nuc is UDP and A is selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. Even more preferably, Nuc is UDP and A is selected from the group consisting of —$N_3$, —$C(O)CH_3$, —SH, —CH=$CH_2$ and —$CH_2C\equiv CH$. Most preferably Nuc is UDP and A is $N_3$.

In another preferred embodiment of the process according to the invention, $R^{14}$ is —$N_3$. In this embodiment, sugar derivative nucleotide Su(A)-Nuc is therefore according to formula (3d):

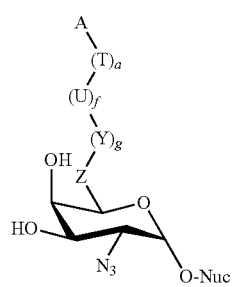

3d wherein Nuc, Z, Y, U, T, A, g, f and a are as defined above.

Also when sugar derivative nucleotide Su(A)-Nuc is according to formula (3d), or preferred embodiments thereof, it is preferred that Nuc is UDP.

Furthermore, also in Su(A)-Nuc (3d) A is preferably selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. More preferably, A is selected from the group consisting of —$N_3$, —$C(O)CH_3$, —SH, —CH=$CH_2$ and —$CH_2C\equiv CH$. Most preferably A is $N_3$.

In a particular preferred embodiment, in Su(A)-Nuc (3d) Nuc is UDP and A is selected from the group consisting of —$N_3$, —$C(O)R^3$, —SH, —$(CH_2)_iC\equiv CR^4$ and $R^{12}$, wherein i, $R^3$, $R^4$, $R^{12}$, and preferred embodiments thereof, are as defined above. Even more preferably, Nuc is UDP and A is selected from the group consisting of —N$_3$, —C(O)CH$_3$, —SH, —CH═CH$_2$ and —CH$_2$C≡CH. Most preferably Nuc is UDP and A is N$_3$.

In Su(A)-Nuc (3), and preferred embodiments thereof such as e.g. (34), (3a), (3b), (3c) or (3d), T is a C$_3$-C$_{12}$ (hetero)arylene group, wherein the (hetero)arylene group is optionally substituted. In a preferred embodiment, T is absent (a is 0). In another preferred embodiment, T is present (a is 1). When a is 1, (hetero)arylene group T in (3) is substituted with A, wherein A is as defined above.

(Hetero)arylene group T is optionally further substituted with one or more substituents R$^2$, wherein R$^2$ is independently selected from the group consisting of halogen (—F, —Cl, —Br, —I, preferably —F, —Cl, —Br), —CN, —NO$_2$, —C(O)R$^9$, —C(O)OR$^9$, —C(O)N(R$^{10}$)$_2$, C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_5$-C$_{12}$ cycloalkenyl groups, C$_8$-C$_{12}$ cycloalkynyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, amino groups (preferably —N(R$^{10}$)$_2$), oxo groups and —Si(R$^7$)$_3$ groups, wherein the alkyl groups, alkenyl groups, alkynyl groups, cycloalkyl groups, cycloalkenyl groups, cycloalkynyl groups, alkoxy groups, alkenyloxy groups, alkynyloxy groups and cycloalkyloxy groups are optionally interrupted by one of more heteroatoms selected from the group consisting of O, N and S, and wherein R$^7$ is independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups and C$_3$-C$_{12}$ cycloalkyloxy groups wherein the alkyl groups, alkenyl groups, alkynyl groups, cycloalkyl groups, alkoxy groups, alkenyloxy groups, alkynyloxy groups and cycloalkyloxy groups are optionally substituted, wherein R$^9$ is a C$_1$-C$_{12}$ alkyl group, and wherein R$^{10}$ is independently selected from hydrogen and a C$_1$-C$_{12}$ alkyl group. Preferably, R$^9$ is a C$_1$-C$_6$ alkyl group, even more preferably a C$_1$-C$_4$ alkyl group, and most preferably a methyl, ethyl, n-propyl, i-propyl, n-butyl, s-butyl or a t-butyl group. Preferably, R$^{10}$ is a hydrogen or a C$_1$-C$_6$ alkyl group, more preferably hydrogen or a C$_1$-C$_4$ alkyl group, and most preferably R$^{10}$ is hydrogen, a methyl, ethyl, n-propyl, i-propyl, n-butyl, s-butyl or a t-butyl group.

When R$^2$ is a —Si(R$^7$)$_3$ group, preferably R$^7$ is, independently, a C$_1$-C$_{12}$ alkyl group, more preferably independently a C$_1$-C$_6$ alkyl group, even more preferably independently a C$_1$-C$_4$ alkyl group, and most preferably R$^7$ is, independently, a methyl, ethyl, n-propyl, i-propyl, n-butyl, s-butyl or a t-butyl group.

Preferably, R$^2$, when present, is independently selected from the group consisting of —F, —Cl, —Br, —I, —CN, —NO$_2$, —C(O)R$^9$, —C(O)OR$^9$, —C(O)N(R$^{10}$)$_2$, C$_1$-C$_{12}$ alkyl groups, C$_1$-C$_{12}$ alkoxy groups, amino groups (—N(R$^{10}$)$_2$), oxo groups and —Si(R$^7$)$_3$ groups, wherein R$^7$, R$^9$, R$^{10}$ and preferred embodiments of R$^7$, R$^9$, R$^{10}$ are as defined above.

More preferably, R$^2$, when present, is independently selected from the group consisting of —F, —Cl, —Br, —CN, —NO$_2$, —C(O)R$^9$, —C(O)OR$^9$, —C(O)N(R$^{10}$)$_2$, C$_1$-C$_6$ alkyl groups, C$_1$-C$_6$ alkoxy groups, amino groups, oxo groups and —Si(R$^7$)$_3$ groups, wherein R$^7$, R$^9$, R$^{10}$ and preferred embodiments of R$^7$, R$^9$, R$^{10}$ are as defined above.

Even more preferably, R$^2$, when present, is independently selected from the group consisting of —F, —Cl, —Br, —CN, —NO$_2$, —C(O)R$^9$, —C(O)OR$^9$, —C(O)N(R$^{10}$)$_2$, C$_1$-C$_4$ alkyl groups and C$_1$-C$_4$ alkoxy groups, wherein R$^9$ and R$^{10}$, and preferred embodiments of R$^9$ and R$^{10}$, are as defined above.

Yet even more preferably, R$^2$, when present, is independently selected from the group consisting of —F, —Cl, —Br, —CN, —NO$_2$, methyl, methoxy, ethyl, ethoxy, n-propyl, n-propoxy, i-propyl, i-propoxy, n-butyl, n-butoxy, s-butyl, s-butoxy, t-butyl and t-butoxy. Most preferably, R$^2$, when present, is independently selected from the group consisting of —F, —Cl, —Br, —CN, —NO$_2$, methyl and methoxy.

In a preferred embodiment, the (hetero)arylene group in (3) is unsubstituted. In another preferred embodiment, the (hetero)arylene group in (3) comprises one or more substituents R$^2$, wherein R$^2$ and preferred embodiments of R$^2$ are defined above.

The term "(hetero)arylene group" herein refers to arylene groups as well as to heteroarylene groups. The term "(hetero)arylene group" herein refers to monocyclic (hetero) arylene groups as well as to bicyclic (hetero)arylene groups. The (hetero)arylene group in Su(A)-Nuc (3) may be any arylene group or any heteroarylene group.

In a preferred embodiment of the process according to the invention, (hetero)arylene group T in (3) is selected from the group consisting of phenylene groups, naphthylene groups, anthracylene groups, pyrrolylene groups, pyrroliumylene groups, furanylene groups, thiophenylene groups (i.e. thiofuranylene groups), pyrazolylene groups, imidazolylene groups, pyrimidiniumylene groups, imidazoliumylene groups, isoxazolylene groups, oxazolylene groups, oxazoliumylene groups, isothiazolylene groups, thiazolylene groups, 1,2,3-triazolylene groups, 1,3,4-triazolylene groups, diazolylene groups, 1-oxa-2,3-diazolylene groups, 1-oxa-2,4-diazolylene groups, 1-oxa-2,5-diazolylene groups, 1-oxa-3,4-diazolylene groups, 1-thia-2,3-diazolylene groups, 1-thia-2,4-diazolylene groups, 1-thia-2,5-diazolylene groups, 1-thia-3,4-diazolylene groups, tetrazolylene groups, pyridinylene groups, pyridazinylene groups, pyrimidinylene groups, pyrazinylene groups, pyradizinylene groups, pyridiniumylene groups, pyrimidiniumylene groups, benzofuranylene groups, benzothiophenylene groups, benzimidazolylene groups, indazolylene groups, benzotriazolylene groups, pyrrolo[2,3-b]pyridinylene groups, pyrrolo[2,3-c]pyridinylene groups, pyrrolo[3,2-c]pyridinylene groups, pyrrolo[3,2-b]pyridinylene groups, imidazo[4,5-b]pyridinylene groups, imidazo[4,5-c]pyridinylene groups, pyrazolo[4,3-d]pyridinylene groups, pyrazolo[4,3-c]pyridinylene groups, pyrazolo[3,4-c]pyridinylene groups, pyrazolo[3,4-b]pyridinylene groups, isoindolylene groups, indazolylene groups, purinylene groups, indolininylene groups, imidazo[1,2-a]pyridinylene groups, imidazo[1,5-a]pyridinylene groups, pyrazolo[1,5-a]pyridinylene groups, pyrrolo[1,2-b]pyridazinylene groups, imidazo[1,2-c]pyrimidinylene groups, quinolinylene groups, isoquinolinylene groups, cinnolinylene groups, quinazolinylene groups, quinoxalinylene groups, phthalazinylene groups, 1,6-naphthyridinylene groups, 1,7-naphthyridinylene groups, 1,8-naphthyridinylene groups, 1,5-naphthyridinylene groups, 2,6-naphthyridinylene groups, 2,7-naphthyridinylene groups, pyrido[3,2-d]pyrimidinylene groups, pyrido[4,3-d]pyrimidinylene groups, pyrido[3,4-d]pyrimidinylene groups, pyrido[2,3-d]pyrimidinylene groups, pyrido[2,3-b]pyrazinylene groups, pyrido[3,4-b]pyrazinylene groups, pyrimido[5,4-d]pyrimidinylene groups, pyrazino[2,3-b]pyrazinylene groups and pyrimido[4,5-d]pyrimidinylene groups, all groups optionally substituted with one or more substituents R$^2$, wherein R$^2$ and preferred embodiments of R$^2$ are as defined above.

In a further preferred embodiment, (hetero)arylene group T is selected from the group consisting of phenylene groups, pyridinylene groups, pyridiniumylene groups, pyrimidinylene groups, pyrimidiniumylene groups, pyrazinylene groups, pyradizinylene groups, pyrrolylene groups, pyrroliumylene groups, furanylene groups, thiophenylene groups (i.e. thiofuranylene groups), diazolylene groups, quinolinylene groups, imidazolylene groups, pyrimidiniumylene groups, imidazoliumylene groups, oxazolylene groups and oxazoliumylene groups, all groups optionally substituted with one or more substituents $R^2$, wherein $R^2$ and preferred embodiments of $R^2$ are as defined above.

Even more preferably, (hetero)arylene group T is selected from the group consisting of phenylene groups, pyridinylene groups, pyridiniumylene groups, pyrimidinylene groups, pyrimidiniumylene groups, imidazolylene groups, pyrimidiniumylene groups, imidazoliumylene groups, pyrrolylene groups, furanylene groups and thiophenylene groups, all groups optionally substituted with one or more substituents $R^2$, wherein $R^2$ and preferred embodiments of $R^2$ are as defined above.

Most preferably, (hetero)aryl group T is selected from the group consisting of phenylene groups, imidazolylene groups, imidazoliumylene groups, pyrimidiniumylene groups, pyridinylene groups and pyridiniumylene groups, all groups optionally substituted with one or more substituents $R^2$, wherein $R^2$ and preferred embodiments of $R^2$ are as defined above.

In Su(A)-Nuc (3), and preferred embodiments thereof such as e.g. (34), (3a), (3b), (3c) or (3d), U may be present (f is 1) or absent (f is 0). When present, U is $[C(R^1)_2]_n$ wherein n is an integer in the range of 1 to 24; or U is $[C(R^1)_2]_p$—O—$[C(R^1)_2C(R^1)_2O]_o$—$[C(R^1)_2]_q$, wherein o is an integer in the range of 0 to 12, p and q are independently 0, 1 or 2, and $R^1$ is independently selected from the group consisting of H, F, Cl, Br, I, OH and an optionally substituted $C_1$-$C_{24}$ alkyl group. When U is $[C(R^1)_2]_p$—O—$[C(R^1)_2C(R^1)_2O]_o$—$[C(R^1)_2]_q$ it is preferred that at least one of p, o and q is not 0.

In a preferred embodiment U is absent, i.e. f is 0.

In another preferred embodiment U is present, i.e. f is 1.

When U is $[C(R^1)_2]_n$, n is an integer in the range of 1 to 24, preferably an integer in the range of 1 to 12. More preferably n is 1, 2, 3, 4, 5, 6, 7 or 8, even more preferably n is 1, 2, 3, 4, 5 or 6, yet even more preferably n is 1, 2, 3 or 4, yet even more preferably n is 1, 2 or 3, and most preferably, n is 1 or 2.

$R^1$ is independently selected from the group consisting of H, F, Cl, Br, I and an optionally substituted $C_1$-$C_{24}$ alkyl group, preferably from the group consisting of H, F, Cl, Br, I and an optionally substituted $C_1$-$C_{12}$ alkyl group, and more preferably from the group consisting of H, F, Cl, Br, I and an optionally substituted $C_1$-$C_6$ alkyl group. Even more preferably, $R^1$ is independently selected from the group consisting of H, F, Cl, Br, I, a methyl group, an ethyl group, an n-propyl group, an i-propyl group, an n-butyl group, an s-butyl group or a t-butyl group. Even more preferably, $R^1$ is independently selected from the group consisting of H, F, Cl and methyl, and most preferably, $R^1$ is independently selected from the group consisting of H and F.

When U is $[C(R^1)_2]_n$ and n is 1 or 2, preferred examples of the —$[C(R^1)_2]_n$— moiety in Su(A)-Nuc include —(CH$_2$)—, —(CF$_2$)—, —(CCl$_2$)—, —(CBr$_2$)—, —(CMe$_2$)—, —(CH$_2$CH$_2$)—, —(CH$_2$CF$_2$)—, —(CH$_2$CCl$_2$)—, —(CH$_2$CBr$_2$)—, —(CH$_2$Cl$_2$)—, —(CH$_2$CMe$_2$)—, —(CF$_2$CF$_2$)—, —(CCl$_2$CCl$_2$)—, —(CBr$_2$CBr$_2$)— and —(CMe$_2$CMe$_2$)—, more preferably —(CH$_2$)—, —(CF$_2$)—, —(CH$_2$CH$_2$)—, —(CH$_2$CF$_2$)— and —(CF$_2$CF$_2$)—.

When U is $[C(R^1)_2]_n$ and n is 3 or more, preferred examples of the —$[C(R^1)_2]_n$-moiety in Su(A)-Nuc include —(C$_n$H$_{2n}$)—, —(C$_n$F$_{2n}$)—, —(C$_n$Cl$_{2n}$)—, —(C$_n$Br$_{2n}$)—, —(C$_{(n-1)}$H$_{2(n-1)}$CF$_2$)—, —(C$_{(n-1)}$H$_{2(n-1)}$CCl$_2$)—, —(C$_{(n-1)}$H$_{2(n-1)}$CBr$_2$)— and —(C$_{(n-1)}$H$_{2(n-1)}$CMe$_2$)—, for example —(C$_3$H$_6$)—, —(C$_3$F$_6$)—, —(C$_3$Cl$_6$)—, —(C$_3$Br$_6$)—, —(CH$_2$CH$_2$CF$_2$)—, —(CH$_2$CH$_2$CCl$_2$)—, —(CH$_2$CH$_2$CBr$_2$)— and —(C$_4$H$_8$)—. More preferred examples include —(C$_n$H$_{2n}$)—, —(C$_n$F$_{2n}$)—, e.g. —(C$_3$H$_6$)—, —(C$_4$H$_8$)—, —(C$_3$F$_6$)— and —(C$_4$F$_8$)—.

When U is $[C(R^1)_2]_p$—O—$[C(R^1)_2C(R^1)_2O]_o$—$[C(R^1)_2]_q$, o is an integer in the range of 0 to 12 and p and q are independently 0, 1 or 2. Preferably, o is an integer in the range of 1 to 10, more preferably o is 1, 2, 3, 4, 5, 6, 7 or 8, even more preferably o is 1, 2, 3, 4, 5 or 6, yet even more preferably o is 1, 2, 3 or 4, yet even more preferably o is 1, 2 or 3, yet even more preferably, o is 1 or 2 and most preferably o is 1. In another preferred embodiment, o is 0. It is particularly preferred that o is 0, 1 or 2. When o is 0, it is further preferred that when p is 0, q is 1 or 2, and that when q is 0, p is 1 or 2.

When U is $[C(R^1)_2]_p$—O—$[C(R^1)_2C(R^1)_2O]_o$—$[C(R^1)_2]_q$ and o and/or p and/or q are 1 or more, $R^1$ is independently selected from the group consisting of H, F, Cl, Br, I and an optionally substituted $C_1$-$C_{24}$ alkyl group, preferably from the group consisting of H, F, Cl, Br, I and an optionally substituted $C_1$-$C_{12}$ alkyl group, and more preferably from the group consisting of H, F, Cl, Br, I and an optionally substituted $C_1$-$C_6$ alkyl group. Even more preferably, $R^1$ is independently selected from the group consisting of H, F, Cl, Br, I, a methyl group, an ethyl group, an n-propyl group, an i-propyl group, an n-butyl group, an s-butyl group or a t-butyl group. Even more preferably, $R^1$ is independently selected from the group consisting of H, F, Cl and methyl. Most preferably, $R^1$ is H.

When U is $[C(R^1)_2]_p$—O—$[C(R^1)_2C(R^1)_2O]_o$—$[C(R^1)_2]_q$, preferred examples of the —$[C(R^1)_2]_p$—O—$[C(R^1)_2C(R^1)_2O]_o$—$[C(R^1)_2]_q$— moiety in Su(A)-Nuc include —CH$_2$—O—, —(CH$_2$)$_2$—O—, —O—CH$_2$—, —O—(CH$_2$)$_2$—, —CH$_2$—O—(CH$_2$CH$_2$O)$_o$—, —(CH$_2$)$_2$—O—(CH$_2$CH$_2$O)$_o$—, —O—(CH$_2$CH$_2$O)$_o$—, —O—(CH$_2$CH$_2$O)$_o$—CH$_2$—, —O—(CH$_2$CH$_2$O)$_o$—(CH$_2$)$_2$—, —CH$_2$—O—(CH$_2$CH$_2$O)$_o$—CH$_2$—, —CH$_2$—O—(CH$_2$CH$_2$O)$_o$—(CH$_2$)$_2$—, —(CH$_2$)$_2$—O—(CH$_2$CH$_2$O)$_o$—CH$_2$— and —(CH$_2$)$_2$—O—(CH$_2$CH$_2$O)$_o$—(CH$_2$)$_2$—, wherein o is 1, 2, 3, 4, 5 or 6, preferably o is 1, 2, 3 or 4, more preferably o is 1 or 2 and most preferably o is 1.

In sugar-derivative nucleotide Su(A)-Nuc (3), and preferred embodiments thereof such as e.g. (34), (3a), (3b), (3c) or (3d), it is preferred that a and f are not both 0. In another preferred embodiment, a is 0 and f is 1 or that a is 1 and f is 0. In these embodiments, g may be 0 or 1.

In a preferred embodiment of the process according to the invention, a is 0, f is 1 and U is $[C(R^1)_2]_n$. In this embodiment it is further preferred that a is 0, f is 1 and n is in the range of 1 to 12, more preferably a is 0, f is 1 and n is 1, 2, 3, 4, 5, 6, 7 or 8, even more preferably a is 0, f is 1 and n is 1, 2, 3, 4, 5 or 6, yet even more preferably a is 0, f is 1 and n is 1, 2, 3 or 4, yet even more preferably a is 0, f is 1 and n is 1 or 2, and most preferably a is 0, f is 1 and n is 1. Preferred examples of $[C(R^1)_2]_n$ are as described in more detail above.

In another preferred embodiment of the process according to the invention, a is 0, f is 1 and U is $[C(R^1)_2]_p$—O—[C $(R^1)_2C(R^1)_2O]_o$—$[C(R^1)_2]_q$. More preferably p, o and q are not all 0, i.e. o is an integer in the range of 1 to 12 and/or p is 1 or 2 and/or q is 1 or 2. In this embodiment it is further preferred that a is 0, f is 1 and o is in the range of 1 to 12, more preferably a is 0, f is 1 and o is in the range of 1 to 10, even more preferably a is 0, f is 1 and o is 1, 2, 3, 4, 5, 6, 7 or 8, yet even more preferably a is 0, f is 1 and o is 1, 2, 3, 4, 5 or 6, yet even more preferably a is 0, f is 1 and o is 1, 2, 3 or 4, yet even more preferably a is 0, f is 1 and o is 1 or 2, and most preferably a is 0, f is 1 and o is 1. Also in this embodiment, p and q are independently 0, 1 or 2. Preferred examples of $[C(R^1)_2]_p$—O—$[C(R^1)_2C(R^1)_2O]_o$—$[C(R^1)_2]_q$ are as described in more detail above.

In yet another preferred embodiment, a is 1, f is 1 and U is $[C(R^1)_2]_n$. In this embodiment it is further preferred that n is in the range of 1 to 12, more preferably n is 1, 2, 3, 4, 5, 6, 7 or 8, even more preferably n is 1, 2, 3, 4, 5 or 6, yet even more preferably n is 1, 2, 3 or 4, yet even more preferably n is 1 or 2, and most preferably n is 1. Preferred examples of $[C(R^1)_2]_n$ are as described in more detail above.

In yet another preferred embodiment, a is 1, f is 1 and U is $[C(R^1)_2]_p$—O—$[C(R^1)_2C(R^1)_2O]_o$—$[C(R^1)_2]_q$, o is an integer in the range of 1 to 12 and p and q are independently 0, 1 or 2. In this embodiment it is further preferred that o is in the range of 1 to 10, more preferably o is 1, 2, 3, 4, 5, 6, 7 or 8, even more preferably o is 1, 2, 3, 4, 5 or 6, yet even more preferably o is 1, 2, 3 or 4, yet even more preferably o is 1 or 2, and most preferably o is 1. Also in this embodiment, p and q are independently 0, 1 or 2. Preferred examples of $[C(R^1)_2]_p$—O—$[C(R^1)_2C(R^1)_2O]_o$—$[C(R^1)_2]_q$ are as described in more detail above.

As defined above, Z in Su(A)-Nuc (3), and preferred embodiments thereof such as e.g. (34), (3a), (3b), (3c) or (3d), is $CH_2$, $CF_2$ or C(O); or Z is CHOH with the proviso that g is 0, f is 1 and a is 0 or 1. In a preferred embodiment, Z is selected from the group consisting of $CH_2$, $CF_2$ and C(O). In another preferred embodiment, Z is CHOH with the proviso that g is 0, f is 1 and a is 0 or 1.

In Su(A)-Nuc (3), and preferred embodiments thereof such as e.g. (34), (3a), (3b), (3c) or (3d), Y may be absent (g is 0) or present (g is 1). When Y is present, Y is selected from the group consisting of O, S, $N(R^{15})$, $N(R^{15})C(O)$, $N(R^{15})C(O)N(R^{15})$, $N(R^{15})C(O)O$, $OC(O)N(R^{15})S(O)_2N(R^{15})$ and $N(R^{15})C(O)N(R^{15})S(O)_2O$, wherein $R^{15}$ is independently selected from the group consisting of H, $C_1$-$C_{12}$ alkyl groups and $(U)_f$-$(T)_a$-A wherein f, a, U, T and A are as defined above. Preferably, Y is selected from the group consisting of O, S, $N(R^{15})$, NHC(O), NHC(O)N($R^{15}$), NHC(O)O, OC(O) $NHS(O)_2NH$ and NHC(O) $NHS(O)_2O$, wherein $R^{15}$ is independently selected from the group consisting of H, $C_1$-$C_{12}$ alkyl groups and $(U)_f$-$(T)_a$-A wherein f, a, U, T and A are as defined above. In these embodiments it is further preferred that $R^{15}$ is independently selected from the group consisting of H, $C_1$-$C_6$ alkyl groups and $(U)_f$-$(T)_a$-A wherein f, a, U, T and A are as defined above. More preferably $R^{15}$ is independently selected from the group consisting of H, methyl, ethyl, i-propyl, n-propyl and $(U)_f$-$(T)_a$-A wherein f, a, U, T and A are as defined above. Most preferably $R^{15}$ is selected from the group consisting of H and methyl.

In a preferred embodiment, Z is $CH_2$ and g is 1. In this embodiment it is further preferred that Y is selected from the group consisting of O, S, $N(R^{15})$, $N(R^{15})C(O)$, $N(R^{15})C(O)N(R^{15})$ and $N(R^{15})C(O)O$, more preferably from the group consisting of O, S, $N(R^{15})$, NHC(O), NHC(O)N($R^{15}$) and NHC(O)O, wherein $R^{15}$ and preferred embodiments of $R^{15}$ are as defined above.

In another preferred embodiment Z is C(O) g is 1. In this embodiment it is further preferred that Y is N($R^{15}$), wherein $R^{15}$ and preferred embodiments of $R^{15}$ are as defined above.

Therefore, in a preferred embodiment of the process according to the invention, sugar-derivative nucleotide Su(A)-Nuc is according to formula (15), (16), (17) or (18):

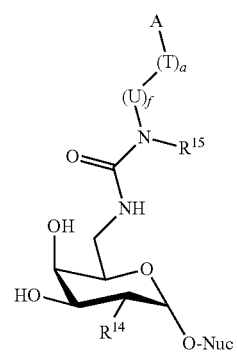

15

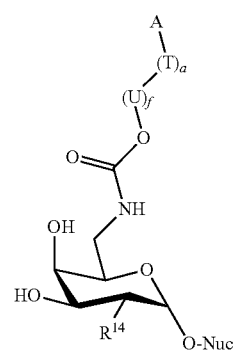

16

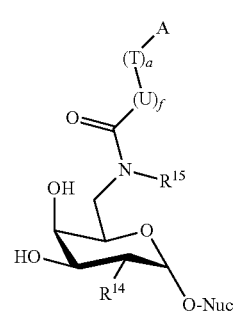

17

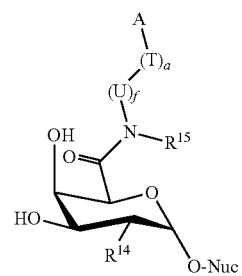

18 wherein Nuc, a, f, $R^{14}$, $R^{15}$, A, U and T are as defined above.

In a preferred embodiment of (15), (16), (17) and (18), $R^{14}$ is —OH. In another preferred embodiment, $R^{14}$ is —$N_3$. In another preferred embodiment, $R^{14}$ is —NHC(O)$CH_3$. In another preferred embodiment $R^{14}$ is —NHC(O)—$(W)_h$—

(U)$_f$-(T)$_a$-A, wherein W, U, T, A, h, f and a are as defined above. In these embodiments it is further preferred that Nuc is UDP.

Preferred embodiments for U, T, a and fin (15), (16), (17) and (18) are as described above. Preferred embodiments for A as defined above also hold for (15), (16), (17) and (18).

In a particularly preferred embodiment of (15), (16), (17) and (18), a is 0, f is 1 and U is —CH$_2$CF$_2$—. In this embodiment it is further preferred that A is N$_3$.

In another particularly preferred embodiment of (15), (16), (17) and (18), a is 1 and T is preferably an, optionally substituted, phenyl group. As described above, the phenyl group is optionally substituted with R$^2$, and preferably R$^2$ is selected from the group consisting of H, F, Cl and Br, more preferably from the group consisting of H, F and Cl and most preferably from the group consisting of H and F. In this embodiment, f is 0 or 1, and when f is 1, U is preferably —CH$_2$—. In these embodiments it is further preferred that A is N$_3$. Preferably A is present on the para-position of the, optionally substituted, phenyl group.

In a preferred embodiment of the process according to the invention, sugar-derivative nucleotide Su(A)-Nuc is according to formula (19), (20), (21), (22), (23), (24), (25), (26), (65) or (66), preferably according to formula (19), (20), (21), (22), (23), (24), (25) or (26):

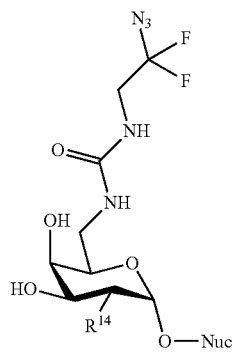

19

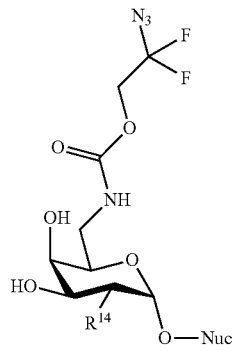

20

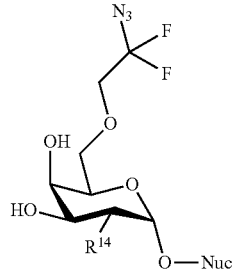

21

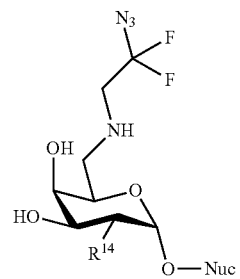

22

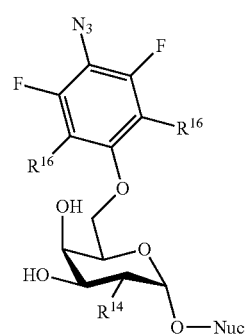

23

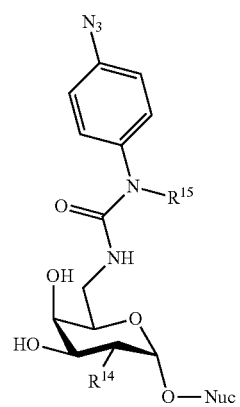

24

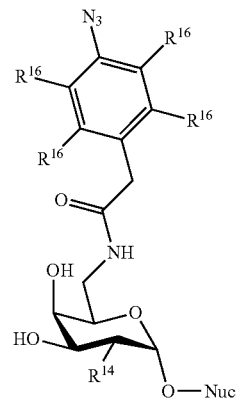

25

-continued

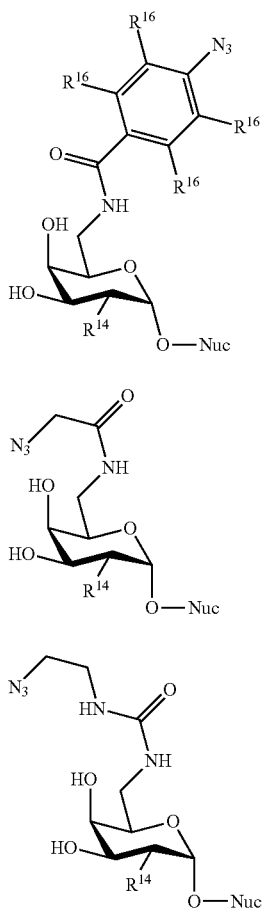

wherein:

$R^{14}$ and $R^{15}$ are as defined above; and $R^{16}$ is independently selected from the group consisting of H and F.

In a preferred embodiment of the process according to the invention, sugar-derivative nucleotide Su(A)-Nuc is according to formula (67), (68) or (69):

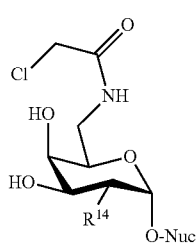

67

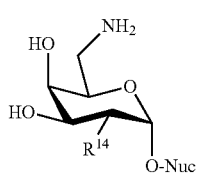

68

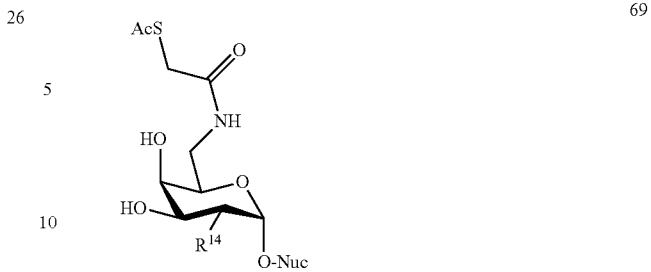

69 wherein $R^{14}$ is as defined above.

In a further preferred embodiment $R^{15}$ is selected from the group consisting of H and $C_1$-$C_{12}$ alkyl groups, preferably from the group consisting of H and $C_1$-$C_6$ alkyl groups, more preferably from the group consisting of H, methyl, ethyl, i-propyl, n-propyl, n-butyl, s-butyl and t-butyl, and most preferably from the group consisting of H and methyl. In another further preferred embodiment $R^{15}$ is $(U)_f$-$(T)_a$-A wherein f, a, U, T and A, and preferred embodiments thereof, are as defined above. When $R^{15}$ is $(U)_f$-$(T)_a$-A, it is preferred that the $(U)_f$-$(T)_a$-A group of $R^{15}$ corresponds to the $(U)_f$-$(T)_a$-A group originating from the Z—$(Y)_g$—$(U)_f$-$(T)_a$-A moiety in Su(A)-Nuc (3). For example, when $R^{15}$ in (24) is $(U)_f$-$(T)_a$-A it is preferred that $R^{15}$ is —($C_6H_4(N_3)$), with $N_3$ on the para position of phenyl. In these embodiments it is further preferred that Nuc is UDP.

In a preferred embodiment of (19), (20), (21), (22), (23), (24), (25), (26), (65), (66), (67), (68) and (69) and preferred embodiments thereof as described above, $R^{14}$ is —OH. In another preferred embodiment $R^{14}$ is —$N_3$. In another preferred embodiment $R^{14}$ is —NHC(O)$CH_3$. In another preferred embodiment $R^{14}$ is —NHC(O)—(W)$_h$—(U)$_f$-$(T)_a$-A, wherein W, U, T, A, h, f and a are as defined above. Also in these embodiments it is further preferred that Nuc is UDP.

In a preferred embodiment, $R^{14}$ is —$N_3$. In another preferred embodiment of the process according to the invention $R^{14}$ is selected from the group consisting of:

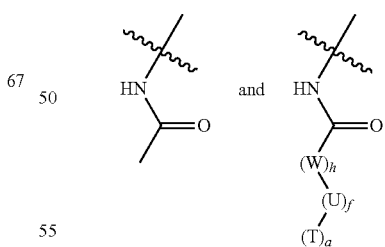

wherein a, f, h, T, A, U and W, and preferred embodiments thereof, are as described above.

In a further preferred embodiment of the process according to the invention, sugar-derivative nucleotide Su(A)-Nuc is according to formula (27), (28), (29), (30) or (31), or according to formula (36):

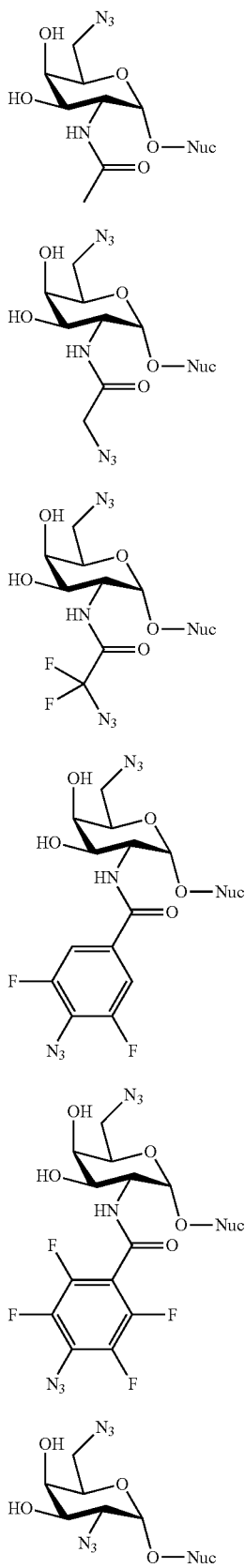

wherein Nuc is as defined above.

In another preferred embodiment of the process according to the invention, $R^{14}$ is OH. In this embodiment it is further preferred that sugar-derivative nucleotide Su(A)-Nuc is according to formula (35):

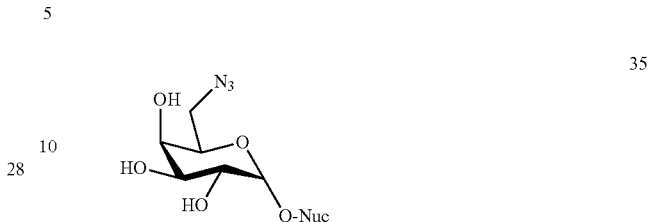

wherein Nuc is as defined above.

Also when Su(A)-Nuc is according to formula (27), (28), (29), (30), (31), (35) or (36), it is preferred that Nuc is UDP.

Enzyme

The process according to the invention comprises the step of contacting a glycoprotein comprising a glycan comprising a terminal GlcNAc moiety with a sugar-derivative nucleotide Su(A)-Nuc in the presence of, more particularly under the action of, a glycosyltransferase, wherein the glycosyltransferase is or is derived from a β-(1,4)-N-acetylgalactosaminyltransferase, in order to provide a modified glycoprotein. A β-(1,4)-N-acetylgalactosaminyltransferase is herein also referred to as a β-(1,4)-GalNAcT enzyme, or β-(1,4)-GalNAcT, or GalNAcT.

β-(1,4)-N-Acetylgalactosaminyltransferases (β-(1,4)-GalNAcTs) are known in the art. Typically, a β-(1,4)-GalNAcT is an enzyme that catalyzes the transfer of N-acetylgalactosamine (GalNAc) from uridine diphosphate-GalNAc (UDP-GalNAc, also referred to as GalNAc-UDP) to a terminal GlcNAc moiety of a glycoprotein glycan, wherein C1 of the GalNAc moiety is attached to C4 of the GlcNAc moiety via a β-1,4-O-glycosidic bond. As described in more detail above, the GlcNAc moiety in a glycan according to formula (1) wherein b is 1, i.e. the GlcNAc moiety in a glycan consisting of a fucosylated GlcNAc, is herein also considered a terminal GlcNAc moiety.

In the process according to the invention, the glycosyltransferase that is, or is derived from, a β-(1,4)-GalNAcT catalyzes the transfer of sugar-derivative Su(A) from a sugar-derivative nucleotide Su(A)-Nuc to a terminal GlcNAc moiety of a glycoprotein glycan to provide a modified glycoprotein, wherein Su(A) is according to formula (6), Su(A)-Nuc is according to formula (3), the glycan comprising a terminal GlcNAc-moiety is according to formula (1) or (2), and the modified glycoprotein is according to formula (4) or (5), as described above. In this process, C1 of the Su(A) moiety is attached to C4 of the GlcNAc moiety via a β-1,4-O-glycosidic bond.

Preferably, the β-(1,4)-GalNAcT enzyme used in the process of the invention is or is derived from an invertebrate β-(1,4)-GalNAcT enzyme, i.e. is or is derived from a β-(1,4)-GalNAcT that originates from invertebrate animal species. The β-(1,4)-GalNAcT enzyme can be, or can be derived from, any invertebrate β-(1,4)-GalNAcT enzyme known by a person skilled in the art. Preferably, the β-(1,4)-GalNAcT enzyme is, or is derived from, a β-(1,4)-GalNAcT enzyme that originates from the phylum of Nematoda, preferably of the class of Chromadorea or Secernentea, or from the phylum of Arthropoda, preferably of the class of Insecta. Preferably, the β-(1,4)-GalNAcT enzyme is, or is derived from, a β-(1,4)-GalNAcT enzyme that originates from *Caenorhabditis elegans, Caenorhabditis remanei, Caenorhabditis briggsae, Ascaris suum, Trichoplusia ni,*

Drosophila melanogaster, Wuchereria bancrofti, Loa loa, Cerapachys biroi, Zootermopsis nevadensis, Camponotus floridanus, Crassostrea gigas or Danaus plexippus, preferably from Caenorhabditis elegans, Ascaris suum, Trichoplusia ni, or Drosophila melanogaster. More preferably, the β-(1,4)-GalNAcT enzyme is, or is derived from, a β-(1,4)-GalNAcT enzyme that originates from Caenorhabditis elegans, Ascaris suum or Trichoplusia ni. In a further preferred embodiment, the β-(1,4)-GalNAcT enzyme is, or is derived from, a β-(1,4)-GalNAcT enzyme that originates from Ascaris suum. In another further preferred embodiment, the β-(1,4)-GalNAcT enzyme is, or is derived from, a β-(1,4)-GalNAcT enzyme that originates from Trichoplusia ni. In another further preferred embodiment, the β-(1,4)-GalNAcT enzyme is, or is derived from, a β-(1,4)-GalNAcT enzyme that originates from Caenorhabditis elegans.

Caenorhabditis elegans is herein also referred to as Ce, Ascaris suum as As, Trichoplusia ni as Tn and Drosophila melanogaster as Dm.

Preferably, the β-(1,4)-GalNAcT enzyme used in the process of the invention has at least 40%, 45%, 50%, 55%, 60%, 65%, 70%, 75%, 80%, 85%, 90%, 91%, 92%, 93%, 94%, 95%, 96%, 97%, 98%, 99% or preferably 100% sequence identity to a sequence selected from the group consisting of SEQ ID NO: 2-5 and 15-23, more preferably to a sequence selected from the group consisting of SEQ ID NO: 2-5. In other words, preferably the β-(1,4)-GalNAcT enzyme used in the process of the invention has at least 40%, 45%, 50%, 55%, 60%, 65%, 70%, 75%, 80%, 85%, 90%, 91%, 92%, 93%, 94%, 95%, 96%, 97%, 98%, 99% or preferably 100% sequence identity to a sequence selected from the group consisting of SEQ ID NO: 2, SEQ ID NO: 3, SEQ ID NO: 4 and SEQ ID NO: 5, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23, more preferably to a sequence selected from the group consisting of SEQ ID NO: 2, SEQ ID NO: 3, SEQ ID NO: 4 and SEQ ID NO: 5, even more preferably to a sequence selected from the group consisting of SEQ ID NO: 2, SEQ ID NO: 3 and SEQ ID NO: 4, even more preferably to a sequence selected from the group consisting of SEQ ID NO: 3 and SEQ ID NO: 4, and most preferably to SEQ ID NO: 4.

Preferably, the β-(1,4)-GalNAcT enzyme used in the process of the invention is or is derived from any of the naturally occurring or wild type β-(1,4)-GalNAcT enzymes selected from the group consisting of Caenorhabditis elegans β-(1,4)-GalNAcT denominated herein as CeGalNAcT (SEQ ID NO: 2), Ascaris suum β-(1,4)-GalNAcT denominated herein as AsGalNAcT (SEQ ID NO: 3), Trichoplusia ni β-(1,4)-GalNAcT denominated herein as TnGalNAcT (SEQ ID NO: 4), Drosophila melanogaster β-(1,4)-GalNAcT denominated herein as DmGalNAcT (SEQ ID NO: 5), Caenorhabditis remanei β-(1,4)-GalNAcT (SEQ ID NO: 15), Caenorhabditis briggsae β-(1,4)-GalNAcT (SEQ ID NO: 16), Wuchereria bancrofti β-(1,4)-GalNAcT (SEQ ID NO: 17), Loa loa β-(1,4)-GalNAcT (SEQ ID NO: 18), Cerapachys biroi β-(1,4)-GalNAcT (SEQ ID NO: 19), Zootermopsis nevadensis β-(1,4)-GalNAcT (SEQ ID NO: 20), Camponotus floridanus β-(1,4)-GalNAcT (SEQ ID NO: 21), Crassostrea gigas β-(1,4)-GalNAcT (SEQ ID NO: 22) and Danaus plexippus β-(1,4)-GalNAcT (SEQ ID NO: 23).

In preferred embodiment, the β-(1,4)-GalNAcT enzyme used in the process of the invention is or is derived from any of the naturally occurring or wild type β-(1,4)-GalNAcT enzymes selected from the group consisting of Caenorhabditis elegans β-(1,4)-GalNAcT denominated herein as CeGalNAcT (SEQ ID NO: 2), Ascaris suum β-(1,4)-GalNAcT denominated herein as AsGalNAcT (SEQ ID NO: 3), Trichoplusia ni β-(1,4)-GalNAcT denominated herein as TnGalNAcT (SEQ ID NO: 4) and Drosophila melanogaster β-(1,4)-GalNAcT denominated herein as DmGalNAcT (SEQ ID NO: 5).

In another preferred embodiment, the β-(1,4)-GalNAcT enzyme used in the process of the invention is, or is derived from, any of the naturally occurring or wild type β-(1,4)-GalNAcT enzymes selected from the group consisting of Caenorhabditis elegans β-(1,4)-GalNAcT denominated herein as CeGalNAcT (SEQ ID NO: 2), Ascaris suum β-(1,4)-GalNAcT denominated herein as AsGalNAcT (SEQ ID NO: 3) and Trichoplusia ni β-(1,4)-GalNAcT denominated herein as TnGalNAcT (SEQ ID NO: 4).

In another preferred embodiment, the β-(1,4)-GalNAcT enzyme used in the process of the invention is, or is derived from, any of the naturally occurring or wild type β-(1,4)-GalNAcT enzymes selected from the group consisting of Ascaris suum β-(1,4)-GalNAcT denominated herein as AsGalNAcT (SEQ ID NO: 3) and Trichoplusia ni β-(1,4)-GalNAcT denominated herein as TnGalNAcT (SEQ ID NO: 4).

In a particularly preferred embodiment, the β-(1,4)-GalNAcT enzyme used in the process of the invention is or is derived from Trichoplusia ni β-(1,4)-GalNAcT denominated herein as TnGalNAcT (SEQ ID NO: 4).

In another preferred embodiment the β-(1,4)-GalNAcT enzyme used in the process of the invention is a β-(1,4)-GalNAcT enzyme that is or is derived from a β-(1,4)-GalNAcT enzyme that originates from an invertebrate species of the phylum Nematode, preferably of the class Chromadorea, preferably of the order Rhabditida, preferably of the family Rhabditidae, preferably of the genus Caenorhabditis. Preferably, the β-(1,4)-GalNAcT enzyme used in the process of the invention has at least 40%, 45%, 50%, 55%, 60%, 65%, 70%, 75%, 80%, 85%. 90%, 91%, 92%, 93%, 94%, 95%, 96%, 97%, 98%, 99% or preferably 100% sequence identity to a sequence of the group consisting of SEQ ID NO: 2, 15 and 16. More preferably, said invertebrate species is of Caenorhabditis Elegans. Preferably, the β-(1,4)-GalNAcT enzyme used in the process of the invention has at least 40%, 45%, 50%, 55%, 60%, 65%, 70%, 75%, 80%, 85%, 90%, 91%, 92%, 93%, 94%, 95%, 96%, 97%, 98%, 99% or preferably 100% sequence identity to SEQ ID NO: 2.

In another preferred embodiment the β-(1,4)-GalNAcT enzyme used in the process of the invention is a β-(1,4)-GalNAcT enzyme that is or is derived from a β-(1,4)-GalNAcT enzyme that originates from an invertebrate species of the phylum Nematode, preferably of the class Secementea, preferably of the order Ascaridida, preferably of the family Ascarididae, preferably of the genus Ascaris. More preferably, said invertebrate species is of Ascaris Sum. Preferably, the β-(1,4)-GalNAcT enzyme used in the process of the invention has at least 40%, 45%, 50%, 55%, 60%, 65%, 70%, 75%, 80%, 85%. 90%, 91%, 92%, 93%, 94%, 95%, 96%, 97%, 98%, 99% or preferably 100% sequence identity to a sequence of the group consisting of SEQ ID NO: 3.

In another preferred embodiment the β-(1,4)-GalNAcT enzyme used in the process of the invention is a β-(1,4)-GalNAcT enzyme that is or is derived from a β-(1,4)-GalNAcT enzyme that originates from an invertebrate species of the phylum Anthropoda, preferably of the class Insecta, preferably of the order Lepidoptera, preferably of the family Noctuidae, preferably of the genus *Trichoplusia*. More preferably, said invertebrate species is of *Trichoplusia Ni*. *Trichoplusia Ni* may sometimes also be referred to as *Phytometra brassicae*, *Plusia innata* or cabbage looper. Preferably, the β-(1,4)-GalNAcT enzyme used in the process of the invention has at least 40%, 45%, 50%, 55%, 60%, 65%, 70%, 75%, 80%, 85%. 90%, 91%, 92%, 93%, 94%, 95%, 96%, 97%, 98%, 99% or preferably 100% sequence identity to a sequence of the group consisting of SEQ ID NO: 4.

In another preferred embodiment the β-(1,4)-GalNAcT enzyme used in the process of the invention is a β-(1,4)-GalNAcT enzyme that is or is derived from a β-(1,4)-GalNAcT enzyme that originates from an invertebrate species of the phylum Anthropoda, preferably of the class Insecta, preferably of the order Diptera, preferably of the family Drosophilidae, preferably of the genus *Drosophila*. More preferably, said invertebrate species is of *Drosophila melanogaster*. Preferably, the β-(1,4)-GalNAcT enzyme used in the process of the invention has at least 40%, 45%, 50%, 55%, 60%, 65%, 70%, 75%, 80%, 85%. 90%, 91%, 92%, 93%, 94%, 95%, 96%, 97%, 98%, 99% or preferably 100% sequence identity to a sequence of the group consisting of SEQ ID NO: 5.

"Derived from" a β-(1,4)-GalNAcT enzyme is to be understood herein as a β-(1,4)-GalNAcT enzyme having an amino acid sequence that is altered from a naturally occurring β-(1,4)-GalNAcT enzyme by substituting, inserting, deleting or adding one or more, preferably 1, 2, 3, 4, 5, 6, 7, 8, 9, 10, 12, 14, 16, 18, 20 or more amino acids, respectively. A β-(1,4)-GalNAcT enzyme that is derived from a β-(1,4)-GalNAcT enzyme is herein also referred to as a derived β-(1,4)-GalNAcT enzyme or a modified β-(1,4)-GalNAcT enzyme or a β-(1,4)-GalNAcT mutant enzyme or a β-(1,4)-GalNAcT mutant.

Derived enzymes are known in the art and include enzymes which have undergone conventional and standard modification of the amino acid sequence, such as removal of the transmembrane domain, inclusion of a tag, such as a solubility and/or purification tag as mentioned herein. Such procedures that lead to an enzyme having a modified amino acid sequence are well-known in the art, and are covered by the process according to the present invention.

In one embodiment, the derived enzyme, i.e. having less than 100% sequence identity to the naturally occurring β-(1,4)-GalNAcT enzymes mentioned herein, preferably have enzyme activity that is at least 10%, 20%, 30%, 40%, 50%, 60%, 70% or preferably at least 80% or 90% or at least 100% of the enzyme activity of the naturally occurring β-(1,4)-GalNAcT enzyme. Herein, activity is conveniently measured as efficacy in incorporating a (modified) GalNAc residue onto the terminal GlcNAc residue of a glycoprotein.

The enzyme is not a galactosyltranferase. In one embodiment, the enzyme is not an enzyme categorized as E.C. 2.4.1.38 or as E.C. 2.4.1.133, preferably not as E.C. 2.4.1.22, as E.C. 2.4.1.38, as E.C. 2.4.1.90 or as E.C. 2.4.1.133.

In one embodiment, the enzyme is enzyme categorized as E.C. 2.4.1.41, as E.C. 2.4.1.92, as E.C. 2.4.1.174 or as E.C. 2.4.1.244, preferably as E.C. 2.4.1.92 or as E.C. 2.4.1.244.

Preferably, said derived β-(1,4)-GalNAcT enzyme is modified by adding additional N- or C-terminal amino acids or chemical moieties or by deleting N- or C-terminal amino acids to increase stability, solubility, activity and/or ease of purification.

Preferably the β-(1,4)-GalNAcT enzyme is modified by deleting the N-terminal cytoplasmic domain and transmembrane domain, which is denominated herein as a truncated enzyme. Deletion of these domains is known in the art to result in an enzyme that shows an increased solubility in aqueous solutions.

For instance, CeGalNAcT(30-383) is to be understood herein as a truncated *Caenorhabditis elegans* β-(1,4)-GalNAcT enzyme consisting of the amino acid sequence represented by the amino acids on position 30-383 of SEQ ID NO: 2. Similarly, AsGalNAcT(30-383) is to be understood herein as a truncated *Ascaris Sum* β-(1,4)-GalNAcT enzyme consisting of the amino acid sequence represented by the amino acids on position 30-383 of SEQ ID NO: 3, TnGalNAcT(33-421) is to be understood herein as a truncated *Trichoplusia Ni* β-(1,4)-GalNAcT enzyme consisting of the amino acid sequence represented by the amino acids on position 33-421 of SEQ ID NO: 4, and DmGalNAcT(47-403) is to be understood herein as a truncated *Drosophila melanogaster* β-(1,4)-GalNAcT enzyme consisting of the amino acid sequence represented by the amino acids on position 47-403 of SEQ ID NO: 5.

Preferably, the β-(1,4)-GalNAcT enzyme used in the process of the invention has at least 40%, 45%, 50%, 55% 60%, 65%, 70%, 75% 80%, 85% 90%, 91%, 92%, 93%, 94%, 95%, 96%, 97%, 98%, 99% or preferably at least 100% sequence identity to any of the sequences of SEQ ID NO: 6, SEQ ID NO: 7, SEQ ID NO: 8 or SEQ ID NO: 9, more preferably of the sequences of SEQ ID NO: 6, SEQ ID NO: 7 or SEQ ID NO: 8, even more preferably of the sequences of SEQ ID NO: 7 or SEQ ID NO: 8, and even more preferably SEQ ID NO: 8.

A β-(1,4)-GalNAcT enzyme wherein one or more amino acid has been substituted, added or deleted is herein also referred to as a derived β-(1,4)-GalNAcT enzyme. Preferably, the β-(1,4)-GalNAcT enzyme is modified by deleting the N-terminal cytoplasmic domain and transmembrane domain, and by substituting one or more amino acids. A substitution of one or more amino acids is herein also referred to as a mutation. An enzyme comprising one or more substituted amino acids is also referred to as a mutant enzyme.

In the process according to the invention, when the glycosyltransferase is derived from *Caenorhabditis elegans* β-(1,4)-GalNAcT enzyme or truncated β-(1,4)-GalNAcT enzyme, it is preferred that the enzyme further comprises one or more mutations. Preferred mutations include substitution of the isoleucine (Ile, also referred to as I) at position 257 by leucine (Leu, also referred to as L), methionine (Met, also referred to as M) or alanine (Ala, also referred to as A). Preferred mutations also include substitution of the methionine (Met, also referred to as M) at position 312 by histidine (His, also referred to as H). Consequently, when the glycosyltransferase is derived from CeGalNAcT or CeGalNAcT (30-383) it is preferred that the enzyme comprises a I257L, I257M or a I257A mutation, and/or a M312H mutation.

It should be noted that the numbering of amino acid position is herein based on the numbering of amino acid position in the wild-type β-(1,4)-GalNAcT enzyme. When a β-(1,4)-GalNAcT enzyme is e.g. a truncated enzyme, the number used herein to indicate e.g. the position of an amino acid substitution corresponds to the numbering of amino acid position in the corresponding wild-type β-(1,4)-GalNAcT enzyme.

As an example, in wild-type CeGalNAcT (SEQ ID NO: 2) an isoleucine (Ile, I) is present on amino acid position 257. In CeGalNAcT(I257L) the isoleucine amino acid at position 257 is substituted by a leucine amino acid (Leu, L). As described above, CeGalNAcT(30-383) is herein to be understood as a truncated CeGalNAcT enzyme consisting of the amino acid sequence represented by the amino acids on position 30-383 of SEQ ID NO: 2, whereas CeGalNAcT (30-383) itself is represented by SEQ ID NO: 6. In CeGalNAcT(30-383; I257L), the number "257" in I257L indicates that it is the I amino acid on position 257 in the corresponding wild-type CeGalNAcT (i.e. number 257 of SEQ ID NO:2 that is substituted with an L amino acid. The isoleucine amino acid on position 257 SEQ ID NO:2 is represented by the isoleucine amino acid on position 228 of SEQ ID NO:6.

Preferred truncated *Caenorhabditis elegans* β-(1,4)-GalNAcT mutant enzymes include CeGalNAcT(30-383; I257L) (SEQ ID NO: 10), CeGalNAcT(30-383; I257M) (SEQ ID NO: 11), CeGalNAcT(30-383; I257A) (SEQ ID NO: 12) and CeGalNAcT(30-383; M312H) (SEQ ID NO: 13).

In the process according to the invention, when the glycosyltransferase is derived from *Trichoplusia Ni* β-(1,4)-GalNAcT enzyme or truncated *Trichoplusia Ni* β-(1,4)-GalNAcT enzyme, it is preferred that the enzyme further comprises one or more mutations. Preferred mutations include substitution of the tryptophan (Trp, also referred to as W) on position 336 by phenylalanine (Phe, also referred to as F), histidine (His, also referred to as H) or valine (Val, also referred to as V). Consequently, when the glycosyltransferase is derived from TnGalNAcT or TnGalNAcT(33-421), it is preferred that the enzyme comprises a W336F, W336H or W336V mutation. Preferred mutations of TnGalNAcT or TnGalNAcT(33-421) also include substitution of the glutamic acid (Glu, also referred to as E) on position 339 by alanine (Ala, also referred to as A), glycine (Gly, also referred to as G), aspartic acid (Asp, also referred to as D) or serine (Ser, also referred to as S). Consequently, when the glycosyltransferase is derived from TnGalNAcT or TnGalNAcT(33-421), it is preferred that the enzyme comprises a E339A, E339G, E339D or E339S mutation. More preferably, when the glycosyltransferase is derived from TnGalNAcT or TnGalNAcT(33-421), both the 336 and the 339 position are mutated as described above. Consequently, when the glycosyltransferase is derived from TnGalNAcT or TnGalNAcT(33-421) it is preferred that the enzyme comprises a W336F, W336H or W336V mutation and a E339A, E339G, E339D or E339S mutation.

Preferred mutations of TnGalNAcT or TnGalNAcT(33-421) also include substitution of the isoleucine (Ile, also referred to as I) on position 311 by a tyrosine (Tyr, also referred to as Y). Consequently, when the glycosyltransferase is derived from TnGalNAcT or TnGalNAcT(33-421) it is preferred that the enzyme comprises a I311Y mutation.

When the glycosyltransferase is derived from TnGalNAcT or TnGalNAcT(33-421) and comprises a I311Y mutation, the enzyme may further comprise a mutation on the 336 position as described above and/or a mutation on the 339 position as described above. Consequently, when the glycosyltransferase is derived from TnGalNAcT or TnGalNAcT(33-421) comprising a I311Y mutation, the enzyme may further comprise a W336F, W336H or W336V mutation, and/or a E339A, E339G, E339D or E339S mutation.

In a preferred embodiment of the process according to the invention, the glycosyltransferase that is, or is derived from, a β-(1,4)-GalNAcT enzyme is a *Trichoplusia Ni* β-(1,4)-GalNAcT enzyme selected from the group consisting of TnGalNAcT(33-421; W336F) (SEQ ID NO: 25), TnGalNAcT(33-421; W336H) (SEQ ID NO: 26), TnGalNAcT(33-421; W336V) (SEQ ID NO: 27), TnGalNAcT(33-421; E339A) (SEQ ID NO: 28), TnGalNAcT(33-421; E339G) (SEQ ID NO: 29), TnGalNAcT(33-421; E339D) (SEQ ID NO: 30) and TnGalNAcT(33-421; E339S) (SEQ ID NO: 31).

In another preferred embodiment of the process according to the invention, the glycosyltransferase that is, or is derived from, a β-(1,4)-GalNAcT enzyme is a *Trichoplusia Ni* β-(1,4)-GalNAcT enzyme selected from the group consisting of TnGalNAcT(33-421; W336H, E339A) (SEQ ID NO: 32), TnGalNAcT(33-421; W336H, E339D) (SEQ ID NO: 33 and TnGalNAcT(33-421; W336H, E339S) (SEQ ID NO: 34).

In another preferred embodiment of the process according to the invention, the glycosyltransferase that is, or is derived from, a β-(1,4)-GalNAcT enzyme is *Trichoplusia Ni* β-(1,4)-GalNAcT enzyme TnGalNAcT(33-421; I311Y) (SEQ ID NO: 35).

In another preferred embodiment of the process according to the invention, the glycosyltransferase that is, or is derived from, a β-(1,4)-GalNAcT enzyme is a *Trichoplusia Ni* β-(1,4)-GalNAcT enzyme selected from the group consisting of TnGalNAcT(33-421; I311Y, W336F) (SEQ ID NO: 36), TnGalNAcT(33-421; I311Y, W336H) (SEQ ID NO: 37), TnGalNAcT(33-421; I311Y, W336V) (SEQ ID NO: 38), TnGalNAcT(33-421; I311Y, E339A) (SEQ ID NO: 39), TnGalNAcT(33-421; I311Y, E339G) (SEQ ID NO: 40), TnGalNAcT(33-421; I311Y, E339D) (SEQ ID NO: 41) and TnGalNAcT(33-421; I311Y, E339S) (SEQ ID NO: 42).

In another preferred embodiment of the process according to the invention, the glycosyltransferase that is, or is derived from, a β-(1,4)-GalNAcT enzyme is a *Trichoplusia Ni* β-(1,4)-GalNAcT enzyme selected from the group consisting of TnGalNAcT(33-421; I311Y, W336H, E339A) (SEQ ID NO: 43), TnGalNAcT(33-421; I311Y, W336H, E339D) (SEQ ID NO: 44) and TnGalNAcT(33-421; I311Y, W336H, E339S) (SEQ ID NO: 45).

In the process according to the invention, when the glycosyltransferase is derived from *Ascaris Sum* β-(1,4)-GalNAcT enzyme or truncated *Ascaris Sum* β-(1,4)-GalNAcT enzyme, it is preferred that the enzyme further comprises one or more mutations. Preferred mutations include substitution of tryptophan (Trp, also referred to as W) on position 282 by histidine (His, also referred to as H), and/or substitution of glutamic acid (Glu, also referred to as E) on position 285 by aspartic acid (Asp, also referred to as D), and/or substitution of isoleucine (Ile, also referred to as I) on position 257 by tyrosine (Tyr, also referred to as Y). Consequently, when the glycosyltransferase is derived from AsGalNAcT or AsGalNAcT(30-383) it is preferred that the enzyme comprises a W282H mutation, an E285D mutation and/or I257Y mutation.

In a preferred embodiment of the process according to the invention, the glycosyltransferase that is or is derived from a β-(1,4)-GalNAcT enzyme is a *Ascaris Sum* β-(1,4)-GalNAcT selected from the group consisting of AsGalNAcT (30-383; W282H) (SEQ ID NO: 46) and AsGalNAcT(30-383; E285D) (SEQ ID NO: 47).

In another preferred embodiment of the process according to the invention, the glycosyltransferase that is or is derived from a β-(1,4)-GalNAcT enzyme is *Ascaris Sum* β-(1,4)-GalNAcT AsGalNAcT(30-383; I257Y) (SEQ ID NO: 48).

In another preferred embodiment of the process according to the invention, the glycosyltransferase that is or is derived from a β-(1,4)-GalNAcT enzyme is *Ascaris Sum* β-(1,4)-GalNAcT selected from the group consisting of AsGalNAcT (30-383; I257Y, W282H) and AsGalNAcT(30-383; I257Y, E285D).

In a preferred embodiment of the process according to the invention, the glycosyltransferase that is or is derived from a β-(1,4)-GalNAcT enzyme as defined herein comprises a sequence encoding a tag for ease of purification. Preferably, said tag is selected from, but is not limited to, the group consisting of a FLAG-tag, poly(His)-tag, HA-tag, Myc-tag, SUMO-tag, GST-tag, MBP-tag or CBP-tag, more preferably said tag is a 6×His tag. Other preferred tags to be incorporated in the enzyme are solubility tags, such as an AFV-tag, a SlyD-tag, a Tsf-tag, a SUMO-tag, a Bla-tag, a MBP-tag and a GST-tag. In a further preferred embodiment, said tag or tags is/are covalently linked to the β-(1,4)-GalNAcT enzyme at the C-terminus of the enzyme. In another further preferred embodiment, said tag is covalently linked to the β-(1,4)-GalNAcT enzyme at the N-terminus of the enzyme.

When the β-(1,4)-GalNAcT enzyme is derived from *C. Elegans* β-(1,4)-GalNAcT, the His-tagged β-(1,4)-GalNAcT enzyme is preferably CeGalNAcT(30-383)-His (SEQ ID NO: 14).

In a preferred embodiment of the process according to the invention, when the β-(1,4)-GalNAcT enzyme is, or is derived from, *Trichoplusia Ni* β-(1,4)-GalNAcT, the His-tagged β-(1,4)-GalNAcT enzyme is, or is derived from, His-TnGalNAcT(33-421) (SEQ ID NO: 49).

In another preferred embodiment of the process according to the invention, when the β-(1,4)-GalNAcT enzyme is, or is derived from, *Trichoplusia Ni* β-(1,4)-GalNAcT, the His-tagged β-(1,4)-GalNAcT enzyme is, or is derived from, His-TnGalNAcT(33-421; W336F) (SEQ ID NO: 50), His-TnGalNAcT(33-421; W336H) (SEQ ID NO: 51), His-TnGalNAcT(33-421; W336V) (SEQ ID NO: 52), His-TnGalNAcT(33-421; 339A) (SEQ ID NO: 53), His-TnGalNAcT(33-421; E339G) (SEQ ID NO: 54), His-TnGalNAcT(33-421; E339D) (SEQ ID NO: 55), His-TnGalNAcT(33-421; E339S) (SEQ ID NO: 56), His-TnGalNAcT(33-421; W336H,E339A) (SEQ ID NO: 57), His-TnGalNAcT(33-421; W336H,E339D) (SEQ ID NO: 58) or His-TnGalNAcT(33-421; W336H,E339S) (SEQ ID NO: 59).

In another preferred embodiment of the process according to the invention, when the β-(1,4)-GalNAcT enzyme is, or is derived from, *Trichoplusia Ni* β-(1,4)-GalNAcT, the His-tagged β-(1,4)-GalNAcT enzyme is, or is derived from, His-TnGalNAcT(33-421; I311Y) SEQ ID NO: 60.

In another preferred embodiment of the process according to the invention, when the β-(1,4)-GalNAcT enzyme is, or is derived from, *Trichoplusia Ni* β-(1,4)-GalNAcT, the His-tagged β-(1,4)-GalNAcT enzyme is, or is derived from, His-TnGalNAcT(33-421; I311Y,W336F)(SEQ ID NO: 61), His-TnGalNAcT(33-421; I311Y,W336H) (SEQ ID NO: 62), His-TnGalNAcT(33-421; I311Y,W336V) (SEQ ID NO: 63), His-TnGalNAcT(33-421; I311Y,E339A) (SEQ ID NO: 64), His-TnGalNAcT(33-421; I311Y,E339G) (SEQ ID NO: 65), His-TnGalNAcT(33-421; I311Y,E339D) (SEQ ID NO: 66), His-TnGalNAcT(33-421; I311Y,E339S) (SEQ ID NO: 67), His-TnGalNAcT(33-421; I311Y,W336H,E339A) (SEQ ID NO: 68), His-TnGalNAcT(33-421; I311Y,W336H,E339D) (SEQ ID NO: 69) or His-TnGalNAcT(33-421; I311Y, W336H,E339S) (SEQ ID NO: 70).

In another preferred embodiment of the process according to the invention, when the β-(1,4)-GalNAcT enzyme is, or is derived from, *Ascaris Sum* β-(1,4)-GalNAcT, the His-tagged β-(1,4)-GalNAcT enzyme is, or is derived from, His-AsGalNAcT(30-383) (SEQ ID NO: 71).

In another preferred embodiment of the process according to the invention, when the β-(1,4)-GalNAcT enzyme is, or is derived from, *Ascaris Sum* β-(1,4)-GalNAcT, the His-tagged β-(1,4)-GalNAcT enzyme is, or is derived from, His-AsGalNAcT(30-383; W282H) (SEQ ID NO: 72), His-AsGalNAcT(30-383; E285D) (SEQ ID NO: 73) or His-AsGalNAcT(30-383; I257Y) (SEQ ID NO: 74).

In a preferred embodiment of the process according to the invention, the β-(1,4)-N-acetylgalactosaminyltransferase used in the process is, or is derived from, a sequence selected from the group consisting of SEQ ID NO: 2-23 and SEQ ID NO: 25-74.

In a preferred embodiment of the process according to the invention, the β-(1,4)-N-acetylgalactosaminyltransferase used in the process is, or is derived from, a sequence selected from the group consisting of SEQ ID NO: 2-23. In other words, in a preferred embodiment, the β-(1,4)-N-acetylgalactosaminyltransferase used in the process according to the invention is, or is derived from, a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

Herein, the term "derived from" comprises e.g. truncated enzymes, mutant enzymes and enzymes comprising a tag for ease of purification, and these modifications are described in more detail above. The term "derived from" also comprises enzymes comprising a combination of the modifications described in more detail above.

In another preferred embodiment, the β-(1,4)-N-acetylgalactosaminyltransferase used in the process according to the invention has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2-23, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

In a preferred embodiment of the process according to the invention, the β-(1,4)-N-acetylgalactosaminyltransferase used in the process is, or is derived from, a sequence selected from the group consisting of SEQ ID NO: 2-9. In other words, in a preferred embodiment, the β-(1,4)-N-acetylgalactosaminyltransferase used in the process according to the invention is, or is derived from, a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

In another preferred embodiment, the β-(1,4)-N-acetylgalactosaminyltransferase used in the process according to the invention has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

In another preferred embodiment of the process according to the invention, the β-(1,4)-N-acetylgalactosaminyltransferase used in the process is, or is derived from, a sequence selected from the group consisting of SEQ ID NO: 25-45 and SEQ ID NO: 50-70. In other words, in a preferred embodiment, the β-(1,4)-N-acetylgalactosaminyltransferase used in the process according to the invention is, or is derived from, a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 and SEQ ID NO: 70.

In another preferred embodiment, the β-(1,4)-N-acetylgalactosaminyltransferase used in the process according to the invention has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 25-45 and SEQ ID NO: 50-70, i.e. from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 and SEQ ID NO: 70.

In another preferred embodiment of the process according to the invention, the β-(1,4)-N-acetylgalactosaminyltransferase used in the process is, or is derived from, a sequence selected from the group consisting of SEQ ID NO: 46-49 and SEQ ID NO: 71-74. In other words, in a preferred embodiment, the β-(1,4)-N-acetylgalactosaminyltransferase used in the process according to the invention is, or is derived from, a sequence selected from the group consisting of SEQ ID NO: 46, SEQ ID NO: 47, SEQ ID NO: 48, SEQ ID NO: 49, SEQ ID NO: 71, SEQ ID NO: 72, SEQ ID NO: 73 and SEQ ID NO: 74.

In another preferred embodiment, the β-(1,4)-N-acetylgalactosaminyltransferase used in the process according to the invention has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 46-49 and SEQ ID NO: 71-74, i.e. from the group consisting of SEQ ID NO: 46, SEQ ID NO: 47, SEQ ID NO: 48, SEQ ID NO: 49, SEQ ID NO: 71, SEQ ID NO: 72, SEQ ID NO: 73 and SEQ ID NO: 74.

In the process according the invention, sugar derivative nucleotide Su(A)-Nuc is according to formula (3), or preferred embodiments thereof, as described in more detail above. $R^{14}$ is selected from the group consisting of:

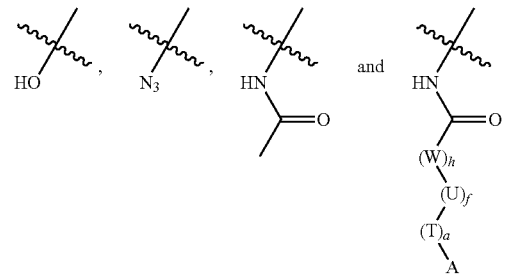

wherein W, h, a, f, T, A and U, and preferred embodiments thereof, are as defined above.

Preferred Glycosyltransferases when $R^{14}$ is —NHC(O) CH$_3$

In a preferred embodiment of the process according to the invention, $R^{14}$ is —NHC(O)CH$_3$. In this embodiment, sugar derivative nucleotide Su(A)-Nuc is according to formula (3a), as defined above.

When Su(A)-Nuc is according to formula (3a), or preferred embodiments of (3a) as described above, in a preferred embodiment of the process the glycosyltransferase that is, or is derived from, a β-(1,4)-GalNAcT is, or is derived from, a wild-type β-(1,4)-GalNAcT, preferably an invertebrate β-(1,4)-GalNAcT. In another preferred embodiment of the process, the glycosyltransferase is, or is derived from, an invertebrate β-(1,4)-GalNAcT. In a further preferred embodiment, the glycosyltransferase is, or is derived from, *Caenorhabditis elegans* β-(1,4)-GalNAcT (CeGalNAcT), *Ascaris Sum* β-(1,4)-GalNAcT (AsGalNAcT) or *Trichoplusia Ni* β-(1,4)-GalNAcT (TnGalNAcT). β-(1,4)-GalNAcTs that are, or are derived from, (CeGalNAcT), (AsGalNAcT) or (TnGalNAcT) are described in more detail above.

When $R^{14}$ in the sugar-derivative nucleotide Su(A)-Nuc is —NHC(O)CH$_3$, it is particularly preferred that the β-(1,4)-N-acetylgalactosaminyltransferase used in the process is, or is derived from, a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —NHC(O)CH$_3$, the β-(1,4)-N-acetylgalactosaminyltransferase used in the process is, or is derived from, a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process is, or is derived from SEQ ID NO: 8.

In another particularly preferred embodiment, when $R^{14}$ in the sugar-derivative nucleotide Su(A)-Nuc is —NHC(O) CH$_3$, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —NHC(O) CH$_3$, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 8.

In another particularly preferred embodiment of the process according to the invention wherein $R^{14}$ is —NHC(O)CH$_3$, the glycosyltransferase is or is derived from *Caenorhabditis elegans* β-(1,4)-GalNAcT (CeGalNAcT).

In another particularly preferred embodiment of the process wherein $R^{14}$ is —NHC(O)CH$_3$, the CeGalNAcT is or is derived from SEQ ID NO: 2 or SEQ ID NO: 6.

In another particularly preferred embodiment of the process wherein $R^{14}$ is —NHC(O)CH$_3$, the CeGalNAcT used in the process is or is derived from SEQ ID NO: 10, SEQ ID NO: 11, SEQ ID NO: 12, SEQ ID NO: 13 or SEQ ID NO: 14.

In another particularly preferred embodiment of the process wherein $R^{14}$ is —NHC(O)CH$_3$, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 2 or SEQ ID NO: 6.

In another particularly preferred embodiment of the process wherein $R^{14}$ is —NHC(O)CH$_3$, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence SEQ ID NO: 10, SEQ ID NO: 11, SEQ ID NO: 12, SEQ ID NO: 13 or SEQ ID NO: 14.

In another particularly preferred embodiment of the process according to the invention wherein $R^{14}$ is —NHC(O)CH$_3$, the glycosyltransferase is, or is derived from, *Trichoplusia Ni* β-(1,4)-GalNAcT (TnGalNAcT).

In a further preferred embodiment of the process wherein $R^{14}$ is —NHC(O)CH$_3$, the TnGalNAcT is or is derived from SEQ ID NO: 4 or SEQ ID NO: 8.

In another further preferred embodiment of the process wherein $R^{14}$ is —NHC(O)CH$_3$, the TnGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 4 or SEQ ID NO: 8.

In another preferred embodiment of the process wherein $R^{14}$ is —NHC(O)CH$_3$, the TnGalNAcT used in the process is, or is derived from, a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another preferred embodiment, the TnGalNAcT used in the process wherein $R^{14}$ is —NHC(O)CH$_3$, has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another particularly preferred embodiment of the process according to the invention wherein $R^{14}$ is —NHC(O)CH$_3$, the glycosyltransferase is or is derived from *Ascaris Sum* β-(1,4)-GalNAcT (AsGalNAcT).

In this embodiment of the process wherein $R^{14}$ is —NHC(O)CH$_3$, it is further preferred that the AsGalNAcT is or is derived from SEQ ID NO: 3 or SEQ ID NO: 7.

In another further preferred embodiment of the process wherein $R^{14}$ is —NHC(O)CH$_3$, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 3 or SEQ ID NO: 7.

In another further preferred embodiment of the process wherein $R^{14}$ is —NHC(O)CH$_3$, the AsGalNAcT used in the process is, or is derived from, a sequence selected from the group consisting of SEQ ID NO: 46, SEQ ID NO: 47, SEQ ID NO: 71, SEQ ID NO: 72 and SEQ ID NO: 73.

In another further preferred embodiment of the process wherein $R^{14}$ is —NHC(O)CH$_3$, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 46, SEQ ID NO: 47, SEQ ID NO: 71, SEQ ID NO: 72 and SEQ ID NO: 73.

In the here described preferred embodiments of the process according to the invention wherein $R^{14}$ is —NHC(O)CH$_3$ and the glycosyltransferase as described above, it is further preferred that sugar-derivative nucleotide Su(A)-Nuc is according to formula (15), (16), (17) or (18) as defined above, wherein $R^{14}$ is —NHC(O)CH$_3$; or according to formula (19), (20), (21), (22), (23), (24), (25), (26), (65), (66), (67), (68) or (69) as defined above, wherein $R^{14}$ is —NHC(O)CH$_3$; or according to formula (27) as defined above. In these particularly preferred embodiments it is further preferred that Nuc is UDP.

Preferred Glycosyltransferases when $R^{14}$ is —NHC(O)—$(W)_h$—$(U)_f$—$(T)_a$-A In another preferred embodiment of the process according to the invention, $R^{14}$ is —NHC(O)—$(W)_h$—$(U)_f$—$(T)_a$-A. In this embodiment, sugar derivative nucleotide Su(A)-Nuc is according to formula (3b), as defined above.

When Su(A)-Nuc is according to formula (3b), or preferred embodiments of (3b) as described above, in a preferred embodiment of the process the glycosyltransferase that is or is derived from a β-(1,4)-GalNAcT is or is derived from a wild-type β-(1,4)-GalNAcT, preferably an invertebrate β-(1,4)-GalNAcT. In another preferred embodiment of the process, the glycosyltransferase is or is derived from an invertebrate β-(1,4)-GalNAcT. In a further preferred embodiment, the glycosyltransferase is or is derived from *Caenorhabditis elegans* β-(1,4)-GalNAcT (CeGalNAcT), *Ascaris Sum* 3-(1,4)-GalNAcT (AsGalNAcT) or *Trichoplusia Ni* β-(1,4)-GalNAcT (TnGalNAcT). β-(1,4)-GalNAcTs that are or are derived from (CeGalNAcT), (AsGalNAcT) or (TnGalNAcT) are described in more detail above.

When $R^{14}$ in the sugar-derivative nucleotide Su(A)-Nuc is —NHC(O)—$(W)_h$—$(U)_f$—$(T)_a$-A, it is particularly preferred that the β-(1,4)-N-acetylgalactosaminyltransferase used in the process is, or is derived from, a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —NHC(O)—$(W)_h$—$(U)_f$-$(T)_a$-A, the β-(1,4)-N-acetylgalactosaminyltransferase used in the process is, or is derived from, a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process is, or is derived from SEQ ID NO: 8.

In another particularly preferred embodiment, when $R^{14}$ in the sugar-derivative nucleotide Su(A)-Nuc is —NHC(O)—$(W)_h$—$(U)_f$-$(T)_a$-A, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —NHC(O)—$(W)_h$—$(U)_f$-$(T)_a$-A, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 8.

In another particularly preferred embodiment of the process according to the invention wherein $R^{14}$ is —NHC(O)—$(W)_h$—$(U)_f$-$(T)_a$-A, the glycosyltransferase is, or is derived from, *Caenorhabditis elegans* β-(1,4)-GalNAcT (CeGalNAcT).

In another particularly preferred embodiment of the process wherein $R^{14}$ is —NHC(O)—$(W)_h$—$(U)_f$-$(T)_a$-A, the CeGalNAcT is, or is derived from, SEQ ID NO: 2 or SEQ ID NO: 6.

In another particularly preferred embodiment of the process wherein $R^{14}$ is —NHC(O)—$(W)_h$—$(U)_f$-$(T)_a$-A, the CeGalNAcT used in the process is, or is derived from, SEQ ID NO: 10, SEQ ID NO: 11, SEQ ID NO: 12, SEQ ID NO: 13 or SEQ ID NO: 14.

In another particularly preferred embodiment of the process wherein $R^{14}$ is —NHC(O)—$(W)_h$—$(U)_f$-$(T)_a$-A, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 2 or SEQ ID NO: 6.

In another particularly preferred embodiment of the process wherein $R^{14}$ is —NHC(O)—$(W)_h$—$(U)_f$-$(T)_a$-A, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence SEQ ID NO: 10, SEQ ID NO: 11, SEQ ID NO: 12, SEQ ID NO: 13 or SEQ ID NO: 14.

In another particularly preferred embodiment of the process according to the invention wherein $R^{14}$ is —NHC(O)—$(W)_h$—$(U)_f$-$(T)_a$-A, the glycosyltransferase is, or is derived from, *Trichoplusia Ni* β-(1,4)-GalNAcT (TnGalNAcT).

In a further preferred embodiment of the process wherein $R^{14}$ is —NHC(O)—$(W)_h$—$(U)_f$-$(T)_a$-A, the TnGalNAcT is or is derived from SEQ ID NO: 4 or SEQ ID NO: 8.

In another further preferred embodiment of the process wherein $R^{14}$ is —NHC(O)—$(W)_h$—$(U)_f$-$(T)_a$-A, the TnGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 4 or SEQ ID NO: 8.

In another preferred embodiment of the process wherein $R^{14}$ is —NHC(O)—$(W)_h$—$(U)_f$-$(T)_a$-A, the TnGalNAcT used in the process is, or is derived from, a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another preferred embodiment, the TnGalNAcT used in the process wherein $R^{14}$ is —NHC(O)—$(W)_h$—$(U)_f$-$(T)_a$-A, has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another particularly preferred embodiment of the process according to the invention wherein $R^{14}$ is —NHC(O)—$(W)_h$—$(U)_f$-$(T)_a$-A, the glycosyltransferase is, or is derived from, *Ascaris Sum* β-(1,4)-GalNAcT (AsGalNAcT).

In this embodiment of the process wherein $R^{14}$ is —NHC(O)—$(W)_h$—$(U)_f$-$(T)_a$-A, it is further preferred that the AsGalNAcT is or is derived from SEQ ID NO: 3 or SEQ ID NO: 7.

In another further preferred embodiment of the process wherein $R^{14}$ is —NHC(O)—$(W)_h$—$(U)_f$-$(T)_a$-A, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 3 or SEQ ID NO: 7.

In another further preferred embodiment of the process wherein $R^{14}$ is —NHC(O)—$(W)_h$—$(U)_f$-$(T)_a$-A, the AsGalNAcT used in the process is, or is derived from, a sequence selected from the group consisting of SEQ ID NO: 46, SEQ ID NO: 47, SEQ ID NO: 71, SEQ ID NO: 72 and SEQ ID NO: 73.

In another further preferred embodiment of the process wherein $R^{14}$ is —NHC(O)—$(W)_h$—$(U)_f$-$(T)_a$-A, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 46, SEQ ID NO: 47, SEQ ID NO: 71, SEQ ID NO: 72 and SEQ ID NO: 73.

In the here described preferred embodiments of the process according to the invention wherein $R^{14}$ is —NHC(O)—$(W)_h$—$(U)_f$—$(T)_a$-A and the glycosyltransferase as described above, it is further preferred that sugar-derivative nucleotide Su(A)-Nuc is according to formula (15), (16), (17) or (18) as defined above, wherein $R^{14}$ is —NHC(O)—$(W)_h$—$(U)_f$-$(T)_a$-A; or according to formula (19), (20), (21), (22), (23), (24), (25), (26), (65), (66), (67), (68) or (69) as defined above, wherein $R^{14}$ is —NHC(O)—$(W)_h$—$(U)_f$-$(T)_a$-A; or according to formula (28), (29), (30) or (31) as defined above. In these particularly preferred embodiments it is further preferred that Nuc is UDP.

Preferred Glycosyltransferases when $R^{14}$ is —OH

In a preferred embodiment of the process according to the invention, $R^{14}$ is —OH. In this embodiment, sugar derivative nucleotide Su(A)-Nuc is according to formula (3c), as defined above.

When Su(A)-Nuc is according to formula (3c), or preferred embodiments of (3c) as described above, in a preferred embodiment of the process the glycosyltransferase is derived from a wild-type β-(1,4)-GalNAcT, preferably an invertebrate β-(1,4)-GalNAcT. In another preferred embodiment of the process, the glycosyltransferase is derived from an invertebrate β-(1,4)-GalNAcT. In a further preferred embodiment, the glycosyltransferase is derived from *Caenorhabditis elegans* β-(1,4)-GalNAcT (CeGalNAcT), *Ascaris Sum* β-(1,4)-GalNAcT (AsGalNAcT) or *Trichoplusia Ni* β-(1,4)-GalNAcT (TnGalNAcT). β-(1,4)-GalNAcTs that are derived from (CeGalNAcT), (AsGalNAcT) or (TnGalNAcT) are described in more detail above.

In another particularly preferred embodiment of the process according to the invention wherein $R^{14}$ is —OH, the glycosyltransferase is derived from *Caenorhabditis elegans* β-(1,4)-GalNAcT (CeGalNAcT).

In another particularly preferred embodiment of the process according to the invention wherein $R^{14}$ is —OH, the glycosyltransferase is derived from *Trichoplusia Ni* 3-(1,4)-GalNAcT (TnGalNAcT).

In a further preferred embodiment of the process wherein $R^{14}$ is —OH, the TnGalNAcT is, or is derived from, SEQ ID NO: 35 or SEQ ID NO: 60.

In another further preferred embodiment of the process wherein $R^{14}$ is —OH, the TnGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 35 or SEQ ID NO: 60.

In another preferred embodiment of the process wherein $R^{14}$ is —OH, the TnGalNAcT used in the process is, or is derived from, a sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 and SEQ ID NO: 70.

In another preferred embodiment, the TnGalNAcT used in the process wherein $R^{14}$ is —OH, has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 and SEQ ID NO: 70.

In another particularly preferred embodiment of the process according to the invention wherein $R^{14}$ is —OH, the glycosyltransferase is derived from *Ascaris Sum* 3-(1,4)-GalNAcT (AsGalNAcT).

In this embodiment of the process wherein $R^{14}$ is —OH, it is further preferred that the AsGalNAcT is, or is derived from, SEQ ID NO: 48 or SEQ ID NO: 74.

In another further preferred embodiment of the process wherein $R^{14}$ is —OH, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 48 or SEQ ID NO: 74.

In the here described preferred embodiments of the process according to the invention wherein $R^{14}$ is —OH and the glycosyltransferase as described above, it is further preferred that sugar-derivative nucleotide Su(A)-Nuc is according to formula (15), (16), (17) or (18) as defined above, wherein $R^{14}$ is —OH; or according to formula (19), (20), (21), (22), (23), (24), (25), (26), (65), (66), (67), (68) or (69) as defined above, wherein $R^{14}$ is —OH; or according to formula (35) as defined above. In these particularly preferred embodiments it is further preferred that Nuc is UDP.

Preferred Glycosyltransferases when $R^{14}$ is —$N_3$

In a preferred embodiment of the process according to the invention, $R^{14}$ is —$N_3$. In this embodiment, sugar derivative nucleotide Su(A)-Nuc is according to formula (3d), as defined above.

When Su(A)-Nuc is according to formula (3d), or preferred embodiments of (3d) as described above, in a preferred embodiment of the process the glycosyltransferase that is, or is derived from, a β-(1,4)-GalNAcT is, or is derived from, a wild-type β-(1,4)-GalNAcT, preferably an invertebrate β-(1,4)-GalNAcT. In another preferred embodiment of the process, the glycosyltransferase is, or is derived from, an invertebrate β-(1,4)-GalNAcT. In a further preferred embodiment, the glycosyltransferase is, or is derived from, *Caenorhabditis elegans* β-(1,4)-GalNAcT (CeGalNAcT), *Ascaris Sum* β-(1,4)-GalNAcT (AsGalNAcT) or *Trichoplusia Ni* β-(1,4)-GalNAcT (TnGalNAcT). β-(1,4)-GalNAcTs that are, or are derived from, (CeGalNAcT), (AsGalNAcT) or (TnGalNAcT) are described in more detail above.

When $R^{14}$ in the sugar-derivative nucleotide Su(A)-Nuc is —$N_3$, it is particularly preferred that the β-(1,4)-N-acetylgalactosaminyltransferase used in the process is, or is derived from, a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —$N_3$, the β-(1,4)-N-acetylgalactosaminyltransferase used in the process is, or is derived from, a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process is, or is derived from SEQ ID NO: 8.

In another particularly preferred embodiment, when $R^{14}$ in the sugar-derivative nucleotide Su(A)-Nuc is —$N_3$, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2-9, i.e. from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9. More preferably, when $R^{14}$ is —$N_3$, the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 2, SEQ ID NO: 3, SEQ ID NO: 4, SEQ ID NO: 6, SEQ ID NO: 7 and SEQ ID NO: 8, more preferably from the group consisting of SEQ ID NO: 6, SEQ ID NO: 7 and SEQ ID NO: 8, even more preferably from the group consisting of SEQ ID NO: 7 and SEQ ID NO: 8. Most preferably the β-(1,4)-N-acetylgalactosaminyltransferase used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 8.

In another particularly preferred embodiment of the process according to the invention wherein $R^{14}$ is —$N_3$, the glycosyltransferase is or is derived from *Caenorhabditis elegans* β-(1,4)-GalNAcT (CeGalNAcT).

In another particularly preferred embodiment of the process wherein $R^{14}$ is —$N_3$, the CeGalNAcT is or is derived from SEQ ID NO: 2 or SEQ ID NO: 6.

In another particularly preferred embodiment of the process wherein $R^{14}$ is —$N_3$, the CeGalNAcT used in the process is or is derived from SEQ ID NO: 10, SEQ ID NO: 11, SEQ ID NO: 12, SEQ ID NO: 13 or SEQ ID NO: 14.

In another particularly preferred embodiment of the process wherein $R^{14}$ is —$N_3$, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 2 or SEQ ID NO: 6.

In another particularly preferred embodiment of the process wherein $R^{14}$ is —$N_3$, the CeGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence SEQ ID NO: 10, SEQ ID NO: 11, SEQ ID NO: 12, SEQ ID NO: 13 or SEQ ID NO: 14.

In another particularly preferred embodiment of the process according to the invention wherein $R^{14}$ is —$N_3$, the glycosyltransferase is, or is derived from, *Trichoplusia Ni* β-(1,4)-GalNAcT (TnGalNAcT).

In a further preferred embodiment of the process wherein $R^{14}$ is —$N_3$, the TnGalNAcT is or is derived from SEQ ID NO: 4 or SEQ ID NO: 8.

In another further preferred embodiment of the process wherein $R^{14}$ is —$N_3$, the TnGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 4 or SEQ ID NO: 8.

In another preferred embodiment of the process wherein $R^{14}$ is —$N_3$, the TnGalNAcT used in the process is, or is derived from, a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another preferred embodiment, the TnGalNAcT used in the process wherein $R^{14}$ is —$N_3$, has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58 and SEQ ID NO: 59.

In another particularly preferred embodiment of the process according to the invention wherein $R^{14}$ is —$N_3$, the glycosyltransferase is or is derived from *Ascaris Sum* 3-(1,4)-GalNAcT (AsGalNAcT).

In this embodiment of the process wherein $R^{14}$ is —$N_3$, it is further preferred that the AsGalNAcT is or is derived from SEQ ID NO: 3 or SEQ ID NO: 7.

In another further preferred embodiment of the process wherein $R^{14}$ is —$N_3$, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to SEQ ID NO: 3 or SEQ ID NO: 7.

In another further preferred embodiment of the process wherein $R^{14}$ is —$N_3$, the AsGalNAcT used in the process is, or is derived from, a sequence selected from the group consisting of SEQ ID NO: 46, SEQ ID NO: 47, SEQ ID NO: 71, SEQ ID NO: 72 and SEQ ID NO: 73.

In another further preferred embodiment of the process wherein $R^{14}$ is —$N_3$, the AsGalNAcT used in the process has at least 50% sequence identity, preferably at least 55% 60%, 65%, 70%, 75% 80%, 85% 90%, 91%, 92%, 93%, 94%, 95%, 96%, 97%, 98%, 99% or preferably 100% sequence identity, to a sequence selected from the group consisting of SEQ ID NO: 46, SEQ ID NO: 47, SEQ ID NO: 71, SEQ ID NO: 72 and SEQ ID NO: 73.

In the here described preferred embodiments of the process according to the invention wherein $R^{14}$ is —$N_3$ and the glycosyltransferase as described above, it is further preferred that sugar-derivative nucleotide Su(A)-Nuc is according to formula (15), (16), (17) or (18) as defined above, wherein $R^{14}$ is —$N_3$; or according to formula (19), (20), (21), (22), (23), (24), (25), (26), (65), (66), (67), (68) or (69) as defined above, wherein $R^{14}$ is —$N_3$; or according to formula (36) as defined above. In these particularly preferred embodiments it is further preferred that Nuc is UDP.

Enzymes

In one aspect, the invention concerns the enzyme as defined herein, i.e. glycosyltransferases that are, or are derived from, β-(1,4)-GalNAcT, in particular the glycosyltransferases that are derived from β-(1,4)-GalNAcT, i.e. derived β-(1,4)-GalNAcT enzymes. In one embodiment, the enzyme is derived from an invertebrate species. In one embodiment, the enzymes according to this aspect are in isolated form. The enzymes and preferred embodiments thereof are further defined above in the context of the process according to the invention, which equally applies to the enzyme itself, according to the present aspect.

In one embodiment, the enzyme according to this aspect of the invention as derived from a β-(1,4)-N-acetylgalactosaminyltransferases, preferably derived from a β-(1,4)-N-acetylgalactosaminyltransferases having a sequence selected from the group consisting of SEQ ID NO: 2-23 and SEQ ID NO: 25-74, more preferably from the group consisting of SEQ ID NO: 10-14 and SEQ ID NO: 25-74, most preferably from the group consisting of SEQ ID NO: 10-13, SEQ ID NO: 25-48, SEQ ID NO: 50-70 and SEQ ID NO: 72-74. The enzymes according to this embodiment are typically in isolated form.

In one embodiment, the enzyme according to this aspect of the invention concerns β-(1,4)-N-acetylgalactosaminyltransferases having at least 40% sequence identity, preferably at least 45%, 50%, 55%, 60%, 65%, 70%, 75%, 80%, 85%, 90%, 91%, 92%, 93%, 94%, 95%, 96%, 97%, 98%, 99% or preferably 100% sequence identity, to a sequence selected from the group consisting of SEQ ID NO: 2-23 and SEQ ID NO: 25-74. The enzymes according to this embodiment are typically in isolated form. Preferably, the invention concerns β-(1,4)-N-acetylgalactosaminyltransferases having at least 40% sequence identity, preferably at least 45%, 50%, 55%, 60%, 65%, 70%, 75%, 80%, 85%, 90%, 91%, 92%, 93%, 94%, 95%, 96%, 97%, 98%, 99% or preferably 100% sequence identity, to a sequence selected from the group consisting of SEQ ID NO: 10-14 and SEQ ID NO: 25-74, most preferably from the group consisting of SEQ ID NO: 10-13, SEQ ID NO: 25-48, SEQ ID NO: 50-70 and SEQ ID NO: 72-74.

In a preferred embodiment, the enzyme according to this aspect of the invention concerns β-(1,4)-N-acetylgalactosaminyltransferases having at least 40% sequence identity, preferably at least 45%, 50%, 55%, 60%, 65%, 70%, 75%, 80%, 85%, 90%, 91%, 92%, 93%, 94%, 95%, 96%, 97%, 98%, 99% or preferably 100% sequence identity, to a sequence selected from the group consisting of SEQ ID NO: 6-14, i.e. from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14, preferably from the group consisting of SEQ ID NO: 10-13, i.e. from the group consisting of SEQ ID NO: 10, SEQ ID NO: 11, SEQ ID NO: 12 and SEQ ID NO: 13.

In another preferred embodiment, the enzyme according to this aspect of the invention concerns β-(1,4)-N-acetylgalactosaminyltransferase having at least 40% sequence identity, preferably at least 45%, 50%, 55%, 60%, 65%, 70%, 75%, 80%, 85%, 90%, 91%, 92%, 93%, 94%, 95%, 96%, 97%, 98%, 99% or preferably 100% sequence identity, to a sequence selected from the group consisting of SEQ ID NO: 25-45 and SEQ ID NO: 50-70, i.e. from the group consisting of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 and SEQ ID NO: 70.

In another preferred embodiment, the enzyme according to this aspect of the invention concerns β-(1,4)-N-acetylgalactosaminyltransferase having at least 40% sequence identity, preferably at least 45%, 50%, 55%, 60%, 65%, 70%, 75%, 80%, 85%, 90%, 91%, 92%, 93%, 94%, 95%, 96%, 97%, 98%, 99% or preferably 100% sequence identity, to a sequence selected from the group consisting of SEQ ID NO: 46-48 and SEQ ID NO: 72-74, i.e. from the group consisting of SEQ ID NO: 46, SEQ ID NO: 47, SEQ ID NO: 48, SEQ ID NO: 72, SEQ ID NO: 73 and SEQ ID NO: 74.

The invention also pertains to the use of the enzyme according to the invention, as defined hereinabove, in a process for modification of a glycoprotein, preferably in the process according to the invention. The process comprises contacting a glycoprotein comprising a glycan comprising a terminal GlcNAc moiety, with a sugar-derivative nucleotide in the presence of the enzyme. In a preferred embodiment, the glycoprotein is as defined herein, most preferably a glycoprotein comprising a glycan according to formula (1) or (2) as further defined herein. In a preferred embodiment, the sugar-derivative nucleotide is a sugar-derivative nucleotide Su(A)-Nuc according to formula (3) as further defined herein.

Modified Glycoprotein

The present invention further relates to a modified glycoprotein obtainable by the process according to the invention for the modification of a glycoprotein. More in particular, the invention relates to a glycoprotein comprising a glycan according to formula (4) or (5):

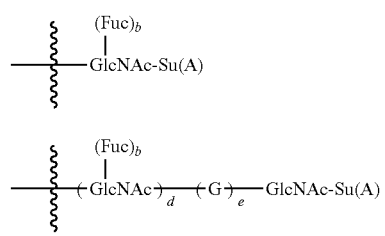

wherein:
b is 0 or 1;
d is 0 or 1;
e is 0 or 1;
G is a monosaccharide, or a linear or branched oligosaccharide comprising 2 to 20 sugar moieties; and
Su(A) is according to formula (6):

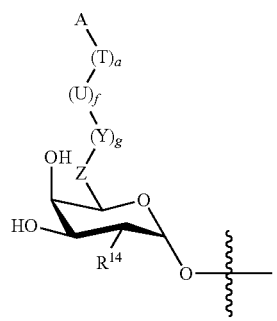

wherein $R^{14}$, Z, Y, U, T, A, g, f and a are as defined above for (3).

Preferred embodiments of $R^{14}$, Z, Y, U, T, A, g, f and a in (6) are as described above in more detail for (3) and preferred embodiments of (3) such as e.g. (3a), (3b), (3c) and (3d).

In the modified glycoprotein according to the invention, C1 of the Su(A) moiety is attached to C4 of the GlcNAc moiety via a β-1,4-O-glycosidic bond.

The modified glycoprotein according to the invention may comprise more than one glycan according to formula (4) or (5). When this is the case, the two or more glycans may differ from each other. The glycoprotein may also comprise one or more additional glycans that do not comprise a Su(A) moiety.

In a preferred embodiment, the modified glycoprotein comprises a glycan according to formula (4), wherein b is 0. In another preferred embodiment, the modified glycoprotein comprises a glycan according to formula (4), wherein b is 1.

In another preferred embodiment, the modified glycoprotein comprises a glycan according to formula (5), wherein b is 0. In another preferred embodiment, the modified glycoprotein comprises a glycan according to formula (5), wherein b is 1. In a glycan according to formula (5), G represents a monosaccharide, or a linear or branched oligosaccharide comprising 1 to 20, preferably 1 to 12, more preferably 1 to 10, even more preferably 1, 2, 3, 4, 5, 6, 7 or 8, and most preferably 1, 2, 3, 4, 5 or 6 sugar moieties. In glycan (5) it is preferred that when d is 0 then e is 1, and when e is 0 then d is 1. More preferably, in glycan (5) d is 1, and even more preferably d is 1 and e is 1. Sugar moieties that may be present in a glycan are known to a person skilled in the art, and include e.g. glucose (Glc), galactose (Gal), mannose (Man), fucose (Fuc), N-acetylglucosamine (GlcNAc), N-acetylgalactosamine (GalNAc), N-acetylneuraminic acid (NeuNAc) or sialic acid and xylose (Xyl). When the glycan is according to formula (5), it is further preferred that the glycan is according to formula (37), (38), (39), (40), (41) or (42):

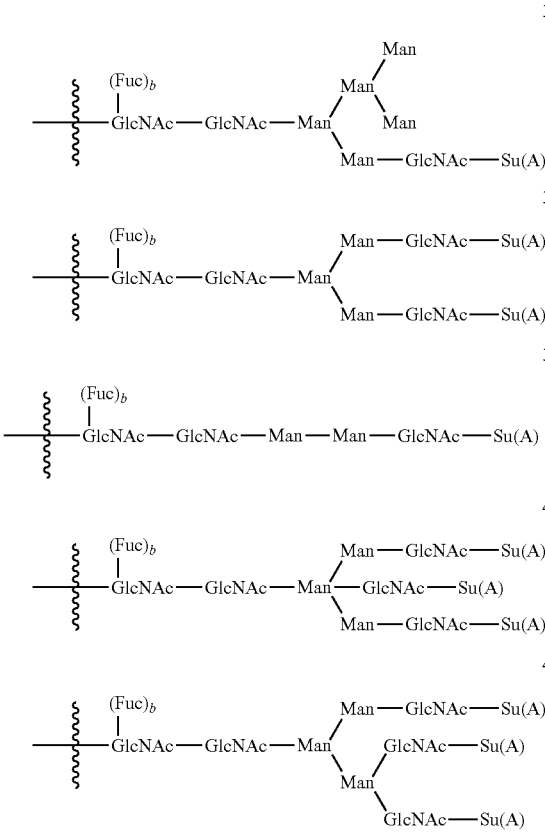

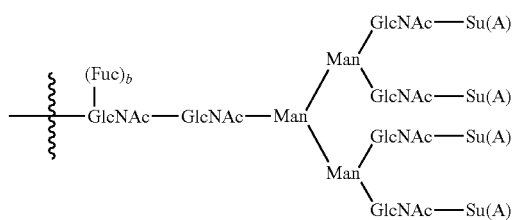

wherein b is 0 or 1; and
Su(A) is according to formula (6) as defined above.

In a preferred embodiment the modified glycoprotein according to the invention comprises a glycan according to formula (4), (37), (38), (39), (40), (41) or (42), more preferably an N-linked glycan according to formula (4), (37), (38), (39), (40), (41) or (42). In a further preferred embodiment, the modified glycoprotein according to the invention comprises a glycan according to formula (4), (37), (38) or (39), more preferably an N-linked glycan according to formula (4), (37), (38) or (39). Most preferably the modified glycoprotein according to the invention comprises a glycan according to formula (4) or (38), more preferably an N-linked glycan according to formula (4) or (38).

The modified glycoprotein according to the invention is preferably according to formula (43), (44) or (45):

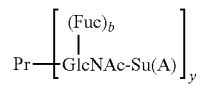

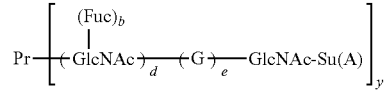

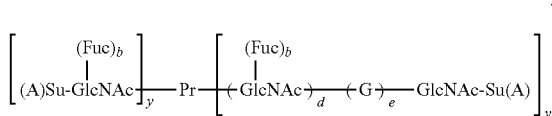

wherein:
b, d, e and G, and preferred embodiments thereof, are as defined above;
Su(A) is according to formula (6) as defined above;
y is independently an integer in the range of 1 to 24; and
Pr is a protein.

The modified glycoprotein may comprise one or more glycans (4) or (5) (y is 1 to 24). Preferably y is an integer in the range of 1 to 12, more preferably an integer in the range of 1 to 10. More preferably, y is 1, 2, 3, 4, 5, 6, 7 or 8, and yet more preferably y is 1, 2, 3, 4, 5 or 6. Even more preferably, y is 1, 2, 3 or 4. When y is 2 or more, the glycans may differ from each other. The modified glycoprotein may also comprise a combination of one or more glycans (4) and one or more glycans (5). As was described above, the glycoprotein may further comprise one or more glycans not having a Su(A) moiety.

When the modified glycoprotein according to the invention is according to formula (43), (44) or (45), it is also preferred that the glycoprotein comprises a glycan according to formula (4), (37), (38), (39), (40), (41) or (42) as described above, more preferably a glycan, preferably an N-linked glycan according to formula (4), (37), (38) or (39) and even more preferably according to formula (4) or (38). Most preferably the glycan comprising a terminal GlcNAc-moiety is an N-linked glycan according to formula (4) or (38).

In a preferred embodiment of the process according to the invention, the glycoprotein comprising a glycan comprising a terminal GlcNAc moiety is an antibody, more preferably an antibody according to formula (43), (44) or (45), wherein the protein (Pr) is an antibody (Ab), or more specifically Pr is the polypeptide part of an antibody. Also when the glycoprotein to be modified is an antibody and the antibody comprises more than one glycan (y is 2 or more), the glycans may differ from each other. The antibody may further comprise one or more glycans not having a Su(A) moiety. Also when the modified glycoprotein is an antibody, it is preferred that the modified antibody comprises a glycan according to formula (4), (37), (38), (39), (40), (41) or (42) as defined above, more preferably according to formula (4), (37), (38) or (39), even more preferably according to formula (4) or (38). In this embodiment it is further preferred that the antibody comprises an N-linked glycan according to formula (4), (37), (38), (39), (40), (41) or (42), more preferably an N-linked glycan according to formula (4), (37), (38) or (39), and most preferably an N-linked glycan according to formula (4) or (38).

When the modified glycoprotein is an antibody, it is preferred that y is 1, 2, 3, 4, 5, 6, 7 or 8, more preferably y is 1, 2, 4, 6 or 8, even more preferably y is 1, 2 or 4, and most preferably y is 1 or 2.

As was defined above, said antibody may be a whole antibody, but also an antibody fragment. When the antibody is a whole antibody, said antibody preferably comprises one or more, more preferably one, glycan on each heavy chain. Said whole antibody thus preferably comprises 2 or more, preferably 2, 4, 6 or 8 of said glycans, more preferably 2 or 4, and most preferably 2 glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a preferred embodiment, said antibody is a monoclonal antibody (mAb). Preferably, said antibody is selected from the group consisting of IgA, IgD, IgE, IgG and IgM antibodies. More preferably, said antibody is an IgG1, IgG2, IgG3 or IgG4 antibody, and most preferably said antibody is an IgG1 antibody.

In the modified glycoprotein according to the invention, $R^{14}$ in Su(A) according to formula (6) is selected from the group consisting of:

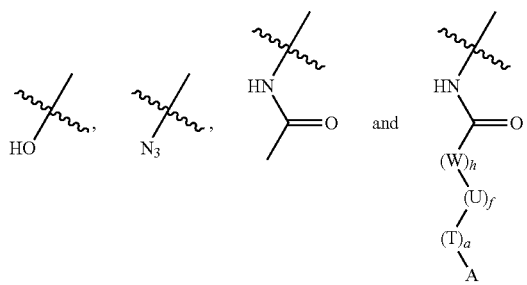

wherein W, h, a, f, T, A and U are as defined above.

In a preferred embodiment of modified glycoprotein according to the invention, $R^{14}$ in Su(A) according to formula (6) is selected from the group consisting of:

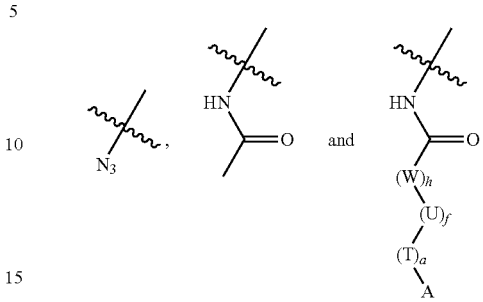

wherein W, h, a, f, T, A and U are as defined above.

Most preferably $R^{14}$ in Su(A) according to formula (6) is —NHAc.

In a further preferred embodiment, the modified glycoprotein according to the invention comprises a glycan, more preferably an N-linked glycan, according to formula (4) or (5), wherein $R^{14}$ in Su(A) (6) is —OH. In this embodiment it is preferred that the modified glycoprotein is according to formula (43), (44) or (45).

In another further preferred embodiment, the modified glycoprotein according to the invention comprises a glycan, more preferably an N-linked glycan, according to formula (4) or (5), wherein $R^{14}$ in Su(A) (6) is —N$_3$. In this embodiment it is preferred that the modified glycoprotein is according to formula (43), (44) or (45).

In another further preferred embodiment, the modified glycoprotein according to the invention comprises a glycan, more preferably an N-linked glycan, according to formula (4) or (5), wherein $R^{14}$ in Su(A) (6) is —NHC(O)CH$_3$. In this embodiment it is preferred that the modified glycoprotein is according to formula (43), (44) or (45).

In another further preferred embodiment, the modified glycoprotein according to the invention comprises a glycan, more preferably an N-linked glycan, according to formula (4) or (5), wherein $R^{14}$ in Su(A) (6) is —NHC(O)—(W)$_h$—(U)$_f$-(T)$_a$-A wherein W, h, U, f, T, a and A, and preferred embodiments thereof, are as described in more detail above. In this embodiment it is preferred that the modified glycoprotein is according to formula (43), (44) or (45).

In another further preferred embodiment the modified glycoprotein according to the invention comprises a glycan, more preferably an N-linked glycan, according to formula (37), (38), (39), (40), (41) or (42), wherein $R^{14}$ in Su(A) (6) is —OH. In this embodiment it is preferred that the modified glycoprotein is according to formula (43), (44) or (45).

In another further preferred embodiment the modified glycoprotein according to the invention comprises a glycan, more preferably an N-linked glycan, according to formula (37), (38), (39), (40), (41) or (42), wherein $R^{14}$ in Su(A) (6) is —N$_3$. In this embodiment it is preferred that the modified glycoprotein is according to formula (43), (44) or (45).

In another further preferred embodiment the modified glycoprotein according to the invention comprises a glycan, more preferably an N-linked glycan, according to formula (37), (38), (39), (40), (41) or (42), wherein $R^{14}$ in Su(A) (6) is —NHC(O)CH$_3$. In this embodiment it is preferred that the modified glycoprotein is according to formula (43), (44) or (45).

In another further preferred embodiment the modified glycoprotein according to the invention comprises a glycan, more preferably an N-linked glycan, according to formula (37), (38), (39), (40), (41) or (42), wherein $R^{14}$ in Su(A) (6) is —NHC(O)—(W)$_h$—(U)$_f$-(T)$_a$-A. In this embodiment it is preferred that the modified glycoprotein is according to formula (43), (44) or (45).

In another further preferred embodiment the modified glycoprotein according to the invention comprises a glycan, preferably an N-linked glycan, according to formula (4) or (5), more preferably a glycan, even more preferably an N-linked glycan according to formula (37), (38), (39), (40), (41) or (42), wherein Su(A) (6) is according to formula (46), (47), (48) or (49):

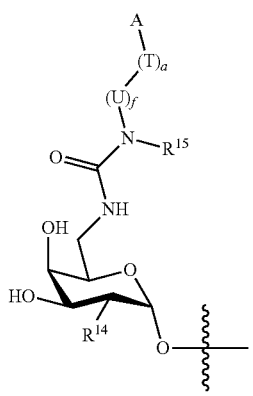

46

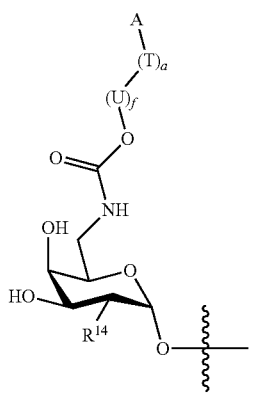

47

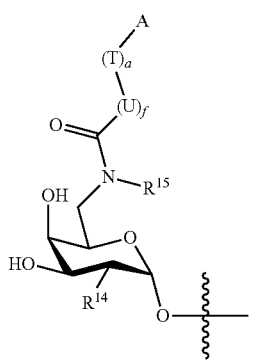

48

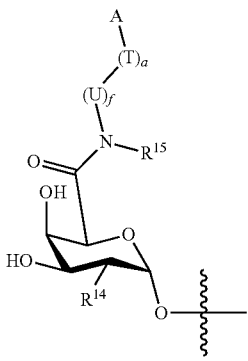

49 wherein a, f, $R^{14}$, $R^{15}$, A, U and T, and preferred embodiments thereof, are as defined above for (15), (16), (17) and (18).

In these embodiments wherein Su(A) (6) is according to formula (46), (47), (48) or (49), in a further preferred embodiment $R^{14}$ is —OH. In another further preferred embodiment $R^{14}$ is —N$_3$. In another further preferred embodiment $R^{14}$ is —NHC(O)CH$_3$. In another further preferred embodiment, $R^{14}$ is —NHC(O)—(W)$_h$—(U)$_f$-(T)$_a$-A wherein W, h, U, f, T, a and A, and preferred embodiments thereof, are as described in more detail above. Also in these embodiments it is preferred that the modified glycoprotein is according to formula (43), (44) or (45).

In another further preferred embodiment the modified glycoprotein according to the invention comprises a glycan, preferably an N-linked glycan, according to formula (4) or (5), more preferably a glycan, even more preferably an N-linked glycan according to formula (37), (38), (39), (40), (41) or (42), wherein Su(A) (6) is according to formula (50), (51), (52), (53), (54), (55), (56), (57), (70) or (71), preferably according to formula (50), (51), (52), (53), (54), (55), (56) or (57):

50

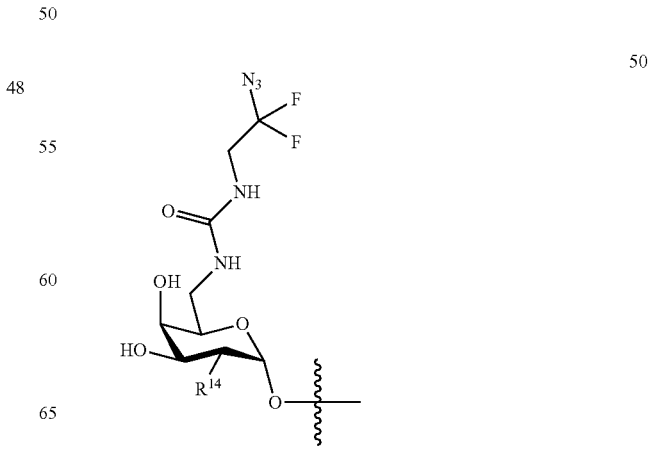

50

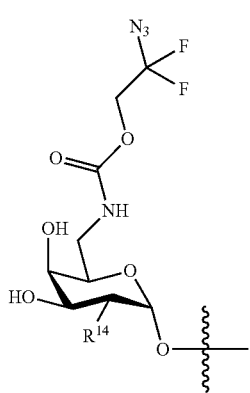
51
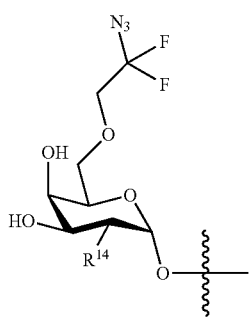
52
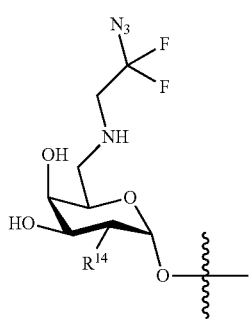
53
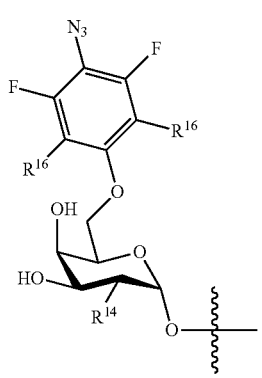
54
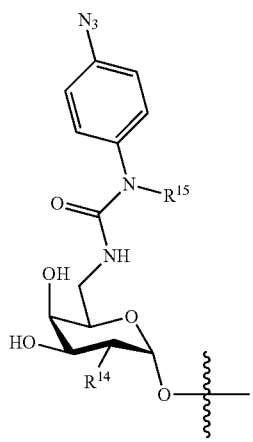
55
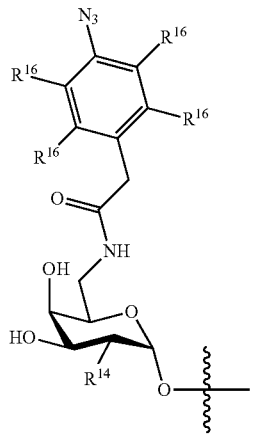
56
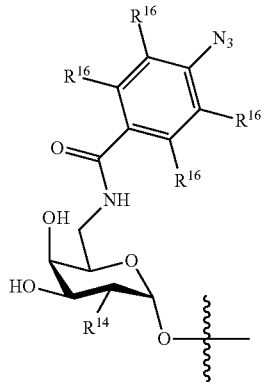
57
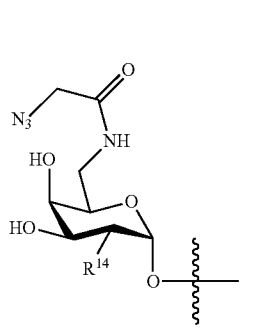
70

-continued

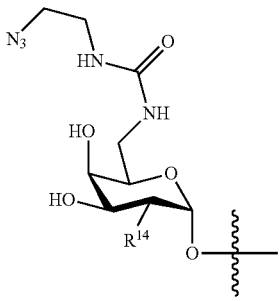

71 wherein $R^{14}$, $R^{15}$ and $R^{16}$, and preferred embodiments thereof, are as defined above for (19), (20), (21), (22), (23), (24), (25), (26), (65), (66), (67), (68) and (69).

In another further preferred embodiment the modified glycoprotein according to the invention comprises a glycan, preferably an N-linked glycan, according to formula (4) or (5), more preferably a glycan, even more preferably an N-linked glycan according to formula (37), (38), (39), (40), (41) or (42), wherein Su(A) (6) is according to formula (72), (73) or (74):

72

73

74 wherein $R^{14}$ and preferred embodiments thereof, are as defined above for (72), (73) and (74).

In a further preferred embodiment the modified glycoprotein according to the invention comprises a glycan, preferably an N-linked glycan, according to formula (37), wherein Su(A) (6) is according to formula (50), (51), (52), (53), (54), (55), (56), (57), (70), (71), (72), (73) or (74), preferably according to formula (50), (51), (52), (53), (54), (55), (56) or (57). In another further preferred embodiment the modified glycoprotein according to the invention comprises a glycan, preferably an N-linked glycan, according to formula (38), wherein Su(A) (6) is according to formula (50), (51), (52), (53), (54), (55), (56), (57), (70), (71), (72), (73) or (74), preferably according to formula (50), (51), (52), (53), (54), (55), (56) or (57). In another further preferred embodiment the modified glycoprotein according to the invention comprises a glycan, preferably an N-linked glycan, according to formula (39), wherein Su(A) (6) is according to formula (50), (51), (52), (53), (54), (55), (56), (57), (70), (71), (72), (73) or (74), preferably according to formula (50), (51), (52), (53), (54), (55), (56) or (57). In another further preferred embodiment the modified glycoprotein according to the invention comprises a glycan, preferably an N-linked glycan, according to formula (40), wherein Su(A) (6) is according to formula (50), (51), (52), (53), (54), (55), (56), (57), (70), (71), (72), (73) or (74), preferably according to formula (50), (51), (52), (53), (54), (55), (56) or (57). In another further preferred embodiment the modified glycoprotein according to the invention comprises a glycan, preferably an N-linked glycan, according to formula (41), wherein Su(A) (6) is according to formula (50), (51), (52), (53), (54), (55), (56), (57), (70), (71), (72), (73) or (74), preferably according to formula (50), (51), (52), (53), (54), (55), (56) or (57). In another further preferred embodiment the modified glycoprotein according to the invention comprises a glycan, preferably an N-linked glycan, according to formula (42), wherein Su(A) (6) is according to formula (50), (51), (52), (53), (54), (55), (56), (57), (70), (71), (72), (73) or (74), preferably according to formula (50), (51), (52), (53), (54), (55), (56) or (57).

In these embodiments wherein Su(A) (6) is according to formula (50), (51), (52), (53), (54), (55), (56), (57), (70), (71), (72), (73) or (74), preferably according to formula (50), (51), (52), (53), (54), (55), (56) or (57), in a further preferred embodiment $R^{14}$ is —OH. In another further preferred embodiment $R^{14}$ is —$N_3$. In another further preferred embodiment $R^{14}$ is —NHC(O)$CH_3$. In another further preferred embodiment $R^{14}$ is —NHC(O)—(W)$_h$—(U)$_f$-(T)$_a$-A wherein W, h, U, f, T, a and A, and preferred embodiments thereof, are as described in more detail above. Also in these embodiments it is preferred that the modified glycoprotein is according to formula (43), (44) or (45).

In another further preferred embodiment the modified glycoprotein according to the invention comprises a glycan, preferably an N-linked glycan, according to formula (4) or (5), more preferably a glycan, even more preferably an N-linked glycan according to formula (37), (38), (39), (40), (41) or (42), wherein Su(A) (6) is according to formula (58), (59), (60), (61) or (62):

58

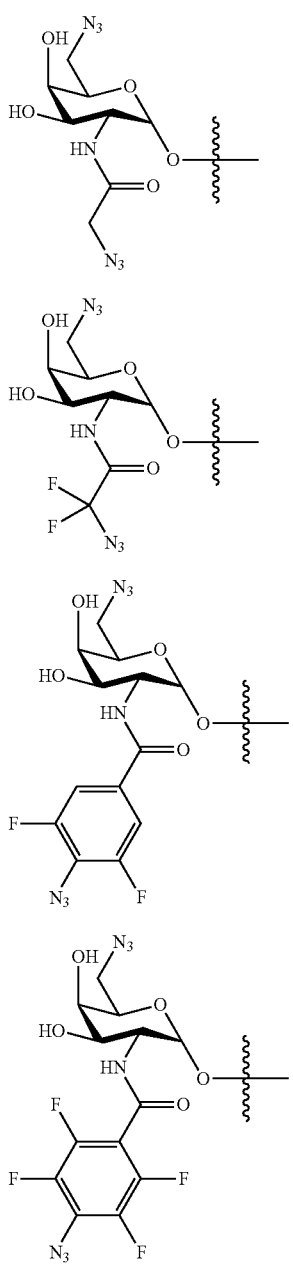

59

60

61

62

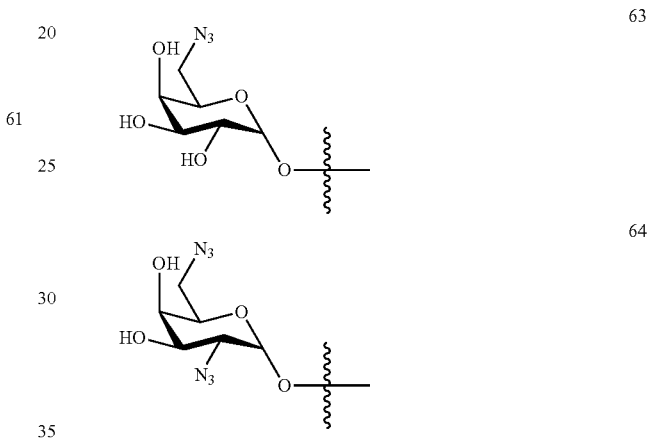

63

64

In a further preferred embodiment the modified glycoprotein according to the invention comprises a glycan, preferably an N-linked glycan, according to formula (38), wherein Su(A) (6) is according to formula (58), (59), (60), (61) or (62). In another further preferred embodiment the modified glycoprotein according to the invention comprises a glycan, preferably an N-linked glycan, according to formula (39), wherein Su(A) (6) is according to formula (58), (59), (60), (61) or (62). In another further preferred embodiment the modified glycoprotein according to the invention comprises a glycan, preferably an N-linked glycan, according to formula (40), wherein Su(A) (6) is according to formula (58), (59), (60), (61) or (62). In another further preferred embodiment the modified glycoprotein according to the invention comprises a glycan, preferably an N-linked glycan, according to formula (41), wherein Su(A) (6) is according to formula (58), (59), (60), (61) or (62). In another further preferred embodiment the modified glycoprotein according to the invention comprises a glycan, preferably an N-linked glycan, according to formula (42), wherein Su(A) (6) is according to formula (58), (59), (60), (61) or (62).

In these embodiments wherein Su(A) (6) is according to formula (58), (59), (60), (61) or (62) it is preferred that the modified glycoprotein is according to formula (43), (44) or (45).

In another further preferred embodiment the modified glycoprotein according to the invention comprises a glycan, preferably an N-linked glycan, according to formula (4) or (5), more preferably a glycan, even more preferably an N-linked glycan according to formula (37), (38), (39), (40), (41) or (42), wherein Su(A) (6) is according to formula (63) or (64):

In a further preferred embodiment the modified glycoprotein according to the invention comprises a glycan, preferably an N-linked glycan, according to formula (38), wherein Su(A) (6) is according to formula (63) or (64). In another further preferred embodiment the modified glycoprotein according to the invention comprises a glycan, preferably an N-linked glycan, according to formula (39), wherein Su(A) (6) is according to formula (63) or (64).

In these embodiments wherein Su(A) (6) is according to formula (63) or (64) it is preferred that the modified glycoprotein is according to formula (43), (44) or (45).

The invention also pertains to the use of the modified glycoprotein according to the invention, as defined hereinabove, in a process for preparing a bioconjugate, preferably the bioconjugate according to the invention. The process is preferably for preparing an antibody-drug-conjugate (ADC). The process comprises contacting modified glycoprotein with a linker-conjugate. In a preferred embodiment, the linker-conjugate is as defined herein. In a preferred embodiment, the bioconjugate is a bioconjugate according to formula (75), (76) or (77), as further defined herein below.

Bioconjugate

The present invention further relates to a bioconjugate obtainable by conjugating a linker-conjugate to the modified glycoprotein according to the invention. Linker-conjugates are known in the art as one of the reactants in a bioconjugation reaction, wherein a glycoprotein, such as a modified glycoprotein according to the invention, is the other reactant. A linker-conjugate is herein defined as a compound wherein a target molecule is covalently connected to a reactive group $Q^1$, via a linker. Reactive group $Q^1$ is capable of reacting with functional group A present on the modified glycoprotein according to the invention. A linker-conjugate may comprise more than one reactive groups $Q^1$ and/or more than one target molecules. Suitable linker-conjugates include those disclosed in WO 2014/065661 and WO 2016/053107, which are both incorporated herein by reference.

Bioconjugation reactions are known in the field of antibody-conjugates such as antibody-drug-conjugates (ADCs), wherein they are used to prepare conjugates of an antibody with a target molecule, typically a cytotoxin. In such a bioconjugation reaction, the modified glycoprotein according to the invention is coupled to or conjugated to the linker-conjugate by virtue of a reaction between functional group A present on the modified glycoprotein and a reactive group $Q^1$ present on the linker-conjugate. The bioconjugate according to the invention is preferably an antibody-conjugate, wherein an antibody is conjugated to a target molecule, most preferably such as antibody-drug-conjugate, wherein an antibody is conjugated to a drug, typically a cytotoxin.

More in particular, the invention relates to a bioconjugate according to formula (75), (76) or (77):

wherein $R^{14}$, Z, Y, U, T, g, f and a are as defined above for (3), and Su is connected via C1 to C4 of the GlcNAc moiety via a β-1,4-O-glycosidic bond and to CG via Z, Y, U or T.

Preferred embodiments of Pr and y in (75), (76) or (77) are as described above in more detail for (43), (44) and (45). In a preferred embodiment, the glycoprotein is an antibody. The bioconjugate, in particular the antibody, may comprises more than one functionalized glycan (y is 2 or more), the glycans may differ from each other. The antibody may further comprise one or more glycans not having a Su-(CG-(Sp)$_l$-(D)$_k$)$_j$ moiety. It is further preferred that the functionalized glycan is an N-linked glycan. When the bioconjugate according to the invention is an antibody-conjugate, it is preferred that y is 1, 2, 3, 4, 5, 6, 7 or 8, more preferably y is 1, 2, 4, 6 or 8, even more preferably y is 1, 2 or 4, and most preferably y is 1 or 2.

As defined above, said antibody may be a whole antibody, but also an antibody fragment. When the antibody is a whole antibody, said antibody preferably comprises one or more, more preferably one, glycan on each heavy chain. Said whole antibody thus preferably comprises 2 or more, pref-

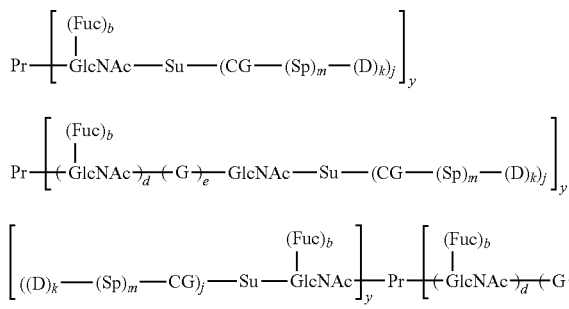

wherein:
Pr is a protein
y is independently as defined above for (43);
b, d, e and G are independently as defined above for (5);
CG is a connecting group that connects Su to Sp or D;
Sp is a spacer;
D is a target molecule;
j is independently 1, 2, 3, 4 or 5, preferably j is 1;
k is independently an integer in the range of 1 to 10, preferably k is 1, 2, 3 or 4, most preferably k is 1;
m is 0 or 1, preferably m is 1.
Su is according to formula (78):

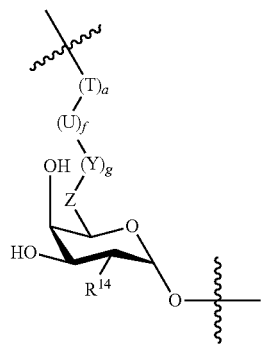

erably 2, 4, 6 or 8 of said functionalized glycans, more preferably 2 or 4, and most preferably 2 functionalized glycans. In other words, when said antibody is a whole antibody, y is preferably 2, 4, 6 or 8, more preferably y is 2 or 4, and most preferably y is 2. When the antibody is an antibody fragment, it is preferred that y is 1, 2, 3 or 4, and more preferably y is 1 or 2.

In a preferred embodiment, said antibody is a monoclonal antibody (mAb). Preferably, said antibody is selected from the group consisting of IgA, IgD, IgE, IgG and IgM antibodies. More preferably, said antibody is an IgG1, IgG2, IgG3 or IgG4 antibody, and most preferably said antibody is an IgG1 antibody.

Preferred embodiments of the glycan chain, in particular of b, d, e and G, in (75), (76) or (77) are as described above in more detail for (4) and (5) and preferred embodiments thereof, such as e.g. (37), (38), (39), (40), (41) or (42).

Preferred embodiments of $R^{14}$, Z, Y, U, T, g, f and a in (78) are as described above in more detail for (3) and preferred embodiments of (3) such as e.g. (3a), (3b), (3c) and (3d). Preferred embodiments for Su according to formula (78) correspond to Su(A) according to any one of (46) to (64) and (70) to (74), and preferred embodiments thereof, as described above in more detail for (6), albeit with A being reacted with $Q^1$ to form CG.

In the bioconjugate according to the invention, $R^{14}$ in Su according to formula (78) is selected from the group consisting of:

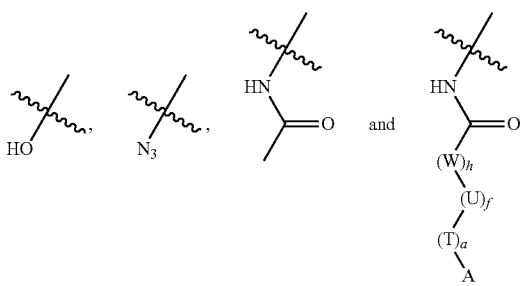

wherein W, h, a, f, T, A and U are as defined above.

In a preferred embodiment of modified glycoprotein according to the invention, $R^{14}$ in Su according to formula (78) is selected from the group consisting of:

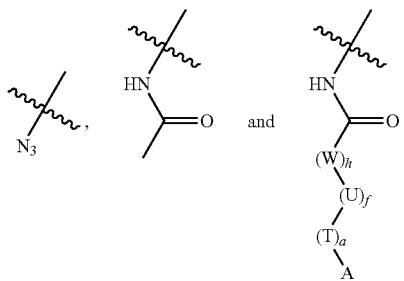

wherein W, h, a, f, T, A and U are as defined above.

Most preferably $R^{14}$ in Su according to formula (78) is —NHAc.

D is a target molecule. Target molecules are herein defined as molecular structures possessing a desired property that is imparted onto the biomolecule upon conjugation. Target molecule D is preferably selected from the group consisting of active substances, reporter molecules, polymers, solid surfaces, hydrogels, nanoparticles, microparticles and biomolecules. Most preferably, target molecule D is an active substance.

The term "active substance" herein relates to a pharmacological and/or biological substance, i.e. a substance that is biologically and/or pharmaceutically active, for example a drug, a prodrug, a diagnostic agent, a protein, a peptide, a polypeptide, a peptide tag, an amino acid, a glycan, a lipid, a vitamin, a steroid, a nucleotide, a nucleoside, a polynucleotide, RNA or DNA. Examples of peptide tags include cell-penetrating peptides like human lactoferrin or polyarginine. An example of a glycan is oligomannose. An example of an amino acid is lysine. When the target molecule is an active substance, the active substance is preferably selected from the group consisting of drugs and prodrugs. More preferably, the active substance is selected from the group consisting of pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs).

The term "reporter molecule" herein refers to a molecule whose presence is readily detected, for example a diagnostic agent, a dye, a fluorophore, a radioactive isotope label, a contrast agent, a magnetic resonance imaging agent or a mass label. A wide variety of fluorophores, also referred to as fluorescent probes, is known to a person skilled in the art. Several fluorophores are described in more detail in e.g. G. T. Hermanson, "Bioconjugate Techniques", Elsevier, $3^{rd}$ Ed. 2013, Chapter 10: "Fluorescent probes", p. 395-463, incorporated by reference. Examples of a fluorophore include all kinds of Alexa Fluor (e.g. Alexa Fluor 555), cyanine dyes (e.g. Cy3 or Cy5) and cyanine dye derivatives, coumarin derivatives, fluorescein and fluorescein derivatives, rhodamine and rhodamine derivatives, boron dipyrromethene derivatives, pyrene derivatives, naphthalimide derivatives, phycobiliprotein derivatives (e.g. allophycocyanin), chromomycin, lanthanide chelates and quantum dot nanocrystals. Examples of a radioactive isotope label include $^{99m}Tc$, $^{111}In$, $^{114m}In$, $^{115}In$, $^{18}F$, $^{14}C$, $^{64}Cu$, $^{131}I$, $^{125}I$, $^{123}I$, $^{212}Bi$, $^{88}Y$, $^{90}Y$, $^{67}Cu$, $^{186}Rh$, $^{188}Rh$, $^{66}Ga$, $^{67}Ga$ and $^{10}B$, which is optionally connected via a chelating moiety such as e.g. DTPA (diethylenetriaminepentaacetic anhydride), DOTA (1,4,7,10-tetraazacyclododecane-N,N',N'',N'''tetraacetic acid), NOTA (1,4,7-triazacyclononane N,N',N''-triacetic acid), TETA (1,4,8,11-tetraazacyclotetradecane-N,N',N'', N'''-tetraacetic acid), DTTA ($N^1$-(p-isothiocyanatobenzyl)-diethylenetriamine-$N^1,N^2,N^3,N^3$-tetraacetic acid), deferoxamine or DFA (N'-[5-[[4-[[5-(acetylhydroxy-amino)pentyl]amino]-1,4-dioxobutyl]hydroxyamino]pentyl]-N-(5-aminopentyl)-N-hydroxybutanediamide) or HYNIC (hydrazinonicotinamide). Isotopic labelling techniques are known to a person skilled in the art, and are described in more detail in e.g. G. T. Hermanson, "Bioconjugate Techniques", Elsevier, $3^{rd}$ Ed. 2013, Chapter 12: "Isotopic labelling techniques", p. 507-534, incorporated by reference.

Polymers suitable for use as a target molecule D in the compound according to the invention are known to a person skilled in the art, and several examples are described in more detail in e.g. G. T. Hermanson, "Bioconjugate Techniques", Elsevier, $3^{rd}$ Ed. 2013, Chapter 18: "PEGylation and synthetic polymer modification", p. 787-838, incorporated by reference. When target molecule D is a polymer, target molecule D is preferably independently selected from the group consisting of a poly(ethyleneglycol) (PEG), a polyethylene oxide (PEO), a polypropylene glycol (PPG), a polypropylene oxide (PPO), a 1,x-diaminoalkane polymer (wherein x is the number of carbon atoms in the alkane, and preferably x is an integer in the range of 2 to 200, preferably 2 to 10), a (poly)ethylene glycol diamine (e.g. 1,8-diamino-3,6-dioxaoctane and equivalents comprising longer ethylene glycol chains), a polysaccharide (e.g. dextran), a poly(amino acid) (e.g. a poly(L-lysine)) and a poly(vinyl alcohol), a poly(2-oxazoline)s (PAOx).

Solid surfaces suitable for use as a target molecule D are known to a person skilled in the art. A solid surface is for example a functional surface (e.g. a surface of a nanomaterial, a carbon nanotube, a fullerene or a virus capsid), a metal surface (e.g. a titanium, gold, silver, copper, nickel, tin, rhodium or zinc surface), a metal alloy surface (wherein the alloy is from e.g. aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc and/or zirconium), a polymer surface (wherein the polymer is e.g. polystyrene, polyvinylchloride, polyethylene, polypropylene, poly(dimethylsiloxane) or polymethylmethacrylate, polyacrylamide), a glass surface, a silicone surface, a chromatography support surface (wherein the chromatography support is e.g. a silica support, an agarose support, a cellulose support or an alumina support), etc. When target molecule D is a solid surface, it is preferred that D is independently selected from the group consisting of a functional surface or a polymer surface.

Hydrogels are known to the person skilled in the art. Hydrogels are water-swollen networks, formed by crosslinks between the polymeric constituents. See for example A. S. Hoffman, *Adv. Drug Delivery Rev.* 2012, 64, 18, incorporated by reference. When the target molecule is a hydrogel, it is preferred that the hydrogel is composed of poly(ethylene)glycol (PEG) as the polymeric basis.

Micro- and nanoparticles suitable for use as a target molecule D are known to a person skilled in the art. A variety of suitable micro- and nanoparticles is described in e.g. G. T. Hermanson, *"Bioconjugate Techniques"*, Elsevier, $3^{rd}$ Ed. 2013, Chapter 14: *"Microparticles and nanoparticles"*, p. 549-587, incorporated by reference. The micro- or nanoparticles may be of any shape, e.g. spheres, rods, tubes, cubes, triangles and cones. Preferably, the micro- or nanoparticles are of a spherical shape. The chemical composition of the micro- and nanoparticles may vary. When target molecule D is a micro- or a nanoparticle, the micro- or nanoparticle is for example a polymeric micro- or nanoparticle, a silica micro- or nanoparticle or a gold micro- or nanoparticle. When the particle is a polymeric micro- or nanoparticle, the polymer is preferably polystyrene or a copolymer of styrene (e.g. a copolymer of styrene and divinylbenzene, butadiene, acrylate and/or vinyltoluene), polymethylmethacrylate (PMMA), polyvinyltoluene, poly(hydroxyethyl methacrylate (pHEMA) or poly(ethylene glycol dimethacrylate/2-hydroxyethylmetacrylae) [poly(EDGMA/HEMA)]. Optionally, the surface of the micro- or nanoparticles is modified, e.g. with detergents, by graft polymerization of secondary polymers or by covalent attachment of another polymer or of spacer moieties, etc.

Target molecule D may also be a biomolecule. When target molecule D is a biomolecule, it is preferred that the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides.

CG is a connecting group. The term "connecting group" herein refers to the structural element connecting one part of a compound and another part of the same compound. Typically, a bioconjugate is prepared via reaction of a reactive group $Q^1$ present in a linker-conjugate with a functional group A present in the modified glycoprotein according to the invention. CG is the moiety formed upon reaction of reactive group $Q^1$ with functional moiety A. As will be understood by the person skilled in the art, the nature of CG depends on the type of organic reaction that was used to establish the connection between the modified glycoprotein according to the invention and the linker-conjugate. In other words, the nature of CG depends on the nature of reactive group $Q^1$ on the linker-conjugate and the nature of functional group A in the biomolecule. Since there is a large number of different chemical reactions available for establishing the connection between the modified glycoprotein and the linker-conjugate, consequently there is a large number of possibilities for CG. Several examples of suitable combinations of $F^1$ and $Q^1$, and of connecting group $Z^3$ that will be present in a bioconjugate when a linker-conjugate comprising $Q^1$ is conjugated to a biomolecule comprising a complementary functional group $F^1$, are shown in FIG. 5.

When A is for example a thiol group, complementary groups $Q^1$ include N-maleimidyl groups and alkenyl groups, and the corresponding connecting groups CG are as shown in FIG. 5. When A is a thiol group, complementary groups $Q^1$ also include allenamide groups.

When A is for example an amino group, complementary groups $Q^1$ include ketone groups, activated ester groups and azido groups, and the corresponding connecting groups CG are as shown in FIG. 5.

When A is for example a ketone group, complementary groups $Q^1$ include (O-alkyl)hydroxylamino groups and hydrazine groups, and the corresponding connecting groups CG are as shown in FIG. 5.

When A is for example an alkynyl group, complementary groups $Q^1$ include azido groups, and the corresponding connecting group CG is as shown in FIG. 5.

When A is for example an alkene group, complementary groups $Q^1$ include thiols, dienes or heterodienes groups which are reactive in a Diels-Alder cycloaddition and tetrazinyl groups, and the corresponding connecting group CG may be thioethers, Diels-Alder adducts (cyclohexenes or analogues thereof) or dihydropyridazine, respectively.

When A is for example an azido group, complementary groups $Q^1$ include alkynyl groups, and the corresponding connecting group CG is as shown in FIG. 5.

When A is for example a cyclopropenyl group, a trans-cyclooctene group or a cyclooctyne group, complementary groups $Q^1$ include tetrazinyl groups, and the corresponding connecting group $Z^3$ is as shown in FIG. 5. In these particular cases, $Z^3$ is only an intermediate structure and will expel $N_2$, thereby generating a dihydropyridazine (from the reaction with alkene) or pyridazine (from the reaction with alkyne).

When A is for example a halogen (X), complementary groups $Q^1$ include thiols and the corresponding connecting groups CG may be a thioether.

When A is for example $—OS(O)_2R^5$, complementary groups $Q^1$ include hydroxyl and (primary and secondary) amine groups, and the corresponding connecting groups CG may be an ether or a (secondary or tertiary) amine groups.

When A is for example an allenyl group, complementary groups $Q^1$ include thiols and the corresponding connecting groups CG may be a thioether, typically a methyl-substituted thioether.

When A is for example $—SC(O)R^8$ or $—SC(V)OR^8$, A typically first reacts to a thiol, and complementary groups $Q^1$ include N-maleimidyl groups, alkenyl groups allenamide groups. Corresponding connecting groups CG may be as shown in FIG. 5 for A is thiol.

Additional suitable combinations of A and $Q^1$, and the nature of resulting connecting group CG are known to a person skilled in the art, and are e.g. described in G. T. Hermanson, *"Bioconjugate Techniques"*, Elsevier, $3^{rd}$ Ed. 2013 (ISBN: 978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, *"Bioconjugate Techniques"*, Elsevier, $3^{rd}$ Ed. 2013 (ISBN: 978-0-12-382239-0), and the content of this Table is expressly incorporated by reference herein.

Sp is a spacer or a linker. A linker is herein defined as a moiety that connects two or more elements of a compound. For example in a bioconjugate, a biomolecule and a target molecule are covalently connected to each other via a linker; in a linker-conjugate a reactive group $Q^1$ is covalently connected to a target molecule via a linker. Any linker known in the art to be suitable for use in bioconjugates, in particular antibody-conjugates can be used as Sp. Such spacer-moieties are known to a person skilled in the art. Examples of suitable spacer-moieties include (poly)ethylene glycol diamines (e.g. 1,8-diamino-3,6-dioxaoctane or equivalents comprising longer ethylene glycol chains), polyethylene glycol chains or polyethylene oxide chains, polypropylene glycol chains or polypropylene oxide chains and 1,x-diaminoalkanes wherein x is the number of carbon atoms in the alkane. Another class of suitable spacer-moieties comprises cleavable spacer-moieties, or cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are disulfide-linkers that are cleaved upon reduction, peptide-linkers that are cleaved upon specific recognition by a protease, e.g. cathepsin, plasmin or metalloproteases, or glycoside-based linkers that are cleaved upon specific recognition by a glycosidase, e.g. glucuronidase, or nitroaromatics that are reduced in oxygen-poor, hypoxic areas. Herein, suitable cleavable spacer-moieties also include spacer moieties comprising a specific, cleavable, sequence of amino acids. Examples include e.g. spacer-moieties comprising a Val-Ala (valine-alanine) or Val-Cit (valine-citrulline) moiety.

In a preferred embodiment, Sp is selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{19}$, wherein $R^{19}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, Sp is selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{19}$, wherein $R^{19}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, Sp is selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{19}$, wherein $R^{19}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, Sp is selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{19}$, wherein $R^{19}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^{19}$, preferably O, wherein $R^{19}$ is independently selected from the group consisting of hydrogen and $C_1$-$C_4$ alkyl groups, preferably hydrogen or methyl.

Most preferably, Sp is selected from the group consisting of linear or branched $C_1$-$C_{20}$ alkylene groups, the alkylene groups being optionally substituted and optionally interrupted by one or more heteroatoms selected from the group of O, S and $NR^{19}$, wherein $R^{19}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^{19}$, preferably O and/or S—S, wherein $R^{19}$ is independently selected from the group consisting of hydrogen and $C_1$-$C_4$ alkyl groups, preferably hydrogen or methyl.

Particularly preferred Sp moieties include —$(CH_2)_n$—, —$(CH_2CH_2)_n$—, —$(CH_2CH_2O)$—, —$(OCH_2CH_2)_n$—, —$(CH_2CH_2O)CH_2CH_2$—, —$CH_2CH_2(OCH_2CH_2)_n$—, —(CH$_2$CH$_2$CH$_2$O)$_n$—, —(OCH$_2$CH$_2$CH$_2$)$_n$—, —(CH$_2$CH$_2$CH$_2$O)CH$_2$CH$_2$CH$_2$— and —CH$_2$CH$_2$CH$_2$(O—CH$_2$CH$_2$CH$_2$)$_n$—, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

EXAMPLES

Example 1. Selection and Design of GalNAc-Transferases

Four specific sequences were selected for initial evaluation, in particular Uniprot accession number: Q9GUM2 (*C. elegans*; identified herein as SEQ ID NO: 2), U1MEV9 (*A. suum*; identified herein as SEQ ID NO: 3), Q6J4T9 (*T. ni*; identified herein as SEQ ID NO: 4) and Q7KN92 (*D. melanogaster*; identified herein as SEQ ID NO: 5). The polypeptides were constructed based on deletion of the predicted cytoplasmatic domain and transmembrane domain. These polypeptides comprise the predicted *C. elegans* (CeGalNAcT [30-383] identified by SEQ ID NO: 6), *A. suum* (AsGalNAcT [30-383] identified by SEQ ID NO: 7), *T. ni* (TnGalNAcT [33-421] identified by SEQ ID NO: 8) and *D. melanogaster* (DmGalNAcT [47-403] identified by SEQ ID NO: 9). In addition, polypeptide variants containing an N-terminal His-tag were constructed for AsGalNAcT [30-383] (His-AsGalNAcT [30-383] identified by SEQ ID NO: 71) and TnGalNAcT [33-421] (His-TnGalNAcT [33-421] identified by SEQ ID NO: 49).

Example 2. Design of *T. ni* GalNAcT Mutants and *A. suum* GalNAcT Mutants

Mutants of TnGalNAcT and AsGalNAcT were designed based on the crystal structure for bovine β(1,4)-Gal-T1 in complex with UDP-N-acetyl-galactosamine (PDB entry 1OQM) and the β(1,4)-Gal-T1(Y289L) mutant reported by Qasba et al. (J. Biol. Chem. 2002, 277: 20833-20839, incorporated by reference). Mutants of TnGalNAcT and AsGalNAcT were designed based on a sequence alignment of TnGalNAcT and AsGalNAcT with bovine β(1,4)Gal-T1. The corresponding amino acid residues between these proteins are shown in Table 1.

TABLE 1

Numbers of corresponding amino acids in different GalNAcT/GalT species

| TnGalNAcT | AsGalNAcT | Bovine β(1,4)-Gal-T1 |
|---|---|---|
| I311 | I257 | Y289 |
| W336 | W282 | W314 |
| E339 | E285 | E317 |

Example 3. Site Directed Mutagenesis of his-TnGalNAcT(33-421) Mutants

A pET15b-vector containing the codon optimized sequence encoding residues 33-421 of TnGalNAcT (identified by SEQ ID NO: 8) between the NdeI-BamHI sites was obtained from Genscript, resulting in His-TnGalNAcT(33-421) (identified by SEQ ID NO: 49). The TnGalNacT mutant genes were amplified from the above described construct using a set of overlapping primers by a linear amplification PCR. The overlapping primer sets used for each mutant are shown in table 2. For the construction of His-TnGalNAcT(33-421; W336F) (identified by SEQ ID NO: 50) the DNA fragment was amplified with a pair of primers defined herein as SEQ ID NO: 79 and SEQ ID NO: 80. For the construction of His-TnGalNAcT(33-421; W336H) (identified by SEQ ID NO: 51) the DNA fragment was amplified with a pair of primers defined herein as SEQ ID NO: 81 and SEQ ID NO: 82. For the construction of His-TnGalNAcT(33-421; W336V) (identified by SEQ ID NO: 52) the DNA fragment was amplified with a pair of primers defined herein as SEQ ID NO: 83 and SEQ ID NO: 84. For the construction of His-TnGalNAcT(33-421; E339A) (identified by SEQ ID NO: 53) the DNA fragment was amplified with a pair of primers defined herein as SEQ ID NO: 85 and SEQ ID NO: 86. For the construction of His-TnGalNAcT(33-421; E339G) (identified by SEQ ID NO: 54) the DNA fragment was amplified with a pair of primers defined herein as SEQ ID NO: 87 and SEQ ID NO: 88. For the construction of His-TnGalNAcT(33-421; E339D) (identified by SEQ ID NO: 55) the DNA fragment was amplified with a pair of primers defined herein as SEQ ID NO: 89 and SEQ ID NO: 90. For the construction of His-TnGalNAcT(33-421; I311Y) (identified by SEQ ID NO: 60) the DNA fragment was amplified with a pair of primers defined herein as SEQ ID NO: 91 and SEQ ID NO: 92. After the PCR amplification, the reaction mixture was treated with DpnI to digest template DNA followed by transformation into NEB 10-beta competent cells (obtained from New England Biolabs). DNA was isolated and sequences were confirmed by sequence analysis for the mutants His-TnGalNAcT(33-421; W336F) (identified by SEQ ID NO: 50), His-TnGalNAcT(33-421; W336V) (identified by SEQ ID NO: 52), His-TnGalNAcT(33-421; E339A) (identified by SEQ ID NO: 53) and His-TnGalNAcT(33-421; I311Y) (identified by SEQ ID NO: 60).

TABLE 2

Sequence identification of the primers used.

| SEQ ID NO | Name | Nucleotide sequence |
|---|---|---|
| SEQ ID NO: 79 | W336F, fwd | C TCG AAT AAA TAT TGG GGT TTT GGC GGT GAA GAT GAC GAT ATG |
| SEQ ID NO: 80 | W336F, rev | CAT ATC GTC ATC TTC ACC GCC AAA ACC CCA ATA TTT ATT CGA G |
| SEQ ID NO: 81 | W336H, fwd | CG AAT AAA TAT TGG GGT CAC GGC GGT GAA GAT GAC G |
| SEQ ID NO: 82 | W336H, rev | C GTC ATC TTC ACC GCC GTG ACC CCA ATA TTT ATT CG |
| SEQ ID NO: 83 | W336V, fwd | CG AAT AAA TAT TGG GGT GTG GGC GGT GAA GAT GAC G |
| SEQ ID NO: 84 | W336V, rev | C GTC ATC TTC ACC GCC CAC ACC CCA ATA TTT ATT CG |
| SEQ ID NO: 85 | E339A, fwd | G GGT TGG GGC GGT GCG GAT GAC GAT ATG AGC |
| SEQ ID NO: 86 | E339A, rev | GCT CAT ATC GTC ATC CGC ACC GCC CCA ACC C |
| SEQ ID NO: 87 | E339G, fwd | G GGT TGG GGC GGT GGA GAT GAC GAT ATG AG |

TABLE 2 -continued

Sequence identification of the primers used.

| SEQ ID NO | Name | Nucleotide sequence |
|---|---|---|
| SEQ ID NO: 88 | E339G, rev | CT CAT ATC GTC ATC TCC ACC GCC CCA ACC C |
| SEQ ID NO: 89 | E339D, fwd | G GGT TGG GGC GGT GAT GAT GAC GAT ATG AGC |
| SEQ ID NO: 90 | E339D, rev | GCT CAT ATC GTC ATC ATC ACC GCC CCA ACC C |
| SEQ ID NO: 91 | I311Y, fwd | G CCG TAC GAA GAT TAT TTC GGC GGT GTC TCA G |
| SEQ ID NO: 92 | I311Y, rev | C TGA GAC ACC GCC GAA ATA ATC TTC GTA CGG C |

Codons corresponding to the mutated amino acid are in bold.

Example 4. Expression and Refolding of his-TnGalNAcT(33-421), his-TnGalNAcT(33-421; W336F), His-TnGalNAcT(33-421; W336V) and His-TnGalNAcT(33-421; E339A) in E. coli His-TnGalNAcT(33-421), His-TnGalNAcT(33-421; W336F), His-TnGalNAcT(33-421; W336V) and His-TnGalNAcT(33-421; E339A) were expressed from the corresponding pET15b-constructs which are obtained as described in Example 3. Expression, inclusion body isolation and refolding was performed according to the reported procedure by Qasba et al. (Prot. Expr. Pur. 2003, 30, 219-76229, incorporated by reference). After refolding, the insoluble protein was removed by centrifugation (10 minutes 8.000×g) followed by filtration through a 0.45 µM-pore diameter filter. The soluble protein was purified and concentrated using a HisTrap HP 5 mL column (GE Healthcare). The column was first washed with buffer A (20 mM Tris buffer, 20 mM imidazole, 500 mM NaCl, pH 7.5). Retained protein was eluted with buffer B (20 mM Tris, 500 mM NaCl, 250 mM imidazole, pH 7.5, 10 mL). Fractions were analyzed by SDS-PAGE on polyacrylamide gels (12%), and the fractions that contained purified target protein were combined and the buffer was exchanged against 20 mM Tris pH 7.5 and 150 mM NaCl by dialysis performed overnight at 4° C. The purified protein was concentrated to at least 2 mg/mL using an Amicon Ultra-0.5, Ultracel-10 Membrane (Millipore) and stored at −80 OC prior to further use.

Example 5. Transient Expression of GalNAcTs and Mutants in CHO

Proteins were transiently expressed in CHO K1 cells by Evitria (Zurich, Switzerland) at 20 mL scale. The following GalNAcT variants were expressed: CeGalNAcT(30-383) (identified by SEQ ID NO: 6), AsGalNAcT(30-383) (identified by SEQ ID NO: 7), TnGalNAcT(33-421) (identified by SEQ ID NO: 8), DmGalNAcT(47-403) (identified by SEQ ID NO: 9) and TnGalNAcT(33-421; E339A) (identified by SEQ ID NO: 28). In a typical purification experiment, CHO-produced supernatant containing the expressed GalNAcT was dialyzed against 20 mM Tris buffer, pH 7.5. The supernatant (typically 25 mL) was filtered through a 0.45 µM-pore diameter filter and subsequently purified over a cation exchange column (HiTrap SP HP 5 mL column, GE Healthcare), which was equilibrated with 20 mM Tris buffer, pH 7.5 prior to use. Purification was performed on an AKTA Prime chromatography system equipped with an external fraction collector. Samples were loaded from system pump A. The non-bound proteins were eluted from the column by washing the column with 10 column volumes (CV) of 20 mM Tris buffer, pH 7.5. Retained protein was eluted with elution buffer (20 mM Tris, 1 NaCl, pH 7.5; 10 mL). Collected fractions were analyzed by SDS-PAGE on polyacrylamide gels (12%), and fractions containing the target protein were combined and concentrated using spin filtration to a volume of 0.5 mL. Except for TnGalNAcT(33-421; E339A), the proteins were next purified on a Superdex200 10/300 GL size exclusion chromatography column (GE Healthcare) using an AKTA purifier-10 system (UNICORN v6.3) to obtain the pure monomeric fractions. Fractions were analyzed by SDS-PAGE and the fractions containing the monomeric protein were stored at −80° C. prior to further use.

General Protocol for Mass Spectral Analysis of IgG

Prior to mass spectral analysis, IgGs were either treated with DTT, which allows analysis of both light and heavy chain, or treated with Fabricator™ (commercially available from Genovis, Lund, Sweden), which allows analysis of the Fc/2 fragment. For analysis of both light and heavy chain, a solution of 20 µg (modified) IgG was incubated for 5 minutes at 37° C. with 100 mM DTT in a total volume of 4 µL. If present, azide-functionalities are reduced to amines under these conditions. For analysis of the Fc/2 fragment, a solution of 20 µg (modified) IgG was incubated for 1 hour at 37° C. with Fabricator™ (1.25 U/µL) in phosphate-buffered saline (PBS) pH 6.6 in a total volume of 10 µL. After reduction or Fabricator-digestion the samples were washed trice with milliQ using an Amicon Ultra-0.5, Ultracel-10 Membrane (Millipore) resulting in a final sample volume of approximately 40 µL. Next, the samples were analyzed by electrospray ionization time-of-flight (ESI-TOF) on a JEOL AccuTOF. Deconvoluted spectra were obtained using Magtran software.

Example 6. Preparation of Trimmed Trastuzumab by Endo S Treatment

Glycan trimming of trastuzumab was performed with endo S from Streptococcus pyogenes (commercially available from Genovis, Lund, Sweden). Thus, trastuzumab (10 mg/mL) was incubated with endo S (40 U/mL) in 25 mM Tris pH 8.0 for approximately 16 hours at 37° C. The deglycosylated IgG was concentrated and washed with 10 mM MnCl2 and 25 mM Tris-HCl pH 8.0 using an Amicon Ultra-0.5, Ultracel-10 Membrane (Millipore). After deconvolution of peaks, the mass spectrum showed one peak of the light chain and two peaks of the heavy chain. The two peaks of heavy chain belonged to one major product (49496 Da, 90% of total heavy chain), resulting from core GlcNAc (Fuc) substituted trastuzumab, and a minor product (49351 Da, ±10% of total heavy chain), resulting from trimmed trastuzumab.

Example 7. Glycosyltransfer of the 6-Azido-Gal-UDP to Trimmed Trastuzumab Under the Action of Bovine β(1,4)-Gal-T1

Trimmed trastuzumab (10 mg/mL), obtained by endo S treatment of trastuzumab as described above, was incubated with the 6-azido-Gal-UDP (1 mM, commercially available from GlycoHub) and either 0.1 or 0.5 mg/mL bovine β(1,4)Gal-T1 (commercially available from Sigma Aldrich) in 10 mM MnCl$_2$ and 25 mM Tris-HCl pH 8.0 at 30° C. overnight. Mass spectral analysis of the reduced samples indicated no product formation for both concentrations of bovine β(1,4)-Gal-T1 (major heavy chain peak of 49494 Da, 90% of total heavy chain, resulting from core GlcNAc(Fuc) substituted trastuzumab).

Example 8. Glycosyltransfer of the 6-Azido-N-Acetylgalactosamine-UDP to Trimmed Trastuzumab Under the Action of Bovine β(1, 4)-Gal-T (130-402; Y289L, C342T)

A mutant derived from bovine β(1,4)-Gal-T1 (identified by SEQ ID NO: 1) was used which contained the Y289L and C342T mutations and contains only the catalytic domain (amino acid residues 130-402). This bovine β(1,4)-Gal-T1 (130-402; Y289L,C342T) mutant is described by Qasba et al. (J. Biol. Chem. 2002, 277, 20833-20839, incorporated by reference) and was expressed, isolated and refolded from inclusion bodies according to the reported procedure by Qasba et al. (Prot. Expr. Pur. 2003, 30, 219-76229, incorporated by reference). Trimmed trastuzumab (10 mg/mL), obtained by endo S treatment of trastuzumab as described above, was incubated with 6-azido-GalNAc-UDP (2.5 mM, commercially available from GlycoHub) and 1 mg/mL β(1,4)-Gal-T1(130-402; Y289L,C342T) in 10 mM MnCl$_2$ and 25 mM Tris-HCl pH 7.5 at 37° C. overnight. Mass spectral analysis of the reduced samples indicated no product formation (major heavy chain peak of 49502 Da, 90% of total heavy chain, resulting from core GlcNAc(Fuc) substituted trastuzumab).

Example 9. Glycosyltransfer of the 6-Azido-N-Acetylgalactosamine-UDP to Trimmed Trastuzumab Under the Action of GalNAcTs Incorporation of 6-azidoGalNAc was tested for CeGalNAcT(30-383) (identified by SEQ ID NO: 6), AsGalNAcT (30-383) (identified by SEQ ID NO: 7), TnGalNAcT(33-421) (identified by SEQ ID NO: 8) and DmGalNAcT(47-403) (identified by SEQ ID NO: 9), which were expressed and purified as described in example 5. Trimmed trastuzumab (10 mg/mL), obtained by endo S treatment of trastuzumab as described above, was incubated with 6-azido-GalNAc-UDP (1 mM, commercially available from GlycoHub) in 10 mM MnCl$_2$ and 25 mM Tris-HCl pH 7.5 and either 0.2 or 0.5 mg/mL of one of the above mentioned GalNAcTs.

Mass spectral analysis of the Fabricator™-digested samples indicated no product formation for both concentrations of CeGalNAcT(30-383) and DmGalNAcT(47-403) (major Fc/2 peak of 24139 Da, 90% of total heavy chain, resulting from core GlcNAc(Fuc) substituted trastuzumab), while both AsGalNAcT(30-383) and TnGalNAcT(33-421) showed partial conversion of core GlcNac(Fuc)-substituted trastuzumab (observed mass 24139 Da) into the product (observed mass 24366 Da), resulting from transfer of 6-azido-GalNAc to core GlcNAc(Fuc)-substituted trastuzumab. The obtained conversions are shown in Table 3.

TABLE 3

Conversions (%) of GlcNAc(Fuc) substituted trastuzumab into 6-azido-GalNAc-GlcNAc(Fuc)-substituted trastuzumab by GalNAcTs at various enzyme concentrations.

|  | 0.2 mg/mL enzyme | 0.5 mg/mL enzyme |
| --- | --- | --- |
| CeGalNAcT (30-383) | 0 | 0 |
| DmGalNAcT (47-403) | 0 | 0 |
| AsGalNAcT (30-383) | 10 | 30 |
| TnGalNAcT (33-421) | 40 | 60 |

Scheme 1: Synthesis of compounds 88-94 and of modified glycoproteins 95-96 (Example 10-26).

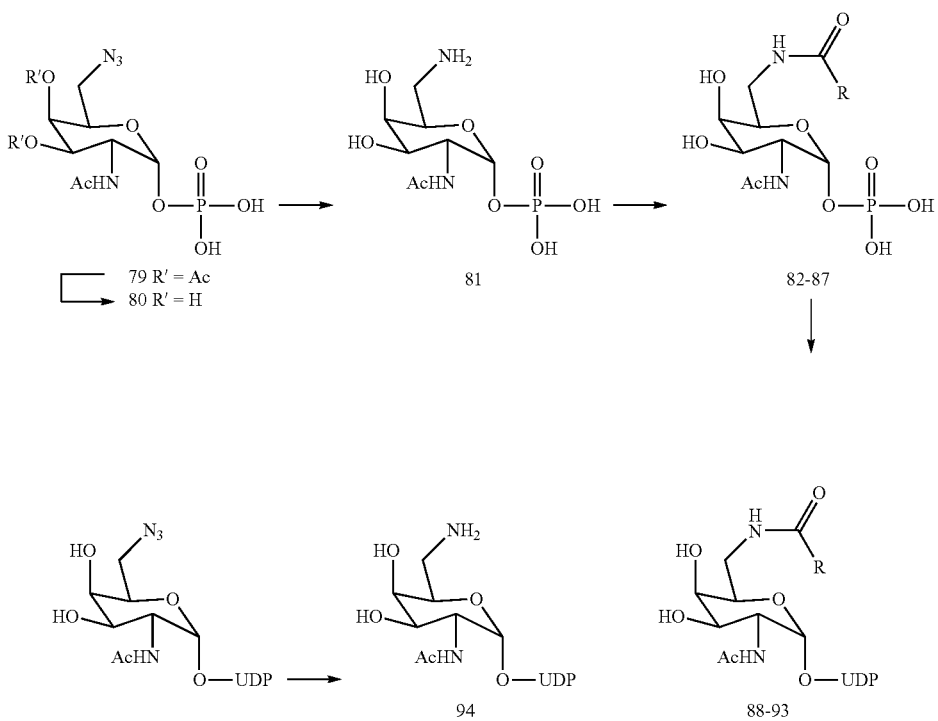

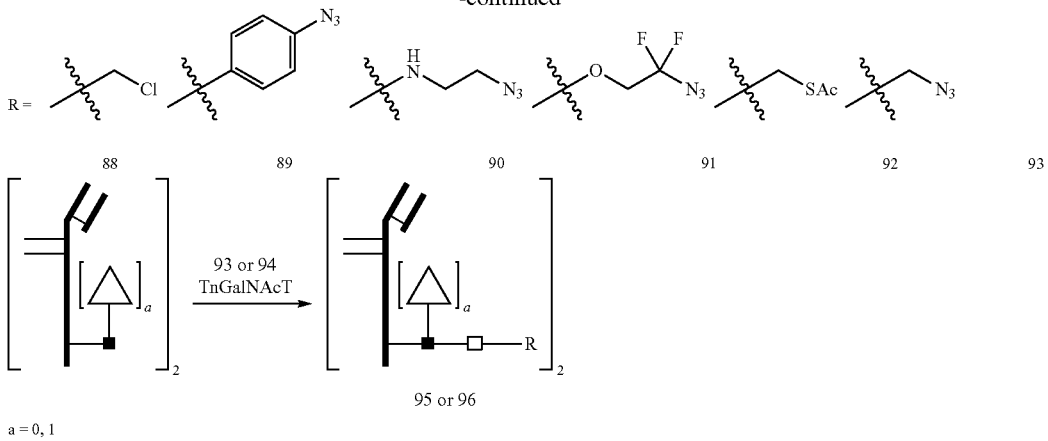

a = 0, 1

Example 10. Synthesis of 6-Azido-6-Deoxy-GalNAc-1-Monophosphate 80

The acetylated sugar 79 can be prepared according to the procedure in Wang et al, *Bioorg. Med. Chem. Lett.,* 2009, 19, 5433.

To a suspension of the acetylated sugar 79 (4.9 g, 11.9 mmol) in MeOH (15 mL), was added 25% aq. NH$_4$OH (60 mL). The reaction was allowed to stir at r.t. and the conversion monitored with LCMS. After 4 h, the mixture was concentrated under reduced pressure and stored at −20° C. for 2 d. The solid was then redissolved in 25% aq. NH$_4$OH (75 mL), stirred at r.t. and after 3 h, MS showed complete conversion. Concentration of the solvent gave the crude product as a yellow solid. A quantitative NMR was taken, showing that 60 wt % was product 80, giving a yield of 3.2 g (83%).

$^1$H-NMR (400 MHz, D$_2$O): δ 5.28 (dd, J=7.2, 3.2 Hz, 1H), 4.12 (dd, J=6.8, 6.4 Hz, 1H), 4.06 (ddd, J=10.8, 3.2, 2.0 Hz, 1H), 3.92-3.81 (m, 2H), 3.47 (dd, J=12.8, 7.2 Hz, 1H), 3.40 (dd, J=12.8 Hz, 6.4 Hz, 1H), 1.88 (s, 3H). LRMS (ESI−) calcd for C$_8$H$_{15}$N$_4$O$_8$P (M-H$^+$) 325.06, found 325.30.

Example 11. Synthesis of 6-amino-6-deoxy-GalNAc-1-monophosphate 81

To a solution of azide 80 (5.9 mmol) in H$_2$O (30 mL) and MeOH (30 mL) was added Pd/C (400 mg) and H$_2$ was bubbled through the reaction mixture for 1 h. The conversion of the reaction was monitored with TLC (7:3 MeOH:MeCN). The reaction mixture was filtered over celite, rinsed thoroughly with MeOH and H$_2$O and concentrated in vacuo to afford the crude product 81 in a yield of 1.8 g (99%).

$^1$H-NMR (400 MHz, D$_2$O): δ 5.28 (dd, J=7.2, 3.6 Hz, 1H), 4.25 (dd, J=8.8, 4.0 Hz, 1H), 4.09-4.04 (m, 1H), 3.90-3.79 (m, 2H), 3.19-3.08 (m, 2H), 1.85 (s, 3H). LRMS (ESI−) calcd for C$_8$H$_{17}$N$_2$O$_8$P (M-H$^+$) 299.06, found 229.29.

Example 12. Synthesis of 6-(2-chloroacetamido)-6-deoxy-GalNAc-1-monophosphate 82

Chloroacetic acid succinimidyl ester was prepared according to the procedure in Hosztafi et al., *Helv. Chim. Acta,* 1996, 79, 133.

To a solution of the sugar 81 (12 mg, 0.040 mmol) in dry DMF (0.5 mL) under a nitrogen atmosphere were added chloroacetic acid succinimidyl ester (9 mg, 0.044 mmol) and Et$_3$N (6.7 μL, 0.048 mmol). The reaction mixture was allowed to stir on at r.t. and concentrated in vacuo to afford the crude product 82.

$^1$H-NMR (400 MHz, D$_2$O): δ 5.42-5.32 (m, 1H), 4.13-4.02 (m, 4H), 3.92-3.81 (m, 2H), 3.53-3.46 (m, 1H), 3.33-3.26 (m, 1H), 1.94 (s, 3H). LRMS (ESI−) calcd for C$_{10}$H$_{18}$ClN$_2$O$_9$P (M-H$^+$) 375.68 (100%), 377.03 (30%), found 3.75.08 (100%), 377.19 (25%).

Example 13. Synthesis of 6-(4-azidobenzamido)-6-deoxy-GalNAc-1-monophosphate 83

4-Azidobenzoic acid succinimidyl ester was prepared according to the Hartman et al., *Chem. Comm.,* 2012, 48, 4755.

To a solution of the sugar 81 (38 mg, 0.127 mmol) in dry DMF (1.5 mL) under a nitrogen atmosphere were added Et$_3$N (21 μL, 0.152 mmol) and 4-azidobenzoic acid succinimidyl ester (36 mg, 0.139 mmol) and the reaction mixture was stirred at r.t. Additional 4-azidobenzoic acid succinimidyl ester (36 mg, 0.139 mmol) and Et$_3$N (42 uL, 0.304 mmol) were added and the reaction was allowed to stir for 5 d at r.t. Product formation was monitored with TLC and MS. The reaction mixture was concentrated after 6 d to afford the crude product 83.

LRMS (ESI−) calcd for C$_{15}$H$_{20}$N$_5$O$_9$P (M-H$^+$) 444.09, found 444.20.

Example 14. Synthesis of 6-(N-2-azido-2,2-difluoroethyl carbamate)-6-deoxy-GalNAc-1-monophosphate 84

2-Azido-2,2-difluoroethanol was prepared according to the procedure described in WO2015/112016.

2-Azido-2,2-difluoroethanol (200 mg, 1.63 mmol) was dissolved in DCM (10 mL) under a nitrogen atmosphere, 4-nitrophenylchloroformate (295 mg, 1.46 mmol) and Et$_3$N (226 μL, 1.63 mmol) were added and the resulting mixture was stirred at r.t. for 1 h. Next, sugar 81 (122 mg, 0.41 mmol) was dissolved in H$_2$O (2 mL), Et$_3$N (113 μL, 0.81 mmol) and DMF (5 mL) were added and the resulting solution was added to the reaction mixture. The reaction was allowed to stir at r.t. for 16 h, when TLC and LCMS confirmed full consumption of the sugar 81. The solvent was removed under reduced pressure to afford the crude product. Purification was performed with ion-exchange chromatography (Q HITRAP, 3×5 mL and 1×15 mL columns). First binding on the column was achieved via loading with buffer A (10 mM $NH_4HCO_3$) and the column was rinsed with buffer A. Next, a gradient to 40% B (250 mM $NH_4HCO_3$) was performed to elute the product and the column was flushed with 100% B to remove remaining byproducts. The fractions containing the product were lyophilized to afford the desired product 84 (147 mg, 0.33 mmol, 80%).

$^1$H-NMR (400 MHz, $D_2O$): δ 5.17 (dd, J=6.4, 3.2 Hz, 1H), 4.40-4.24 (m, 2H), 4.07-3.93 (m, 2H), 3.85-3.70 (m, 2H), 3.28-3.13 (m, 2H), 1.87 (s, 3H). LRMS (ESI-) calcd for $C_{11}H_{18}F2N_5O_{10}P$ (M-H$^+$) 448.07, found 448.14.

Example 15. Synthesis of 6-(N-1-(2-azidoethyl)urea)-6-deoxy-GalNAc-1-monophosphate 85

2-Azidoethylamine was prepared according to the procedure described in Zhang et al, *J. Am. Chem. Soc.*, 2015, 137, 6000. $^1$H-NMR (400 MHz, $CDCl_3$): δ 3.40-3.33 (m, 2H), 2.91-2.81 (m, 2H).

Carbonyldiimidazole (377 mg, 2.32 mmol) was dissolved in dry DMF (10 mL) and stirred under a nitrogen atmosphere. 2-Azidoethylamine (200 mg, 2.32 mmol) was dissolved in dry DMF (5 mL) and added dropwise to the CDI. The resulting solution was stirred for 1 h at r.t., followed by heating to 60° C. The sugar 81 was dissolved in $H_2O$ (2 mL) and DMF (5 mL) and added to the reaction. The resulting suspension was stirred for 16 h at 60° C. The formation of the desired product was monitored with LCMS. After stirring for 16 h, $H_2O$ (5 mL) was added, followed by addition of newly activated 2-azidoethylamine in DCM (15 mL). The resulting mixture was stirred again for 16 h at 60° C. and the solvent was removed under reduced pressure. The crude product was then dissolved in MeOH (10 mL) and $H_2O$ (15 mL) and washed with EtOAc (2×30 mL). The aqueous phase was concentrated to afford the crude product, which was purified with ion-exchange chromatography (Q-HITRAP, 3×5 mL and 1×15 mL columns). First binding on the column was achieved via loading with buffer A (10 mM $NH_4HCO_3$) and the column was rinsed with buffer A. Next, a gradient to 40% B (250 mM $NH_4HCO_3$) was performed to elute the product and the columns was flushed with 100% B to remove remaining byproducts. The fractions containing the product were lyophilized to afford the desired product 85 (147 mg, 0.33 mmol, 80%).

$^1$H-NMR (400 MHz, $D_2O$): δ 5.30 (br s, 1H), 4.13-3.93 (m, 2H), 3.91-3.76 (m, 2H), 3.35-3.10 (m, 5H), 1.92 (s, 3H). LRMS (ESI-) calcd for $C_{11}H_{21}N_6O_9P$ (M-H$^+$) 411.10, found 411.24.

Example 16. Synthesis of 6-(N-(2-S-acetyl)-mercaptoacetamido)-6-deoxy-GalNAc-1-monophosphate 86

The sugar 81 (105 mg, 0.35 mmol) was dissolved in $H_2O$ (1.7 mL) and stirred at r.t. In a separate vial S-acetylthioglycolic acid pentafluorophenyl ester (210 mg, 0.70 mmol) was dissolved in DMF (1.7 mL) and added to the reaction, together with $Et_3N$ (146 μL, 1.05 mmol). The resulting mixture was stirred for 16 h at r.t. when LCMS showed full consumption of the sugar 81. The solvent was removed under reduced pressure and the crude product purified by flash chromatography (6:2:1-4:2:1 EtOAc:MeOH:$H_2O$) to afford the product 86 (95 mg, 0.23 mmol, 65%).

$^1$H-NMR (400 MHz, $D_2O$): δ 5.33 (dd, J=6.8, 3.6 Hz, 1H), 4.11-4.00 (m, 2H), 3.90-3.80 (m, 2H), 3.63-3.53 (m, 2H), 3.44 (dd, J=14.0, 5.2 Hz, 1H), 3.23 (dd, J=14.0, 8.0 Hz, 1H), 2.31 (s, 3H), 1.94 (s, 3H). LRMS (ESI-) calcd for $C_{12}H_{21}N_2O_{10}PS$ (M-H$^+$) 415.06, found 415.18.

Example 17. Synthesis of 6-(N-2-azidoacetamido)-6-deoxy-GalNAc-1-monophosphate 87

Azidoacetic acid (101 mg, 1.0 mmol) was dissolved in DMF (2 mL) and EDC (192 mg, 1.0 mmol), NHS (115 mg, 1.0 mmol) and DMAP (4 mg, 0.03 mmol) were added. Next, the sugar 81 (100 mg, 0.33 mmol) was dissolved in $H_2O$ (3 mL), added to the reaction and stirred for 16 h at r.t. The formation of the desired product was monitored with LCMS. Another portion of azidoacetic acid was activated as described above and added to the reaction. After 4 h, the reaction was concentrated in vacuo. Purification was performed with ion-exchange chromatography (Q-HITRAP, 3×5 mL and 1×15 mL columns). First binding on the column was achieved via loading with buffer A (10 mM $NH_4HCO_3$) and the column was rinsed with buffer A. Next, a gradient to 40% buffer B (250 mM $NH_4HCO_3$) was performed to elute the product and the column was flushed with 100% buffer B to remove remaining byproducts. The fractions containing the product were lyophilized to afford the desired product 87 (100 mg, 0.26 mmol, 79%).

$^1$H-NMR (400 MHz, $D_2O$): δ 5.34 (br s, 1H), 4.13-4.03 (m, 2H), 3.93 (s, 2H), 3.92-3.81 (m, 2H), 3.48 (dd, J=14.0, 4.0 Hz, 1H), 3.29 (dd, J=14.0, 8.0 Hz, 1H), 1.95 (s, 3H). LRMS (ESI-) calcd for $C_{10}H_{18}N_5O_9P$ (M-H$^+$) 382.08, found 382.15.

Example 18. Synthesis of 6-(2-chloroacetamido)-6-deoxy-GalNAc-UDP 88

Monophosphate 82 was coupled to UMP according to a procedure described by Baisch et al. *Bioorg. Med. Chem.*, 1997, 5, 383.

In brief, tributylammonium uridine-5'-monophosphate (31 mg, 0.06 mmol) was dissolved in dry DMF (0.5 mL) under a nitrogen atmosphere. Carbonyldiimidazole (13 mg, 0.04 mmol) was added and the reaction mixture was stirred at r.t. for 30 min. Next, dry MeOH (2.5 μL) was added and stirred for 15 min to remove the excess CDI. The leftover MeOH was removed under high vacuum for 15 min. Subsequently, the monophosphate 82 (15 mg, 0.04 mmol) was dissolved in dry DMF (0.5 mL) and added to the reaction mixture, followed by N-methylimidazole, HCl salt (25 mg, 0.16 mmol). The reaction was allowed to stir at r.t. for o.n. before concentration in vacuo. The consumption of the monophosphate intermediate was monitored by MS. Purification was performed with ion-exchange chromatography (Q-HITRAP, 1×5 mL column). First binding on the column was achieved via loading with buffer A (10 mM $NH_4HCO_3$) and the column was rinsed with buffer A. Next, a gradient to 40% buffer B (250 mM $NH_4HCO_3$) was performed to elute the product and the column was flushed with 100% buffer B to remove remaining byproducts. The fractions containing the product were lyophilized to afford the desired product 88 (1 mg, 1.46 μmol, 4%).

LRMS (ESI-) calcd for $C_{19}H_{29}ClN_4O_{17}P_2$(M-H$^+$) 681.06 (100%), 683.06 (32%), found 681.13 (100%), 683.15 (40%).

Example 19. Synthesis of 6-(4-azidobenzamido)-6-deoxy-GalNAc-UDP 89

Monophosphate 83 was coupled to UMP according to a procedure described by Baisch et al. *Bioorg. Med. Chem.*, 1997, 5, 383.

In brief, tributylammonium uridine-5'-monophosphate (77 mg, 0.15 mmol) was dissolved in dry DMF (1 mL) under a nitrogen atmosphere. Carbonyldiimidazole (41 mg, 0.25 mmol) was added and the reaction mixture was stirred at r.t. for 30 min. Next, dry MeOH (6.2 µL) was added and stirred for 15 min to remove the excess CDI. The leftover MeOH was removed under high vacuum for 15 min. Subsequently, the monophosphate 83 (56 mg, 0.13 mmol) was dissolved in dry DMF (1 mL) and added to the reaction mixture, followed by N-methylimidazole, HCl salt (79 mg, 0.51 mmol). The reaction was allowed to stir at r.t. for o.n. before concentration in vacuo. The consumption of the monophosphate intermediate was monitored by MS. Purification was performed with ion-exchange chromatography (Q-HITRAP, 3×5 mL columns, 1×15 mL column). First binding on the column was achieved via loading with buffer A (10 mM NH$_4$HCO$_3$) and the column was rinsed with buffer A. Next, a gradient to 40% buffer B (250 mM NH$_4$HCO$_3$) was performed to elute the product and the column was flushed with 100% B to remove remaining byproducts. The fractions containing the product were lyophilized to afford the desired product 89 (13 mg, 0.017 mmol, 14%).

LRMS (ESI-) calcd for $C_{24}H_{31}N_7O_{17}P_2$(M-H$^+$) 750.12, found 750.33.

Example 20. Synthesis of 6-(N-2-azido-2,2-difluoroethyl carbamate)-6-deoxy-GalNAc-UDP 90

Monophosphate 84 was coupled to UMP according to a procedure described by Baisch et al. *Bioorg. Med. Chem.*, 1997, 5, 383.

In brief, tributylammonium uridine-5'-monophosphate (200 mg, 0.39 mmol) was dissolved in dry DMF (3 mL) under a nitrogen atmosphere. Carbonyldiimidazole (106 mg, 0.65 mmol) was added and the reaction mixture was stirred at r.t. for 30 min. Next, dry MeOH (16 µL) was added and stirred for 15 min to remove the excess CDI. The leftover MeOH was removed under high vacuum for 15 min. Subsequently, the monophosphate 84 (147 mg, 0.33 mmol) was suspended in dry DMF (3 mL) and added to the reaction mixture, followed by N-methylimidazole, HCl salt (204 mg, 1.31 mmol). The consumption of the monophosphate intermediate was monitored by MS. The reaction was allowed to stir at r.t. for 3 d. Another portion of UMP was activated as described above and added to the reaction together with 1 mL H$_2$O. After stirring for o.n., the reaction went to completion and the solvent was removed under reduced pressure. Purification was performed with ion-exchange chromatography (Q HITRAP, 3×5 mL columns, 1×15 mL column). First binding on the column was achieved via loading with buffer A (10 mM NH$_4$HCO$_3$) and the column was rinsed with buffer A. Next, a gradient to 40% buffer B (250 mM NH$_4$HCO$_3$) was performed to elute the product and the column was flushed with 100% buffer B to remove remaining byproducts. The fractions containing the product were lyophilized to afford the desired product 90 (122 mg, 0.16 mmol, 49%).

LRMS (ESI-) calcd for $C_{20}H_{29}F_2N_7O_{18}P_2$ (M-H$^+$) 754.09, found 754.16.

Example 21. Synthesis of 6-(N-1-(2-azidoethyl) urea)-6-deoxy-GalNAc-UDP 91

Monophosphate 85 was coupled to UMP according to a procedure described by Baisch et al. *Bioorg. Med. Chem.*, 1997, 5, 383.

In brief, tributylammonium uridine-5'-monophosphate (126 mg, 0.25 mmol) was dissolved in dry DMF (2 mL) under a nitrogen atmosphere. Carbonyldiimidazole (67 mg, 0.41 mmol) was added and the reaction mixture was stirred at r.t. for 30 min. Next, dry MeOH (10 µL) was added and stirred for 15 min to remove the excess CDI. The leftover MeOH was removed under high vacuum for 15 min. Subsequently, the monophosphate 85 (85 mg, 0.21 mmol) was dissolved in dry DMF (2 mL) and added to the reaction mixture, followed by N-methylimidazole, HCl salt (129 mg, 0.82 mmol). The reaction was allowed to stir at r.t. for 2 d before concentration in vacuo. The consumption of the monophosphate intermediate was monitored by MS. Purification was performed with ion-exchange chromatography (Q HITRAP, 3×5 mL columns, 1×15 mL column). First binding on the column was achieved via loading with buffer A (10 mM NH$_4$HCO$_3$) and the column was rinsed with buffer A. Next, a gradient to 40% buffer B (250 mM NH$_4$HCO$_3$) was performed to elute the product and the column was flushed with 100% buffer B to remove remaining byproducts. The fractions containing the product were lyophilized to afford the desired product 91 (83 mg, 012 mmol, 56%).

LRMS (ESI-) calcd for $C_{20}H_{32}N_8O_{17}P_2$(M-H$^+$) 717.13, found 717.27.

Example 22. Synthesis of 6-(N-(2-S-acetyl)-mercaptoacetamido)-6-deoxy-GalNAc-UDP 92

Monophosphate 86 was coupled to UMP according to a procedure described by Baisch et al. *Bioorg. Med. Chem.*, 1997, 5, 383.

In brief, tributylammonium uridine-5'-monophosphate (139 mg, 0.27 mmol) was dissolved in dry DMF (2 mL) under a nitrogen atmosphere. Carbonyldiimidazole (74 mg, 0.46 mmol) was added and the reaction mixture was stirred at r.t. for 30 min. Next, dry MeOH (11 µL) was added and stirred for 15 min to remove the excess CDI. The leftover MeOH was removed under high vacuum for 15 min. Subsequently, the monophosphate 86 (95 mg, 0.27 mmol) was dissolved in dry DMF (2 mL) and added to the reaction mixture, followed by N-methylimidazole, HCl salt (142 mg, 0.91 mmol). The reaction was allowed to stir at r.t. for 3 d before concentration in vacuo. The consumption of the monophosphate intermediate was monitored by MS. Purification was performed with flash chromatography (7:2:1-4:2:1 EtOAc:MeOH:H$_2$O) to afford the product 92 (97 mg, 0.13 mmol, 49%).

LRMS (ESI-) calcd for $C_{21}H_{32}N_4O_{18}P_2S$ (M-H$^+$) 721.08, found 721.39.

Example 23. Synthesis of 6-(2-azidoacetamido)-6-deoxy-GalNAc-UDP 93

Monophosphate 87 was coupled to UMP according to a procedure described by Baisch et al. *Bioorg. Med. Chem.*, 1997, 5, 383.

In brief, tributylammonium uridine-5'-monophosphate (191 mg, 0.38 mmol) was dissolved in dry DMF (3 mL) under a nitrogen atmosphere. Carbonyldiimidazole (102 mg, 0.63 mmol) was added and the reaction mixture was stirred at r.t. for 30 min. Next, dry MeOH (16 µL) was added and stirred for 15 min to remove the excess CDI. The leftover MeOH was removed under high vacuum for 15 min. Subsequently, the monophosphate 87 (120 mg, 0.31 mmol) was suspended in dry DMF (3 mL) and added to the reaction mixture, followed by N-methylimidazole, HCl salt (195 mg, 1.25 mmol). The consumption of the monophosphate intermediate was monitored by MS. The reaction was allowed to stir at r.t. for 16 h. To dissolve all components in the reaction, 1 mL H$_2$O was added. After stirring for 3 h, the solvent was removed under reduced pressure. Purification was performed with ion-exchange chromatography (Q-HITRAP, 3×5 mL columns, 1×15 mL column). First binding on the column was achieved via loading with buffer A (10 mM NH$_4$HCO$_3$) and the column was rinsed with buffer A. Next, a gradient to 40% buffer B (250 mM NH$_4$HCO$_3$) was performed to elute the product and the column was flushed with 100% buffer B to remove remaining byproducts. The fractions containing the product were lyophilized to afford the desired product 93 (10 mg, 0.015 mmol, 5%).

LRMS (ESI−) calcd for C$_{19}$H$_{29}$N$_7$O$_{17}$P$_2$ (M-H$^+$) 688.10, found 688.10.

Example 24. Synthesis of 6-amino-6-deoxy-GalNAc-UDP 94

To a solution of 6-azido-GalNAc-UDP (25 mg, 0.04 mmol) in H$_2$O (0.5 mL) were added DTT (6 mg, 0.04 mmol) and add a few drops of Et$_3$N. The reaction was stirred at r.t. for 2 h, and followed with LCMS. To speed up the reaction, extra DTT (12 mg, 0.08 mmol) was added, after 1 h the reaction was complete and concentrated in vacuo. Purification was performed with ion-exchange chromatography (Q-HITRAP, 1×5 mL column). First binding on the column was achieved via loading with buffer A (10 mM NH$_4$HCO$_3$) and the column was rinsed with buffer A. Next, a gradient to 40% buffer B (250 mM NH$_4$HCO$_3$) was performed to elute the product and the column was flushed with 100% buffer B to remove remaining byproducts. The fractions containing the product were lyophilized to afford the desired product 94 (12 mg, 0.019 mmol, 51%).

LRMS (ESI−) calcd for C17H$_{28}$N$_4$O$_{16}$P$_2$(M-H$^+$) 605.09, found 605.11.

Example 25. Preparation of brentuximab-(6-amino-6-deoxy-GalNAc), 95

Bentuximab was trimmed analogues to the trimming of trastuzumab as described in example 6.

Trimmed bentuximab (15 mg/mL) was incubated with 6-amino-6-deoxy-GalNAc-UDP 94 (5 mM) and TnGalNAcT (1.5 mg/mL) in 10 mM MnCl$_2$ and 25 mM Tris-HCl pH 8.0 at 30° C. overnight. A sample of the reaction mixture (2 µL) was incubated for 1 hour at 37° C. with Fabricator™ (1.25 U/µL) in phosphate-buffered saline (PBS) pH 6.6 in a total volume of 10 µL. Mass spectrometric analysis of this sample showed full conversion to the product brentuximab-(6-amino-GalNAc) (24307 Da (70%) and 24435 (30%, C-terminal lysine variant)).

Example 26. Preparation of brentuximab-(6-(2-azidoacetamido)-6-deoxy-GalNAc), 96

Trimmed bentuximab (15 mg/mL) was incubated with 6-(2-azidoacetamido)-6-deoxy-GalNAc 93 (5 mM) and TnGalNAcT (1.5 mg/mL) in 10 mM MnCl$_2$ and 25 mM Tris-HCl pH 8.0 at 30° C. overnight. A sample of the reaction mixture (2 µL) was incubated for 1 hour at 37° C. with Fabricator™ (1.25 U/µL) in phosphate-buffered saline (PBS) pH 6.6 in a total volume of 10 µL. Mass spectrometric analysis of this sample showed 70% conversion to the product brentuximab-(6-(2-azidoacetamido)-6-deoxy-GalNAc) (24391 Da (70%) and 24518 (30%, C-terminal lysine variant)).

The invention claimed is:

1. A process for the modification of a glycoprotein, the process comprising:

contacting a glycoprotein comprising a glycan comprising a terminal GlcNAc moiety, with a sugar-derivative nucleotide Su(A)-Nuc in the presence of a glycosyltransferase, wherein:
(i) the glycosyltransferase is, or is derived from, *Ascaris summ* β-(1,4)-N-acetylgalactosaminytransferase or *Trichoplusia ni* β-(1,4)-N-acetylgalactosaminyltransferase;

(ii) the glycan, comprising a terminal GlcNAc-moiety, is according to formula (1) and optionally (2)

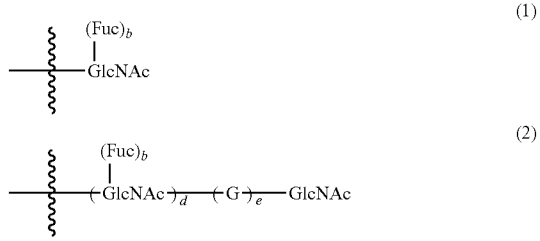

wherein:
b is 0 or 1;
d is 0 or 1;
e is 0 or 1; and
G is a monosaccharide, or a linear or branched oligosaccharide comprising 2 to 20 sugar moieties; and (iii) the sugar-derivative nucleotide Su(A)-Nuc is according to formula (3):

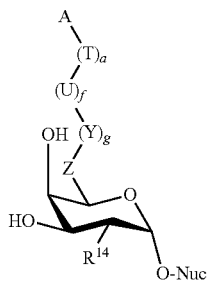
(3)

wherein:
a is 0 or 1;
f is 0 or 1;
g is 0 or 1;
Nuc is a nucleotide;
U is $[C(R^1)_2]n$ or $[C(R^1)_2]_p-O-[C(R^1)_2C(R^1)_2O]_o-[C(R^1)_2]_q$, wherein n is an integer in the range of 1 to 24; o is an integer in the range of 0 to 12; p and q are independently 0, 1 or 2; and $R^1$ is independently selected from the group consisting of H, F, Cl, Br, I, OH and an unsubstituted or substituted $C_1$-$C_{24}$ alkyl group;
T is a $C_3$-$C_{12}$ (hetero)arylene group, wherein the (hetero)arylene group is optionally substituted;
A is selected from the group consisting of:
  (a) —$N_3$
  (b) —C(O)$R^3$
    wherein $R^3$ is an unsubstituted or substituted $C_1$-$C_{24}$ alkyl group;
  (c) (hetero)cycloalkynyl group or a $(CH_2)_iC\equiv C-R^4$ moiety
    wherein i is 0-10 and $R^4$ is hydrogen or an unsubstituted or substituted $C_1$-$C_{24}$ alkyl group;
  (d) —SH
  (e) —SC(O)$R^8$
    wherein $R^8$ is an, unsubstituted or substituted, $C_1$-$C_{24}$ alkyl group or phenyl group;
  (f) —SC(V)O$R^8$
    wherein V is O or S, and $R^8$ is an, unsubstituted or substituted, $C_1$-$C_{24}$ alkyl group or phenyl group;
  (g) —X
    wherein X is selected from the group consisting of F, Cl, Br and I;
  (h) —OS(O)$_2R^5$
    wherein $R^5$ is selected from the group consisting of $C_1$-$C_{24}$ alkyl groups, $C_6$-$C_{24}$ aryl groups, $C_7$-$C_{24}$ alkylaryl groups and $C_7$-$C_{24}$ arylalkyl groups, groups, aryl groups, alkylaryl groups and arylalkyl groups being optionally substituted;
  (i) $R^{12}$
    wherein $R^{12}$ is selected from the group consisting of, unsubstituted or substituted, terminal $C_2$-$C_{24}$ alkenyl groups, $C_3$-$C_5$ cycloalkenyl groups and $C_4$-$C_8$ alkadienyl groups;
  (j) $R^{13}$
    wherein $R^{13}$ is unsubstituted or substituted terminal $C_3$-$C_{24}$ allenyl group; and
  (k) N(R')$_2$
wherein $R^{17}$ is independently selected from the group consisting of H and $C_1$-$C_{12}$ alkyl groups;
Z is $CH_2$, $CF_2$ or C(O); or Z is CHOH with the proviso that g is 0, f is 1 and a is 0 or 1;
Y is selected from the group consisting of O, S, N($R^{15}$), N($R^{15}$)C(O), N($R^{15}$)C(O)N($R^{15}$), N($R^{15}$)C(O)O, OC(O)N($R^{15}$)S(O)$_2$N($R^{15}$) and N($R^{15}$)C(O)N($R^{15}$)S(O)$_2$O, wherein $R^{15}$ is independently selected from the group consisting of H, $C_1$-$C_{12}$ alkyl groups and $(U)_f$-$(T)_a$-A wherein f, a, U, T and A are as defined above; and
$R^{14}$ is selected from the group consisting of:

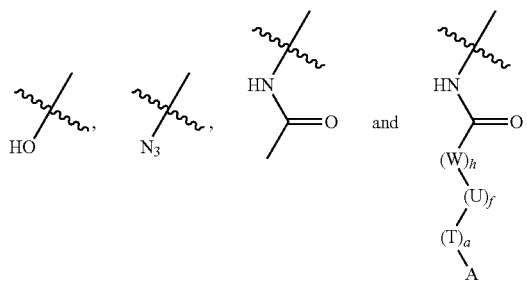

wherein:
a, f, T, A and U are as defined above;
h is 0 or 1; and
W is selected from the group consisting of O, S, $NR^{15}$, $NHS(O)_2O$ and $NHS(O)_2NR^{15}$, wherein $R^{15}$ is as defined above.

2. The process according to claim 1, wherein the β-(1,4)-N-acetylgalactosaminyltransferase is *Trichoplusia ni* β-(1,4)-N-acetylgalactosaminyltransferase.

3. The process according to claim 1, wherein A is selected from the group consisting of —$N_3$, —C(O)$CH_3$, —SH, —CH=$CH_2$ and —$CH_2C\equiv CH$.

4. The process according to claim 1, wherein the sugar-derivative nucleotide Su(A)-Nuc has formula (15), (16), (17) or (18):

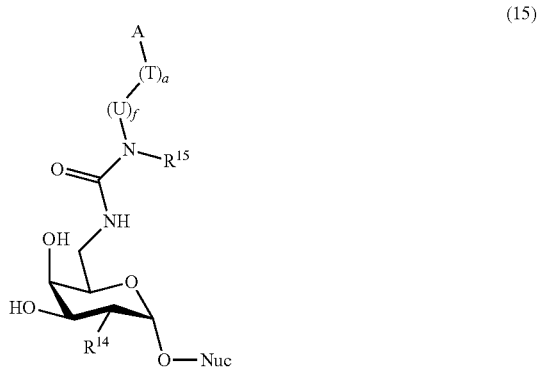
(15)

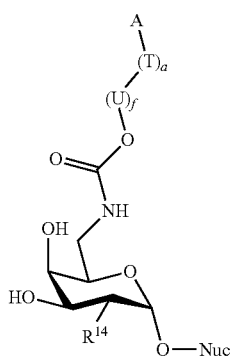
(16)
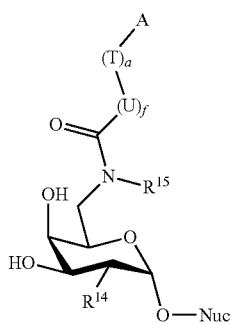
(17)
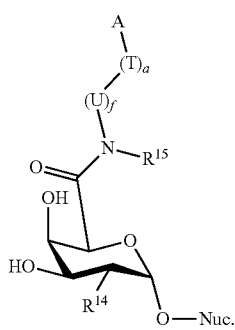
(18)
5. The process according to claim 1, wherein sugar-derivative nucleotide Su(A)-Nuc has formula (19), (20), (21), (22), (23), (24), (25), (26), (65), (66), (67), (68) or (69):
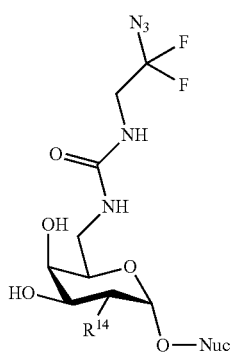
(19)
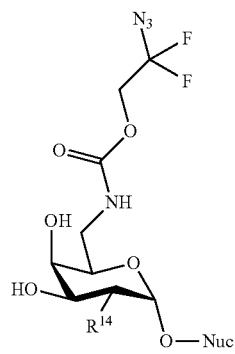
(20)
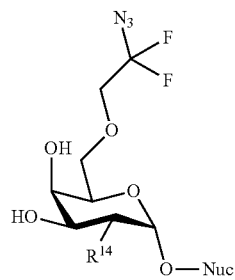
(21)
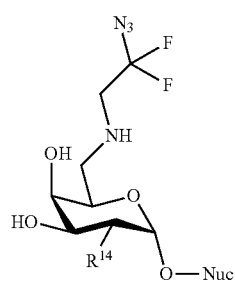
(22)
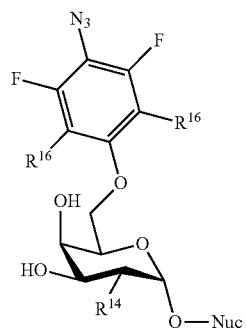
(23)
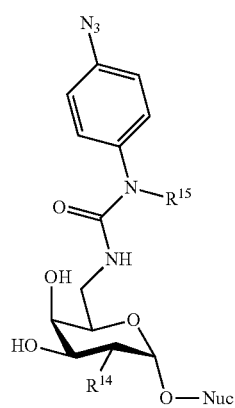
(24)

(25) 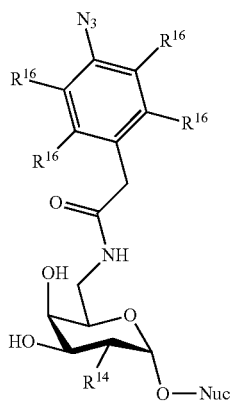

(26) 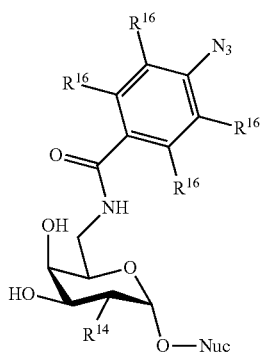

(65) 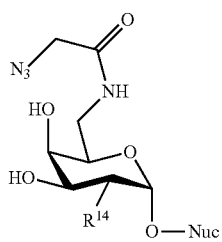

(66) 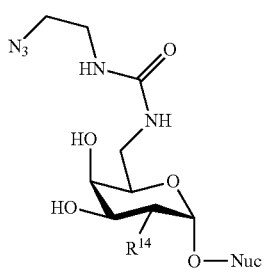

(67) 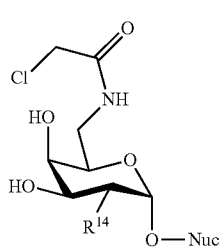

(68) 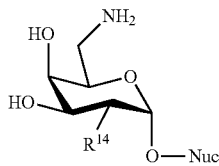

(69) 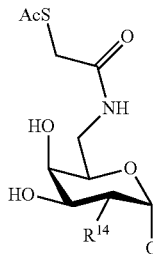

wherein:
$R^{14}$ and $R^{15}$ are as defined in claim; and
$R^{16}$ is independently selected from the group consisting of H and F.

6. The process according to claim 1, wherein the sugar-derivative nucleotide Su(A)-Nuc has formula (27):

(27) 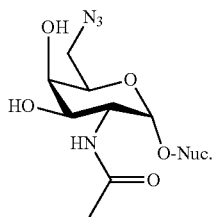

7. The process according to claim 1, wherein the nucleotide in sugar-derivative nucleotide Su(A)-Nuc is uridine diphosphate (UDP).

8. The process according to claim 1, wherein the glycan, comprising a terminal GlcNAc moiety, has formula (1), (9), (10) or (11):

(1) 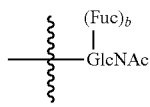

(9) 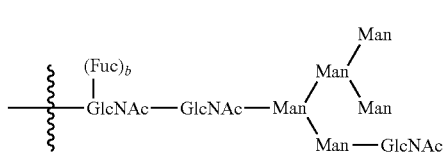

(10) 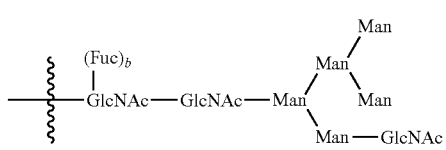

(11) 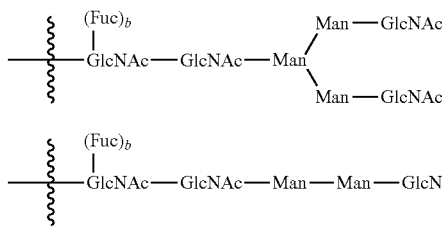

9. The process according to claim 1, wherein the glycoprotein comprising a glycan, comprising a terminal GlcNAc moiety, is according to B formula (7) or (8b):

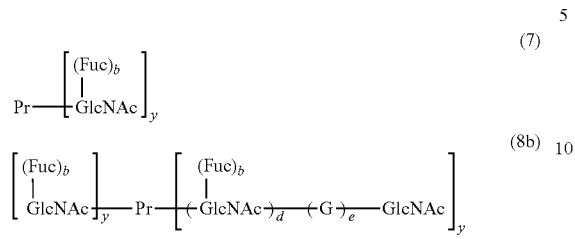

wherein:
b, d, e and G are as defined in claim 1;
y is independently an integer in the range of 1 to 24; and
Pr is a protein.

10. The process according to claim 1, wherein the glycoprotein, comprising a glycan comprising a terminal GlcNAc moiety, is an antibody.

11. The process according to claim 1, wherein $R^{14}$ is —NHC(O)Me.

* * * * *

SEQUENCE LISTING

```
<160> NUMBER OF SEQ ID NOS: 92

<210> SEQ ID NO 1
<211> LENGTH: 402
<212> TYPE: PRT
<213> ORGANISM: Artificial
<220> FEATURE:
<223> OTHER INFORMATION: Bos Taurus GalT Y289L mutant

<400> SEQUENCE: 1

Met Lys Phe Arg Glu Pro Leu Leu Gly Gly Ser Ala Ala Met Pro Gly
1               5                   10                  15

Ala Ser Leu Gln Arg Ala Cys Arg Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125
```

Arg Ser Leu Thr Ala Cys Pro Glu Ser Pro Leu Leu Val Gly Pro
            130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
            180                 185                 190

Glu His Leu Lys Tyr Trp Leu Tyr Tyr Leu His Pro Met Val Gln Arg
            195                 200                 205

Gln Gln Leu Asp Tyr Gly Ile Tyr Val Ile Asn Gln Ala Gly Glu Ser
            210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
            275                 280                 285

Leu Phe Gly Gly Val Ser Ala Leu Ser Lys Gln Gln Phe Leu Ser Ile
            290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
370                 375                 380

Val Gln Arg Tyr Pro Leu Tyr Thr Lys Ile Thr Val Asp Ile Gly Thr
385                 390                 395                 400

Pro Ser

<210> SEQ ID NO 2
<211> LENGTH: 383
<212> TYPE: PRT
<213> ORGANISM: Caenorhabditis elegans

<400> SEQUENCE: 2

Met Ala Phe Arg His Leu Ala Val Ala Arg Leu Lys Ser Leu Leu Val
1               5                   10                  15

Leu Cys Ala Val Leu Leu Leu Val His Ala Met Ile Tyr Lys Ile Pro
            20                  25                  30

Ser Leu Tyr Glu Asn Leu Thr Ile Gly Ser Ser Thr Leu Ile Ala Asp
            35                  40                  45

Val Asp Ala Met Glu Ala Val Leu Gly Asn Thr Ala Ser Thr Ser Asp
        50                  55                  60

Asp Leu Leu Asp Thr Trp Asn Ser Thr Phe Ser Pro Ile Ser Glu Val
65                  70                  75                  80

Asn Gln Thr Ser Phe Met Glu Asp Ile Arg Pro Ile Leu Phe Pro Asp
                85                  90                  95

Asn Gln Thr Leu Gln Phe Cys Asn Gln Thr Pro Pro His Leu Val Gly
            100                 105                 110

Pro Ile Arg Val Phe Leu Asp Glu Pro Asp Phe Lys Thr Leu Glu Lys
            115                 120                 125

Ile Tyr Pro Asp Thr His Ala Gly Gly His Gly Met Pro Lys Asp Cys
            130                 135                 140

Val Ala Arg His Arg Val Ala Ile Ile Val Pro Tyr Arg Asp Arg Glu
145                 150                 155                 160

Ala His Leu Arg Ile Met Leu His Asn Leu His Ser Leu Leu Ala Lys
                165                 170                 175

Gln Gln Leu Asp Tyr Ala Ile Phe Ile Val Glu Gln Val Ala Asn Gln
            180                 185                 190

Thr Phe Asn Arg Gly Lys Leu Met Asn Val Gly Tyr Asp Val Ala Ser
            195                 200                 205

Arg Leu Tyr Pro Trp Gln Cys Phe Ile Phe His Asp Val Asp Leu Leu
210                 215                 220

Pro Glu Asp Asp Arg Asn Leu Tyr Thr Cys Pro Ile Gln Pro Arg His
225                 230                 235                 240

Met Ser Val Ala Ile Asp Lys Phe Asn Tyr Lys Leu Pro Tyr Ser Ala
                245                 250                 255

Ile Phe Gly Gly Ile Ser Ala Leu Thr Lys Asp His Leu Lys Lys Ile
            260                 265                 270

Asn Gly Phe Ser Asn Asp Phe Trp Gly Trp Gly Glu Asp Asp Asp
            275                 280                 285

Leu Ala Thr Arg Thr Ser Met Ala Gly Leu Lys Val Ser Arg Tyr Pro
            290                 295                 300

Thr Gln Ile Ala Arg Tyr Lys Met Ile Lys His Ser Thr Glu Ala Thr
305                 310                 315                 320

Asn Pro Val Asn Lys Cys Arg Tyr Lys Ile Met Gly Gln Thr Lys Arg
                325                 330                 335

Arg Trp Thr Arg Asp Gly Leu Ser Asn Leu Lys Tyr Lys Leu Val Asn
            340                 345                 350

Leu Glu Leu Lys Pro Leu Tyr Thr Arg Ala Val Val Asp Leu Leu Glu
            355                 360                 365

Lys Asp Cys Arg Arg Glu Leu Arg Arg Asp Phe Pro Thr Cys Phe
            370                 375                 380

<210> SEQ ID NO 3
<211> LENGTH: 383
<212> TYPE: PRT
<213> ORGANISM: Ascaris suum

<400> SEQUENCE: 3

Met Asn Ser Lys Leu Lys Leu Val Ile Val Leu Thr Leu Cys Val Ala
1               5                   10                  15

Ile Ile His Phe Leu Leu Ser Asp Cys Pro Ile Ser Pro Asp Tyr Ser
            20                  25                  30

Phe Trp Ser Pro Ala Phe Ile Ile Ser Ala Pro Lys Thr Leu Thr Thr
        35                  40                  45

Leu Gln Pro Phe Ser Gln Ser Thr Ser Thr Asn Asp Leu Ala Val Ser
        50                  55                  60

Ala Leu Glu Ser Val Glu Phe Ser Met Leu Asp Asn Ser Ser Ile Leu
65                  70                  75                  80

His Ala Ser Asp Asn Trp Thr Asn Asp Glu Leu Val Met Arg Ala Gln

```
            85                  90                  95
Asn Glu Asn Leu Gln Leu Cys Pro Met Thr Pro Pro Ala Leu Val Gly
            100                 105                 110

Pro Ile Lys Val Trp Met Asp Ala Pro Ser Phe Ala Glu Leu Glu Arg
            115                 120                 125

Leu Tyr Pro Phe Leu Glu Pro Gly Gly His Gly Met Pro Thr Ala Cys
            130                 135                 140

Arg Ala Arg His Arg Val Ala Ile Val Val Pro Tyr Arg Asp Arg Glu
145                 150                 155                 160

Ser His Leu Arg Thr Phe Leu His Asn Leu His Ser Leu Leu Thr Lys
            165                 170                 175

Gln Gln Leu Asp Tyr Ala Ile Phe Val Val Glu Gln Thr Ala Asn Glu
            180                 185                 190

Thr Phe Asn Arg Ala Lys Leu Met Asn Val Gly Tyr Ala Glu Ala Ile
            195                 200                 205

Arg Leu Tyr Asp Trp Arg Cys Phe Ile Phe His Asp Val Asp Leu Leu
            210                 215                 220

Pro Glu Asp Asp Arg Asn Leu Tyr Ser Cys Pro Asp Glu Pro Arg His
225                 230                 235                 240

Met Ser Val Ala Val Asp Lys Phe Asn Tyr Lys Leu Pro Tyr Gly Ser
            245                 250                 255

Ile Phe Gly Gly Ile Ser Ala Leu Thr Arg Glu Gln Phe Glu Gly Ile
            260                 265                 270

Asn Gly Phe Ser Asn Asp Tyr Trp Gly Trp Gly Gly Glu Asp Asp Asp
            275                 280                 285

Leu Ser Thr Arg Val Thr Leu Ala Gly Tyr Lys Ile Ser Arg Tyr Pro
            290                 295                 300

Ala Glu Ile Ala Arg Tyr Lys Met Ile Lys His Asn Ser Glu Lys Lys
305                 310                 315                 320

Asn Pro Val Asn Arg Cys Arg Tyr Lys Leu Met Ser Ala Thr Lys Ser
            325                 330                 335

Arg Trp Arg Asn Asp Gly Leu Ser Ser Leu Ser Tyr Asp Leu Ile Ser
            340                 345                 350

Leu Gly Arg Leu Pro Leu Tyr Thr His Ile Lys Val Asp Leu Leu Glu
            355                 360                 365

Lys Gln Ser Arg Arg Tyr Leu Arg Thr His Gly Phe Pro Thr Cys
            370                 375                 380

<210> SEQ ID NO 4
<211> LENGTH: 421
<212> TYPE: PRT
<213> ORGANISM: Trichoplusia ni

<400> SEQUENCE: 4

Met Gly Gly Arg Ala Thr Arg Ala Leu Arg Leu Leu Leu Leu Leu Val
1               5                   10                  15

Leu Ala Leu Ala Ala Val Glu Tyr Leu Phe Gly Ser Ile Leu Asp Ala
            20                  25                  30

Ser Pro Leu Arg Thr Tyr Leu Tyr Thr Pro Leu Tyr Asn Ala Thr Gln
            35                  40                  45

Pro Thr Leu Arg Asn Val Glu Arg Leu Ala Ala Asn Trp Pro Lys Lys
            50                  55                  60

Ile Pro Ser Asn Tyr Ile Glu Asp Ser Glu Tyr Ser Ile Lys Asn
65                  70                  75                  80
```

Ile Ser Leu Ser Asn His Thr Thr Arg Ala Ser Val Val His Pro Pro
              85                  90                  95

Ser Ser Ile Thr Glu Thr Ala Ser Lys Leu Asp Lys Asn Met Thr Ile
            100                 105                 110

Gln Asp Gly Ala Phe Ala Met Ile Ser Pro Thr Pro Leu Leu Ile Thr
        115                 120                 125

Lys Leu Met Asp Ser Ile Lys Ser Tyr Val Thr Thr Glu Asp Gly Val
    130                 135                 140

Lys Lys Ala Glu Ala Val Val Thr Leu Pro Leu Cys Asp Ser Met Pro
145                 150                 155                 160

Pro Asp Leu Gly Pro Ile Thr Leu Asn Lys Thr Glu Leu Glu Leu Glu
                165                 170                 175

Trp Val Glu Lys Lys Phe Pro Glu Val Glu Trp Gly Gly Arg Tyr Ser
            180                 185                 190

Pro Pro Asn Cys Thr Ala Arg His Arg Val Ala Ile Ile Val Pro Tyr
        195                 200                 205

Arg Asp Arg Gln Gln His Leu Ala Ile Phe Leu Asn His Met His Pro
    210                 215                 220

Phe Leu Met Lys Gln Gln Ile Glu Tyr Gly Ile Phe Ile Val Glu Gln
225                 230                 235                 240

Glu Gly Asn Lys Asp Phe Asn Arg Ala Lys Leu Met Asn Val Gly Phe
                245                 250                 255

Val Glu Ser Gln Lys Leu Val Ala Glu Gly Trp Gln Cys Phe Val Phe
            260                 265                 270

His Asp Ile Asp Leu Leu Pro Leu Asp Thr Arg Asn Leu Tyr Ser Cys
        275                 280                 285

Pro Arg Gln Pro Arg His Met Ser Ala Ser Ile Asp Lys Leu His Phe
    290                 295                 300

Lys Leu Pro Tyr Glu Asp Ile Phe Gly Gly Val Ser Ala Met Thr Leu
305                 310                 315                 320

Glu Gln Phe Thr Arg Val Asn Gly Phe Ser Asn Lys Tyr Trp Gly Trp
                325                 330                 335

Gly Gly Glu Asp Asp Asp Met Ser Tyr Arg Leu Lys Lys Ile Asn Tyr
            340                 345                 350

His Ile Ala Arg Tyr Lys Met Ser Ile Ala Arg Tyr Ala Met Leu Asp
        355                 360                 365

His Lys Lys Ser Thr Pro Asn Pro Lys Arg Tyr Gln Leu Leu Ser Gln
    370                 375                 380

Thr Ser Leu Thr Phe Gln Lys Asp Gly Leu Ser Thr Leu Glu Tyr Glu
385                 390                 395                 400

Leu Val Gln Val Gln Tyr His Leu Tyr Thr His Ile Leu Val Asn
                405                 410                 415

Ile Asp Glu Arg Ser
            420

<210> SEQ ID NO 5
<211> LENGTH: 403
<212> TYPE: PRT
<213> ORGANISM: Drosophila melanogaster

<400> SEQUENCE: 5

Met Tyr Leu Phe Thr Lys Ala Asn Leu Ile Arg Phe Leu Ala Gly Ala
1               5                   10                  15

Ile Cys Leu Leu Leu Val Leu Asn Phe Val Gly Phe Arg Ser Asp Gly
            20                  25                  30

```
Gly Ser Ala Thr Ser Leu Ser Lys Leu Ser Ile Arg Arg Val His Lys
            35                  40                  45

Tyr Ala His Ile Tyr Gly Asn Ala Ser Ser Asp Gly Ala Gly Gly Ser
 50                  55                  60

Glu Ala Ser Arg Leu Pro Ala Ser Pro Leu Ala Leu Ser Lys Asp Arg
 65                  70                  75                  80

Glu Arg Asp Gln Glu Leu Asn Gly Gly Pro Asn Ser Thr Ile Arg Thr
                 85                  90                  95

Val Ile Ala Thr Ala Asn Phe Thr Ser Ile Pro Gln Asp Leu Thr Arg
                100                 105                 110

Phe Leu Leu Gly Thr Lys Lys Phe Leu Pro Pro Arg Gln Lys Ser Thr
                115                 120                 125

Ser Ala Leu Leu Ala Asn Cys Thr Asp Pro Asp Pro Arg Asp Gly Gly
            130                 135                 140

Pro Ile Thr Pro Asn Thr Thr Leu Glu Ser Leu Asp Val Ile Glu Ala
145                 150                 155                 160

Glu Leu Gly Pro Leu Leu Arg Pro Gly Gly Ala Phe Glu Pro Glu Asn
                165                 170                 175

Cys Asn Ala Gln His His Val Ala Ile Val Pro Phe Arg Asp Arg
            180                 185                 190

Tyr Ala His Leu Leu Leu Phe Leu Arg Asn Ile His Pro Phe Leu Met
            195                 200                 205

Lys Gln Arg Ile Ala Tyr Arg Ile Phe Ile Val Glu Gln Thr Asn Gly
            210                 215                 220

Lys Pro Phe Asn Arg Ala Ala Met Met Asn Ile Gly Tyr Leu Glu Ala
225                 230                 235                 240

Leu Lys Leu Tyr Gln Trp Asp Cys Phe Ile Phe His Asp Val Asp Leu
                245                 250                 255

Leu Pro Leu Asp Asp Arg Asn Leu Tyr Asn Cys Pro Arg Gln Pro Arg
                260                 265                 270

His Met Ser Val Ala Ile Asp Thr Leu Asn Phe Arg Leu Pro Tyr Arg
            275                 280                 285

Ser Ile Phe Gly Gly Val Ser Ala Met Thr Arg Glu His Phe Gln Ala
            290                 295                 300

Val Asn Gly Phe Ser Asn Ser Phe Phe Gly Trp Gly Gly Glu Asp Asp
305                 310                 315                 320

Asp Met Ser Asn Arg Leu Lys His Ala Asn Leu Phe Ile Ser Arg Tyr
                325                 330                 335

Pro Val Asn Ile Ala Arg Tyr Lys Met Leu Lys His Gln Lys Glu Lys
                340                 345                 350

Ala Asn Pro Lys Arg Tyr Glu Asn Leu Gln Asn Gly Met Ser Lys Ile
            355                 360                 365

Glu Gln Asp Gly Ile Asn Ser Ile Lys Tyr Ser Ile Tyr Ser Ile Lys
            370                 375                 380

Gln Phe Pro Thr Phe Thr Trp Tyr Leu Ala Glu Leu Lys Asn Ser Glu
385                 390                 395                 400

Arg Lys Ser

<210> SEQ ID NO 6
<211> LENGTH: 354
<212> TYPE: PRT
<213> ORGANISM: Artificial
<220> FEATURE:
<223> OTHER INFORMATION: CeGalNAcT(30-383)
```

<400> SEQUENCE: 6

```
Lys Ile Pro Ser Leu Tyr Glu Asn Leu Thr Ile Gly Ser Ser Thr Leu
  1               5                  10                  15

Ile Ala Asp Val Asp Ala Met Glu Ala Val Leu Gly Asn Thr Ala Ser
             20                  25                  30

Thr Ser Asp Asp Leu Leu Asp Thr Trp Asn Ser Thr Phe Ser Pro Ile
         35                  40                  45

Ser Glu Val Asn Gln Thr Ser Phe Met Glu Asp Ile Arg Pro Ile Leu
     50                  55                  60

Phe Pro Asp Asn Gln Thr Leu Gln Phe Cys Asn Gln Thr Pro Pro His
 65                  70                  75                  80

Leu Val Gly Pro Ile Arg Val Phe Leu Asp Glu Pro Asp Phe Lys Thr
                 85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ile Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe
```

<210> SEQ ID NO 7
<211> LENGTH: 354
<212> TYPE: PRT
<213> ORGANISM: Artificial
<220> FEATURE:
<223> OTHER INFORMATION: AsGalNAcT (30-383)

<400> SEQUENCE: 7

| | | | | | | | | | | | | | | | |
|---|---|---|---|---|---|---|---|---|---|---|---|---|---|---|---|
Asp Tyr Ser Phe Trp Ser Pro Ala Phe Ile Ile Ser Ala Pro Lys Thr
1               5                   10                  15

Leu Thr Thr Leu Gln Pro Phe Ser Gln Ser Thr Ser Thr Asn Asp Leu
            20                  25                  30

Ala Val Ser Ala Leu Glu Ser Val Glu Phe Ser Met Leu Asp Asn Ser
        35                  40                  45

Ser Ile Leu His Ala Ser Asp Asn Trp Thr Asn Asp Glu Leu Val Met
    50                  55                  60

Arg Ala Gln Asn Glu Asn Leu Gln Leu Cys Pro Met Thr Pro Pro Ala
65                  70                  75                  80

Leu Val Gly Pro Ile Lys Val Trp Met Asp Ala Pro Ser Phe Ala Glu
                85                  90                  95

Leu Glu Arg Leu Tyr Pro Phe Leu Glu Pro Gly Gly His Gly Met Pro
            100                 105                 110

Thr Ala Cys Arg Ala Arg His Arg Val Ala Ile Val Val Pro Tyr Arg
        115                 120                 125

Asp Arg Glu Ser His Leu Arg Thr Phe Leu His Asn Leu His Ser Leu
    130                 135                 140

Leu Thr Lys Gln Gln Leu Asp Tyr Ala Ile Phe Val Val Glu Gln Thr
145                 150                 155                 160

Ala Asn Glu Thr Phe Asn Arg Ala Lys Leu Met Asn Val Gly Tyr Ala
                165                 170                 175

Glu Ala Ile Arg Leu Tyr Asp Trp Arg Cys Phe Ile Phe His Asp Val
            180                 185                 190

Asp Leu Leu Pro Glu Asp Asp Arg Asn Leu Tyr Ser Cys Pro Asp Glu
        195                 200                 205

Pro Arg His Met Ser Val Ala Val Asp Lys Phe Asn Tyr Lys Leu Pro
    210                 215                 220

Tyr Gly Ser Ile Phe Gly Gly Ile Ser Ala Leu Thr Arg Glu Gln Phe
225                 230                 235                 240

Glu Gly Ile Asn Gly Phe Ser Asn Asp Tyr Trp Gly Trp Gly Gly Glu
                245                 250                 255

Asp Asp Asp Leu Ser Thr Arg Val Thr Leu Ala Gly Tyr Lys Ile Ser
            260                 265                 270

Arg Tyr Pro Ala Glu Ile Ala Arg Tyr Lys Met Ile Lys His Asn Ser
        275                 280                 285

Glu Lys Lys Asn Pro Val Asn Arg Cys Arg Tyr Lys Leu Met Ser Ala
    290                 295                 300

Thr Lys Ser Arg Trp Arg Asn Asp Gly Leu Ser Ser Leu Ser Tyr Asp
305                 310                 315                 320

Leu Ile Ser Leu Gly Arg Leu Pro Leu Tyr Thr His Ile Lys Val Asp
                325                 330                 335

Leu Leu Glu Lys Gln Ser Arg Arg Tyr Leu Arg Thr His Gly Phe Pro
            340                 345                 350

Thr Cys

<210> SEQ ID NO 8
<211> LENGTH: 389
<212> TYPE: PRT
<213> ORGANISM: Artificial
<220> FEATURE:
<223> OTHER INFORMATION: TnGalNAcT(33-421)

<400> SEQUENCE: 8

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
                20                  25                  30

Ile Pro Ser Asn Tyr Ile Glu Asp Ser Glu Gly Tyr Ser Ile Lys Asn
            35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65              70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
                100                 105                 110

Lys Lys Ala Glu Ala Val Val Thr Leu Pro Leu Cys Asp Ser Met Pro
            115                 120                 125

Pro Asp Leu Gly Pro Ile Thr Leu Asn Lys Thr Glu Leu Glu Leu Glu
            130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
            210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
            275                 280                 285

Glu Gln Phe Thr Arg Val Asn Gly Phe Ser Asn Lys Tyr Trp Gly Trp
            290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
            370                 375                 380

Ile Asp Glu Arg Ser
385

<210> SEQ ID NO 9
<211> LENGTH: 357

```
<212> TYPE: PRT
<213> ORGANISM: Artificial
<220> FEATURE:
<223> OTHER INFORMATION: DmGalNAcT (47-403)

<400> SEQUENCE: 9

His Lys Tyr Ala His Ile Tyr Gly Asn Ala Ser Ser Asp Gly Ala Gly
  1               5                  10                  15

Gly Ser Glu Ala Ser Arg Leu Pro Ala Ser Pro Leu Ala Leu Ser Lys
             20                  25                  30

Asp Arg Glu Arg Asp Gln Glu Leu Asn Gly Gly Pro Asn Ser Thr Ile
         35                  40                  45

Arg Thr Val Ile Ala Thr Ala Asn Phe Thr Ser Ile Pro Gln Asp Leu
 50                  55                  60

Thr Arg Phe Leu Leu Gly Thr Lys Lys Phe Leu Pro Pro Arg Gln Lys
 65                  70                  75                  80

Ser Thr Ser Ala Leu Leu Ala Asn Cys Thr Asp Pro Asp Pro Arg Asp
                 85                  90                  95

Gly Gly Pro Ile Thr Pro Asn Thr Thr Leu Glu Ser Leu Asp Val Ile
            100                 105                 110

Glu Ala Glu Leu Gly Pro Leu Leu Arg Pro Gly Gly Ala Phe Glu Pro
        115                 120                 125

Glu Asn Cys Asn Ala Gln His His Val Ala Ile Val Val Pro Phe Arg
130                 135                 140

Asp Arg Tyr Ala His Leu Leu Leu Phe Leu Arg Asn Ile His Pro Phe
145                 150                 155                 160

Leu Met Lys Gln Arg Ile Ala Tyr Arg Ile Phe Ile Val Glu Gln Thr
                165                 170                 175

Asn Gly Lys Pro Phe Asn Arg Ala Ala Met Met Asn Ile Gly Tyr Leu
            180                 185                 190

Glu Ala Leu Lys Leu Tyr Gln Trp Asp Cys Phe Ile Phe His Asp Val
        195                 200                 205

Asp Leu Leu Pro Leu Asp Asp Arg Asn Leu Tyr Asn Cys Pro Arg Gln
210                 215                 220

Pro Arg His Met Ser Val Ala Ile Asp Thr Leu Asn Phe Arg Leu Pro
225                 230                 235                 240

Tyr Arg Ser Ile Phe Gly Gly Val Ser Ala Met Thr Arg Glu His Phe
                245                 250                 255

Gln Ala Val Asn Gly Phe Ser Asn Ser Phe Phe Gly Trp Gly Gly Glu
            260                 265                 270

Asp Asp Asp Met Ser Asn Arg Leu Lys His Ala Asn Leu Phe Ile Ser
        275                 280                 285

Arg Tyr Pro Val Asn Ile Ala Arg Tyr Lys Met Leu Lys His Gln Lys
290                 295                 300

Glu Lys Ala Asn Pro Lys Arg Tyr Glu Asn Leu Gln Asn Gly Met Ser
305                 310                 315                 320

Lys Ile Glu Gln Asp Gly Ile Asn Ser Ile Lys Tyr Ser Ile Tyr Ser
                325                 330                 335

Ile Lys Gln Phe Pro Thr Phe Thr Trp Tyr Leu Ala Glu Leu Lys Asn
            340                 345                 350

Ser Glu Arg Lys Ser
        355

<210> SEQ ID NO 10
<211> LENGTH: 354
```

<212> TYPE: PRT
<213> ORGANISM: Artificial
<220> FEATURE:
<223> OTHER INFORMATION: CeGalNacT(30-383; I257L)

<400> SEQUENCE: 10

```
Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
    195                 200                 205

Pro Arg His Met Ser Val Ala Ile Asp Lys Phe Asn Tyr Lys Leu Pro
210                 215                 220

Tyr Ser Ala Leu Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe
```

<210> SEQ ID NO 11
<211> LENGTH: 354
<212> TYPE: PRT

<213> ORGANISM: Artificial
<220> FEATURE:
<223> OTHER INFORMATION: CeGalNAcT(30-383; I257M)

<400> SEQUENCE: 11

```
Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Met Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe
```

<210> SEQ ID NO 12
<211> LENGTH: 354
<212> TYPE: PRT
<213> ORGANISM: Artificial

<220> FEATURE:
<223> OTHER INFORMATION: CeGalNacT(30-383; I257A)

<400> SEQUENCE: 12

Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ala Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe

<210> SEQ ID NO 13
<211> LENGTH: 354
<212> TYPE: PRT
<213> ORGANISM: Artificial
<220> FEATURE:

<223> OTHER INFORMATION: CeGalNacT(30-383; M312H)

<400> SEQUENCE: 13

```
Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ile Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys His Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe
```

<210> SEQ ID NO 14
<211> LENGTH: 360
<212> TYPE: PRT
<213> ORGANISM: Artificial
<220> FEATURE:
<223> OTHER INFORMATION: CeGalNAcT(30-383)-His

<400> SEQUENCE: 14

```
Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ile Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe His His His His His
        355                 360
```

<210> SEQ ID NO 15
<211> LENGTH: 383
<212> TYPE: PRT
<213> ORGANISM: Caenorhabditis remanei

<400> SEQUENCE: 15

```
Met Ala Leu Arg His Leu Ala Val Ala Lys Leu Lys Thr Phe Phe Val
1               5                   10                  15

Leu Cys Ala Ala Leu Leu Val His Thr Met Ile Tyr Lys Ala Pro
            20                  25                  30

Ser Leu Tyr Glu Asn Phe Ser Ile Gly Ser Ser Thr Leu Ile Ala Asp
        35                  40                  45

Val Asp Ala Met Glu Ala Val Leu Gly Asn Thr Ala Ser Thr Ser Tyr
50                  55                  60

Asp Leu Leu Asp Thr Trp Asn Ser Thr Phe Ser Pro Ile Ser Glu Val
65                  70                  75                  80

Asn Gln Thr Ser Phe Leu Glu Asp Val Arg Pro Ile Leu Phe Thr Asp
                85                  90                  95

Asn Gln Thr Lys Pro Phe Cys Asn Gln Thr Pro Pro His Leu Val Gly
            100                 105                 110

Pro Ile Arg Val Phe Leu Asp Glu Pro Asp Phe Ala Thr Leu Glu Lys
        115                 120                 125

Ile Tyr Pro Asp Val His Thr Gly Gly His Gly Ile Pro Asp Glu Cys
        130                 135                 140

Ile Ala Arg His Arg Val Ala Val Ile Val Pro Tyr Arg Asp Arg Glu
145                 150                 155                 160

Ala His Leu Arg Ile Met Leu His Asn Leu His Ser Leu Leu Ala Lys
                165                 170                 175

Gln Gln Leu Asp Tyr Ala Ile Ile Val Val Glu Gln Ile Val Asn Gln
            180                 185                 190

Thr Phe Asn Arg Gly Lys Leu Met Asn Val Gly Tyr Asp Val Ala Ser
        195                 200                 205

Arg Leu Tyr Pro Trp Gln Cys Phe Ile Phe His Asp Val Asp Leu Leu
210                 215                 220

Pro Glu Asp Asp Arg Asn Leu Tyr Thr Cys Pro Ile Gln Pro Arg His
225                 230                 235                 240

Met Ser Val Ala Ile Asp Lys Phe Asp Tyr Lys Leu Pro Tyr Ser Thr
                245                 250                 255

Ile Phe Gly Gly Ile Ser Ala Leu Thr Gln Glu His Val Lys Lys Ile
            260                 265                 270

Asn Gly Phe Ser Asn Asp Phe Trp Gly Trp Gly Gly Glu Asp Asp Asp
        275                 280                 285

Leu Ala Thr Arg Thr Ser Met Ala Gly Leu Lys Val Ser Arg Tyr Pro
290                 295                 300

Ala Gln Ile Ala Arg Tyr Lys Met Ile Lys His Ser Thr Glu Ala Thr
305                 310                 315                 320

Asn Pro Val Asn Lys Cys Arg Tyr Lys Ile Met Gly Gln Thr Lys Arg
                325                 330                 335

Arg Trp Thr Arg Asp Gly Leu Ser Ser Leu Lys Tyr Lys Leu Val Lys
            340                 345                 350

Leu Asp Leu Lys Pro Leu Tyr Thr Arg Ala Val Val Asp Leu Leu Glu
        355                 360                 365

Lys Asp Cys Arg Arg Glu Leu Arg Lys Asp Phe Pro Thr Cys Phe
370                 375                 380
```

<210> SEQ ID NO 16
<211> LENGTH: 384
<212> TYPE: PRT
<213> ORGANISM: Caenorhabditis briggsae

<400> SEQUENCE: 16

```
Met Ala Phe Arg His Leu Ala Ser Ala Lys Leu Lys Thr Phe Phe Val
1               5                   10                  15

Leu Cys Ala Ala Leu Leu Leu Val His Ala Met Ile Tyr Lys Val Pro
            20                  25                  30

Ser Leu Tyr Glu Asn Phe Ser Ile Gly Ser Ser Thr Leu Ile Ala Asp
        35                  40                  45

Val Asp Ala Met Glu Ala Val Leu Gly Asn Thr Ala Ser Thr Ser Asp
    50                  55                  60

Asp Pro Phe Asp Val Trp Asn Ser Thr Phe Ser Pro Ile Ser Glu Val
65                  70                  75                  80

Asn Gln Thr Ala Phe Met Glu Asp Ile Arg Pro Ile Leu Phe Gly Asp
                85                  90                  95

Ala Asn Glu Thr Arg Pro His Cys Asn Gln Thr Pro Pro His Leu Val
            100                 105                 110

Gly Pro Ile Arg Val Phe Leu Asp Glu Pro Asp Phe Ala Thr Leu Glu
        115                 120                 125

Lys Ile Tyr Pro Glu Thr His Pro Gly Gly His Gly Ile Pro Thr Glu
    130                 135                 140

Cys Val Ala Arg His Arg Val Ala Ile Ile Val Pro Tyr Arg Asp Arg
145                 150                 155                 160

Glu Ala His Leu Arg Ile Met Leu His Asn Leu His Ser Leu Leu Ala
                165                 170                 175

Lys Gln Gln Leu Asp Tyr Ala Ile Phe Val Val Glu Gln Val Ala Asn
            180                 185                 190

Gln Thr Phe Asn Arg Gly Lys Leu Met Asn Val Gly Tyr Asp Val Ala
        195                 200                 205

Ser Arg Leu Tyr Pro Trp Gln Cys Phe Ile Phe His Asp Val Asp Leu
    210                 215                 220

Leu Pro Glu Asp Asp Arg Asn Leu Tyr Thr Cys Pro Ile Gln Pro Arg
225                 230                 235                 240

His Met Ser Val Ala Ile Asp Lys Phe His Tyr Lys Leu Pro Tyr Ser
                245                 250                 255

Ala Ile Phe Gly Gly Ile Ser Ala Leu Thr Gln Glu His Val Lys Ala
            260                 265                 270

Ile Asn Gly Phe Ser Asn Asp Phe Trp Gly Trp Gly Gly Glu Asp Asp
        275                 280                 285

Asp Leu Ala Thr Arg Thr Ser Gln Ala Gly Leu Lys Val Ser Arg Tyr
    290                 295                 300

Pro Ala Gln Ile Ala Arg Tyr Lys Met Ile Lys His Ser Thr Glu Ala
305                 310                 315                 320

Thr Asn Pro Val Asn Lys Cys Arg Tyr Lys Ile Met Gly Gln Thr Lys
                325                 330                 335

Arg Arg Trp Lys Thr Asp Gly Leu Ser Ser Leu Lys Tyr Lys Leu Val
            340                 345                 350

Lys Leu Glu Leu Lys Pro Leu Tyr Thr Arg Ala Val Val Asp Leu Leu
        355                 360                 365

Glu Lys Glu Cys Arg Arg Glu Leu Arg Arg Asp Phe Pro Thr Cys Phe
    370                 375                 380
```

<210> SEQ ID NO 17
<211> LENGTH: 464
<212> TYPE: PRT
<213> ORGANISM: Wuchereria bancrofti -continued

<400> SEQUENCE: 17

```
Met Pro Ala Ala Gly Arg Phe Val Ile Ile Leu Leu Ile Phe Gly Ala
1               5                   10                  15

Ala Ala His Ile Phe Leu Gly Gly Leu Ser Phe Ile Ser Asp Tyr
            20                  25                  30

His Ile Trp Arg Pro Val Val Glu Ser Ser Arg Gln Glu Ile Val Leu
            35                  40                  45

Val His Asn Ile Asp Asn Asn Ser Asp Gln Asn Ala Glu Lys Ile Ile
    50                  55                  60

Ser Asn Asn Glu Thr Lys Phe His Leu Thr Ser Ala Thr Pro Ile Asp
65                  70                  75                  80

Asn Leu Val Ser Ile His Ser Asn Phe Tyr Glu Leu Phe Ile Asn Gly
                85                  90                  95

Leu Arg Phe Gly Lys Leu Thr Thr Val Tyr Pro Ile Ile Asn Gln Ser
            100                 105                 110

Ile Asn Asn Gly Ser Thr Thr Asp Lys Ser Thr Glu Thr Tyr Ala Glu
            115                 120                 125

Ser Val Tyr Phe Leu Lys Thr Asp Gly Asn Ile His Ser Asn Thr Leu
130                 135                 140

Leu Ser Thr Ile Thr Asp Ala Gln Ser Thr Arg Gln Leu Phe Gly Asn
145                 150                 155                 160

Glu Thr Leu Ser Ala Cys Asn Val Ile Pro Ser Phe Gln Met Met His
                165                 170                 175

Gln Asn Leu Ser Leu Val Asn Cys Pro Val Thr Pro Pro Gly Leu Val
            180                 185                 190

Gly Pro Ile Lys Val Trp Tyr Asp Glu Pro Thr Phe Glu Glu Ile Glu
            195                 200                 205

Arg Leu Asn Pro Asn Leu Glu Ala Gly Gly His Gly Lys Pro Glu Asn
210                 215                 220

Cys Leu Ser Arg His Arg Val Ala Val Ile Val Pro Tyr Arg Asp Arg
225                 230                 235                 240

Glu Ala His Leu Arg Ile Leu Leu His Asn Leu His Ser Leu Leu Thr
                245                 250                 255

Lys Gln Gln Leu Asp Tyr Gly Ile Phe Val Ile Glu Gln His Glu Asn
            260                 265                 270

Glu Thr Phe Asn Arg Ala Lys Leu Met Asn Val Gly Tyr Val Glu Ala
            275                 280                 285

Leu Lys Leu Tyr Asp Trp Gln Cys Phe Val Phe His Asp Val Asp Leu
            290                 295                 300

Leu Ala Glu Asp Asp Arg Asn Ile Tyr Ser Cys Pro Asp Gln Pro Arg
305                 310                 315                 320

His Met Ser Val Ala Val Asn Lys Phe Lys Tyr Lys Leu Pro Tyr Gly
                325                 330                 335

Ser Ile Phe Gly Gly Val Ser Ala Ile Arg Thr Glu Gln Phe Ala Thr
            340                 345                 350

Leu Asn Gly Phe Ser Asn Ser Tyr Trp Gly Trp Gly Gly Glu Asp Asp
            355                 360                 365

Asp Leu Ser Met Arg Val Thr Ser Ala Gly Tyr Lys Ile Met Arg Tyr
370                 375                 380

Pro Ser Glu Ile Ala Arg Tyr Gln Met Val Gln His Lys Ser Glu Met
385                 390                 395                 400

Lys Asn Pro Ile Asn Arg Cys Arg Tyr Asp Leu Leu Ala Lys Thr Lys
```

```
                    405                 410                 415
Val Arg Gln Gln Thr Asp Gly Ile Ser Ser Leu Lys Tyr Glu Cys Tyr
                420                 425                 430

Asp Leu Gln Phe Phe Thr Leu Phe Thr His Ile Lys Val Lys Leu Phe
                435                 440                 445

Glu Gln Glu Ser Lys Ala Gln Leu Arg Glu Gly Phe Lys Arg Cys
                450                 455                 460

<210> SEQ ID NO 18
<211> LENGTH: 291
<212> TYPE: PRT
<213> ORGANISM: Loa loa

<400> SEQUENCE: 18

Met Glu Arg Gln Asn Leu Ser Leu Val Asp Cys Pro Ile Ile Pro Pro
1               5                   10                  15

Gly Leu Val Gly Pro Ile Lys Val Trp Tyr Asp Glu Pro Thr Phe Glu
                20                  25                  30

Glu Ile Glu Arg Leu Asn Pro Tyr Leu Glu Leu Gly Gly His Gly Lys
            35                  40                  45

Pro Gly Ser Cys Leu Ser Arg His Arg Val Ala Ile Ile Val Pro Tyr
        50                  55                  60

Arg Asp Arg Glu Ala His Leu Arg Ile Leu Leu His Asn Leu His Ser
65                  70                  75                  80

Leu Leu Thr Lys Gln Gln Leu Asp Tyr Ala Ile Phe Val Ile Glu Gln
                85                  90                  95

His Glu Asn Glu Thr Phe Asn Arg Ala Lys Leu Met Asn Val Gly Tyr
            100                 105                 110

Thr Glu Ala Met Lys Leu Tyr Asp Trp Gln Cys Phe Ile Phe His Asp
        115                 120                 125

Val Asp Leu Leu Ala Glu Asp Asp Arg Asn Ile Tyr Ser Cys Pro Asp
    130                 135                 140

Gln Pro Arg His Met Ser Val Ala Ile Asn Lys Phe Lys Tyr Arg Leu
145                 150                 155                 160

Pro Tyr Gly Ser Ile Phe Gly Gly Val Ser Ala Ile Arg Thr Glu Gln
                165                 170                 175

Phe Leu Lys Met Asn Gly Phe Ser Asn Ser Tyr Trp Gly Trp Gly Gly
            180                 185                 190

Glu Asp Asp Asp Leu Ser Ile Arg Val Thr Ser Leu Gly Tyr Lys Ile
        195                 200                 205

Met Arg Tyr Pro Leu Glu Ile Ala Arg Tyr Gln Met Val Lys His Glu
    210                 215                 220

Ser Glu Thr Lys Asn Pro Ile Asn Arg Cys Arg Tyr Asp Leu Leu Ala
225                 230                 235                 240

Lys Thr Lys Val Arg Gln Gln Met Asp Gly Ile Ser Ser Leu Lys Tyr
                245                 250                 255

Glu Cys Tyr Asp Leu His Phe Leu Pro Leu Phe Thr His Ile Lys Val
            260                 265                 270

Lys Leu Phe Glu Gln Glu Ser Lys Ala Gln Leu Arg Glu Gly Phe
        275                 280                 285

Lys Lys Cys
    290

<210> SEQ ID NO 19
<211> LENGTH: 296
```

<212> TYPE: PRT
<213> ORGANISM: Cerapachys biroi

<400> SEQUENCE: 19

Met Pro Ile Arg Asn Leu Ala Gly Asn Gly Thr Ala Arg Glu Leu
1               5                   10                  15

Pro Val Ala Asn Thr Thr Ser Asn Ala Thr Ile Pro Arg Cys Pro Leu
            20                  25                  30

Ile Pro Pro Asn Leu Val Gly Pro Val Ala Val Ser Lys Ser Pro Pro
        35                  40                  45

Pro Leu Ser Glu Met Glu Arg Ser Phe Val Glu Val Lys Ala Gly Gly
    50                  55                  60

Lys Gly Arg Pro Ala Asp Cys Val Ala Arg His Arg Val Ala Ile Ile
65                  70                  75                  80

Ile Pro Phe Arg Asp Arg Pro Gln His Leu Gln Thr Leu Leu Tyr Asn
                85                  90                  95

Leu His Pro Ile Leu Leu Arg Gln Gln Ile Asp Tyr Gln Ile Phe Val
            100                 105                 110

Ile Glu Gln Glu Gly Thr Gly Thr Phe Asn Arg Ala Met Leu Met Asn
        115                 120                 125

Val Gly Tyr Val Glu Ala Leu Lys Glu Arg Ile Phe Asp Cys Phe Ile
    130                 135                 140

Phe His Asp Val Asp Leu Leu Pro Glu Asp Asp Arg Asn Leu Tyr Thr
145                 150                 155                 160

Cys Pro Glu Gln Pro Arg His Met Ser Val Ala Val Asp Lys Phe Lys
                165                 170                 175

Tyr Arg Leu Pro Tyr Ala Asp Leu Phe Gly Gly Val Ser Ala Met Ser
            180                 185                 190

Arg Glu His Phe Gln Leu Val Asn Gly Phe Ser Asn Val Phe Trp Gly
        195                 200                 205

Trp Gly Gly Glu Asp Asp Met Ala Asn Arg Ile Lys Ala His Gly
    210                 215                 220

Leu His Ile Ser Arg Tyr Pro Ala Asn Val Ala Arg Tyr Lys Met Leu
225                 230                 235                 240

Thr His Lys Lys Glu Lys Ala Asn Pro Lys Arg Tyr Glu Phe Leu Lys
                245                 250                 255

Thr Gly Lys Lys Arg Phe Ser Thr Asp Gly Leu Ala Asn Leu Gln Tyr
            260                 265                 270

Glu Leu Cys Asp Lys Arg Lys Pro Lys Leu Tyr Thr Trp Leu Leu Val
        275                 280                 285

Arg Leu Thr Pro Pro Gln Pro Ser
    290                 295

<210> SEQ ID NO 20
<211> LENGTH: 422
<212> TYPE: PRT
<213> ORGANISM: Zootermopsis nevadensis

<400> SEQUENCE: 20

Met Arg Cys Arg Cys Leu Ser Ala Trp Ser Arg Ile Thr Gln His Val
1               5                   10                  15

Pro Arg Gln Pro Cys Leu His Ile His Ser His Leu Cys Lys Val Val
            20                  25                  30

Ile Val Leu Ala Val Leu Ile Ala Leu Gln Phe Leu Thr Thr Ile
        35                  40                  45

Phe Glu Ala Arg Gln Ile Glu Pro Leu Phe Thr Val Asn Phe Thr Tyr
        50                  55                  60

Ser Gly Arg Arg Ser Arg Trp Gly Leu Ile Ser His Ser Arg Gly Leu
65                  70                  75                  80

Leu Ser Pro Ser His Asn Ser Ser Phe Asn Gly Ser Met Arg Val Ser
                85                  90                  95

Val Glu Arg Thr Leu Ser Pro Val Glu Asn Ile Ser Gly Glu Thr Lys
            100                 105                 110

Asn Leu Ser Phe Leu His Thr His Glu Asn Ala Val Arg Asn Ala Ser
        115                 120                 125

Ser Leu Val Leu Asn Ile Ser Leu Pro Ser Asp Leu Asn Pro Thr Thr
130                 135                 140

Ser Pro Ser Leu Thr Val Pro Phe Thr Gly Lys Ser Leu Cys Pro Pro
145                 150                 155                 160

Ile Pro Pro Asn Leu Asn Gly Pro Ile Lys Val Leu Lys Asp Ser Pro
                165                 170                 175

Ser Leu Glu Glu Leu Glu Lys Met Phe Pro Leu Leu Gly Pro Gly Gly
            180                 185                 190

His Tyr His Pro Glu Glu Cys Gln Ala Arg Asp Arg Val Ala Ile Ile
        195                 200                 205

Val Pro Tyr Arg Asp Arg Ala Glu His Leu Ser Thr Phe Leu Leu Asn
210                 215                 220

Leu His Pro Leu Leu Gln Arg Gln Leu Asp Tyr Gly Met Phe Val
225                 230                 235                 240

Ile Glu Gln Gly Gly Asp Gly Pro Phe Asn Arg Ala Met Leu Met Asn
                245                 250                 255

Val Gly Phe Val Glu Ala Leu Lys Leu Tyr Ser Tyr Asp Cys Phe Ile
            260                 265                 270

Phe His Asp Val Asp Leu Leu Pro Glu Asp Asp Arg Asn Leu Tyr Thr
        275                 280                 285

Cys Pro Glu Gln Pro Arg His Met Ser Val Ala Val Asp Val Leu Lys
        290                 295                 300

Tyr Lys Leu Pro Tyr Gln Ala Ile Phe Gly Gly Val Ser Ala Met Thr
305                 310                 315                 320

Lys Thr Gln Phe Gln Lys Val Asn Gly Phe Ser Asn Leu Phe Trp Gly
                325                 330                 335

Trp Gly Gly Glu Asp Asp Asp Met Ser Asn Arg Val Arg His His Gly
            340                 345                 350

Tyr His Ile Ser Arg Tyr Pro Ala Asn Ile Ala Arg Tyr Lys Met Leu
        355                 360                 365

Ala His Arg Lys Gln His Ala Asn Pro Lys Arg Tyr Glu Phe Leu Asn
370                 375                 380

Thr Gly Arg Lys Arg Phe Lys Thr Asp Gly Leu Ser Asn Leu Gln Tyr
385                 390                 395                 400

Asp Arg Lys Glu Leu Asn Leu Gly Lys Leu Tyr Thr Arg Val Leu Val
                405                 410                 415

Glu Leu Ala Thr Pro Ser
            420

<210> SEQ ID NO 21
<211> LENGTH: 295
<212> TYPE: PRT
<213> ORGANISM: Camponotus floridanus

<400> SEQUENCE: 21

Met Pro Thr Arg Asn Leu Val Gly Gly Gly Thr Ala Arg Glu Leu Pro
1               5                   10                  15

Val Ala Asn Ala Thr Asn Asn Thr Thr Met Pro Arg Cys Pro Leu Ile
            20                  25                  30

Pro Pro Asn Leu Val Gly Pro Met Val Val Ser Lys Ser Pro Pro Pro
        35                  40                  45

Leu Ser Glu Met Glu Arg Ser Phe Val Glu Val Asn Ala Gly Gly Arg
    50                  55                  60

Gly Arg Pro Ala Asp Cys Val Ala Arg His Arg Val Ala Ile Ile Ile
65              70                  75                  80

Pro Phe Arg Asp Arg Pro Gln His Leu Gln Thr Leu Leu Tyr Asn Leu
                85                  90                  95

His Pro Ile Leu Leu Arg Gln Gln Ile Glu Tyr Gln Ile Phe Val Ile
            100                 105                 110

Glu Gln Glu Gly Thr Gly Ala Phe Asn Arg Ala Met Leu Met Asn Val
        115                 120                 125

Gly Tyr Val Glu Ala Leu Lys Glu Arg Thr Phe Asp Cys Phe Ile Phe
    130                 135                 140

His Asp Val Asp Leu Leu Pro Glu Asp Arg Asn Leu Tyr Thr Cys
145                 150                 155                 160

Pro Glu Gln Pro Arg His Met Ser Val Ala Val Asp Lys Phe Lys Tyr
                165                 170                 175

Arg Leu Pro Tyr Thr Asp Leu Phe Gly Gly Val Ser Ala Met Ser Arg
            180                 185                 190

Glu His Phe Gln Leu Val Asn Gly Phe Ser Asn Val Phe Trp Gly Trp
        195                 200                 205

Gly Gly Glu Asp Asp Asp Met Ala Asn Arg Ile Lys Ala His Gly Leu
    210                 215                 220

His Ile Ser Arg Tyr Pro Ala Asn Val Ala Arg Tyr Lys Met Leu Thr
225                 230                 235                 240

His Lys Lys Glu Lys Ala Asn Pro Lys Arg Tyr Glu Phe Leu Lys Thr
                245                 250                 255

Gly Lys Lys Arg Phe Ser Thr Asp Gly Leu Ala Asn Leu Gln Tyr Glu
            260                 265                 270

Leu Ser Asp Lys Arg Lys Pro Lys Leu Tyr Thr Trp Leu Leu Val Arg
        275                 280                 285

Leu Thr Pro Pro Gln Pro Ser
    290                 295

<210> SEQ ID NO 22
<211> LENGTH: 310
<212> TYPE: PRT
<213> ORGANISM: Crassostrea gigas

<400> SEQUENCE: 22

Met Asp Arg Gly Cys Lys Pro Met Arg Val Cys Ser Ser Ser Pro Ser
1               5                   10                  15

Asp Leu Val Gly Ser Leu Ala Thr Tyr Lys Glu Ala Pro Ser Tyr Lys
            20                  25                  30

Glu Met Ile Lys Ile Tyr Pro Leu Val Arg Pro Gly Leu Tyr Thr
        35                  40                  45

Pro Pro Asp Cys Ile Ala Arg Glu Arg Val Ala Ile Ile Ile Pro Phe
    50                  55                  60

Arg Asp Arg Glu Glu His Leu Arg Ile Leu Leu His Asn Leu His Pro

```
                65                  70                  75                  80
Met Leu Gln Arg Gln Gln Leu Asp Tyr Gly Ile Tyr Val Val Glu Gln
                    85                  90                  95

Glu Asn Gly Thr Gln Phe Asn Arg Ala Met Leu Met Asn Ile Gly Tyr
                100                 105                 110

Ala Glu Ser Ile Lys Leu Tyr Asn Tyr Thr Cys Phe Ile Phe His Asp
                115                 120                 125

Val Asp Leu Ile Pro Glu Asn Asp Arg Ile Met Tyr Asp Cys Arg Asp
            130                 135                 140

Ser Pro Arg His Leu Ser Ser Ala Val Asp Lys Phe Lys Tyr Lys Leu
145                 150                 155                 160

Pro Tyr Pro Gln Leu Phe Gly Gly Val Thr Ala Ile Lys Arg Ala His
                165                 170                 175

Phe Glu Lys Val Asn Gly His Ser Asn Lys Phe Phe Gly Trp Gly Gly
                180                 185                 190

Glu Asp Asp Asp Met Phe Arg Arg Leu Val Asn Asn Gly Phe Lys Ile
            195                 200                 205

Ser Arg Tyr Gln Ala Ser Leu Ser Lys Tyr Lys Met Ile Lys His Leu
210                 215                 220

His Asp Ala Gly Asn Lys Ala Asn Lys Arg Arg His His Leu Ile Lys
225                 230                 235                 240

Thr Gly Lys Gly Arg Tyr Arg Arg Asp Gly Ile Asn Asn Leu His Tyr
                245                 250                 255

Lys Lys Leu Gly Ile Glu Tyr Gln Tyr Leu His Thr Arg Ile Leu Val
                260                 265                 270

Ser Ile Asn Glu Thr Lys Val Met Thr Val Ser Leu Leu Tyr Met Tyr
            275                 280                 285

Ser Ser Thr Thr Val Tyr Ile Ile Val Asn Ile Tyr Thr Ile Tyr Cys
290                 295                 300

Lys Ser Arg Asn Ile Arg
305                 310

<210> SEQ ID NO 23
<211> LENGTH: 338
<212> TYPE: PRT
<213> ORGANISM: Danaus plexippus

<400> SEQUENCE: 23

Met Ala Lys Lys Leu Leu Thr Gln Gly Thr Glu Ser Val Thr Asn Tyr
1               5                   10                  15

Thr His Thr Thr Asn Ser Ser Asn Lys Asn Pro Ala Lys Glu Thr Phe
                20                  25                  30

Asn Met Thr Lys Pro Asn Leu Ser Asp Asp Thr Ser Thr Pro Leu Leu
            35                  40                  45

Ile Thr Lys Ile Met Glu Ser Ile Lys Asn Leu Val Thr Thr Glu Glu
        50                  55                  60

Asp Phe Arg Asp Glu Pro Ser Leu Pro Leu Cys Asp Glu Met Pro Pro
65                  70                  75                  80

Asp Leu Gly Pro Ile Ser Val Asn Lys Thr Glu Ile Glu Leu Asp Trp
                85                  90                  95

Val Glu Lys Arg Tyr Pro Glu Val Arg Ser Gly Gly Ile Tyr Ser Ser
                100                 105                 110

Ser Asn Cys Thr Ala Arg His Arg Val Ala Ile Val Pro Tyr Arg
            115                 120                 125
```

```
Asp Arg Gln Gln His Leu Ala Ile Phe Leu Asn His Met His Pro Phe
    130                 135                 140

Leu Met Lys Gln Gln Ile Glu Tyr Gly Ile Tyr Ile Ile Glu Gln Glu
145                 150                 155                 160

Gly Thr Ser Glu Phe Asn Arg Ala Lys Leu Met Asn Val Gly Phe Val
                165                 170                 175

Glu Ser Gln Arg Gln Arg Ser Trp Gln Cys Phe Ile Phe His Asp Ile
            180                 185                 190

Asp Leu Leu Pro Leu Asp Ser Arg Asn Met Tyr Ser Cys Pro Lys Gln
        195                 200                 205

Pro Arg His Met Ser Ala Ser Ile Asp Lys Leu Asn Phe Arg Leu Pro
    210                 215                 220

Tyr Glu Asp Ile Phe Gly Gly Val Ser Ala Met Thr Leu Glu Gln Phe
225                 230                 235                 240

Thr Lys Val Asn Gly Phe Ser Asn Lys Tyr Trp Gly Trp Gly Gly Glu
                245                 250                 255

Asp Asp Asp Met Phe Tyr Arg Leu Lys Lys Met Asn Tyr His Ile Ala
            260                 265                 270

Arg Tyr Lys Met Ser Ile Ala Arg Tyr Ala Met Leu Asp His Lys Lys
        275                 280                 285

Ser Ala Pro Asn Pro Lys Arg Tyr Gln Leu Leu Ser Gln Thr Ser Lys
    290                 295                 300

Thr Phe Gln Lys Asp Gly Leu Ser Thr Leu Glu Tyr Glu Val Ile Lys
305                 310                 315                 320

Val Thr Ala Asn His Leu Tyr Thr His Ile Leu Val Asn Ile Asp Glu
                325                 330                 335

Arg Ser

<210> SEQ ID NO 24
<211> LENGTH: 941
<212> TYPE: PRT
<213> ORGANISM: Artificial
<220> FEATURE:
<223> OTHER INFORMATION: HuGalNAcT (57-998)

<400> SEQUENCE: 24

Arg Tyr Gly Ser Trp Arg Glu Leu Ala Lys Ala Leu Ala Ser Arg Asn
1               5                   10                  15

Ile Pro Ala Val Asp Pro His Leu Gln Phe Tyr His Pro Gln Arg Leu
                20                  25                  30

Ser Leu Glu Asp His Asp Ile Asp Gln Gly Val Ser Ser Asn Ser Ser
            35                  40                  45

Tyr Leu Lys Trp Asn Lys Pro Val Pro Trp Leu Ser Glu Phe Arg Gly
        50                  55                  60

Arg Ala Asn Leu His Val Phe Glu Asp Trp Cys Gly Ser Ser Ile Gln
65                  70                  75                  80

Gln Leu Arg Arg Asn Leu His Phe Pro Leu Tyr Pro His Ile Arg Thr
                85                  90                  95

Thr Leu Arg Lys Leu Ala Val Ser Pro Lys Trp Thr Asn Tyr Gly Leu
            100                 105                 110

Arg Ile Phe Gly Tyr Leu His Pro Phe Thr Asp Gly Lys Ile Gln Phe
        115                 120                 125

Ala Ile Ala Ala Asp Asp Asn Ala Glu Phe Trp Leu Ser Leu Asp Asp
    130                 135                 140

Gln Val Ser Gly Leu Gln Leu Leu Ala Ser Val Gly Lys Thr Gly Lys
```

```
            145                 150                 155                 160
Glu Trp Thr Ala Pro Gly Glu Phe Gly Lys Phe Arg Ser Gln Ile Ser
                    165                 170                 175

Lys Pro Val Ser Leu Ser Ala Ser His Arg Tyr Tyr Phe Glu Val Leu
                180                 185                 190

His Lys Gln Asn Glu Glu Gly Thr Asp His Val Glu Val Ala Trp Arg
                195                 200                 205

Arg Asn Asp Pro Gly Ala Lys Phe Thr Ile Ile Asp Ser Leu Ser Leu
            210                 215                 220

Ser Leu Phe Thr Asn Glu Thr Phe Leu Gln Met Asp Glu Val Gly His
225                 230                 235                 240

Ile Pro Gln Thr Ala Ala Ser His Val Asp Ser Ser Asn Ala Leu Pro
                245                 250                 255

Arg Asp Glu Gln Pro Pro Ala Asp Met Leu Arg Pro Asp Pro Arg Asp
                260                 265                 270

Thr Leu Tyr Arg Val Pro Leu Ile Pro Lys Ser His Leu Arg His Val
                275                 280                 285

Leu Pro Asp Cys Pro Tyr Lys Pro Ser Tyr Leu Val Asp Gly Leu Pro
            290                 295                 300

Leu Gln Arg Tyr Gln Gly Leu Arg Phe Val His Leu Ser Phe Val Tyr
305                 310                 315                 320

Pro Asn Asp Tyr Thr Arg Leu Ser His Met Glu Thr His Asn Lys Cys
                325                 330                 335

Phe Tyr Gln Glu Asn Ala Tyr Tyr Gln Asp Arg Phe Ser Phe Gln Glu
                340                 345                 350

Tyr Ile Lys Ile Asp Gln Pro Glu Lys Gln Gly Leu Glu Gln Pro Gly
                355                 360                 365

Phe Glu Glu Asn Leu Leu Glu Ser Gln Tyr Gly Glu Val Ala Glu
            370                 375                 380

Glu Thr Pro Ala Ser Asn Asn Gln Asn Ala Arg Met Leu Glu Gly Arg
385                 390                 395                 400

Gln Thr Pro Ala Ser Thr Leu Glu Gln Asp Ala Thr Asp Tyr Arg Leu
                405                 410                 415

Arg Ser Leu Arg Lys Leu Leu Ala Gln Pro Arg Glu Gly Leu Leu Ala
                420                 425                 430

Pro Phe Ser Lys Arg Asn Ser Thr Ala Ser Phe Pro Gly Arg Thr Ser
                435                 440                 445

His Ile Pro Val Gln Gln Pro Glu Lys Arg Lys Gln Lys Pro Ser Pro
            450                 455                 460

Glu Pro Ser Gln Asp Ser Pro His Ser Asp Lys Trp Pro Pro Gly His
465                 470                 475                 480

Pro Val Lys Asn Leu Pro Gln Met Arg Gly Pro Arg Pro Arg Pro Ala
                485                 490                 495

Gly Asp Ser Pro Arg Lys Thr Gln Trp Leu Asn Gln Val Glu Ser Tyr
            500                 505                 510

Ile Ala Glu Gln Arg Arg Gly Asp Arg Met Arg Pro Gln Ala Pro Gly
                515                 520                 525

Arg Gly Trp His Gly Glu Glu Val Val Ala Ala Gly Gln Glu
                530                 535                 540

Gly Gln Val Glu Gly Glu Glu Gly Glu Glu Glu Glu Glu
545                 550                 555                 560

Asp Met Ser Glu Val Phe Glu Tyr Val Pro Val Phe Asp Pro Val Val
                565                 570                 575
```

Asn Trp Asp Gln Thr Phe Ser Ala Arg Asn Leu Asp Phe Gln Ala Leu
            580                 585                 590

Arg Thr Asp Trp Ile Asp Leu Ser Cys Asn Thr Ser Gly Asn Leu Leu
        595                 600                 605

Leu Pro Glu Gln Glu Ala Leu Glu Val Thr Arg Val Phe Leu Lys Lys
    610                 615                 620

Leu Asn Gln Arg Ser Arg Gly Arg Tyr Gln Leu Gln Arg Ile Val Asn
625                 630                 635                 640

Val Glu Lys Arg Gln Asp Gln Leu Arg Gly Arg Tyr Leu Leu Glu
            645                 650                 655

Leu Glu Leu Leu Glu Gln Gly Gln Arg Val Val Arg Leu Ser Glu Tyr
            660                 665                 670

Val Ser Ala Arg Gly Trp Gln Gly Ile Asp Pro Ala Gly Gly Glu Glu
        675                 680                 685

Val Glu Ala Arg Asn Leu Gln Gly Leu Val Trp Asp Pro His Asn Arg
    690                 695                 700

Arg Arg Gln Val Leu Asn Thr Arg Ala Gln Glu Pro Lys Leu Cys Trp
705                 710                 715                 720

Pro Gln Gly Phe Ser Trp Ser His Arg Ala Val Val His Phe Val Val
            725                 730                 735

Pro Val Lys Asn Gln Ala Arg Trp Val Gln Phe Ile Lys Asp Met
        740                 745                 750

Glu Asn Leu Phe Gln Val Thr Gly Asp Pro His Phe Asn Ile Val Ile
    755                 760                 765

Thr Asp Tyr Ser Ser Glu Asp Met Asp Val Glu Met Ala Leu Lys Arg
770                 775                 780

Ser Lys Leu Arg Ser Tyr Gln Tyr Val Lys Leu Ser Gly Asn Phe Glu
785                 790                 795                 800

Arg Ser Ala Gly Leu Gln Ala Gly Ile Asp Leu Val Lys Asp Pro His
            805                 810                 815

Ser Ile Ile Phe Leu Cys Asp Leu His Ile His Phe Pro Ala Gly Val
        820                 825                 830

Ile Asp Ala Ile Arg Lys His Cys Val Glu Gly Lys Met Ala Phe Ala
    835                 840                 845

Pro Met Val Met Arg Leu His Cys Gly Ala Thr Pro Gln Trp Pro Glu
850                 855                 860

Gly Tyr Trp Glu Val Asn Gly Phe Gly Leu Leu Gly Ile Tyr Lys Ser
865                 870                 875                 880

Asp Leu Asp Arg Ile Gly Gly Met Asn Thr Lys Glu Phe Arg Asp Arg
            885                 890                 895

Trp Gly Gly Glu Asp Trp Glu Leu Leu Asp Arg Ile Leu Gln Gly Leu
        900                 905                 910

Asp Val Glu Arg Leu Ser Leu Arg Asn Phe Phe His His Phe His Ser
    915                 920                 925

Lys Arg Gly Met Trp Ser Arg Arg Gln Met Lys Thr Leu
930                 935                 940

<210> SEQ ID NO 25
<211> LENGTH: 389
<212> TYPE: PRT
<213> ORGANISM: Artificial
<220> FEATURE:
<223> OTHER INFORMATION: TnGalNAcT(33-421; W336F)

<400> SEQUENCE: 25

-continued

Ser Pro Leu Arg Thr Tyr Leu Tyr Thr Pro Leu Tyr Asn Ala Thr Gln
 1               5                  10                  15

Pro Thr Leu Arg Asn Val Glu Arg Leu Ala Ala Asn Trp Pro Lys Lys
                 20                  25                  30

Ile Pro Ser Asn Tyr Ile Glu Asp Ser Glu Glu Tyr Ser Ile Lys Asn
             35                  40                  45

Ile Ser Leu Ser Asn His Thr Thr Arg Ala Ser Val Val His Pro Pro
 50                  55                  60

Ser Ser Ile Thr Glu Thr Ala Ser Lys Leu Asp Lys Asn Met Thr Ile
 65                  70                  75                  80

Gln Asp Gly Ala Phe Ala Met Ile Ser Pro Thr Pro Leu Leu Ile Thr
                 85                  90                  95

Lys Leu Met Asp Ser Ile Lys Ser Tyr Val Thr Thr Glu Asp Gly Val
                100                 105                 110

Lys Lys Ala Glu Ala Val Val Thr Leu Pro Leu Cys Asp Ser Met Pro
            115                 120                 125

Pro Asp Leu Gly Pro Ile Thr Leu Asn Lys Thr Glu Leu Glu Leu Glu
            130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
                180                 185                 190

Phe Leu Met Lys Gln Gln Ile Glu Tyr Gly Ile Phe Ile Val Glu Gln
                195                 200                 205

Glu Gly Asn Lys Asp Phe Asn Arg Ala Lys Leu Met Asn Val Gly Phe
            210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
                260                 265                 270

Lys Leu Pro Tyr Glu Asp Ile Phe Gly Gly Val Ser Ala Met Thr Leu
            275                 280                 285

Glu Gln Phe Thr Arg Val Asn Gly Phe Ser Asn Lys Tyr Trp Gly Phe
            290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
                340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
            370                 375                 380

Ile Asp Glu Arg Ser
385

<210> SEQ ID NO 26
<211> LENGTH: 389

```
<212> TYPE: PRT
<213> ORGANISM: Artificial
<220> FEATURE:
<223> OTHER INFORMATION: TnGalNAcT(33-421; W336H)

<400> SEQUENCE: 26
```

| | | | | | | | | | | | | | | | |
|---|---|---|---|---|---|---|---|---|---|---|---|---|---|---|---|
|Ser|Pro|Leu|Arg|Thr|Tyr|Leu|Tyr|Thr|Pro|Leu|Tyr|Asn|Ala|Thr|Gln|
|1| | | |5| | | |10| | | |15| | | |

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
            35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
            115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
            275                 280                 285

Glu Gln Phe Thr Arg Val Asn Gly Phe Ser Asn Lys Tyr Trp Gly His
    290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 27
<211> LENGTH: 389
<212> TYPE: PRT
<213> ORGANISM: Artificial
<220> FEATURE:
<223> OTHER INFORMATION: TnGalNAcT(33-421; W336V)

<400> SEQUENCE: 27

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly Val
    290                 295                 300

Gly Gly Glu Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

```
Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 28
<211> LENGTH: 389
<212> TYPE: PRT
<213> ORGANISM: Artificial
<220> FEATURE:
<223> OTHER INFORMATION: TnGalNAcT(33-421; E339A)

<400> SEQUENCE: 28

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys His Leu Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Ala Asp Asp Asp Met Ser Tyr Arg Leu Lys Lys Ile Asn Tyr
305                 310                 315                 320
```

His Ile Ala Arg Tyr Lys Met Ser Ile Ala Arg Tyr Ala Met Leu Asp
            325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
370                 375                 380

Ile Asp Glu Arg Ser
385

<210> SEQ ID NO 29
<211> LENGTH: 389
<212> TYPE: PRT
<213> ORGANISM: Artificial
<220> FEATURE:
<223> OTHER INFORMATION: TnGalNAcT(33-421; E339G)

<400> SEQUENCE: 29

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
            35                  40                  45

Ile Ser Leu Ser Asn His Thr Thr Arg Ala Ser Val Val His Pro Pro
        50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

```
Glu Gln Phe Thr Arg Val Asn Gly Phe Ser Asn Lys Tyr Trp Gly Trp
        290                 295                 300
Gly Gly Gly Asp Asp Met Ser Tyr Arg Leu Lys Lys Ile Asn Tyr
305                 310                 315                 320
His Ile Ala Arg Tyr Lys Met Ser Ile Ala Arg Tyr Ala Met Leu Asp
                325                 330                 335
His Lys Lys Ser Thr Pro Asn Pro Lys Arg Tyr Gln Leu Leu Ser Gln
                340                 345                 350
Thr Ser Lys Thr Phe Gln Lys Asp Gly Leu Ser Thr Leu Glu Tyr Glu
                355                 360                 365
Leu Val Gln Val Val Gln Tyr His Leu Tyr Thr His Ile Leu Val Asn
370                 375                 380
Ile Asp Glu Arg Ser
385
```

<210> SEQ ID NO 30
<211> LENGTH: 389
<212> TYPE: PRT
<213> ORGANISM: Artificial
<220> FEATURE:
<223> OTHER INFORMATION: TnGalNAcT(33-421; E339D)

<400> SEQUENCE: 30

```
Ser Pro Leu Arg Thr Tyr Leu Tyr Thr Pro Leu Tyr Asn Ala Thr Gln
1               5                   10                  15
Pro Thr Leu Arg Asn Val Glu Arg Leu Ala Ala Asn Trp Pro Lys Lys
                20                  25                  30
Ile Pro Ser Asn Tyr Ile Glu Asp Ser Glu Tyr Ser Ile Lys Asn
                35                  40                  45
Ile Ser Leu Ser Asn His Thr Thr Arg Ala Ser Val Val His Pro Pro
50                  55                  60
Ser Ser Ile Thr Glu Thr Ala Ser Lys Leu Asp Lys Asn Met Thr Ile
65                  70                  75                  80
Gln Asp Gly Ala Phe Ala Met Ile Ser Pro Thr Pro Leu Leu Ile Thr
                85                  90                  95
Lys Leu Met Asp Ser Ile Lys Ser Tyr Val Thr Thr Glu Asp Gly Val
                100                 105                 110
Lys Lys Ala Glu Ala Val Val Thr Leu Pro Leu Cys Asp Ser Met Pro
                115                 120                 125
Pro Asp Leu Gly Pro Ile Thr Leu Asn Lys Thr Glu Leu Glu Leu Glu
130                 135                 140
Trp Val Glu Lys Lys Phe Pro Glu Val Glu Trp Gly Gly Arg Tyr Ser
145                 150                 155                 160
Pro Pro Asn Cys Thr Ala Arg His Arg Val Ala Ile Ile Val Pro Tyr
                165                 170                 175
Arg Asp Arg Gln Gln His Leu Ala Ile Phe Leu Asn His Met His Pro
                180                 185                 190
Phe Leu Met Lys Gln Gln Ile Glu Tyr Gly Ile Phe Ile Val Glu Gln
                195                 200                 205
Glu Gly Asn Lys Asp Phe Asn Arg Ala Lys Leu Met Asn Val Gly Phe
                210                 215                 220
Val Glu Ser Gln Lys Leu Val Ala Glu Gly Trp Gln Cys Phe Val Phe
225                 230                 235                 240
His Asp Ile Asp Leu Leu Pro Leu Asp Thr Arg Asn Leu Tyr Ser Cys
                245                 250                 255
```

```
Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
385
```

<210> SEQ ID NO 31
<211> LENGTH: 389
<212> TYPE: PRT
<213> ORGANISM: Artificial
<220> FEATURE:
<223> OTHER INFORMATION: TnGalNAcT(33-421; E339S)

<400> SEQUENCE: 31

```
Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Arg Tyr Ser
145                 150                 155                 160

Pro Pro Asn Cys Thr Ala Arg His Arg Val Ala Ile Val Pro Tyr
            165                 170                 175

Arg Asp Arg Gln Gln His Leu Ala Ile Phe Leu Asn His Met His Pro
        180                 185                 190

Phe Leu Met Lys Gln Gln Ile Glu Tyr Gly Ile Phe Ile Val Glu Gln
    195                 200                 205

Glu Gly Asn Lys Asp Phe Asn Arg Ala Lys Leu Met Asn Val Gly Phe
    210                 215                 220
```

```
Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Ser Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
                340                 345                 350

Thr Ser Lys Thr Phe Gln Lys Asp Gly Leu Ser Thr Leu Glu Tyr Glu
                355                 360                 365

Leu Val Gln Val Val Gln Tyr His Leu Tyr Thr His Ile Leu Val Asn
370                 375                 380

Ile Asp Glu Arg Ser
385

<210> SEQ ID NO 32
<211> LENGTH: 389
<212> TYPE: PRT
<213> ORGANISM: Artificial
<220> FEATURE:
<223> OTHER INFORMATION: TnGalNAcT(33-421; W336H, E339A)

<400> SEQUENCE: 32

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
                20                  25                  30

Ile Pro Ser Asn Tyr Ile Glu Asp Ser Glu Tyr Ser Ile Lys Asn
            35                  40                  45

Ile Ser Leu Ser Asn His Thr Thr Arg Ala Ser Val Val His Pro Pro
50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190
```

```
Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
        210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly His
    290                 295                 300

Gly Gly Ala Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Gln Tyr His Leu Tyr Thr His Ile Leu Val Asn
    370                 375                 380

Ile Asp Glu Arg Ser
385

<210> SEQ ID NO 33
<211> LENGTH: 389
<212> TYPE: PRT
<213> ORGANISM: Artificial
<220> FEATURE:
<223> OTHER INFORMATION: TnGalNAcT(33-421; W336H,E339D)

<400> SEQUENCE: 33

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Gly Val Glu Trp Gly Gly Arg Tyr Ser
145                 150                 155                 160
```

```
Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Ile Phe Gly Gly Val Ser Ala Met Thr Leu
        275                 280                 285

Glu Gln Phe Thr Arg Val Asn Gly Phe Ser Asn Lys Tyr Trp Gly His
    290                 295                 300

Gly Gly Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 34
<211> LENGTH: 389
<212> TYPE: PRT
<213> ORGANISM: Artificial
<220> FEATURE:
<223> OTHER INFORMATION: TnGalNAcT(33-421; W336H,E339S)

<400> SEQUENCE: 34

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125
```

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
                180                 185                 190

Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
                260                 265                 270

Lys Leu Pro Tyr Glu Asp Ile Phe Gly Gly Val Ser Ala Met Thr Leu
            275                 280                 285

Glu Gln Phe Thr Arg Val Asn Gly Phe Ser Asn Lys Tyr Trp Gly His
290                 295                 300

Gly Gly Ser Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 35
<211> LENGTH: 389
<212> TYPE: PRT
<213> ORGANISM: Artificial
<220> FEATURE:
<223> OTHER INFORMATION: TnGalNAcT(33-421; I311Y)

<400> SEQUENCE: 35

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

```
Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Val Pro Tyr
                165                 170                 175

Arg Asp Arg Gln Gln His Leu Ala Ile Phe Leu Asn His Met His Pro
                180                 185                 190

Phe Leu Met Lys Gln Gln Ile Glu Tyr Gly Ile Phe Ile Val Glu Gln
                195                 200                 205

Glu Gly Asn Lys Asp Phe Asn Arg Ala Lys Leu Met Asn Val Gly Phe
                210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
                260                 265                 270

Lys Leu Pro Tyr Glu Asp Tyr Phe Gly Gly Val Ser Ala Met Thr Leu
                275                 280                 285

Glu Gln Phe Thr Arg Val Asn Gly Phe Ser Asn Lys Tyr Trp Gly Trp
                290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
                340                 345                 350

Thr Ser Lys Thr Phe Gln Lys Asp Gly Leu Ser Thr Leu Glu Tyr Glu
                355                 360                 365

Leu Val Gln Val Val Gln Tyr His Leu Tyr Thr His Ile Leu Val Asn
                370                 375                 380

Ile Asp Glu Arg Ser
385

<210> SEQ ID NO 36
<211> LENGTH: 389
<212> TYPE: PRT
<213> ORGANISM: Artificial
<220> FEATURE:
<223> OTHER INFORMATION: TnGalNAcT(33-421; I311Y,W336F)

<400> SEQUENCE: 36

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
                20                  25                  30

Ile Pro Ser Asn Tyr Ile Glu Asp Ser Glu Glu Tyr Ser Ile Lys Asn
                35                  40                  45

Ile Ser Leu Ser Asn His Thr Thr Arg Ala Ser Val Val His Pro Pro
                50                  55                  60
```

```
Ser Ser Ile Thr Glu Thr Ala Ser Lys Leu Asp Lys Asn Met Thr Ile
 65                  70                  75                  80

Gln Asp Gly Ala Phe Ala Met Ile Ser Pro Thr Pro Leu Leu Ile Thr
                 85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Gly Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly Phe
    290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 37
<211> LENGTH: 389
<212> TYPE: PRT
<213> ORGANISM: Artificial
<220> FEATURE:
<223> OTHER INFORMATION: TnGalNAcT(33-421; I311Y,W336H)

<400> SEQUENCE: 37

Ser Pro Leu Arg Thr Tyr Leu Tyr Thr Pro Leu Tyr Asn Ala Thr Gln
  1               5                  10                  15

Pro Thr Leu Arg Asn Val Glu Arg Leu Ala Ala Asn Trp Pro Lys Lys
             20                  25                  30
```

Ile Pro Ser Asn Tyr Ile Glu Asp Ser Glu Tyr Ser Ile Lys Asn
            35                  40                  45

Ile Ser Leu Ser Asn His Thr Thr Arg Ala Ser Val Val His Pro Pro
 50                  55                  60

Ser Ser Ile Thr Glu Thr Ala Ser Lys Leu Asp Lys Asn Met Thr Ile
 65                  70                  75                  80

Gln Asp Gly Ala Phe Ala Met Ile Ser Pro Thr Pro Leu Leu Ile Thr
                 85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
            115                 120                 125

Pro Asp Leu Gly Pro Ile Thr Leu Asn Lys Thr Glu Leu Glu Leu Glu
130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
            210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
            275                 280                 285

Glu Gln Phe Thr Arg Val Asn Gly Phe Ser Asn Lys Tyr Trp Gly His
            290                 295                 300

Gly Gly Glu Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
370                 375                 380

Ile Asp Glu Arg Ser
385

<210> SEQ ID NO 38
<211> LENGTH: 389
<212> TYPE: PRT
<213> ORGANISM: Artificial
<220> FEATURE:
<223> OTHER INFORMATION: TnGalNAcT(33-421; I311Y,W336V)

<400> SEQUENCE: 38

```
Ser Pro Leu Arg Thr Tyr Leu Tyr Thr Pro Leu Tyr Asn Ala Thr Gln
  1               5                  10                  15

Pro Thr Leu Arg Asn Val Glu Arg Leu Ala Ala Asn Trp Pro Lys Lys
             20                  25                  30

Ile Pro Ser Asn Tyr Ile Glu Asp Ser Glu Glu Tyr Ser Ile Lys Asn
             35                  40                  45

Ile Ser Leu Ser Asn His Thr Thr Arg Ala Ser Val Val His Pro Pro
 50                  55                  60

Ser Ser Ile Thr Glu Thr Ala Ser Lys Leu Asp Lys Asn Met Thr Ile
 65                  70                  75                  80

Gln Asp Gly Ala Phe Ala Met Ile Ser Pro Thr Pro Leu Leu Ile Thr
                 85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
            115                 120                 125

Pro Asp Leu Gly Pro Ile Thr Leu Asn Lys Thr Glu Leu Glu Leu Glu
            130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
            195                 200                 205

Glu Gly Asn Lys Asp Phe Asn Arg Ala Lys Leu Met Asn Val Gly Phe
        210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
            275                 280                 285

Glu Gln Phe Thr Arg Val Asn Gly Phe Ser Asn Lys Tyr Trp Gly Val
            290                 295                 300

Gly Gly Glu Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
370                 375                 380

Ile Asp Glu Arg Ser
385

<210> SEQ ID NO 39
<211> LENGTH: 389
<212> TYPE: PRT
```

<213> ORGANISM: Artificial
<220> FEATURE:
<223> OTHER INFORMATION: TnGalNAcT(33-421; I311Y,E339A)

<400> SEQUENCE: 39

```
Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Ala Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
```

<210> SEQ ID NO 40
<211> LENGTH: 389
<212> TYPE: PRT
<213> ORGANISM: Artificial
<220> FEATURE:
<223> OTHER INFORMATION: TnGalNAcT(33-421; I311Y,E339G)

<400> SEQUENCE: 40

```
Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Gly Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
```

-continued

```
                355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 41
<211> LENGTH: 389
<212> TYPE: PRT
<213> ORGANISM: Artificial
<220> FEATURE:
<223> OTHER INFORMATION: TnGalNAcT(33-421; I311Y,E339D)

<400> SEQUENCE: 41

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly Trp
    290                 295                 300

Gly Gly Asp Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
```

```
                    325                 330                 335
His Lys Lys Ser Thr Pro Asn Pro Lys Arg Tyr Gln Leu Leu Ser Gln
                340                 345                 350

Thr Ser Lys Thr Phe Gln Lys Asp Gly Leu Ser Thr Leu Glu Tyr Glu
            355                 360                 365

Leu Val Gln Val Val Gln Tyr His Leu Tyr Thr His Ile Leu Val Asn
        370                 375                 380

Ile Asp Glu Arg Ser
385

<210> SEQ ID NO 42
<211> LENGTH: 389
<212> TYPE: PRT
<213> ORGANISM: Artificial
<220> FEATURE:
<223> OTHER INFORMATION: TnGalNAcT(33-421; I311Y,E339S)

<400> SEQUENCE: 42

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly Trp
```

```
              290                 295                 300
Gly Gly Ser Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
    370                 375                 380

Ile Asp Glu Arg Ser
385

<210> SEQ ID NO 43
<211> LENGTH: 389
<212> TYPE: PRT
<213> ORGANISM: Artificial
<220> FEATURE:
<223> OTHER INFORMATION: TnGalNAcT(33-421; I311Y,W336H,E339A)

<400> SEQUENCE: 43

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
            20                  25                  30

Ile Pro Ser Asn Tyr Ile Glu Asp Ser Glu Glu Tyr Ser Ile Lys Asn
        35                  40                  45

Ile Ser Leu Ser Asn His Thr Thr Arg Ala Ser Val Val His Pro Pro
    50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
    130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
```

```
                            260                 265                 270
Lys Leu Pro Tyr Glu Asp Tyr Phe Gly Gly Val Ser Ala Met Thr Leu
                275                 280                 285

Glu Gln Phe Thr Arg Val Asn Gly Phe Ser Asn Lys Tyr Trp Gly His
            290                 295                 300

Gly Gly Ala Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
                340                 345                 350

Thr Ser Lys Thr Phe Gln Lys Asp Gly Leu Ser Thr Leu Glu Tyr Glu
                355                 360                 365

Leu Val Gln Val Val Gln Tyr His Leu Tyr Thr His Ile Leu Val Asn
            370                 375                 380

Ile Asp Glu Arg Ser
385
```

<210> SEQ ID NO 44
<211> LENGTH: 389
<212> TYPE: PRT
<213> ORGANISM: Artificial
<220> FEATURE:
<223> OTHER INFORMATION: TnGalNAcT(33-421; I311Y,W336H,E339D)

<400> SEQUENCE: 44

```
Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
                20                  25                  30

Ile Pro Ser Asn Tyr Ile Glu Asp Ser Glu Glu Tyr Ser Ile Lys Asn
            35                  40                  45

Ile Ser Leu Ser Asn His Thr Thr Arg Ala Ser Val Val His Pro Pro
50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
            100                 105                 110

Lys Lys Ala Glu Ala Val Val Thr Leu Pro Leu Cys Asp Ser Met Pro
        115                 120                 125

Pro Asp Leu Gly Pro Ile Thr Leu Asn Lys Thr Glu Leu Glu Leu Glu
130                 135                 140

Trp Val Glu Lys Lys Phe Pro Glu Val Glu Trp Gly Gly Arg Tyr Ser
145                 150                 155                 160

Pro Pro Asn Cys Thr Ala Arg His Arg Val Ala Ile Ile Val Pro Tyr
                165                 170                 175

Arg Asp Arg Gln Gln His Leu Ala Ile Phe Leu Asn His Met His Pro
            180                 185                 190

Phe Leu Met Lys Gln Gln Ile Glu Tyr Gly Ile Phe Ile Val Glu Gln
        195                 200                 205

Glu Gly Asn Lys Asp Phe Asn Arg Ala Lys Leu Met Asn Val Gly Phe
    210                 215                 220

Val Glu Ser Gln Lys Leu Val Ala Glu Gly Trp Gln Cys Phe Val Phe
```

```
                225                 230                 235                 240
His Asp Ile Asp Leu Leu Pro Leu Asp Thr Arg Asn Leu Tyr Ser Cys
                    245                 250                 255

Pro Arg Gln Pro Arg His Met Ser Ala Ser Ile Asp Lys Leu His Phe
                    260                 265                 270

Lys Leu Pro Tyr Glu Asp Tyr Phe Gly Gly Val Ser Ala Met Thr Leu
                    275                 280                 285

Glu Gln Phe Thr Arg Val Asn Gly Phe Ser Asn Lys Tyr Trp Gly His
                    290                 295                 300

Gly Gly Asp Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                    325                 330                 335

His Lys Lys Ser Thr Pro Asn Pro Lys Arg Tyr Gln Leu Leu Ser Gln
                    340                 345                 350

Thr Ser Lys Thr Phe Gln Lys Asp Gly Leu Ser Thr Leu Glu Tyr Glu
                    355                 360                 365

Leu Val Gln Val Val Gln Tyr His Leu Tyr Thr His Ile Leu Val Asn
                    370                 375                 380

Ile Asp Glu Arg Ser
385

<210> SEQ ID NO 45
<211> LENGTH: 389
<212> TYPE: PRT
<213> ORGANISM: Artificial
<220> FEATURE:
<223> OTHER INFORMATION: TnGalNAcT(33-421; I311Y,W336H,E339S)

<400> SEQUENCE: 45

Ser Pro Leu Arg Thr Tyr Leu Tyr Thr Pro Leu Tyr Asn Ala Thr Gln
1               5                   10                  15

Pro Thr Leu Arg Asn Val Glu Arg Leu Ala Ala Asn Trp Pro Lys Lys
                20                  25                  30

Ile Pro Ser Asn Tyr Ile Glu Asp Ser Glu Glu Tyr Ser Ile Lys Asn
                35                  40                  45

Ile Ser Leu Ser Asn His Thr Thr Arg Ala Ser Val Val His Pro Pro
        50                  55                  60

Ser Ser Ile Thr Glu Thr Ala Ser Lys Leu Asp Lys Asn Met Thr Ile
65                  70                  75                  80

Gln Asp Gly Ala Phe Ala Met Ile Ser Pro Thr Pro Leu Leu Ile Thr
                85                  90                  95

Lys Leu Met Asp Ser Ile Lys Ser Tyr Val Thr Thr Glu Asp Gly Val
                100                 105                 110

Lys Lys Ala Glu Ala Val Val Thr Leu Pro Leu Cys Asp Ser Met Pro
                115                 120                 125

Pro Asp Leu Gly Pro Ile Thr Leu Asn Lys Thr Glu Leu Glu Leu Glu
                130                 135                 140

Trp Val Glu Lys Lys Phe Pro Glu Val Glu Trp Gly Arg Tyr Ser
145                 150                 155                 160

Pro Pro Asn Cys Thr Ala Arg His Arg Val Ala Ile Val Pro Tyr
                165                 170                 175

Arg Asp Arg Gln Gln His Leu Ala Ile Phe Leu Asn His Met His Pro
                180                 185                 190

Phe Leu Met Lys Gln Gln Ile Glu Tyr Gly Ile Phe Ile Val Glu Gln
```

```
                195                 200                 205
Glu Gly Asn Lys Asp Phe Asn Arg Ala Lys Leu Met Asn Val Gly Phe
210                 215                 220

Val Glu Ser Gln Lys Leu Val Ala Glu Gly Trp Gln Cys Phe Val Phe
225                 230                 235                 240

His Asp Ile Asp Leu Leu Pro Leu Asp Thr Arg Asn Leu Tyr Ser Cys
                245                 250                 255

Pro Arg Gln Pro Arg His Met Ser Ala Ser Ile Asp Lys Leu His Phe
            260                 265                 270

Lys Leu Pro Tyr Glu Asp Tyr Phe Gly Gly Val Ser Ala Met Thr Leu
        275                 280                 285

Glu Gln Phe Thr Arg Val Asn Gly Phe Ser Asn Lys Tyr Trp Gly His
290                 295                 300

Gly Gly Ser Asp Asp Met Ser Tyr Arg Leu Lys Lys Ile Asn Tyr
305                 310                 315                 320

His Ile Ala Arg Tyr Lys Met Ser Ile Ala Arg Tyr Ala Met Leu Asp
                325                 330                 335

His Lys Lys Ser Thr Pro Asn Pro Lys Arg Tyr Gln Leu Leu Ser Gln
            340                 345                 350

Thr Ser Lys Thr Phe Gln Lys Asp Gly Leu Ser Thr Leu Glu Tyr Glu
        355                 360                 365

Leu Val Gln Val Val Gln Tyr His Leu Tyr Thr His Ile Leu Val Asn
370                 375                 380

Ile Asp Glu Arg Ser
385

<210> SEQ ID NO 46
<211> LENGTH: 354
<212> TYPE: PRT
<213> ORGANISM: Artificial
<220> FEATURE:
<223> OTHER INFORMATION: AsGalNAcT(30-383; W282H)

<400> SEQUENCE: 46

Asp Tyr Ser Phe Trp Ser Pro Ala Phe Ile Ile Ser Ala Pro Lys Thr
1               5                   10                  15

Leu Thr Thr Leu Gln Pro Phe Ser Gln Ser Thr Ser Thr Asn Asp Leu
            20                  25                  30

Ala Val Ser Ala Leu Glu Ser Val Glu Phe Ser Met Leu Asp Asn Ser
        35                  40                  45

Ser Ile Leu His Ala Ser Asp Asn Trp Thr Asn Asp Glu Leu Val Met
50                  55                  60

Arg Ala Gln Asn Glu Asn Leu Gln Leu Cys Pro Met Thr Pro Pro Ala
65                  70                  75                  80

Leu Val Gly Pro Ile Lys Val Trp Met Asp Ala Pro Ser Phe Ala Glu
                85                  90                  95

Leu Glu Arg Leu Tyr Pro Phe Leu Glu Pro Gly Gly His Gly Met Pro
            100                 105                 110

Thr Ala Cys Arg Ala Arg His Arg Val Ala Ile Val Val Pro Tyr Arg
        115                 120                 125

Asp Arg Glu Ser His Leu Arg Thr Phe Leu His Asn Leu His Ser Leu
130                 135                 140

Leu Thr Lys Gln Gln Leu Asp Tyr Ala Ile Phe Val Val Glu Gln Thr
145                 150                 155                 160

Ala Asn Glu Thr Phe Asn Arg Ala Lys Leu Met Asn Val Gly Tyr Ala
```

```
                      165                 170                 175
Glu Ala Ile Arg Leu Tyr Asp Trp Arg Cys Phe Ile Phe His Asp Val
            180                 185                 190

Asp Leu Leu Pro Glu Asp Arg Asn Leu Tyr Ser Cys Pro Asp Glu
        195                 200                 205

Pro Arg His Met Ser Val Ala Val Asp Lys Phe Asn Tyr Lys Leu Pro
    210                 215                 220

Tyr Gly Ser Ile Phe Gly Gly Ile Ser Ala Leu Thr Arg Glu Gln Phe
225                 230                 235                 240

Glu Gly Ile Asn Gly Phe Ser Asn Asp Tyr Trp Gly His Gly Gly Glu
            245                 250                 255

Asp Asp Asp Leu Ser Thr Arg Val Thr Leu Ala Gly Tyr Lys Ile Ser
        260                 265                 270

Arg Tyr Pro Ala Glu Ile Ala Arg Tyr Lys Met Ile Lys His Asn Ser
    275                 280                 285

Glu Lys Lys Asn Pro Val Asn Arg Cys Arg Tyr Lys Leu Met Ser Ala
        290                 295                 300

Thr Lys Ser Arg Trp Arg Asn Asp Gly Leu Ser Ser Leu Ser Tyr Asp
305                 310                 315                 320

Leu Ile Ser Leu Gly Arg Leu Pro Leu Tyr Thr His Ile Lys Val Asp
            325                 330                 335

Leu Leu Lys Gln Ser Arg Arg Tyr Leu Arg Thr His Gly Phe Pro
        340                 345                 350

Thr Cys

<210> SEQ ID NO 47
<211> LENGTH: 354
<212> TYPE: PRT
<213> ORGANISM: Artificial
<220> FEATURE:
<223> OTHER INFORMATION: AsGalNAcT(30-383; E285D)

<400> SEQUENCE: 47

Asp Tyr Ser Phe Trp Ser Pro Ala Phe Ile Ile Ser Ala Pro Lys Thr
1               5                   10                  15

Leu Thr Thr Leu Gln Pro Phe Ser Gln Ser Thr Ser Thr Asn Asp Leu
            20                  25                  30

Ala Val Ser Ala Leu Glu Ser Val Glu Phe Ser Met Leu Asp Asn Ser
        35                  40                  45

Ser Ile Leu His Ala Ser Asp Asn Trp Thr Asn Asp Glu Leu Val Met
    50                  55                  60

Arg Ala Gln Asn Glu Asn Leu Gln Leu Cys Pro Met Thr Pro Pro Ala
65                  70                  75                  80

Leu Val Gly Pro Ile Lys Val Trp Met Asp Ala Pro Ser Phe Ala Glu
                85                  90                  95

Leu Glu Arg Leu Tyr Pro Phe Leu Glu Pro Gly Gly His Gly Met Pro
            100                 105                 110

Thr Ala Cys Arg Ala Arg His Arg Val Ala Ile Val Val Pro Tyr Arg
        115                 120                 125

Asp Arg Glu Ser His Leu Arg Thr Phe Leu His Asn Leu His Ser Leu
    130                 135                 140

Leu Thr Lys Gln Gln Leu Asp Tyr Ala Ile Phe Val Val Glu Gln Thr
145                 150                 155                 160

Ala Asn Glu Thr Phe Asn Arg Ala Lys Leu Met Asn Val Gly Tyr Ala
                165                 170                 175
```

-continued

```
Glu Ala Ile Arg Leu Tyr Asp Trp Arg Cys Phe Ile Phe His Asp Val
            180                 185                 190

Asp Leu Leu Pro Glu Asp Arg Asn Leu Tyr Ser Cys Pro Asp Glu
        195                 200                 205

Pro Arg His Met Ser Val Ala Val Asp Lys Phe Asn Tyr Lys Leu Pro
    210                 215                 220

Tyr Gly Ser Ile Phe Gly Ile Ser Ala Leu Thr Arg Glu Gln Phe
225                 230                 235                 240

Glu Gly Ile Asn Gly Phe Ser Asn Asp Tyr Trp Gly Trp Gly Gly Asp
                245                 250                 255

Asp Asp Asp Leu Ser Thr Arg Val Thr Leu Ala Gly Tyr Lys Ile Ser
        260                 265                 270

Arg Tyr Pro Ala Glu Ile Ala Arg Tyr Lys Met Ile Lys His Asn Ser
    275                 280                 285

Glu Lys Lys Asn Pro Val Asn Arg Cys Arg Tyr Lys Leu Met Ser Ala
290                 295                 300

Thr Lys Ser Arg Trp Arg Asn Asp Gly Leu Ser Ser Leu Ser Tyr Asp
305                 310                 315                 320

Leu Ile Ser Leu Gly Arg Leu Pro Leu Tyr Thr His Ile Lys Val Asp
                325                 330                 335

Leu Leu Glu Lys Gln Ser Arg Arg Tyr Leu Arg Thr His Gly Phe Pro
            340                 345                 350

Thr Cys

<210> SEQ ID NO 48
<211> LENGTH: 354
<212> TYPE: PRT
<213> ORGANISM: Artificial
<220> FEATURE:
<223> OTHER INFORMATION: AsGalNAcT(30-383; I257Y)

<400> SEQUENCE: 48

Asp Tyr Ser Phe Trp Ser Pro Ala Phe Ile Ile Ser Ala Pro Lys Thr
1               5                   10                  15

Leu Thr Thr Leu Gln Pro Phe Ser Gln Ser Thr Ser Thr Asn Asp Leu
            20                  25                  30

Ala Val Ser Ala Leu Glu Ser Val Glu Phe Ser Met Leu Asp Asn Ser
        35                  40                  45

Ser Ile Leu His Ala Ser Asp Asn Trp Thr Asn Asp Glu Leu Val Met
    50                  55                  60

Arg Ala Gln Asn Glu Asn Leu Gln Leu Cys Pro Met Thr Pro Pro Ala
65                  70                  75                  80

Leu Val Gly Pro Ile Lys Val Trp Met Asp Ala Pro Ser Phe Ala Glu
                85                  90                  95

Leu Glu Arg Leu Tyr Pro Phe Leu Glu Pro Gly Gly His Gly Met Pro
            100                 105                 110

Thr Ala Cys Arg Ala Arg His Arg Val Ala Ile Val Val Pro Tyr Arg
        115                 120                 125

Asp Arg Glu Ser His Leu Arg Thr Phe Leu His Asn Leu His Ser Leu
    130                 135                 140

Leu Thr Lys Gln Gln Leu Asp Tyr Ala Ile Phe Val Val Glu Gln Thr
145                 150                 155                 160

Ala Asn Glu Thr Phe Asn Arg Ala Lys Leu Met Asn Val Gly Tyr Ala
                165                 170                 175
```

```
Glu Ala Ile Arg Leu Tyr Asp Trp Arg Cys Phe Ile Phe His Asp Val
                180                 185                 190

Asp Leu Leu Pro Glu Asp Arg Asn Leu Tyr Ser Cys Pro Asp Glu
            195                 200                 205

Pro Arg His Met Ser Val Ala Val Asp Lys Phe Asn Tyr Lys Leu Pro
        210                 215                 220

Tyr Gly Ser Tyr Phe Gly Gly Ile Ser Ala Leu Thr Arg Glu Gln Phe
225                 230                 235                 240

Glu Gly Ile Asn Gly Phe Ser Asn Asp Tyr Trp Gly Trp Gly Gly Glu
                245                 250                 255

Asp Asp Asp Leu Ser Thr Arg Val Thr Leu Ala Gly Tyr Lys Ile Ser
            260                 265                 270

Arg Tyr Pro Ala Glu Ile Ala Arg Tyr Lys Met Ile Lys His Asn Ser
        275                 280                 285

Glu Lys Lys Asn Pro Val Asn Arg Cys Arg Tyr Lys Leu Met Ser Ala
    290                 295                 300

Thr Lys Ser Arg Trp Arg Asn Asp Gly Leu Ser Ser Leu Ser Tyr Asp
305                 310                 315                 320

Leu Ile Ser Leu Gly Arg Leu Pro Leu Tyr Thr His Ile Lys Val Asp
                325                 330                 335

Leu Leu Glu Lys Gln Ser Arg Arg Tyr Leu Arg Thr His Gly Phe Pro
            340                 345                 350

Thr Cys

<210> SEQ ID NO 49
<211> LENGTH: 410
<212> TYPE: PRT
<213> ORGANISM: Artificial
<220> FEATURE:
<223> OTHER INFORMATION: His-TnGalNAcT(33-421)

<400> SEQUENCE: 49

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
```

180                 185                 190
Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
            245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
            290                 295                 300

Ser Ala Met Thr Leu Glu Gln Phe Thr Arg Val Asn Gly Phe Ser Asn
305                 310                 315                 320

Lys Tyr Trp Gly Trp Gly Gly Glu Asp Asp Asp Met Ser Tyr Arg Leu
            325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
            405                 410

<210> SEQ ID NO 50
<211> LENGTH: 410
<212> TYPE: PRT
<213> ORGANISM: Artificial
<220> FEATURE:
<223> OTHER INFORMATION: His-TnGalNAcT(33-421; W336F)

<400> SEQUENCE: 50

Met Gly Ser Ser His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
            85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu

```
                    130                 135                 140
Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                    165                 170                 175

Gly Gly Arg Tyr Ser Pro Pro Asn Cys Thr Ala Arg His Val Ala
                180                 185                 190

Ile Ile Val Pro Tyr Arg Asp Arg Gln Gln His Leu Ala Ile Phe Leu
                195                 200                 205

Asn His Met His Pro Phe Leu Met Lys Gln Gln Ile Glu Tyr Gly Ile
            210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                    245                 250                 255

Gln Cys Phe Val Phe His Asp Ile Asp Leu Leu Pro Leu Asp Thr Arg
                260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
        290                 295                 300

Ser Ala Met Thr Leu Glu Gln Phe Thr Arg Val Asn Gly Phe Ser Asn
305                 310                 315                 320

Lys Tyr Trp Gly Phe Gly Gly Glu Asp Asp Met Ser Tyr Arg Leu
                    325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
        370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 51
<211> LENGTH: 410
<212> TYPE: PRT
<213> ORGANISM: Artificial
<220> FEATURE:
<223> OTHER INFORMATION: His-TnGalNAcT(33-421; W336H)

<400> SEQUENCE: 51

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
        50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
```

```
                85                  90                  95
Lys Asn Met Thr Ile Gln Asp Gly Ala Phe Ala Met Ile Ser Pro Thr
                100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Ile Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly His Gly Gly Glu Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Gln Tyr His Leu Tyr Thr
385                 390                 395                 400

His Ile Leu Val Asn Ile Asp Glu Arg Ser
                405                 410

<210> SEQ ID NO 52
<211> LENGTH: 410
<212> TYPE: PRT
<213> ORGANISM: Artificial
<220> FEATURE:
<223> OTHER INFORMATION: His-TnGalNAcT(33-421; W336V)

<400> SEQUENCE: 52

Met Gly Ser Ser His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
```

```
            35                  40                  45
Asn Trp Pro Lys Lys Ile Pro Ser Asn Tyr Ile Glu Asp Ser Glu Glu
 50                  55                  60

Tyr Ser Ile Lys Asn Ile Ser Leu Ser Asn His Thr Thr Arg Ala Ser
 65                  70                  75                  80

Val Val His Pro Pro Ser Ser Ile Thr Glu Thr Ala Ser Lys Leu Asp
                 85                  90                  95

Lys Asn Met Thr Ile Gln Asp Gly Ala Phe Ala Met Ile Ser Pro Thr
                100                 105                 110

Pro Leu Leu Ile Thr Lys Leu Met Asp Ser Ile Lys Ser Tyr Val Thr
                115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
                180                 185                 190

Ile Ile Val Pro Tyr Arg Asp Arg Gln Gln His Leu Ala Ile Phe Leu
                195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
                260                 265                 270

Asn Leu Tyr Ser Cys Pro Arg Gln Pro Arg His Met Ser Ala Ser Ile
                275                 280                 285

Asp Lys Leu His Phe Lys Leu Pro Tyr Glu Asp Ile Phe Gly Gly Val
290                 295                 300

Ser Ala Met Thr Leu Glu Gln Phe Thr Arg Val Asn Gly Phe Ser Asn
305                 310                 315                 320

Lys Tyr Trp Gly Val Gly Gly Glu Asp Asp Met Ser Tyr Arg Leu
                325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
                355                 360                 365

Gln Leu Leu Ser Gln Thr Ser Lys Thr Phe Gln Lys Asp Gly Leu Ser
                370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 53
<211> LENGTH: 410
<212> TYPE: PRT
<213> ORGANISM: Artificial
<220> FEATURE:
<223> OTHER INFORMATION: His-TnGalNAcT(33-421; E339A)
```

```
<400> SEQUENCE: 53

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
290                 295                 300

Ser Ala Met Thr Leu Glu Gln Phe Thr Arg Val Asn Gly Phe Ser Asn
305                 310                 315                 320

Lys Tyr Trp Gly Trp Gly Gly Ala Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410
```

<210> SEQ ID NO 54
<211> LENGTH: 410
<212> TYPE: PRT
<213> ORGANISM: Artificial
<220> FEATURE:
<223> OTHER INFORMATION: His-TnGalNAcT(33-421; E339G)

<400> SEQUENCE: 54

| | | | | | | | | | | | | | | | |
|---|---|---|---|---|---|---|---|---|---|---|---|---|---|---|---|
| Met | Gly | Ser | Ser | His | His | His | His | His | Ser | Ser | Gly | Leu | Val | Pro | |
| 1 | | | | 5 | | | | | 10 | | | | | 15 | |
| Arg | Gly | Ser | His | Met | Ser | Pro | Leu | Arg | Thr | Tyr | Leu | Tyr | Thr | Pro | Leu |
| | | | 20 | | | | | 25 | | | | | 30 | | |
| Tyr | Asn | Ala | Thr | Gln | Pro | Thr | Leu | Arg | Asn | Val | Glu | Arg | Leu | Ala | Ala |
| | | 35 | | | | | 40 | | | | | 45 | | | |
| Asn | Trp | Pro | Lys | Lys | Ile | Pro | Ser | Asn | Tyr | Ile | Glu | Asp | Ser | Glu | Glu |
| | 50 | | | | | 55 | | | | | 60 | | | | |
| Tyr | Ser | Ile | Lys | Asn | Ile | Ser | Leu | Ser | Asn | His | Thr | Thr | Arg | Ala | Ser |
| 65 | | | | | 70 | | | | | 75 | | | | | 80 |
| Val | Val | His | Pro | Pro | Ser | Ser | Ile | Thr | Glu | Thr | Ala | Ser | Lys | Leu | Asp |
| | | | | 85 | | | | | 90 | | | | | 95 | |
| Lys | Asn | Met | Thr | Ile | Gln | Asp | Gly | Ala | Phe | Ala | Met | Ile | Ser | Pro | Thr |
| | | | 100 | | | | | 105 | | | | | 110 | | |
| Pro | Leu | Leu | Ile | Thr | Lys | Leu | Met | Asp | Ser | Ile | Lys | Ser | Tyr | Val | Thr |
| | | | 115 | | | | | 120 | | | | | 125 | | |
| Thr | Glu | Asp | Gly | Val | Lys | Lys | Ala | Glu | Ala | Val | Val | Thr | Leu | Pro | Leu |
| | 130 | | | | | 135 | | | | | 140 | | | | |
| Cys | Asp | Ser | Met | Pro | Pro | Asp | Leu | Gly | Pro | Ile | Thr | Leu | Asn | Lys | Thr |
| 145 | | | | | 150 | | | | | 155 | | | | | 160 |
| Glu | Leu | Glu | Leu | Glu | Trp | Val | Glu | Lys | Lys | Phe | Pro | Glu | Val | Glu | Trp |
| | | | | 165 | | | | | 170 | | | | | 175 | |
| Gly | Gly | Arg | Tyr | Ser | Pro | Pro | Asn | Cys | Thr | Ala | Arg | His | Arg | Val | Ala |
| | | | 180 | | | | | 185 | | | | | 190 | | |
| Ile | Ile | Val | Pro | Tyr | Arg | Asp | Arg | Gln | Gln | His | Leu | Ala | Ile | Phe | Leu |
| | | | 195 | | | | | 200 | | | | | 205 | | |
| Asn | His | Met | His | Pro | Phe | Leu | Met | Lys | Gln | Gln | Ile | Glu | Tyr | Gly | Ile |
| | 210 | | | | | 215 | | | | | 220 | | | | |
| Phe | Ile | Val | Glu | Gln | Glu | Gly | Asn | Lys | Asp | Phe | Asn | Arg | Ala | Lys | Leu |
| 225 | | | | | 230 | | | | | 235 | | | | | 240 |
| Met | Asn | Val | Gly | Phe | Val | Glu | Ser | Gln | Lys | Leu | Val | Ala | Glu | Gly | Trp |
| | | | | 245 | | | | | 250 | | | | | 255 | |
| Gln | Cys | Phe | Val | Phe | His | Asp | Ile | Asp | Leu | Leu | Pro | Leu | Asp | Thr | Arg |
| | | | 260 | | | | | 265 | | | | | 270 | | |
| Asn | Leu | Tyr | Ser | Cys | Pro | Arg | Gln | Pro | Arg | His | Met | Ser | Ala | Ser | Ile |
| | | | 275 | | | | | 280 | | | | | 285 | | |
| Asp | Lys | Leu | His | Phe | Lys | Leu | Pro | Tyr | Glu | Asp | Ile | Phe | Gly | Gly | Val |
| | 290 | | | | | 295 | | | | | 300 | | | | |
| Ser | Ala | Met | Thr | Leu | Glu | Gln | Phe | Thr | Arg | Val | Asn | Gly | Phe | Ser | Asn |
| 305 | | | | | 310 | | | | | 315 | | | | | 320 |
| Lys | Tyr | Trp | Gly | Trp | Gly | Gly | Glu | Asp | Asp | Met | Ser | Tyr | Arg | Leu | |
| | | | | 325 | | | | | 330 | | | | | 335 | |
| Lys | Lys | Ile | Asn | Tyr | His | Ile | Ala | Arg | Tyr | Lys | Met | Ser | Ile | Ala | Arg |
| | | | 340 | | | | | 345 | | | | | 350 | | |
| Tyr | Ala | Met | Leu | Asp | His | Lys | Lys | Ser | Thr | Pro | Asn | Pro | Lys | Arg | Tyr |
| | | | 355 | | | | | 360 | | | | | 365 | | |

Gln Leu Leu Ser Gln Thr Ser Lys Thr Phe Gln Lys Asp Gly Leu Ser
        370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
        405                 410

<210> SEQ ID NO 55
<211> LENGTH: 410
<212> TYPE: PRT
<213> ORGANISM: Artificial
<220> FEATURE:
<223> OTHER INFORMATION: His-TnGalNAcT(33-421; E339D)

<400> SEQUENCE: 55

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Ile Phe Gly Gly Val
    290                 295                 300

Ser Ala Met Thr Leu Glu Gln Phe Thr Arg Val Asn Gly Phe Ser Asn
305                 310                 315                 320

```
Lys Tyr Trp Gly Trp Gly Gly Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
            405                 410

<210> SEQ ID NO 56
<211> LENGTH: 410
<212> TYPE: PRT
<213> ORGANISM: Artificial
<220> FEATURE:
<223> OTHER INFORMATION: His-TnGalNAcT(33-421; E339S)

<400> SEQUENCE: 56

Met Gly Ser Ser His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Thr Leu Pro Leu
            130                 135                 140

Cys Asp Ser Met Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
            210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270
```

```
Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
        290                 295                 300

Ser Ala Met Thr Leu Glu Gln Phe Thr Arg Val Asn Gly Phe Ser Asn
305                 310                 315                 320

Lys Tyr Trp Gly Trp Gly Gly Ser Asp Asp Met Ser Tyr Arg Leu
                325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
        370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 57
<211> LENGTH: 410
<212> TYPE: PRT
<213> ORGANISM: Artificial
<220> FEATURE:
<223> OTHER INFORMATION: His-TnGalNAcT(33-421; W336H,E339A)

<400> SEQUENCE: 57

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
        50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
            210                 215                 220
```

```
Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
            245                 250                 255

Gln Cys Phe Val Phe His Asp Ile Asp Leu Leu Pro Leu Asp Thr Arg
        260                 265                 270

Asn Leu Tyr Ser Cys Pro Arg Gln Pro Arg His Met Ser Ala Ser Ile
    275                 280                 285

Asp Lys Leu His Phe Lys Leu Pro Tyr Glu Asp Ile Phe Gly Gly Val
290                 295                 300

Ser Ala Met Thr Leu Glu Gln Phe Thr Arg Val Asn Gly Phe Ser Asn
305                 310                 315                 320

Lys Tyr Trp Gly His Gly Gly Ala Asp Asp Met Ser Tyr Arg Leu
            325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 58
<211> LENGTH: 410
<212> TYPE: PRT
<213> ORGANISM: Artificial
<220> FEATURE:
<223> OTHER INFORMATION: His-TnGalNAcT(33-421; W336H, E339D)

<400> SEQUENCE: 58

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175
```

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
            245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
            290                 295                 300

Ser Ala Met Thr Leu Glu Gln Phe Thr Arg Val Asn Gly Phe Ser Asn
305                 310                 315                 320

Lys Tyr Trp Gly His Gly Gly Asp Asp Asp Met Ser Tyr Arg Leu
            325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
            405                 410

<210> SEQ ID NO 59
<211> LENGTH: 410
<212> TYPE: PRT
<213> ORGANISM: Artificial
<220> FEATURE:
<223> OTHER INFORMATION: His-TnGalNAcT(33-421; W336H, E339S)

<400> SEQUENCE: 59

Met Gly Ser Ser His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
        50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

```
Thr Glu Asp Gly Val Lys Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
                180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
                260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Ile Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly His Gly Gly Ser Asp Asp Asp Met Ser Tyr Arg Leu
                325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 60
<211> LENGTH: 410
<212> TYPE: PRT
<213> ORGANISM: Artificial
<220> FEATURE:
<223> OTHER INFORMATION: His-TnGalNAcT(33-421; I311Y)

<400> SEQUENCE: 60

Met Gly Ser Ser His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80
```

Val Val His Pro Pro Ser Ser Ile Thr Glu Thr Ala Ser Lys Leu Asp
             85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Tyr Phe Gly Gly Val
            290                 295                 300

Ser Ala Met Thr Leu Glu Gln Phe Thr Arg Val Asn Gly Phe Ser Asn
305                 310                 315                 320

Lys Tyr Trp Gly Trp Gly Gly Glu Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 61
<211> LENGTH: 410
<212> TYPE: PRT
<213> ORGANISM: Artificial
<220> FEATURE:
<223> OTHER INFORMATION: His-TnGalNAcT(33-421; I311Y,W336F)

<400> SEQUENCE: 61

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

```
Tyr Asn Ala Thr Gln Pro Thr Leu Arg Asn Val Glu Arg Leu Ala Ala
             35                  40                  45

Asn Trp Pro Lys Lys Ile Pro Ser Asn Tyr Ile Glu Asp Ser Glu Glu
 50                      55                  60

Tyr Ser Ile Lys Asn Ile Ser Leu Ser Asn His Thr Thr Arg Ala Ser
 65                  70                  75                  80

Val Val His Pro Pro Ser Ser Ile Thr Glu Thr Ala Ser Lys Leu Asp
                 85                  90                  95

Lys Asn Met Thr Ile Gln Asp Gly Ala Phe Ala Met Ile Ser Pro Thr
                100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly Phe Gly Gly Glu Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Gln Tyr His Leu Tyr Thr
385                 390                 395                 400

His Ile Leu Val Asn Ile Asp Glu Arg Ser
                405                 410

<210> SEQ ID NO 62
<211> LENGTH: 410
<212> TYPE: PRT
<213> ORGANISM: Artificial
<220> FEATURE:
```

<223> OTHER INFORMATION: His-TnGalNAcT(33-421; I311Y,W336H)

<400> SEQUENCE: 62

```
Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Thr Leu Pro Leu
            130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
        210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly His Gly Gly Glu Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Val Gln Tyr His Leu Tyr Thr
385                 390                 395                 400
```

His Ile Leu Val Asn Ile Asp Glu Arg Ser
              405                 410

<210> SEQ ID NO 63
<211> LENGTH: 409
<212> TYPE: PRT
<213> ORGANISM: Artificial
<220> FEATURE:
<223> OTHER INFORMATION: His-TnGalNAcT(33-421; I311Y,W336V)

<400> SEQUENCE: 63

Gly Ser Ser His His His His His Ser Ser Gly Leu Val Pro Arg
1               5                   10                  15

Gly Ser His Met Ser Pro Leu Arg Thr Tyr Leu Tyr Thr Pro Leu Tyr
            20                  25                  30

Asn Ala Thr Gln Pro Thr Leu Arg Asn Val Glu Arg Leu Ala Ala Asn
        35                  40                  45

Trp Pro Lys Lys Ile Pro Ser Asn Tyr Ile Glu Asp Ser Glu Glu Tyr
50                  55                  60

Ser Ile Lys Asn Ile Ser Leu Ser Asn His Thr Thr Arg Ala Ser Val
65                  70                  75                  80

Val His Pro Pro Ser Ser Ile Thr Glu Thr Ala Ser Lys Leu Asp Lys
                85                  90                  95

Asn Met Thr Ile Gln Asp Gly Ala Phe Ala Met Ile Ser Pro Thr Pro
            100                 105                 110

Leu Leu Ile Thr Lys Leu Met Asp Ser Ile Lys Ser Tyr Val Thr Thr
        115                 120                 125

Glu Asp Gly Val Lys Lys Ala Glu Ala Val Val Thr Leu Pro Leu Cys
130                 135                 140

Asp Ser Met Pro Pro Asp Leu Gly Pro Ile Thr Leu Asn Lys Thr Glu
145                 150                 155                 160

Leu Glu Leu Glu Trp Val Glu Lys Lys Phe Pro Glu Val Glu Trp Gly
                165                 170                 175

Gly Arg Tyr Ser Pro Pro Asn Cys Thr Ala Arg His Arg Val Ala Ile
            180                 185                 190

Ile Val Pro Tyr Arg Asp Arg Gln Gln His Leu Ala Ile Phe Leu Asn
        195                 200                 205

His Met His Pro Phe Leu Met Lys Gln Gln Ile Glu Tyr Gly Ile Phe
210                 215                 220

Ile Val Glu Gln Glu Gly Asn Lys Asp Phe Asn Arg Ala Lys Leu Met
225                 230                 235                 240

Asn Val Gly Phe Val Glu Ser Gln Lys Leu Val Ala Glu Gly Trp Gln
                245                 250                 255

Cys Phe Val Phe His Asp Ile Asp Leu Leu Pro Leu Thr Arg Asn
            260                 265                 270

Leu Tyr Ser Cys Pro Arg Gln Pro Arg His Met Ser Ala Ser Ile Asp
        275                 280                 285

Lys Leu His Phe Lys Leu Pro Tyr Glu Asp Tyr Phe Gly Gly Val Ser
290                 295                 300

Ala Met Thr Leu Glu Gln Phe Thr Arg Val Asn Gly Phe Ser Asn Lys
305                 310                 315                 320

Tyr Trp Gly Val Gly Gly Glu Asp Asp Asp Met Ser Tyr Arg Leu Lys
                325                 330                 335

Lys Ile Asn Tyr His Ile Ala Arg Tyr Lys Met Ser Ile Ala Arg Tyr
            340                 345                 350

Ala Met Leu Asp His Lys Lys Ser Thr Pro Asn Pro Lys Arg Tyr Gln
              355                 360                 365

Leu Leu Ser Gln Thr Ser Lys Thr Phe Gln Lys Asp Gly Leu Ser Thr
370                 375                 380

Leu Glu Tyr Glu Leu Val Gln Val Val Gln Tyr His Leu Tyr Thr His
385                 390                 395                 400

Ile Leu Val Asn Ile Asp Glu Arg Ser
              405

<210> SEQ ID NO 64
<211> LENGTH: 410
<212> TYPE: PRT
<213> ORGANISM: Artificial
<220> FEATURE:
<223> OTHER INFORMATION: His-TnGalNAcT(33-421; I311Y,E339A)

<400> SEQUENCE: 64

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
        290                 295                 300

```
Ser Ala Met Thr Leu Glu Gln Phe Thr Arg Val Asn Gly Phe Ser Asn
305                 310                 315                 320

Lys Tyr Trp Gly Trp Gly Gly Ala Asp Asp Met Ser Tyr Arg Leu
            325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 65
<211> LENGTH: 410
<212> TYPE: PRT
<213> ORGANISM: Artificial
<220> FEATURE:
<223> OTHER INFORMATION: His-TnGalNAcT(33-421; I311Y, E339G)

<400> SEQUENCE: 65

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
                35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
            210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
            245                 250                 255
```

```
Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Tyr Phe Gly Gly Val
            290                 295                 300

Ser Ala Met Thr Leu Glu Gln Phe Thr Arg Val Asn Gly Phe Ser Asn
305                 310                 315                 320

Lys Tyr Trp Gly Trp Gly Gly Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
            355                 360                 365

Gln Leu Leu Ser Gln Thr Ser Lys Thr Phe Gln Lys Asp Gly Leu Ser
            370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
            405                 410

<210> SEQ ID NO 66
<211> LENGTH: 410
<212> TYPE: PRT
<213> ORGANISM: Artificial
<220> FEATURE:
<223> OTHER INFORMATION: His-TnGalNAcT(33-421; I311Y,E339D)

<400> SEQUENCE: 66

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
            35                  40                  45

Asn Trp Pro Lys Lys Ile Pro Ser Asn Tyr Ile Glu Asp Ser Glu Glu
            50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
            85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
            165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205
```

```
Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
                260                 265                 270

Asn Leu Tyr Ser Cys Pro Arg Gln Pro Arg His Met Ser Ala Ser Ile
                275                 280                 285

Asp Lys Leu His Phe Lys Leu Pro Tyr Glu Asp Tyr Phe Gly Gly Val
290                 295                 300

Ser Ala Met Thr Leu Glu Gln Phe Thr Arg Val Asn Gly Phe Ser Asn
305                 310                 315                 320

Lys Tyr Trp Gly Trp Gly Gly Asp Asp Asp Met Ser Tyr Arg Leu
                325                 330                 335

Lys Lys Ile Asn Tyr His Ile Ala Arg Tyr Lys Met Ser Ile Ala Arg
                340                 345                 350

Tyr Ala Met Leu Asp His Lys Lys Ser Thr Pro Asn Pro Lys Arg Tyr
                355                 360                 365

Gln Leu Leu Ser Gln Thr Ser Lys Thr Phe Gln Lys Asp Gly Leu Ser
370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 67
<211> LENGTH: 410
<212> TYPE: PRT
<213> ORGANISM: Artificial
<220> FEATURE:
<223> OTHER INFORMATION: His-TnGalNAcT(33-421; I311Y,E339S)

<400> SEQUENCE: 67

Met Gly Ser Ser His His His His His Ser Ser Gly Leu Val Pro
1               5                   10                  15

Arg Gly Ser His Met Ser Pro Leu Arg Thr Tyr Leu Tyr Thr Pro Leu
                20                  25                  30

Tyr Asn Ala Thr Gln Pro Thr Leu Arg Asn Val Glu Arg Leu Ala Ala
                35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
                100                 105                 110

Pro Leu Leu Ile Thr Lys Leu Met Asp Ser Ile Lys Ser Tyr Val Thr
                115                 120                 125

Thr Glu Asp Gly Val Lys Lys Ala Glu Ala Val Val Thr Leu Pro Leu
                130                 135                 140

Cys Asp Ser Met Pro Pro Asp Leu Gly Pro Ile Thr Leu Asn Lys Thr
145                 150                 155                 160
```

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
            195                 200                 205

Asn His Met His Pro Phe Leu Met Lys Gln Gln Ile Glu Tyr Gly Ile
        210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
            275                 280                 285

Asp Lys Leu His Phe Lys Leu Pro Tyr Glu Asp Tyr Phe Gly Gly Val
        290                 295                 300

Ser Ala Met Thr Leu Glu Gln Phe Thr Arg Val Asn Gly Phe Ser Asn
305                 310                 315                 320

Lys Tyr Trp Gly Trp Gly Gly Ser Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 68
<211> LENGTH: 410
<212> TYPE: PRT
<213> ORGANISM: Artificial
<220> FEATURE:
<223> OTHER INFORMATION: His-TnGalNAcT(33-421; I311Y,W336H,E339A)

<400> SEQUENCE: 68

Met Gly Ser Ser His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

```
Pro Leu Leu Ile Thr Lys Leu Met Asp Ser Ile Lys Ser Tyr Val Thr
            115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
    210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly His Gly Gly Ala Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 69
<211> LENGTH: 410
<212> TYPE: PRT
<213> ORGANISM: Artificial
<220> FEATURE:
<223> OTHER INFORMATION: His-TnGalNAcT(33-421; I311Y,W336H,E339D)

<400> SEQUENCE: 69

Met Gly Ser Ser His His His His His His Ser Ser Gly Leu Val Pro
1               5                   10                  15

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
    50                  55                  60
```

```
Tyr Ser Ile Lys Asn Ile Ser Leu Ser Asn His Thr Thr Arg Ala Ser
 65                  70                  75                  80

Val Val His Pro Pro Ser Ser Ile Thr Glu Thr Ala Ser Lys Leu Asp
                 85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
    130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
    290                 295                 300

Ser Ala Met Thr Leu Glu Gln Phe Thr Arg Val Asn Gly Phe Ser Asn
305                 310                 315                 320

Lys Tyr Trp Gly His Gly Gly Asp Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Lys Thr Phe Gln Lys Asp Gly Leu Ser
    370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 70
<211> LENGTH: 410
<212> TYPE: PRT
<213> ORGANISM: Artificial
<220> FEATURE:
<223> OTHER INFORMATION: His-TnGalNAcT(33-421; I311Y,W336H,E339S)

<400> SEQUENCE: 70

Met Gly Ser Ser His His His His His Ser Ser Gly Leu Val Pro
 1               5                  10                  15
```

Arg Gly Ser His Met Ser Pro Leu Arg Thr Tyr Leu Tyr Thr Pro Leu
            20                  25                  30

Tyr Asn Ala Thr Gln Pro Thr Leu Arg Asn Val Glu Arg Leu Ala Ala
        35                  40                  45

Asn Trp Pro Lys Lys Ile Pro Ser Asn Tyr Ile Glu Asp Ser Glu Glu
50                  55                  60

Tyr Ser Ile Lys Asn Ile Ser Leu Ser Asn His Thr Thr Arg Ala Ser
65                  70                  75                  80

Val Val His Pro Pro Ser Ser Ile Thr Glu Thr Ala Ser Lys Leu Asp
                85                  90                  95

Lys Asn Met Thr Ile Gln Asp Gly Ala Phe Ala Met Ile Ser Pro Thr
            100                 105                 110

Pro Leu Leu Ile Thr Lys Leu Met Asp Ser Ile Lys Ser Tyr Val Thr
        115                 120                 125

Thr Glu Asp Gly Val Lys Lys Ala Glu Ala Val Val Thr Leu Pro Leu
130                 135                 140

Cys Asp Ser Met Pro Pro Asp Leu Gly Pro Ile Thr Leu Asn Lys Thr
145                 150                 155                 160

Glu Leu Glu Leu Glu Trp Val Glu Lys Lys Phe Pro Glu Val Glu Trp
                165                 170                 175

Gly Gly Arg Tyr Ser Pro Pro Asn Cys Thr Ala Arg His Arg Val Ala
            180                 185                 190

Ile Ile Val Pro Tyr Arg Asp Arg Gln Gln His Leu Ala Ile Phe Leu
        195                 200                 205

Asn His Met His Pro Phe Leu Met Lys Gln Gln Ile Glu Tyr Gly Ile
210                 215                 220

Phe Ile Val Glu Gln Glu Gly Asn Lys Asp Phe Asn Arg Ala Lys Leu
225                 230                 235                 240

Met Asn Val Gly Phe Val Glu Ser Gln Lys Leu Val Ala Glu Gly Trp
                245                 250                 255

Gln Cys Phe Val Phe His Asp Ile Asp Leu Leu Pro Leu Asp Thr Arg
            260                 265                 270

Asn Leu Tyr Ser Cys Pro Arg Gln Pro Arg His Met Ser Ala Ser Ile
        275                 280                 285

Asp Lys Leu His Phe Lys Leu Pro Tyr Glu Asp Tyr Phe Gly Gly Val
290                 295                 300

Ser Ala Met Thr Leu Glu Gln Phe Thr Arg Val Asn Gly Phe Ser Asn
305                 310                 315                 320

Lys Tyr Trp Gly His Gly Gly Ser Asp Asp Met Ser Tyr Arg Leu
                325                 330                 335

Lys Lys Ile Asn Tyr His Ile Ala Arg Tyr Lys Met Ser Ile Ala Arg
            340                 345                 350

Tyr Ala Met Leu Asp His Lys Lys Ser Thr Pro Asn Pro Lys Arg Tyr
        355                 360                 365

Gln Leu Leu Ser Gln Thr Ser Leu Thr Phe Gln Lys Asp Gly Leu Ser
370                 375                 380

Thr Leu Glu Tyr Glu Leu Val Gln Val Val Gln Tyr His Leu Tyr Thr
385                 390                 395                 400

His Ile Leu Val Asn Ile Asp Glu Arg Ser
                405                 410

<210> SEQ ID NO 71
<211> LENGTH: 375
<212> TYPE: PRT

<213> ORGANISM: Artificial
<220> FEATURE:
<223> OTHER INFORMATION: His-AsGalNAcT(30-383)

<400> SEQUENCE: 71

```
Met Gly Ser Ser His His His His His His Ser Ser Gly Leu Val Pro
1               5                   10                  15

Arg Gly Ser His Met Asp Tyr Ser Phe Trp Ser Pro Ala Phe Ile Ile
            20                  25                  30

Ser Ala Pro Lys Thr Leu Thr Thr Leu Gln Pro Phe Ser Gln Ser Thr
        35                  40                  45

Ser Thr Asn Asp Leu Ala Val Ser Ala Leu Glu Ser Val Glu Phe Ser
    50                  55                  60

Met Leu Asp Asn Ser Ser Ile Leu His Ala Ser Asp Asn Trp Thr Asn
65                  70                  75                  80

Asp Glu Leu Val Met Arg Ala Gln Asn Glu Asn Leu Gln Leu Cys Pro
                85                  90                  95

Met Thr Pro Pro Ala Leu Val Gly Pro Ile Lys Val Trp Met Asp Ala
            100                 105                 110

Pro Ser Phe Ala Glu Leu Glu Arg Leu Tyr Pro Phe Leu Glu Pro Gly
        115                 120                 125

Gly His Gly Met Pro Thr Ala Cys Arg Ala Arg His Arg Val Ala Ile
    130                 135                 140

Val Val Pro Tyr Arg Asp Arg Glu Ser His Leu Arg Thr Phe Leu His
145                 150                 155                 160

Asn Leu His Ser Leu Leu Thr Lys Gln Gln Leu Asp Tyr Ala Ile Phe
                165                 170                 175

Val Val Glu Gln Thr Ala Asn Glu Thr Phe Asn Arg Ala Lys Leu Met
            180                 185                 190

Asn Val Gly Tyr Ala Glu Ala Ile Arg Leu Tyr Asp Trp Arg Cys Phe
        195                 200                 205

Ile Phe His Asp Val Asp Leu Leu Pro Glu Asp Arg Asn Leu Tyr
    210                 215                 220

Ser Cys Pro Asp Glu Pro Arg His Met Ser Val Ala Val Asp Lys Phe
225                 230                 235                 240

Asn Tyr Lys Leu Pro Tyr Gly Ser Ile Phe Gly Gly Ile Ser Ala Leu
                245                 250                 255

Thr Arg Glu Gln Phe Glu Gly Ile Asn Gly Phe Ser Asn Asp Tyr Trp
            260                 265                 270

Gly Trp Gly Gly Glu Asp Asp Leu Ser Thr Arg Val Thr Leu Ala
        275                 280                 285

Gly Tyr Lys Ile Ser Arg Tyr Pro Ala Glu Ile Ala Arg Tyr Lys Met
    290                 295                 300

Ile Lys His Asn Ser Glu Lys Lys Asn Pro Val Asn Arg Cys Arg Tyr
305                 310                 315                 320

Lys Leu Met Ser Ala Thr Lys Ser Arg Trp Arg Asn Asp Gly Leu Ser
                325                 330                 335

Ser Leu Ser Tyr Asp Leu Ile Ser Leu Gly Arg Leu Pro Leu Tyr Thr
            340                 345                 350

His Ile Lys Val Asp Leu Leu Glu Lys Gln Ser Arg Arg Tyr Leu Arg
        355                 360                 365

Thr His Gly Phe Pro Thr Cys
    370                 375
```

```
<210> SEQ ID NO 72
<211> LENGTH: 375
<212> TYPE: PRT
<213> ORGANISM: Artificial
<220> FEATURE:
<223> OTHER INFORMATION: His-AsGalNAcT(30-383; W282H)

<400> SEQUENCE: 72
```

| | | | | | | | | | | | | | | |
|---|---|---|---|---|---|---|---|---|---|---|---|---|---|---|
|Met|Gly|Ser|Ser|His|His|His|His|His|Ser|Ser|Gly|Leu|Val|Pro|
|1| | | |5| | | | |10| | | | |15|
|Arg|Gly|Ser|His|Met|Asp|Tyr|Ser|Phe|Trp|Ser|Pro|Ala|Phe|Ile|Ile|
| | | | |20| | | | |25| | | | |30|
|Ser|Ala|Pro|Lys|Thr|Leu|Thr|Thr|Leu|Gln|Pro|Phe|Ser|Gln|Ser|Thr|
| | | |35| | | | |40| | | | |45| |
|Ser|Thr|Asn|Asp|Leu|Ala|Val|Ser|Ala|Leu|Glu|Ser|Val|Glu|Phe|Ser|
| | |50| | | | |55| | | | |60| | |
|Met|Leu|Asp|Asn|Ser|Ser|Ile|Leu|His|Ala|Ser|Asp|Asn|Trp|Thr|Asn|
|65| | | | |70| | | | |75| | | | |80|
|Asp|Glu|Leu|Val|Met|Arg|Ala|Gln|Asn|Glu|Asn|Leu|Gln|Leu|Cys|Pro|
| | | | |85| | | | |90| | | | |95| |
|Met|Thr|Pro|Pro|Ala|Leu|Val|Gly|Pro|Ile|Lys|Val|Trp|Met|Asp|Ala|
| | | |100| | | | |105| | | | |110| | |
|Pro|Ser|Phe|Ala|Glu|Leu|Glu|Arg|Leu|Tyr|Pro|Phe|Leu|Glu|Pro|Gly|
| | |115| | | | |120| | | | |125| | | |
|Gly|His|Gly|Met|Pro|Thr|Ala|Cys|Arg|Ala|Arg|His|Arg|Val|Ala|Ile|
| |130| | | | |135| | | | |140| | | | |
|Val|Val|Pro|Tyr|Arg|Asp|Arg|Glu|Ser|His|Leu|Arg|Thr|Phe|Leu|His|
|145| | | | |150| | | | |155| | | | |160|
|Asn|Leu|His|Ser|Leu|Leu|Thr|Lys|Gln|Gln|Leu|Asp|Tyr|Ala|Ile|Phe|
| | | | |165| | | | |170| | | | |175| |
|Val|Val|Glu|Gln|Thr|Ala|Asn|Glu|Thr|Phe|Asn|Arg|Ala|Lys|Leu|Met|
| | | |180| | | | |185| | | | |190| | |
|Asn|Val|Gly|Tyr|Ala|Glu|Ala|Ile|Arg|Leu|Tyr|Asp|Trp|Arg|Cys|Phe|
| | |195| | | | |200| | | | |205| | | |
|Ile|Phe|His|Asp|Val|Asp|Leu|Leu|Pro|Glu|Asp|Asp|Arg|Asn|Leu|Tyr|
| |210| | | | |215| | | | |220| | | | |
|Ser|Cys|Pro|Asp|Glu|Pro|Arg|His|Met|Ser|Val|Ala|Val|Asp|Lys|Phe|
|225| | | | |230| | | | |235| | | | |240|
|Asn|Tyr|Lys|Leu|Pro|Tyr|Gly|Ser|Ile|Phe|Gly|Gly|Ile|Ser|Ala|Leu|
| | | | |245| | | | |250| | | | |255| |
|Thr|Arg|Glu|Gln|Phe|Glu|Gly|Ile|Asn|Gly|Phe|Ser|Asn|Asp|Tyr|Trp|
| | | |260| | | | |265| | | | |270| | |
|Gly|His|Gly|Gly|Glu|Asp|Asp|Leu|Ser|Thr|Arg|Val|Thr|Leu|Ala|
| | |275| | | | |280| | | | |285| | | |
|Gly|Tyr|Lys|Ile|Ser|Arg|Tyr|Pro|Ala|Glu|Ile|Ala|Arg|Tyr|Lys|Met|
| |290| | | | |295| | | | |300| | | | |
|Ile|Lys|His|Asn|Ser|Glu|Lys|Lys|Asn|Pro|Val|Asn|Arg|Cys|Arg|Tyr|
|305| | | | |310| | | | |315| | | | |320|
|Lys|Leu|Met|Ser|Ala|Thr|Lys|Ser|Arg|Trp|Arg|Asn|Asp|Gly|Leu|Ser|
| | | | |325| | | | |330| | | | |335| |
|Ser|Leu|Ser|Tyr|Asp|Leu|Ile|Ser|Leu|Gly|Arg|Leu|Pro|Leu|Tyr|Thr|
| | | |340| | | | |345| | | | |350| | |
|His|Ile|Lys|Val|Asp|Leu|Leu|Glu|Lys|Gln|Ser|Arg|Arg|Tyr|Leu|Arg|
| | |355| | | | |360| | | | |365| | | |
|Thr|His|Gly|Phe|Pro|Thr|Cys| | | | | | | | | |

370                 375

<210> SEQ ID NO 73
<211> LENGTH: 375
<212> TYPE: PRT
<213> ORGANISM: Artificial
<220> FEATURE:
<223> OTHER INFORMATION: His-AsGalNAcT(30-383; E285D)

<400> SEQUENCE: 73

```
Met Gly Ser Ser His His His His His Ser Gly Leu Val Pro
1               5                   10                  15

Arg Gly Ser His Met Asp Tyr Ser Phe Trp Ser Pro Ala Phe Ile Ile
            20                  25                  30

Ser Ala Pro Lys Thr Leu Thr Thr Leu Gln Pro Phe Ser Gln Ser Thr
        35                  40                  45

Ser Thr Asn Asp Leu Ala Val Ser Ala Leu Glu Ser Val Glu Phe Ser
    50                  55                  60

Met Leu Asp Asn Ser Ser Ile Leu His Ala Ser Asp Asn Trp Thr Asn
65                  70                  75                  80

Asp Glu Leu Val Met Arg Ala Gln Asn Glu Asn Leu Gln Leu Cys Pro
                85                  90                  95

Met Thr Pro Pro Ala Leu Val Gly Pro Ile Lys Val Trp Met Asp Ala
            100                 105                 110

Pro Ser Phe Ala Glu Leu Glu Arg Leu Tyr Pro Phe Leu Glu Pro Gly
        115                 120                 125

Gly His Gly Met Pro Thr Ala Cys Arg Ala Arg His Arg Val Ala Ile
    130                 135                 140

Val Val Pro Tyr Arg Asp Arg Glu Ser His Leu Arg Thr Phe Leu His
145                 150                 155                 160

Asn Leu His Ser Leu Leu Thr Lys Gln Gln Leu Asp Tyr Ala Ile Phe
                165                 170                 175

Val Val Glu Gln Thr Ala Asn Glu Thr Phe Asn Arg Ala Lys Leu Met
            180                 185                 190

Asn Val Gly Tyr Ala Glu Ala Ile Arg Leu Tyr Asp Trp Arg Cys Phe
        195                 200                 205

Ile Phe His Asp Val Asp Leu Leu Pro Glu Asp Arg Asn Leu Tyr
    210                 215                 220

Ser Cys Pro Asp Glu Pro Arg His Met Ser Val Ala Val Asp Lys Phe
225                 230                 235                 240

Asn Tyr Lys Leu Pro Tyr Gly Ser Ile Phe Gly Gly Ile Ser Ala Leu
                245                 250                 255

Thr Arg Glu Gln Phe Glu Gly Ile Asn Gly Phe Ser Asn Asp Tyr Trp
            260                 265                 270

Gly Trp Gly Gly Asp Asp Asp Leu Ser Thr Arg Val Thr Leu Ala
        275                 280                 285

Gly Tyr Lys Ile Ser Arg Tyr Pro Ala Glu Ile Ala Arg Tyr Lys Met
    290                 295                 300

Ile Lys His Asn Ser Glu Lys Lys Asn Pro Val Asn Arg Cys Arg Tyr
305                 310                 315                 320

Lys Leu Met Ser Ala Thr Lys Ser Arg Trp Arg Asn Asp Gly Leu Ser
                325                 330                 335

Ser Leu Ser Tyr Asp Leu Ile Ser Leu Gly Arg Leu Pro Leu Tyr Thr
            340                 345                 350

His Ile Lys Val Asp Leu Leu Glu Lys Gln Ser Arg Arg Tyr Leu Arg
```

```
            355                 360                 365
Thr His Gly Phe Pro Thr Cys
    370             375

<210> SEQ ID NO 74
<211> LENGTH: 375
<212> TYPE: PRT
<213> ORGANISM: Artificial
<220> FEATURE:
<223> OTHER INFORMATION: His-AsGalNAcT(30-383; I257Y)

<400> SEQUENCE: 74

Met Gly Ser Ser His His His His His Ser Ser Gly Leu Val Pro
1               5                   10                  15

Arg Gly Ser His Met Asp Tyr Ser Phe Trp Ser Pro Ala Phe Ile Ile
            20                  25                  30

Ser Ala Pro Lys Thr Leu Thr Leu Gln Pro Phe Ser Gln Ser Thr
        35                  40                  45

Ser Thr Asn Asp Leu Ala Val Ser Ala Leu Glu Ser Val Glu Phe Ser
    50                  55                  60

Met Leu Asp Asn Ser Ser Ile Leu His Ala Ser Asp Asn Trp Thr Asn
65                  70                  75                  80

Asp Glu Leu Val Met Arg Ala Gln Asn Glu Asn Leu Gln Leu Cys Pro
                85                  90                  95

Met Thr Pro Pro Ala Leu Val Gly Pro Ile Lys Val Trp Met Asp Ala
            100                 105                 110

Pro Ser Phe Ala Glu Leu Glu Arg Leu Tyr Pro Phe Leu Glu Pro Gly
        115                 120                 125

Gly His Gly Met Pro Thr Ala Cys Arg Ala Arg His Arg Val Ala Ile
    130                 135                 140

Val Val Pro Tyr Arg Asp Arg Glu Ser His Leu Arg Thr Phe Leu His
145                 150                 155                 160

Asn Leu His Ser Leu Leu Thr Lys Gln Gln Leu Asp Tyr Ala Ile Phe
                165                 170                 175

Val Val Glu Gln Thr Ala Asn Glu Thr Phe Asn Arg Ala Lys Leu Met
            180                 185                 190

Asn Val Gly Tyr Ala Glu Ala Ile Arg Leu Tyr Asp Trp Arg Cys Phe
        195                 200                 205

Ile Phe His Asp Val Asp Leu Leu Pro Glu Asp Asp Arg Asn Leu Tyr
    210                 215                 220

Ser Cys Pro Asp Glu Pro Arg His Met Ser Val Ala Val Asp Lys Phe
225                 230                 235                 240

Asn Tyr Lys Leu Pro Tyr Gly Ser Tyr Phe Gly Gly Ile Ser Ala Leu
                245                 250                 255

Thr Arg Glu Gln Phe Glu Gly Ile Asn Gly Phe Ser Asn Asp Tyr Trp
            260                 265                 270

Gly Trp Gly Gly Glu Asp Asp Asp Leu Ser Thr Arg Val Thr Leu Ala
        275                 280                 285

Gly Tyr Lys Ile Ser Arg Tyr Pro Ala Glu Ile Ala Arg Tyr Lys Met
    290                 295                 300

Ile Lys His Asn Ser Glu Lys Lys Asn Pro Val Asn Arg Cys Arg Tyr
305                 310                 315                 320

Lys Leu Met Ser Ala Thr Lys Ser Arg Trp Arg Asn Asp Gly Leu Ser
                325                 330                 335

Ser Leu Ser Tyr Asp Leu Ile Ser Leu Gly Arg Leu Pro Leu Tyr Thr
```

|  |  |  | 340 |  |  | 345 |  |  | 350 |  |  |
|---|---|---|---|---|---|---|---|---|---|---|---|

His Ile Lys Val Asp Leu Leu Glu Lys Gln Ser Arg Arg Tyr Leu Arg
            355                    360                    365

Thr His Gly Phe Pro Thr Cys
            370                    375

<210> SEQ ID NO 75
<211> LENGTH: 1173
<212> TYPE: DNA
<213> ORGANISM: Artificial
<220> FEATURE:
<223> OTHER INFORMATION: TnGalNAcT(33-421)

<400> SEQUENCE: 75

| atgtcaccgc | tgcgtaccta | cctgtatacc | ccgctgtata | atgccaccca | accgaccctg | 60 |
|---|---|---|---|---|---|---|
| cgtaatgtgg | aacgtctggc | tgcgaactgg | ccgaagaaaa | ttccgagcaa | ctatatcgaa | 120 |
| gattcagaag | aatactcgat | caaaaacatc | agtctgtcca | atcataccac | gcgtgcgagt | 180 |
| gtggttcacc | cgccgagctc | tatcaccgaa | acggcctcca | aactggacaa | aaatatgacc | 240 |
| attcaggatg | gcgcgttcgc | catgattagc | ccgaccccgc | tgctgatcac | gaaactgatg | 300 |
| gacagcatta | atcttatgt | caccacgaa | gatggcgtga | agaaagcgga | agctgtcgtt | 360 |
| accctgccgc | tgtgtgactc | catgccgcca | gatctgggtc | cgattaccct | gaacaaaacg | 420 |
| gaactggaac | tggaatgggt | tgagaaaaaa | tttccggaag | tcgaatgggg | cggtcgctat | 480 |
| agtccgccga | actgtaccgc | acgtcatcgc | gtggctatta | tcgttccgta | ccgtgaccgc | 540 |
| cagcaacacc | tggcaatctt | tctgaatcac | atgcacccgt | tcctgatgaa | acagcaaatt | 600 |
| gaatacggca | tttttatcgt | ggaacaggaa | ggtaataaag | atttcaatcg | tgcaaaactg | 660 |
| atgaacgttg | gctttgtcga | atctcagaaa | ctggtggctg | aaggttggca | atgctttgtt | 720 |
| ttccatgaca | tcgatctgct | gccgctggat | acccgcaatc | tgtatagttg | tccgcgccag | 780 |
| ccgcgtcaca | tgtcagccag | catcgacaaa | ctgcactta | aactgccgta | cgaagatatt | 840 |
| tcggcggtg | tctcagccat | gaccctggaa | caatttacgc | gtgttaacgg | cttctcgaat | 900 |
| aaatattggg | gttggggcgg | tgaagatgac | gatatgagct | accgcctgaa | gaaaattaac | 960 |
| tatcatatcg | cccgttacaa | aatgagcatt | gcgcgctatg | ccatgctgga | ccacaaaaaa | 1020 |
| tctaccccga | atccgaaacg | ttaccagctg | ctgagtcaaa | ccagcaaaac | gtttcagaaa | 1080 |
| gatggtctgt | ctacgctgga | atatgaactg | gtccaagttg | tgcagtatca | tctgtacacg | 1140 |
| catattctgg | tgaacattga | cgaacgctct | tga |  |  | 1173 |

<210> SEQ ID NO 76
<211> LENGTH: 1233
<212> TYPE: DNA
<213> ORGANISM: Artificial
<220> FEATURE:
<223> OTHER INFORMATION: His-TnGalNAcT(33-421)

<400> SEQUENCE: 76

| atgggcagca | gccatcatca | tcatcatcac | agcagcggcc | tggtgccgcg | cggcagccat | 60 |
|---|---|---|---|---|---|---|
| atgtcaccgc | tgcgtaccta | cctgtatacc | ccgctgtata | atgccaccca | accgaccctg | 120 |
| cgtaatgtgg | aacgtctggc | tgcgaactgg | ccgaagaaaa | ttccgagcaa | ctatatcgaa | 180 |
| gattcagaag | aatactcgat | caaaaacatc | agtctgtcca | atcataccac | gcgtgcgagt | 240 |
| gtggttcacc | cgccgagctc | tatcaccgaa | acggcctcca | aactggacaa | aaatatgacc | 300 |
| attcaggatg | gcgcgttcgc | catgattagc | ccgaccccgc | tgctgatcac | gaaactgatg | 360 |

```
gacagcatta aatcttatgt caccacggaa gatggcgtga agaaagcgga agctgtcgtt    420
accctgccgc tgtgtgactc catgccgcca gatctgggtc cgattaccct gaacaaaacg    480
gaactggaac tggaatgggt tgagaaaaaa tttccggaag tcgaatgggg cggtcgctat    540
agtccgccga actgtaccgc acgtcatcgc gtggctatta tcgttccgta ccgtgaccgc    600
cagcaacacc tggcaatctt tctgaatcac atgcaccgt tcctgatgaa acagcaaatt    660
gaatacggca tttttatcgt ggaacaggaa ggtaataaag atttcaatcg tgcaaaactg    720
atgaacgttg gctttgtcga atctcagaaa ctggtggctg aaggttggca atgctttgtt    780
ttccatgaca tcgatctgct gccgctggat acccgcaatc tgtatagttg tccgcgccag    840
ccgcgtcaca tgtcagccag catcgacaaa ctgcacttta aactgccgta cgaagatatt    900
ttcggcggtg tctcagccat gaccctggaa caatttacgc gtgttaacgg cttctcgaat    960
aaatattggg gttggggcgg tgaagatgac gatatgagct accgcctgaa gaaaattaac   1020
tatcatatcg cccgttacaa aatgagcatt gcgcgctatg ccatgctgga ccacaaaaaa   1080
tctaccccga atccgaaacg ttaccagctg ctgagtcaaa ccagcaaaac gtttcagaaa   1140
gatggtctgt ctacgctgga atatgaactg gtccaagttg tgcagtatca tctgtacacg   1200
catattctgg tgaacattga cgaacgctct tga                               1233
```

<210> SEQ ID NO 77
<211> LENGTH: 1068
<212> TYPE: DNA
<213> ORGANISM: Artificial
<220> FEATURE:
<223> OTHER INFORMATION: AsGalNAcT(30-383)

<400> SEQUENCE: 77

```
atggattact cattctggag cccggcgttc atcatctctg ccccgaaaac cctgaccacc     60
ctgcaaccgt tctctcagtc tacctctacc aacgacctgg cagtctcagc tctggaatcg    120
gtggaattta gcatgctgga taatagctct attctgcatg cgtctgacaa ctggaccaat    180
gatgaactgg tgatgcgcgc ccagaacgaa aatctgcaac tgtgtccgat gacgccgccg    240
gcgctggttg gcccgatcaa agtttggatg gatgcgccga gctttgccga actggaacgt    300
ctgtatccgt tcctggaacc gggcggtcat ggtatgccga ccgcctgtcg tgcacgtcac    360
cgtgttgcca ttgtggttcc gtatcgcgac cgtgaatccc acctgcgcac cttcctgcat    420
aacctgcact cactgctgac gaaacagcaa ctggattacg caatctttgt cgtggaacag    480
accgcaaacg aaacgttcaa tcgtgctaaa ctgatgaatt tggctatgc ggaagccatt    540 cgcctgtacg attggcgttg ctttatcttc catgacgtcg atctgctgcc ggaagatgac    600
cgcaacctgt attcttgtcc ggacgaaccg gtcacatga gtgttgcagt cgataaattc    660
aactacaaac tgccgtacgg ttcgattttc ggcggtatca gcgctctgac ccgcgaacaa    720
tttgaaggca ttaacggttt cagcaatgat tactggggct ggggcggtga agatgacgat    780
ctgtcgaccc gtgtgacgct ggcgggttat aaaatcagcc gctacccggc agaaatcgct    840
cgttacaaaa tgatcaaaca taacagtgaa aagaaaaacc cggttaatcg ctgccgttac    900
aaactgatgt ctgccaccaa aagtcgctgg cgtaatgacg gcctgagttc cctgtcctat    960
gatctgattt cactgggtcg cctgccgctg tacacgcaca tcaaagttga cctgctggaa   1020
aaacaatctc gccgctatct gcgtacccac ggcttcccga cctgctga               1068
```

<210> SEQ ID NO 78

<211> LENGTH: 1128
<212> TYPE: DNA
<213> ORGANISM: Artificial
<220> FEATURE:
<223> OTHER INFORMATION: His-AsGalNAcT(30-383)

<400> SEQUENCE: 78

| | | |
|---|---|---|
| atgggcagca gccatcatca tcatcatcac agcagcggcc tggtgccgcg cggcagccat | 60 |
| atggattact cattctggag cccggcgttc atcatctctg ccccgaaaac cctgaccacc | 120 |
| ctgcaaccgt tctctcagtc tacctctacc aacgacctgg cagtctcagc tctggaatcg | 180 |
| gtggaattta gcatgctgga taatagctct attctgcatg cgtctgacaa ctggaccaat | 240 |
| gatgaactgg tgatgcgcgc ccagaacgaa atctgcaac tgtgtccgat gacgccgccg | 300 |
| gcgctggttg cccgatcaa agtttggatg gatgcgccga gctttgccga actggaacgt | 360 |
| ctgtatccgt tcctggaacc gggcggtcat ggtatgccga ccgcctgtcg tgcacgtcac | 420 |
| cgtgttgcca ttgtggttcc gtatcgcgac cgtgaatccc acctgcgcac cttcctgcat | 480 |
| aacctgcact cactgctgac gaaacagcaa ctggattacg caatctttgt cgtggaacag | 540 |
| accgcaaacg aaacgttcaa tcgtgctaaa ctgatgaatg ttggctatgc ggaagccatt | 600 |
| cgcctgtacg attggcgttg ctttatcttc catgacgtcg atctgctgcc ggaagatgac | 660 |
| cgcaacctgt attcttgtcc ggacgaaccg cgtcacatga gtgttgcagt cgataaattc | 720 |
| aactacaaac tgccgtacgg ttcgattttc ggcggtatca cgctctgac ccgcgaacaa | 780 |
| tttgaaggca ttaacggttt cagcaatgat tactggggct ggggcggtga agatgacgat | 840 |
| ctgtcgaccc gtgtgacgct ggcggggttat aaaatcagcc gctacccggc agaaatcgct | 900 |
| cgttacaaaa tgatcaaaca taacagtgaa agaaaaaacc cggttaatcg ctgccgttac | 960 |
| aaactgatgt ctgccaccaa agtcgctgg cgtaatgacg gcctgagttc cctgtcctat | 1020 |
| gatctgattt cactgggtcg cctgccgctg tacacgcaca tcaaagttga cctgctggaa | 1080 |
| aaacaatctc gccgctatct gcgtacccac ggcttcccga cctgctga | 1128 |

<210> SEQ ID NO 79
<211> LENGTH: 43
<212> TYPE: DNA
<213> ORGANISM: Artificial
<220> FEATURE:
<223> OTHER INFORMATION: primer sequence W336F, fwd

<400> SEQUENCE: 79
ctcgaataaa tattggggtt ttggcggtga agatgacgat atg    43

<210> SEQ ID NO 80
<211> LENGTH: 43
<212> TYPE: DNA
<213> ORGANISM: Artificial
<220> FEATURE:
<223> OTHER INFORMATION: primer sequence W336F,rev

<400> SEQUENCE: 80
catatcgtca tcttcaccgc caaaaccca atatttattc gag    43

<210> SEQ ID NO 81
<211> LENGTH: 36
<212> TYPE: DNA
<213> ORGANISM: Artificial
<220> FEATURE:
<223> OTHER INFORMATION: primer sequence W336H,fwd

<400> SEQUENCE: 81

```
cgaataaata ttggggtcac ggcggtgaag atgacg                              36
```

<210> SEQ ID NO 82
<211> LENGTH: 36
<212> TYPE: DNA
<213> ORGANISM: Artificial
<220> FEATURE:
<223> OTHER INFORMATION: primer sequence W336H,rev

<400> SEQUENCE: 82

```
cgtcatcttc accgccgtga ccccaatatt tattcg                              36
```

<210> SEQ ID NO 83
<211> LENGTH: 36
<212> TYPE: DNA
<213> ORGANISM: Artificial
<220> FEATURE:
<223> OTHER INFORMATION: primer sequence W336V,fwd

<400> SEQUENCE: 83

```
cgaataaata ttggggtgtg ggcggtgaag atgacg                              36
```

<210> SEQ ID NO 84
<211> LENGTH: 36
<212> TYPE: DNA
<213> ORGANISM: Artificial
<220> FEATURE:
<223> OTHER INFORMATION: primer sequence W336V,rev

<400> SEQUENCE: 84

```
cgtcatcttc accgcccaca ccccaatatt tattcg                              36
```

<210> SEQ ID NO 85
<211> LENGTH: 31
<212> TYPE: DNA
<213> ORGANISM: Artificial
<220> FEATURE:
<223> OTHER INFORMATION: primer sequence E339A,fwd

<400> SEQUENCE: 85

```
gggttggggc ggtgcggatg acgatatgag c                                   31
```

<210> SEQ ID NO 86
<211> LENGTH: 31
<212> TYPE: DNA
<213> ORGANISM: Artificial
<220> FEATURE:
<223> OTHER INFORMATION: primer sequence E339A,rev

<400> SEQUENCE: 86

```
gctcatatcg tcatccgcac cgccccaacc c                                   31
```

<210> SEQ ID NO 87
<211> LENGTH: 30
<212> TYPE: DNA
<213> ORGANISM: Artificial
<220> FEATURE:
<223> OTHER INFORMATION: primer sequence E339G,fwd

<400> SEQUENCE: 87

```
gggttggggc ggtggagatg acgatatgag                                     30
```

<210> SEQ ID NO 88
<211> LENGTH: 30
<212> TYPE: DNA

```
<213> ORGANISM: Artificial
<220> FEATURE:
<223> OTHER INFORMATION: primer sequence E339G,rev

<400> SEQUENCE: 88
ctcatatcgt catctccacc gccccaaccc                                30

<210> SEQ ID NO 89
<211> LENGTH: 31
<212> TYPE: DNA
<213> ORGANISM: Artificial
<220> FEATURE:
<223> OTHER INFORMATION: primer sequence E339D,fwd

<400> SEQUENCE: 89
gggttggggc ggtgatgatg acgatatgag c                              31

<210> SEQ ID NO 90
<211> LENGTH: 31
<212> TYPE: DNA
<213> ORGANISM: Artificial
<220> FEATURE:
<223> OTHER INFORMATION: primer sequence E339D,rev

<400> SEQUENCE: 90
gctcatatcg tcatcatcac cgccccaacc c                              31

<210> SEQ ID NO 91
<211> LENGTH: 32
<212> TYPE: DNA
<213> ORGANISM: Artificial
<220> FEATURE:
<223> OTHER INFORMATION: primer sequence I311Y,fwd

<400> SEQUENCE: 91
gccgtacgaa gattatttcg gcggtgtctc ag                             32

<210> SEQ ID NO 92
<211> LENGTH: 32
<212> TYPE: DNA
<213> ORGANISM: Artificial
<220> FEATURE:
<223> OTHER INFORMATION: primer sequence I311Y,rev

<400> SEQUENCE: 92
ctgagacacc gccgaaataa tcttcgtacg gc                             32
```